US010927178B2

(12) United States Patent
Liu et al.

(10) Patent No.: US 10,927,178 B2
(45) Date of Patent: Feb. 23, 2021

(54) ANTI-CXCR4 ANTIBODIES AND ANTIBODY-DRUG CONJUGATES

(71) Applicant: PFIZER INC., New York, NY (US)

(72) Inventors: Shu-Hui Liu, Redwood City, CA (US); Flavia Mercer Pernasetti, San Diego, CA (US); Wei-Hsien Ho, Belmont, CA (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 16/535,477

(22) Filed: Aug. 8, 2019

(65) Prior Publication Data

US 2020/0102394 A1 Apr. 2, 2020

Related U.S. Application Data

(62) Division of application No. 16/166,830, filed on Oct. 22, 2018, now Pat. No. 10,421,815, which is a division of application No. 15/610,417, filed on May 31, 2017, now Pat. No. 10,144,781, which is a division of application No. 14/449,478, filed on Aug. 1, 2014, now Pat. No. 9,708,405.

(60) Provisional application No. 61/861,706, filed on Aug. 2, 2013.

(51) Int. Cl.

| | |
|---|---|
| ***C12N 15/09*** | (2006.01) |
| ***C12N 5/10*** | (2006.01) |
| ***C07K 16/28*** | (2006.01) |
| *C07K 14/715* | (2006.01) |
| *A61K 39/395* | (2006.01) |
| *C07H 21/04* | (2006.01) |
| *A61K 49/00* | (2006.01) |
| *A61K 47/68* | (2017.01) |
| *A61K 39/00* | (2006.01) |

(52) U.S. Cl.

CPC ............ *C07K 16/2866* (2013.01); *C12N 5/10* (2013.01); *C12N 15/09* (2013.01); *A61K 39/3955* (2013.01); *A61K 47/6803* (2017.08); *A61K 47/6809* (2017.08); *A61K 47/6847* (2017.08); *A61K 47/6849* (2017.08); *A61K 47/6851* (2017.08); *A61K 49/0002* (2013.01); *A61K 2039/505* (2013.01); *C07H 21/04* (2013.01); *C07K 14/7158* (2013.01); *C07K 2317/24* (2013.01); *C07K 2317/33* (2013.01); *C07K 2317/56* (2013.01); *C07K 2317/565* (2013.01); *C07K 2317/73* (2013.01); *C07K 2317/732* (2013.01); *C07K 2317/734* (2013.01); *C07K 2317/76* (2013.01); *C07K 2317/92* (2013.01); *C12N 2330/50* (2013.01); *C12N 2510/02* (2013.01); *C12N 2800/107* (2013.01)

(58) Field of Classification Search

CPC ....... C12N 15/09; C07K 14/715; C07K 16/28
See application file for complete search history.

*Primary Examiner* — Zachary C Howard
(74) *Attorney, Agent, or Firm* — Pfizer Inc.

(57) ABSTRACT

The present invention provides antibodies and related molecules that bind to chemokine receptor 4 (CXCR4). The invention further provides antibody-drug conjugates comprising such antibodies, antibody encoding nucleic acids, and methods of obtaining such antibodies. The invention further relates to therapeutic methods for use of these antibodies and anti-CXCR4 antibody-drug conjugates for the treatment of a disorder associated with CXCR4 function or expression (e.g., cancer), such as colon, RCC, esophageal, gastric, head and neck, lung, ovarian, pancreatic cancer or hematological cancers.

3 Claims, 16 Drawing Sheets

Specification includes a Sequence Listing.

FIG. 1

| | | |
|---|---|---|
| h3G10 | VH | EVQLVESGGGLVQPGGSLRLSCAASGFTFSDYYMSWVRQAPGKGLEWVGFIRHKANGYT |
| h3G10.A57 | VH | EVQLVESGGGLVQPGGSLRLSCAASGFTFSDYYMSWVRQAPGKGLEWVGFIRHKANFYT |
| h3G10.2.42 | VH | EVQLVESGGGLVQPGGSLRLSCAASGFTFSDYYMSWVRQAPGKGLEWVGFIRHKVNFYT |
| h3G10.1.7 | VH | EVQLVESGGGLVQPGGSLRLSCAASGFTFSDYYMSWVRQAPGKGLEWVGFIRHKANKYT |
| h3G10.1.60 | VH | EVQLVESGGGLVQPGGSLRLSCAASGFTFSDYYMSWVRQAPGKGLEWVGFIRHKANVYT |
| h3G10.2.5 | VH | EVQLVESGGGLVQPGGSLRLSCAASGFTFSDYYMSWVRQAPGKGLEWVGFIRHKANIYT |
| h3G10.1.91 | VH | EVQLVESGGGLVQPGGSLRLSCAASGFTFSDYYMSWVRQAPGKGLEWVGFIRHKANFET |
| h3G10.2.37 | VH | EVQLVESGGGLVQPGGSLRLSCAASGFTFSDYYMSWVRQAPGKGLEWVGFIRHKANFYT |
| h3G10.2.45 | VH | EVQLVESGGGLVQPGGSLRLSCAASGFTFSDYYMSWVRQAPGKGLEWVGFIRHKANFYT |
| h3G10.3.25 | VH | EVQLVESGGGLVQPGGSLRLSCAASGFTFSDYYMSWVRQAPGKGLEWVGFIRHKANFYT |
| h3G10.1.33 | VH | EVQLVESGGGLVQPGGSLRLSCAASGFTFSDYYMSWVRQAPGKGLEWVGFIRHKANFYT |
| h3G10.2.54 | VH | EVQLVESGGGLVQPGGSLRLSCAASGFTFSDYYMSWVRQAPGKGLEWVGFIRHKANFYT |
| h3G10.A59 | VH | EVQLVESGGGLVQPGGSLRLSCAASGFTFSDYYMSWVRQAPGKGLEWVGFIRHKANTYT |
| h3G10.A62 | VH | EVQLVESGGGLVQPGGSLRLSCAASGFTFSDYYMSWVRQAPGKGLEWVGFIRHKANLYT |
| h3G10.B44 | VH | EVQLVESGGGLVQPGGSLRLSCAASGFTFSDYYMSWVRQAPGKGLEWVSFIRHKANFYT |

| | | |
|---|---|---|
| h3G10 | VH | TEYSTSVKGRFTISRDDSKNSLYLQMNSLKTEDTAVYYCARDLPGFAYWGQGTLVTVSS |
| h3G10.A57 | VH | TEYSTSVKGRFTISRDDSKNSLYLQMNSLKTEDTAVYYCARDLPGFAYWGQGTLVTVSS |
| h3G10.2.42 | VH | TEYSTSVKGRFTISRDDSKNSLYLQMNSLKTEDTAVYYCARDLPGFAYWGQGTLVTVSS |
| h3G10.1.7 | VH | TEYSTSVKGRFTISRDDSKNSLYLQMNSLKTEDTAVYYCARDLPGFAYWGQGTLVTVSS |
| h3G10.1.60 | VH | TEYSTSVKGRFTISRDDSKNSLYLQMNSLKTEDTAVYYCARDLPGFAYWGQGTLVTVSS |
| h3G10.2.5 | VH | TEYSTSVKGRFTISRDDSKNSLYLQMNSLKTEDTAVYYCARDLPGFAYWGQGTLVTVSS |
| h3G10.1.91 | VH | TEYSTSVKGRFTISRDDSKNSLYLQMNSLKTEDTAVYYCARDLPGFAYWGQGTLVTVSS |
| h3G10.2.37 | VH | REYSTSVKGRFTISRDDSKNSLYLQMNSLKTEDTAVYYCARDLPGFAYWGQGTLVTVSS |
| h3G10.2.45 | VH | TEYSTWVKGRFTISRDDSKNSLYLQMNSLKTEDTAVYYCARDLPGFAYWGQGTLVTVSS |
| h3G10.3.25 | VH | TEYSTSDKGRFTISRDDSKNSLYLQMNSLKTEDTAVYYCARDLPGFAYWGQGTLVTVSS |
| h3G10.1.33 | VH | TEYSTSVTGRFTISRDDSKNSLYLQMNSLKTEDTAVYYCARDLPGFAYWGQGTLVTVSS |
| h3G10.2.54 | VH | TEYSTSVRGRFTISRDDSKNSLYLQMNSLKTEDTAVYYCARDLPGFAYWGQGTLVTVSS |
| h3G10.A59 | VH | TEYSTSVRGRFTISRDDSKNSLYLQMNSLKTEDTAVYYCARDLPGFAYWGQGTLVTVSS |
| h3G10.A62 | VH | TEYSTSVRGRFTISRDDSKNSLYLQMNSLKTEDTAVYYCARDLPGFAYWGQGTLVTVSS |
| h3G10.B44 | VH | TEYSTSVKGRFTISRDNSKNTLYLQMNSLRAEDTAVYYCAKDLPGFAYWGQGTLVTVSS |

FIG. 2

| | | |
|---|---|---|
| h3G10 | VL | DIVMTQSPDSLAVSLGERATINCKSSQSLFNSRTRKNYLAWYQQKPGQPPKLLIY |
| h3G10.2.72 | VL | DIVMTQSPDSLAVSLGERATINCKSSQSLFNSRTRKNYLAWYQQKPGQPPKLLIY |
| h3G10.2.25 | VL | DIVMTQSPDSLAVSLGERATINCRSSQSLFNSRTRKNYLAWYQQKPGQPPKLLIY |
| h3G10.A11A | VL | DIVMTQSPDSLAVSLGERATINCKSAQSLFNSRTRKNYLAWYQQKPGQPPKLLIY |
| h3G10.A11B | VL | DIVMTQSPDSLAVSLGERATINCKSAQSLFNSRTRKNYLAWYQQKPGQPPKLLIY |
| h3G10.A18A | VL | DIVMTQSPDSLAVSLGERATINCKSSWSLFNSRTRKNYLAWYQQKPGQPPKLLIY |
| h3G10.A18B | VL | DIVMTQSPDSLAVSLGERATINCKSSWSLFNSRTRKNYLAWYQQKPGQPPKLLIY |
| h3G10.A19A | VL | DIVMTQSPDSLAVSLGERATINCKSSNSLFNSRTRKNYLAWYQQKPGQPPKLLIY |
| h3G10.A19B | VL | DIVMTQSPDSLAVSLGERATINCKSSNSLFNSRTRKNYLAWYQQKPGQPPKLLIY |
| h3G10.A58A | VL | DIVMTQSPDSLAVSLGERATINCKSSQSLFNSHTRKNYLAWYQQKPGQPPKLLIY |
| h3G10.A58B | VL | DIVMTQSPDSLAVSLGERATINCKSSQSLFNSHTRKNYLAWYQQKPGQPPKLLIY |
| h3G10.A65A | VL | DIVMTQSPDSLAVSLGERATINCKSSQSLFNSRFRKNYLAWYQQKPGQPPKLLIY |
| h3G10.A65B | VL | DIVMTQSPDSLAVSLGERATINCKSSQSLFNSRFRKNYLAWYQQKPGQPPKLLIY |
| h3G10.B12A | VL | DIVMTQSPDSLAVSLGERATINCKSSQSLFNSRTRKNYLLWYQQKPGQPPKLLIY |
| h3G10.B12B | VL | DIVMTQSPDSLAVSLGERATINCKSSQSLFNSRTRKNYLLWYQQKPGQPPKLLIY |
| h3G10.B13A | VL | DIVMTQSPDSLAVSLGERATINCKSSQSLFNSRTRKNYLNWYQQKPGQPPKLLIY |
| h3G10.B13B | VL | DIVMTQSPDSLAVSLGERATINCKSSQSLFNSRTRKNYLNWYQQKPGQPPKLLIY |
| h3G10.B18 | VL | DIVMTQSPDSLAVSLGERATINCKSSQSLFNSRTRKNYLMWYQQKPGQPPKLLIY |
| h3G10.B18B | VL | DIVMTQSPDSLAVSLGERATINCKSSQSLFNSRTRKNYLMWYQQKPGQPPKLLIY |
| h3G10.L94D | VL | DIVMTQSPDSLAVSLGERATINCKSSQSLFNSRTRKNYLAWYQQKPGQPPKLLIY |

| | | |
|---|---|---|
| h3G10 | VL | WASARESGVPDRFSGSGSGTDFTLTISSLQAEDVAVYYCKQSFNLRTFGGGTKVEIK |
| h3G10.2.72 | VL | WASARESGVPDRFSGSGSGTDFTLTISSLQAEDVAVYYCKQSFRLRTFGGGTKVEIK |
| h3G10.2.25 | VL | WASARESGVPDRFSGSGSGTDFTLTISSLQAEDVAVYYCKQSFRLRTFGGGTKVEIK |
| h3G10.A11A | VL | WASARESGVPDRFSGSGSGTDFTLTISSLQAEDVAVYYCKQSFRLRTFGGGTKVEIK |
| h3G10.A11B | VL | WASARESGVPDRFSGSGSGTDFTLTISSLQAEDVAVYYCKQSFNLRTFGGGTKVEIK |
| h3G10.A18A | VL | WASARESGVPDRFSGSGSGTDFTLTISSLQAEDVAVYYCKQSFRLRTFGGGTKVEIK |
| h3G10.A18B | VL | WASARESGVPDRFSGSGSGTDFTLTISSLQAEDVAVYYCKQSFNLRTFGGGTKVEIK |
| h3G10.A19A | VL | WASARESGVPDRFSGSGSGTDFTLTISSLQAEDVAVYYCKQSFRLRTFGGGTKVEIK |
| h3G10.A19B | VL | WASARESGVPDRFSGSGSGTDFTLTISSLQAEDVAVYYCKQSFNLRTFGGGTKVEIK |
| h3G10.A58A | VL | WASARGSGVPDRFSGSGSGTDFTLTISSLQAEDVAVYYCKQSFRLRTFGGGTKVEIK |
| h3G10.A58B | VL | WASARGSGVPDRFSGSGSGTDFTLTISSLQAEDVAVYYCKQSFNLRTFGGGTKVEIK |
| h3G10.A65A | VL | WASARESGVPDRFSGSGSGTDFTLTISSLQAEDVAVYYCKQSFRLRTFGGGTKVEIK |
| h3G10.A65B | VL | WASARESGVPDRFSGSGSGTDFTLTISSLQAEDVAVYYCKQSFNLRTFGGGTKVEIK |
| h3G10.B12A | VL | WASARESGVPDRFSGSGSGTDFTLTISSLQAEDVAVYYCKQSFRLRTFGGGTKVEIK |
| h3G10.B12B | VL | WASARESGVPDRFSGSGSGTDFTLTISSLQAEDVAVYYCKQSFNLRTFGGGTKVEIK |
| h3G10.B13A | VL | WASARESGVPDRFSGSGSGTDFTLTISSLQAEDVAVYYCKQSFRLRTFGGGTKVEIK |
| h3G10.B13B | VL | WASARESGVPDRFSGSGSGTDFTLTISSLQAEDVAVYYCKQSFNLRTFGGGTKVEIK |
| h3G10.B18A | VL | WASARESGVPDRFSGSGSGTDFTLTISSLQAEDVAVYYCKQSFRLRTFGGGTKVEIK |
| h3G10.B18B | VL | WASARESGVPDRFSGSGSGTDFTLTISSLQAEDVAVYYCKQSFNLRTFGGGTKVEIK |
| h3G10.L94D | VL | WASARESGVPDRFSGSGSGTDFTLTISSLQAEDVAVYYCKQSFNDRTFGGGTKVEIK |

| | HPB-ALL | CHO-CynoCXCR4 |
|---|---|---|
| EC50 (nM) | 0.27 | 0.16 |

| | Raji | HSC-F |
|---|---|---|
| EC50 (nM) | 3.050 | 2.585 |

| | 3G10 | 6B6 | 12A11 |
|---|---|---|---|
| IC50nM | 1.555 | 1.418 | 27.07 |

| | Isotype Control | h3G10.1.91.A58B | Melphalan |
|---|---|---|---|
| Median Survival (Days) | 33.5 | Undefined | 36 |

ANTI-CXCR4 ANTIBODIES AND ANTIBODY-DRUG CONJUGATES

This application is a Divisional of U.S. application Ser. No. 16/166,830, filed Oct. 22, 2018, which is a Divisional of U.S. application Ser. No. 15/610,417, filed May 31, 2017, which issued as U.S. Pat. No. 10,144,781 which is a Divisional of U.S. application Ser. No. 14/449,478, filed Aug. 1, 2014, which issued as U.S. Pat. No. 9,708,405 and which claims the benefit of U.S. Provisional Application No. 61/861,706 filed on Aug. 2, 2013, hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC71971D_SEQListing_ST25.txt" created on Jul. 31, 2019 and having a size of 101 KB. The sequence listing contained in this .txt file is part of the specification and is herein incorporated by reference in its entirety.

FIELD OF THE INVENTION

The present invention relates to antibodies and related molecules that bind to chemokine receptor 4 (CXCR4). The present invention also relates to molecules comprising, or alternatively consisting of, full-length antibodies, antibody fragments or variants thereof. The present invention further relates to the amino acid and nucleic acid sequences coding for such antibodies. The present invention also relates to antibody conjugates (e.g., antibody-drug conjugates) comprising the anti-CXCR4 antibodies, compositions comprising the anti-CXCR4 antibodies, and methods of using the anti-CXCR4 antibodies, and their conjugates for treating conditions associated with CXCR4 expression (e.g., cancer). The invention further comprises the use of said antibodies, antigen-binding fragment thereof, or antibody-drug conjugates and corresponding processes, for detecting and diagnosing pathological disorders associated with expression of CXCR4. In certain aspects, the disorders are oncogenic disorders associated with increased expression of CXCR4 relative to normal or any other pathology connected with the overexpression of CXCR4. In other aspects, the disorders are inflammatory and immune disorders, allergic disorders, infections (HIV infection, etc.), auto-immune disorders (e.g., rheumatoid arthritis), fibrosis disorders (e.g., pulmonary), and cardiovascular disorders. The invention finally comprises products and/or compositions or kits comprising at least such antibody or antibody-drug conjugate for the prognosis or diagnostic or therapy monitoring of such disorders.

BACKGROUND OF INVENTION

Chemokines are small, secreted peptides that control the migration of leukocytes along a chemical gradient of ligand, known as chemokine gradient, especially during immune reactions (Zlotnik et al., 2000, Immunity, 12:121-127). They are classified into four classes according to the location of the Cys residues at the N-terminus. The CXC class consists of chemokines with a pair of Cys separated by a single residue. The most prominent members of this class are interleukin-8 (IL-8, CXCL8), stromal derived factor-1 (SDF-I, CXCL12), gamma-interferon inducible protein-10 (IP-10, CXCL10), platelet factor-4 (PF-4, CXCL4), neutrophil activating protein-2 (NAP-2, CXCL7) and melanoma growth stimulating activity (MGSA, CXCLI). The CC class of chemokines have two adjacent Cys at the N-terminus and include macrophage inflammatory protein-1 (MIP-Iα, CCL3; MIP-IjSa, CCL4), regulated upon activation of normal T expressed and secreted (RANTES, CCL5), monocyte chemoattractant protein-1 (MCP-I, CCL2). The CX3C class of chemokines contains two Cys separated by three residues at the N-terminus and are represented by fractalkine/neurotactin (CX3CL1). The C-class chemokines contain a single Cys at the N-terminus and are represented by lymphotactin/ATAC/SCM (CLI). Chemokine receptors are grouped according to their binding selectivity to chemokines. For example, CXCR4 binds SDF-I and CXCR5 binds B cell-attracting chemokine 1 (BCAI). The CXCR4 and SDF-1 interaction plays an important role in multiple phases of tumorigenesis, including tumor growth, invasion, angiogenesis, and metastasis.

CXCR4 is a seven transmembrane G protein coupled receptor (GPCR) (Herzog et al. DNA Cell Biol. 12: 465 (1993); Rimland et al. Mol. Pharmacol. 40: 869 (1991); WO03014153, WO02061087). Many medically significant biological processes are mediated by signal transduction pathways that involve G-proteins (Lefkowitz, Nature, 351: 353-354, (1991)). G protein-coupled receptors (GPCRs) are integral membrane proteins containing 7 putative transmembrane domains (TMs). These proteins mediate signals to the interior of the cell via activation of heterotrimeric G proteins that in turn activate various effector proteins, ultimately resulting in a physiologic response.

CXCR4 plays a role in embryogenesis, homeostasis and inflammation. Moreover, CXCR4 has been shown to function as a coreceptor for T lymphotrophic HIV-1 isolates (Feng, Y. et al. Science 272:872 (1996)). CXCR4 also plays a pleiotropic role in human cancer. Its expression is upregulated in many tumor types, including cancers of the breast, lung, colon, pancreas, brain, prostate, ovary, as well as hematopoietic cancers. Some literature reports suggest that SDF-1 may act through CXCR4 as a growth and/or survival factor for some tumors. CXCR4 is expressed on stem cell-like or tumor initiating subpopulations of many tumors, and may mediate the ability of these cells to support the recurrence and metastatic spread of cancers. Additionally, CXCR4 is expressed on endothelial precursor cells (EPCs), and its activity is required for incorporation of EPCs into functional vessels during angiogenesis. This may make a significant contribution to the vascularization and survival of tumors. CXCR4 signaling can also lead to induction of pro-angiogenic cytokines (e.g. VEGF), as well as integrins, adhesion molecules and matrix degrading enzymes that may mediate invasion by tumor cells. Furthermore, CXCR4 expression is detected on tumor infiltrating lymphocytes and fibroblasts, as well as tumor associated macrophages. These cells tend to suppress immune recognition and attack on the tumor, and remodel the tumor micro environment to encourage tumor growth and metastasis.

The multiple roles of CXCR4 in tumor growth, and metastasis, and its broad expression in many common tumor types, make this receptor an attractive target for therapeutic intervention using inhibitory agents. While peptide and small molecule inhibitors of CXCR4 and anti-CXCR antibodies have been identified or entered into the clinic, their utility has been limited by pharmacokinetic properties and toxicology. An agent, such as antibody or antibody-drug conjugate, that is selective, has a long half-life, improved efficacy and safety profile would be a desirable agent for use in the treatment of cancers.

Although there are various agents under development that target CXCR4, there exists a need for additional therapeutic agents targeting CXCR4 (such as antibodies or antibody-drug conjugates) that have improved efficacy and safety profile, and which are suitable for use with human patients. The antibodies and antibody-drug conjugates of the present invention are therapeutically useful anti-CXCR4 antibodies possessing a number of desirable properties such as reducing tumorigenesis, tumor growth, angiogenesis, and metastasis. Additionally, antibodies and antibody-drug conjugates of the present invention induce apoptosis of tumor cells.

SUMMARY OF THE INVENTION

The present invention provides isolated antibodies, antigen-binding fragments and derivatives thereof and antibody-drug conjugates that bind to chemokine receptors 4 (CXCR4). The invention includes the amino acid sequences of the variable heavy and light chain of the antibodies and their corresponding nucleic acid sequences.

In one aspect, the present invention includes the complementary determining regions (CDR) sequences of the antibodies to obtain binding molecules that comprise one or more CDR regions, or CDR-derived regions, that retain CXCR4-binding capacity of the parent molecule from which the CDR was (were) obtained.

In another aspect, the invention provides antibody-drug conjugate comprising the anti-CXCR4 antibodies disclosed herein.

In another aspect, the invention comprises the use of anti-CXCR4 antibody, antigen-binding fragments thereof, and antibody-drug conjugates and corresponding processes, for detecting and diagnosing disorders associated with expression or function of CXCR4. In one aspect, the disorders are cancer disorders associated with increased expression of CXCR4 relative to normal or any other pathology connected with the overexpression of CXCR4.

In another aspect, the invention comprises products and/or compositions or kits comprising at least such antibody, antigen binding fragment or antibody-drug conjugates for the prognosis or diagnostic or therapy monitoring of certain cancers.

In one aspect, the invention provides an isolated antibody, or an antigen binding fragment thereof, that binds to chemokine receptor 4 (CXCR4) and comprises: a) a heavy chain variable (VH) region comprising (i) a VH CDR1 selected from the group consisting of SEQ ID NOs:107, 113, 114, 108, 109, 115, 116, 117, 121 and 122; (ii) a VH CDR2 selected from the group consisting of SEQ ID NOs: 162, 128, 110, 111, 118, 119, 154, 123, 158, 124, 159, 125, 160, 126, 161, 127, 163, 164, 165, 166, 167, 168, 155, 129, 156, and 130, and, (iii) a VH CDR3 selected from the group consisting of SEQ ID NOs: 112, and 120; and/or; b) a light chain variable region (VL) region comprising (i) a VL CDR1 selected from the group consisting of SEQ ID NOs: 144, 131, 135, 138, 141, 142, 143, 146, 147, 148, 149, 150, and 151; (ii) a VL CDR2 selected from the group consisting of 145, 132, 136, and 152; and (iii) a VL CDR3 selected from the group consisting of SEQ ID NO: 139, 133, 137, 140, and 153.

In another aspect, the invention provides an isolated antibody, or an antigen-binding fragment thereof, that binds to chemokine receptor 4 (CXCR4) and comprises: a) a heavy chain variable (VH) region comprising complementary determining regions selected from the group consisting of (i) a VH CDR1 comprising the sequence set forth as SEQ ID NOs: 107, 113, 114, 108, 109, 115, 116, 117, 121 or 122; (ii) a VH CDR2 comprising the sequence set forth as SEQ ID NOs: 162, 128, 110, 111, 118, 119, 154, 123, 158, 124, 159, 125, 160, 126, 161, 127, 163, 164, 165, 166, 167, 168, 155, 129, 156, or 130, and; (iii) a VH CDR3 comprising the sequence set forth as SEQ ID NOs: 112, or 120; and/or b) a light chain variable region (VL) region comprising complementary determining regions selected from the group consisting of (i) a VL CDR1 comprising the sequence set forth as SEQ ID NOs: 144, 131, 135, 138, 141, 142, 143, 146, 147, 148, 149, 150, or 151; (ii) a VL CDR2 comprising the sequence set forth as SEQ ID NOs 145, 132, 136, or 152; and (iii) a VL CDR3 comprising the sequence set forth as SEQ ID NOs: 139, 133, 137, 140, or 153.

In another aspect, the invention provides an isolated antibody, or an antigen binding fragment thereof, that binds to chemokine receptor 4 (CXCR4) and comprises: a) a light chain variable (VL) region comprising (i) VL CDR1 comprising the sequence $X_1SX_2X_3SLFNSX_4X_5RKNYLX_6$ wherein $X_1$ is R or K; $X_2$ is S or A; $X_3$ is W, N or Q; $X_4$ is H or R; $X_5$ is T or F; and/or $X_6$ is A, L, N, or M (SEQ ID NO: 151); (ii) a VL CDR2 comprising the sequence $WASARX_1S$ Wherein $X_1$ is G or E (SEQ ID NOs: 152), and (iii) VL CDR3 comprising the sequence $KQSFX_1LRT$ Wherein $X_1$ is N or R (SEQ ID NO: 153); and/or b) a heavy chain variable (VH) region comprising (i) VH CDR1 comprising the sequence set forth as SEQ ID NOs: 107, 108, 109, 113, or 114; (ii) a VH CDR2 comprising the sequence set forth as SEQ ID NO: 157 and (iii) a VH CDR3 comprising the sequence set forth as SEQ ID NO: 112.

In one aspect, the invention provides an isolated antibody, or an antigen-binding fragment thereof, that binds to CXCR4 and comprises: a heavy chain variable (VH) region sequence comprising: EVQLVESGGGLVQPGGSLRLSCAASGFTFSDYYMSW VRQAPGKGLEWVX$_1$FIRHKX$_2$NX$_3$X$_4$TX$_5$EYSTX$_6$ X$_7$X$_8$GRFTISRDX$_9$SKNX$_{10}$LYLQMNSLX$_{11}$X$_{12}$EDTAVYYCAX$_{13}$DLPGFAYWGQGTLVTVSS (SEQ ID NO: 106), wherein $X_1$ is G or S; $X_2$ is V or A; $X_3$ is G, F, K, V, T, L, or I; $X_4$ is E or Y; $X_5$ is T or R; $X_6$ is W or S; $X_7$ is D or V; $X_8$ is K, T, or R; X is D or N; $X_{10}$ is T or S; $X_{11}$ is R or K; $X_{12}$ is A or T; and/or $X_{13}$ is K or R.

In one aspect, the invention provides an isolated antibody or antigen binding fragment thereof that binds to chemokine receptor 4 (CXCR4) is selected from the group consisting of: a) a heavy chain variable (VH) region having a VH CDR1 of SEQ ID NO:107, 113 or 114; a VH CDR2 of SEQ ID NO:162 or 128 and a VH CDR3 of SEQ ID NO:112 and a light chain variable (VL) region having a VL CDR1 of SEQ ID NO:144; a VL CDR2 of SEQ ID NO:145 and a VL CDR3 of SEQ ID NO:139; b) a VH region having a VH CDR1 of SEQ ID NO:115, 116, 117, 121 or 122; a VH CDR2 of SEQ ID NO:118 or 119 and a VH CDR3 of SEQ ID NO:120 and a VL region having a VL CDR1 of SEQ ID NO:135; a VL CDR2 of SEQ ID NO:136 and a VL CDR3 of SEQ ID NO:137; c) a VH region having a VH CDR1 of SEQ ID NO:107, 108, 109, 113 or 114; a VH CDR2 of SEQ ID NO:110 or 111 and a VH CDR3 of SEQ ID NO:112 and a VL region having a VL CDR1 of SEQ ID NO:131; a VL CDR2 of SEQ ID NO:132 and a VL CDR3 of SEQ ID NO:133; d) a VH region having a VH CDR1 of SEQ ID NO:107, 108, 109, 113 or 114; a VH CDR2 of SEQ ID NO:154 or 123 and a VH CDR3 of SEQ ID NO:112 and a VL region having a VL CDR1 of SEQ ID NO:138; a VL CDR2 of SEQ ID NO:132 and a VL CDR3 of SEQ ID NO:139; and e) a VH region having a VH CDR1 of SEQ ID NO:107, 108, 109, 113 or 114; a VH CDR2 of SEQ ID NO:157 and a VH CDR3 of SEQ ID NO:112 and a VL region having a VL CDR1 of SEQ ID NO:151; a VL CDR2 of SEQ ID NO:152 and a VL CDR3 of SEQ ID NO:153.

In one aspect, the invention provides an isolated antibody or antigen binding fragment thereof is selected from the group consisting of: a) a heavy chain variable (VH) region having a VH CDR1 of SEQ ID NO:107; a VH CDR2 of SEQ ID NO:162 and a VH CDR3 of SEQ ID NO:112 and a light chain variable (VL) region having a VL CDR1 of SEQ ID NO:144; a VL CDR2 of SEQ ID NO:145 and a VL CDR3 of SEQ ID NO:139; b) a VH region having a VH CDR1 of SEQ ID NO:115; a VH CDR2 of SEQ ID NO:118 and a VH CDR3 of SEQ ID NO:120 and a VL region having a VL CDR1 of SEQ ID NO:135; a VL CDR2 of SEQ ID NO:136 and a VL CDR3 of SEQ ID NO:137; c) a VH region having a VH CDR1 of SEQ ID NO:107; a VH CDR2 of SEQ ID NO:110 and a VH CDR3 of SEQ ID NO:112 and a VL region having a VL CDR1 of SEQ ID NO:131; a VL CDR2 of SEQ ID NO:132 and a VL CDR3 of SEQ ID NO:133; d) a VH region having a VH CDR1 of SEQ ID NO:107; a VH CDR2 of SEQ ID NO:154 and a VH CDR3 of SEQ ID NO:112 and a VL region having a VL CDR1 of SEQ ID NO:138; a VL CDR2 of SEQ ID NO:132 and a VL CDR3 of SEQ ID NO:139; and e) a VH region having a VH CDR1 of SEQ ID NO:107; a VH CDR2 of SEQ ID NO:157 and a VH CDR3 of SEQ ID NO:112 and a VL region having a VL CDR1 of SEQ ID NO:151; a VL CDR2 of SEQ ID NO:152 and a VL CDR3 of SEQ ID NO:153.

In one aspect, the invention provides an isolated antibody or antigen binding fragment thereof is selected from the group consisting of: a) a heavy chain variable (VH) region having a VH CDR1 of SEQ ID NO:107; a VH CDR2 of SEQ ID NO:158 and a VH CDR3 of SEQ ID NO:112 and a light chain variable (VL) region having a VL CDR1 of SEQ ID NO:138; a VL CDR2 of SEQ ID NO:132 and a VL CDR3 of SEQ ID NO:139; b) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:138; a VL CDR2 of SEQ ID NO:132 and a VL CDR3 of SEQ ID NO:140; c) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:150; a VL CDR2 of SEQ ID NO:132 and a VL CDR3 of SEQ ID NO:140; d) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:141; a VL CDR2 of SEQ ID NO:132 and a VL CDR3 of SEQ ID NO:140; e) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:144; a VL CDR2 of SEQ ID NO:145 and a VL CDR3 of SEQ ID NO:140; f) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:147; a VL CDR2 of SEQ ID NO:132 and a VL CDR3 of SEQ ID NO:140; g) a VH region having a VH CDR1 of SEQ ID NO:107; a VH CDR2 of SEQ ID NO:159 and a VH CDR3 of SEQ ID NO:112 and a VL region having a VL CDR1 of SEQ ID NO:138; a VL CDR2 of SEQ ID NO:132 and a VL CDR3 of SEQ ID NO:140; h) a VH region having a VH CDR1 of SEQ ID NO:107; a VH CDR2 of SEQ ID NO:160 and a VH CDR3 of SEQ ID NO:112 and a VL region having a VL CDR1 of SEQ ID NO:138; a VL CDR2 of SEQ ID NO:132 and a VL CDR3 of SEQ ID NO:140; i) a VH region having a VH CDR1 of SEQ ID NO:107; a VH CDR2 of SEQ ID NO:161 and a VH CDR3 of SEQ ID NO:112 and a VL region having a VL CDR1 of SEQ ID NO:138; a VL CDR2 of SEQ ID NO:132 and a VL CDR3 of SEQ ID NO:140; j) a VH region having a VH CDR1 of SEQ ID NO:107; a VH CDR2 of SEQ ID NO:162 and a VH CDR3 of SEQ ID NO:112 and a VL region having a VL CDR1 of SEQ ID NO:138; a VL CDR2 of SEQ ID NO:132 and a VL CDR3 of SEQ ID NO:140; k) a VH region having a VH CDR1 of SEQ ID NO:107; a VH CDR2 of SEQ ID NO:163 and a VH CDR3 of SEQ ID NO:112 and a VL region having a VL CDR1 of SEQ ID NO:138; a VL CDR2 of SEQ ID NO:132 and a VL CDR3 of SEQ ID NO:140; I) a VH region having a VH CDR1 of SEQ ID NO:107; a VH CDR2 of SEQ ID NO:164 and a VH CDR3 of SEQ ID NO:112 and a VL region having a VL CDR1 of SEQ ID NO:138; a VL CDR2 of SEQ ID NO:132 and a VL CDR3 of SEQ ID NO:140; m) a VH region having a VH CDR1 of SEQ ID NO:107; a VH CDR2 of SEQ ID NO:165 and a VH CDR3 of SEQ ID NO:112 and a VL region having a VL CDR1 of SEQ ID NO:138; a VL CDR2 of SEQ ID NO:132 and a VL CDR3 of SEQ ID NO:140; o) a VH region having a VH CDR1 of SEQ ID NO:107; a VH CDR2 of SEQ ID NO:166 and a VH CDR3 of SEQ ID NO:112 and a VL region having a VL CDR1 of SEQ ID NO:138; a VL CDR2 of SEQ ID NO:132 and a VL CDR3 of SEQ ID NO:140; p) a VH region having a VH CDR1 of SEQ ID NO:107; a VH CDR2 of SEQ ID NO:167 and a VH CDR3 of SEQ ID NO:112 and a VL region having a VL CDR1 of SEQ ID NO:138; a VL CDR2 of SEQ ID NO:132 and a VL CDR3 of SEQ ID NO:140; q) a VH region having a VH CDR1 of SEQ ID NO:107; a VH CDR2 of SEQ ID NO:168 and a VH CDR3 of SEQ ID NO:112 and a VL region having a VL CDR1 of SEQ ID NO:138; a VL CDR2 of SEQ ID NO:132 and a VL CDR3 of SEQ ID NO:140; r) a VH region having a VH CDR1 of SEQ ID NO:107; a VH CDR2 of SEQ ID NO:168 and a VH CDR3 of SEQ ID NO:112 and a VL region having a VL CDR1 of SEQ ID NO:138; a VL CDR2 of SEQ ID NO:132 and a VL CDR3 of SEQ ID NO:140; s) a VH region having a VH CDR1 of SEQ ID NO:107; a VH CDR2 of SEQ ID NO:163 and a VH CDR3 of SEQ ID NO:112 and a VL region having a VL CDR1 of SEQ ID NO:144; a VL CDR2 of SEQ ID NO:145 and a VL CDR3 of SEQ ID NO:140; t) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:144; a VL CDR2 of SEQ ID NO:145 and a VL CDR3 of SEQ ID NO:139; u) a VH region having a VH CDR1 of SEQ ID NO:107; a VH CDR2 of SEQ ID NO:162 and a VH CDR3 of SEQ ID NO:112 and a VL region having a VL CDR1 of SEQ ID NO:144; a VL CDR2 of SEQ ID NO:145 and a VL CDR3 of SEQ ID NO:139; v) a VH region having a VH CDR1 of SEQ ID NO:107; a VH CDR2 of SEQ ID NO:163 and a VH CDR3 of SEQ ID NO:112 and a VL region having a VL CDR1 of SEQ ID NO:144; a VL CDR2 of SEQ ID NO:145 and a VL CDR3 of SEQ ID NO:139; and w) a VH region having a VH CDR1 of SEQ ID NO:107; a VH CDR2 of SEQ ID NO:162 and a VH CDR3 of SEQ ID NO:112 and a VL region having a VL CDR1 of SEQ ID NO:144; a VL CDR2 of SEQ ID NO:145 and a VL CDR3 of SEQ ID NO:140.

In particular aspects of the invention, the antibody or antigen binding fragment thereof comprises: a heavy chain variable (VH) region comprising three CDRs set forth as SEQ ID NOs: 107, 162 and 112. In some aspect, the antibody or antigen binding fragment thereof of comprises: a light chain variable (VL) region comprising three CDRs set forth as SEQ ID NOs: 144, 145 and 139. In some aspects, the antibody or antigen binding fragment thereof comprises:

a heavy chain variable (VH) region comprising three CDRs set forth as SEQ ID NOs: 107, 162 and 112; and a light chain variable (VL) region comprising three CDRs set forth as SEQ ID NOs: 144, 145 and 139.

In some aspects of the invention, the antibody or antigen binding fragment thereof comprises: a heavy chain variable (VH) region comprising VH CDR1, VH CDR2 and VH CDR3 from a VH region of SEQ ID NO: 33. In other aspects, the antibody or antigen binding fragment thereof comprises: a light chain variable (VL) region comprising VL CDR1, VL CDR2 and VL CDR3 from a VL region of SEQ ID NO: 73.

In some aspects of the invention, the isolated antibody, or an antigen binding fragment thereof comprises: a heavy chain variable (VH) region comprising VH CDR1, VH CDR2 and VH CDR3 from a VH region of SEQ ID NO: 33; and a light chain variable (VL) region comprising VL CDR1, VL CDR2 and VL CDR3 from a VL region of SEQ ID NO: 73.

In some aspects of the invention, the isolated antibody or antigen binding fragment thereof is selected from the group consisting of: a) an antibody or antigen-binding fragment thereof comprising a VH region of SEQ ID NO:33 and a VL region of SEQ ID NO:73; b) an antibody or antigen-binding fragment thereof comprising a VH region of SEQ ID NO:13 and a VL region of SEQ ID NO:15; c) an antibody or antigen-binding fragment thereof comprising a VH region of SEQ ID NO:5 and a VL region of SEQ ID NO:7; d) an antibody or antigen-binding fragment thereof comprising a VH region of SEQ ID NO:21 and a VL region of SEQ ID NO:47; and e) an antibody or antigen-binding fragment thereof comprising a VH region of SEQ ID NO:106 and a VL region having a VL CDR1 of SEQ ID NO:138; a VL CDR2 of SEQ ID NO:132; and a VL CDR3 of SEQ ID NO:139.

In some aspects of the invention, the isolated antibody or antigen fragment thereof comprises a heavy chain variable region having an amino acid sequence that is at least 95% identical to SEQ ID NO: 33 and a light chain variable having an amino acid sequence that is at least 95% identical to SEQ ID NO: 73.

In particular aspects of the invention, the antibody or antigen binding fragment thereof comprises: a) a heavy chain variable (VH) region of SEQ ID NO: 33; and/or b) a light chain variable (VL) region of SEQ ID NO: 73.

In some aspects of the invention, the antibody or the antigen binding fragment comprises a heavy chain variable (VH) region produced by the expression vector with ATCC Accession No. PTA-121353. In some aspects of the invention, the antibody or the antigen binding fragment comprises a light chain variable (VL) region produced by the expression vector with ATCC Accession No. PTA-121354.

In some aspects of the invention, the isolated antibody or antigen binding fragment thereof is selected from the group consisting of:

a) a heavy chain variable (VH) region having a VH CDR1 of SEQ ID NO:107; a VH CDR2 of SEQ ID NO:158 and a VH CDR3 of SEQ ID NO:112 and a light chain variable (VL) region having a VL CDR1 of SEQ ID NO:138; a VL CDR2 of SEQ ID NO:132 and a VL CDR3 of SEQ ID NO:139;

b) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:138; a VL CDR2 of SEQ ID NO:132 and a VL CDR3 of SEQ ID NO:140; c) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:150; a VL CDR2 of SEQ ID NO:132 and a VL CDR3 of SEQ ID NO:140; d) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:141; a VL CDR2 of SEQ ID NO:132 and a VL CDR3 of SEQ ID NO:140; e) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:144; a VL CDR2 of SEQ ID NO:145 and a VL CDR3 of SEQ ID NO:140; f) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:147; a VL CDR2 of SEQ ID NO:132 and a VL CDR3 of SEQ ID NO:140; g) a VH region having a VH CDR1 of SEQ ID NO:107; a VH CDR2 of SEQ ID NO:159 and a VH CDR3 of SEQ ID NO:112 and a VL region having a VL CDR1 of SEQ ID NO:138; a VL CDR2 of SEQ ID NO:132 and a VL CDR3 of SEQ ID NO:140; h) a VH region having a VH CDR1 of SEQ ID NO:107; a VH CDR2 of SEQ ID NO:160 and a VH CDR3 of SEQ ID NO:112 and a VL region having a VL CDR1 of SEQ ID NO:138; a VL CDR2 of SEQ ID NO:132 and a VL CDR3 of SEQ ID NO:140; i) a VH region having a VH CDR1 of SEQ ID NO:107; a VH CDR2 of SEQ ID NO:161 and a VH CDR3 of SEQ ID NO:112 and a VL region having a VL CDR1 of SEQ ID NO:138; a VL CDR2 of SEQ ID NO:132 and a VL CDR3 of SEQ ID NO:140; j) a VH region having a VH CDR1 of SEQ ID NO:107; a VH CDR2 of SEQ ID NO:162 and a VH CDR3 of SEQ ID NO:112 and a VL region having a VL CDR1 of SEQ ID NO:138; a VL CDR2 of SEQ ID NO:132 and a VL CDR3 of SEQ ID NO:140; k) a VH region having a VH CDR1 of SEQ ID NO:107; a VH CDR2 of SEQ ID NO:163 and a VH CDR3 of SEQ ID NO:112 and a VL region having a VL CDR1 of SEQ ID NO:138; a VL CDR2 of SEQ ID NO:132 and a VL CDR3 of SEQ ID NO:140; I) a VH region having a VH CDR1 of SEQ ID NO:107; a VH CDR2 of SEQ ID NO:164 and a VH CDR3 of SEQ ID NO:112 and a VL region having a VL CDR1 of SEQ ID NO:138; a VL CDR2 of SEQ ID NO:132 and a VL CDR3 of SEQ ID NO:140; m) a VH region having a VH CDR1 of SEQ ID NO:107; a VH CDR2 of SEQ ID NO:165 and a VH CDR3 of SEQ ID NO:112 and a VL region having a VL CDR1 of SEQ ID NO:138; a VL CDR2 of SEQ ID NO:132 and a VL CDR3 of SEQ ID NO:140; n) a VH region having a VH CDR1 of SEQ ID NO:107; a VH CDR2 of SEQ ID NO:166 and a VH CDR3 of SEQ ID NO:112 and a VL region having a VL CDR1 of SEQ ID NO:138; a VL CDR2 of SEQ ID NO:132 and a VL CDR3 of SEQ ID NO:140; o) a VH region having a VH CDR1 of SEQ ID NO:107; a VH CDR2 of SEQ ID NO:167 and a VH CDR3 of SEQ ID NO:112 and a VL region having a VL CDR1 of SEQ ID NO:138; a VL CDR2 of SEQ ID NO:132 and a VL CDR3 of SEQ ID NO:140; p) a VH region having a VH CDR1 of SEQ ID NO:107; a VH CDR2 of SEQ ID NO:168 and a VH CDR3 of SEQ ID NO:112 and a VL region having a VL CDR1 of SEQ ID NO:138; a VL CDR2 of SEQ ID NO:132 and a VL CDR3 of SEQ ID NO:140; q) a VH region having a VH CDR1 of SEQ ID NO:107; a VH CDR2 of SEQ ID NO:168 and a VH CDR3 of SEQ ID NO:112 and a VL region having a VL CDR1 of SEQ ID NO:138; a VL CDR2 of SEQ ID NO:132 and a VL CDR3 of SEQ ID NO:140; r) a VH region having a VH CDR1 of SEQ ID NO:107; a VH CDR2 of SEQ ID NO:163 and a VH CDR3 of SEQ ID NO:112 and a VL region having a VL CDR1 of SEQ ID NO:144; a VL CDR2 of SEQ ID NO:145 and a VL CDR3 of SEQ ID NO:140; s) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:144; a VL CDR2 of SEQ ID NO:145 and a VL CDR3 of SEQ ID NO:139; t) a VH region having a VH CDR1 of SEQ ID NO:107; a VH CDR2 of SEQ ID NO:162 and a VH CDR3 of SEQ ID NO:112 and a VL region having a VL CDR1 of SEQ ID NO:144; a VL CDR2 of SEQ ID NO:145 and a VL CDR3 of SEQ ID NO:139; u) a VH region having a VH CDR1 of SEQ ID NO: 107; a VH CDR2 of SEQ ID NO:163 and a VH CDR3 of SEQ ID NO:112 and a VL region having a VL CDR1 of SEQ ID NO:144; a VL CDR2 of SEQ ID NO:145 and a VL CDR3 of SEQ ID NO:139; and v) a VH region having a VH CDR1 of SEQ ID NO:107; a VH CDR2 of SEQ ID NO:162 and a VH CDR3 of SEQ ID NO:112 and a VL region having a VL CDR1 of SEQ ID NO:144; a VL CDR2 of SEQ ID NO:145 and a VL CDR3 of SEQ ID NO:140.

In some aspects of the invention, an isolated antibody or antigen binding fragment thereof, that binds CXCR4, competes for binding to CXCR4 with and/or binds to the same epitope of CXCR4 as an antibody or antigen binding fragment thereof disclosed herein.

In some aspects of the invention, the isolated antibody or antigen binding fragment thereof comprises a VH region having a VH CDR1 of SEQ ID NO: 107; a VH CDR2 of SEQ ID NO: 162 and a VH CDR3 of SEQ ID NO: 112 and a VL region having a VL CDR1 of SEQ ID NO: 144; a VL CDR2 of SEQ ID NO:145 and a VL CDR3 of SEQ ID NO:139.

In some aspects of the invention, the antibody or antigen binding fragment thereof is a humanized, chimeric, CDR grafted, or recombinant human antibody. In other aspects of the invention, the antibody or antigen binding fragment thereof is not caninized or felinized.

In some aspects of the invention, the antibody or antigen binding fragment thereof comprises an acyl donor glutamine-containing tag engineered at a specific site.

In some aspects of the invention, provided are anti-CXCR4 antibody-drug conjugates. The antibody-drug conjugate of the invention is generally of the formula: Ab-(T-L-D), wherein: Ab is an antibody or antigen-binding fragment thereof that binds to chemokine receptor 4 (CXC4); T is an acyl donor glutamine-containing tag that can be optionally included; L is a linker; and D is a drug.

In particular aspects, the antibody drug conjugate of the invention, is selected from the group consisting of: a) an antibody or antigen-binding fragment thereof comprising a VH region comprising CDRs of SEQ ID NOs: 107, 162 and 112 and a VL region comprising CDRs of SEQ ID NOs: 144, 145 and 139; b) an antibody or antigen-binding fragment thereof comprising a VH region comprising CDRs of SEQ ID NOs: 115, 118 and 120 and a VL region comprising CDRs of SEQ ID NOs:135, 136 and 137; c) an antibody or antigen-binding fragment thereof comprising a VH region comprising CDRs of SEQ ID NOs: 107, 110 and 112 and a VL region comprising CDRs of SEQ ID NOs:131, 132 and 133; d) an antibody or antigen-binding fragment thereof comprising a VH region comprising CDRs of SEQ ID NOs: 107, 154 and 112 and a VL region comprising CDRs of SEQ ID NOs:138, 132 and 139; e) an antibody or antigen-binding fragment thereof comprising a VH region comprising CDRs of SEQ ID NOs: 107, 157 and 112 and a VL region comprising CDRs of SEQ ID NOs:151, 152 and 153; f) an antibody or antigen-binding fragment thereof comprising a VH region of SEQ ID NO:33 and a VL region of SEQ ID NO:73; g) an antibody or antigen-binding fragment thereof comprising a VH region of SEQ ID NO:13 and a VL region of SEQ ID NO:15; h) an antibody or antigen-binding fragment thereof comprising a VH region of SEQ ID NO:5 and a VL region of SEQ ID NO:7; and i) an antibody or antigen-binding fragment thereof comprising a VH region of SEQ ID NO:21 and a VL region of SEQ ID NO:47.

In some antibody-drug conjugates of the invention, the Ab is a humanized, chimeric, CDR grafted, or recombinant human antibody or antigen binding fragment thereof. In some antibody-drug conjugates of the invention, the T is selected from the group consisting of SEQ ID NOs: 171, 90, 91, 92, 93, 94, 95, 96, 97, 98, 99, 100, 101, 172, 173, 102, 103 and LLQ. In some antibody-drug conjugates of the invention, the L is selected from the group consisting of acetyl-lysine-valine-citrulline-p-aminobenzyloxycarbonyl (AcLys-VC-PABC), amino PEG6-propionyl, maleimidocapronic-valine-citruline-p-aminobenzyloxycarbonyl (vc) and maleimidocaproyl (mc). In some antibody-drug conjugates of the invention, the D is selected from the group consisting of a cytotoxic agent, an immunomodulating agent, an imaging agent, a therapeutic protein, a biopolymer, and an oligonucleotide.

Any antibody-drug conjugate of the invention may be prepared with a drug that is a cytotoxic agent, The cytotoxic agent may be an anthracycline, an auristatin, a camptothecin, a combretastain, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, and calicheamicin. Any antibody-drug conjugate of the invention may be prepared with a drug that is auristatin. In one aspect, the auristatin may be 0101 (2-methylalanyl-N-[(3R,4S,5S)-3-methoxy-1-{(2S)-2-[(1R,2R)-1-methoxy-2-methyl-3-oxo-3-{[(1 S)-2-phenyl-1-(1,3-thiazol-2-yl)ethyl]amino}propyl]pyrrolidin-1-yl}-5-methyl-1-oxoheptan-4-yl]-N-methyl-L-valinamide), MMAD (Monomethyl Auristatin D or monomethyl dolastatin 10 and 8261 (2-Methylalanyl-N-[(3R,4S,5S)-1-{(2S)-2-[(1R,2R)-3-{[(1 S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide).

In particular aspects, the antibody-drug conjugate of the invention is selected from the group consisting of: a) Ab-LLQGA (SEQ ID NO: 91)-(acetyl-lysine-valine-citrulline-p-aminobenzyloxycarbonyl (AcLys-VC-PABC))-0101; Ab-LLQGA (SEQ ID NO: 91)-(AcLys-VC-PABC)-MMAD; c) Ab-LLQ$X_1X_2X_3X_4X_5$ (SEQ ID NO: 102)-(AcLys-VC-PABC)-0101; d) Ab-LLQ$X_1X_2X_3X_4X_5$ (SEQ ID NO: 102)-(AcLys-VC-PABC)-MMAD; e) Ab-GGLLQGA (SEQ ID NO: 92)-(AcLys-VC-PABC)-0101; and f) Ab-GGLLQGA (SEQ ID NO: 92)-(AcLys-VC-PABC)-M MAD.

In some aspects of the invention, a CXCR4 antibody-drug conjugate comprises any of the antibodies or antigen binding fragments thereof, disclosed herein, In a particular aspect of the invention, the antibody-drug conjugate of the invention comprises an antibody wherein the antibody comprises a VH region comprising CDRs of SEQ ID NOs: 107, 162 and 112 and a VL region comprising CDRs of SEQ ID NOs: 144, 145 and 139.

Further provided are pharmaceutical compositions comprising CXCR4 antibody, antigen binding fragment thereof, or antibody-drug conjugate, disclosed herein and a pharmaceutically acceptable carrier.

In some aspects of the invention, provided are isolated polynucleotide comprising a nucleotide sequence encoding any of the anti-CXCR4 antibodies or antigen binding fragments thereof, disclosed herein. In some aspects, provided are host cells that recombinantly produce the antibody or antigen binding fragment thereof, disclosed herein.

In other aspects are provided methods of treating a disorder associated with CXCR4 function or expression in a subject comprising administering to the subject an effective amount of the pharmaceutical composition of the present invention. In particular aspects of the invention, the disorder is cancer.

In other aspects are provided methods decreasing metastasis of CXCR4 expressing cancer cells in a subject, comprising administering to the subject in need thereof an effective amount of the pharmaceutical composition disclosed herein. In other aspects are provided methods inducing tumor regression in a subject who has a CXCR4 expressing tumor, comprising administering to the subject in need thereof an effective amount of the pharmaceutical composition, disclosed herein.

These and other aspects of the invention will be appreciated by a review of the application as a whole.

BRIEF DESCRIPTION OF THE DRAWINGS

FIG. 1 shows the h3G10 Heavy Chain variable region (VH) alignment.

FIG. 2 shows the h3G10 Light Chain variable region (VL) alignment.

DETAILED DESCRIPTION OF THE INVENTION

Figure 3A:
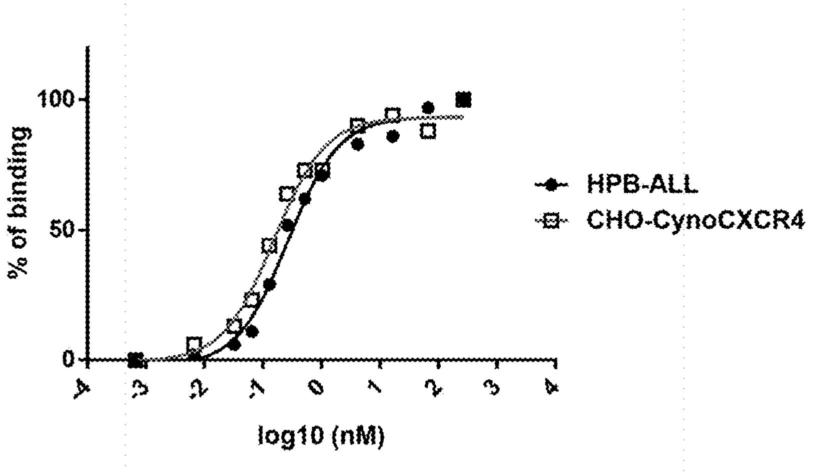
FIG. 3A shows the cross reactivity of anti-human CXCR4 Ab h3G10.1.91.A58B to the cynomolgus CXCR4 by flow cytometry in a dilution series (0.007-267 nM) on HPB-ALL (Human T cell leukemia) and Cyno-CXCR4 transfected CHO cells.

The invention disclosed herein provides antibodies and antibody conjugates (e.g., antibody-drug conjugates) that bind to CXCR4 (e.g., human CXCR4). The invention also provides polynucleotides encoding these antibodies, compositions comprising these antibodies, and methods of making and using these antibodies. In certain aspects, the antibodies of this disclosure are derived from particular heavy and light chain germline sequences and/or comprise particular structural features such as CDR regions comprising particular amino acid sequences. This disclosure provides isolated antibodies, methods of making such antibodies, antigen binding fragment thereof, antibody-drug conjugates and bispecific molecules comprising such antibodies and pharmaceutical compositions containing the antibodies, antigen binding fragment thereof, antibody-drug conjugates or bispecific molecules of this disclosure. This disclosure also relates to methods of using the antibodies, such as to detect CXCR4, to modulate CXCR4 activity and/or for targeting to CXCR4 expressing cells for destruction (e.g., ADCC, CDC, toxin), in disorders associated with function or expression of CXCR4 such as cancer. The invention also provides methods for the preventive and/or therapeutic treatment of a disorder associated with CXCR4 function or expression in a subject, such as cancer (e.g., solid tumor cancers or hematological cancers). Finally, the invention comprises compositions comprising such antibodies in conjugation (e.g., antibody-drug conjugates) or in combination with other anti-cancer compounds, such as antibodies, toxins, cytotoxic/cytostatic, and the use of same for the prevention and/or treatment of in disorders associated with function or expression of CXCR4 such as cancer.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); and, The Antibodies (M. Zanetti and J. D. Capra, eds., Harwood Academic Publishers, 1995).

Definitions and Abbreviations

The terms “Chemokine (C-X-C motif) receptor 4” and “CXCR4” as used herein refer to a G protein-coupled, 7-transmembrane domain chemokine receptor that is normally embedded within the membrane of a cell. The terms also include variants, isoforms, homologs, orthologs and paralogs. Nucleic acid and polypeptide sequences of human CXCR4 are disclosed as GenBank Accession Nos. NM_003467 and NP_003458, respectively. Further description of human CXCR4 can be found in Federsppiel, B. et al. Genomics 16(3):707-712 (1993); Herzog, H. et al. DNA Cell Biol. 12(6):465-471 (1993); Jazin, E. E. et al. Regul. Pept 47(3):247-258 (1993); Nomura, H. et al. Int. Immunol. 5(10):1239-1249 (1993); Loetscher, M. et al. J. Biol. Chem. 269(1):232-237 (1994); Moriuchi, M. et al. J. Immunol. 159(9):4322-4329 (1997); Caruz, A. et al. FEBS Lett. 426 (2):271-278 (1998); and Wegner, S. A. et al. J. Biol. Chem. 273(8):4754-4760 (1998).

CXCR4 is also known in the art as, for example, LESTR, CD 184, CD184 antigen, C-X-C chemokine receptor type 4, CXCR-4, CXCL-12, CXCR-R4, D2S201E, FB22, fusion, Fusin, HM89, HSY3RR, LAP3, LCR1, Leukocyte-derived seven transmembrane domain receptor, NPY3R, NPYR, NPYRL, NPYY3R, SDF-1 receptor, or Stromal cell derived factor 1 receptor.

For purposes of the present invention, the term “CXCR4 antigen” encompasses any CXCR4, including human CXCR4, CXCR4 of another mammal (such as mouse CXCR4, rat CXCR4, Canine CXCR4, feline CXCR4 protein or primate CXCR4), as well as different forms of CXCR4 (e.g., glycosylated CXCR4).

The terms “antibody” and “Ab” as used herein refer to an immunoglobulin molecule capable of recognizing and binding to a specific target or antigen, such as a carbohydrate, polynucleotide, lipid, polypeptide, etc., through at least one antigen recognition site, located in the variable region of the immunoglobulin molecule. As used herein, the term “antibody” can encompass any type of antibody, including but not limited to monoclonal antibodies, polyclonal antibodies and antigen binding fragments of intact antibodies that retain the ability to specifically bind to a given antigen (e.g. CXCR4), bispecific antibodies, heteroconjugate antibodies, mutants thereof, fusion proteins having an antibody, single chain (ScFv) and single domain antibodies (e.g., shark and camelid antibodies), maxibodies, minibodies, intrabodies, diabodies, triabodies, tetrabodies, v-NAR and bis-scFv (see, e.g., Hollinger and Hudson, 2005, Nature Biotechnology 23(9): 1126-1136), humanized antibodies, chimeric antibodies and any other modified configuration of the immunoglobulin molecule that includes an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some aspects of the invention, the antibody, or antigen binding fragment thereof for use in the methods of the invention is a chimeric, humanized, or a recombinant human antibody, or CXCR4-binding fragment thereof.

There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy chain constant regions that correspond to the different classes of immunoglobulins are called alpha, delta, epsilon, gamma, and mu, respectively. The subunit structures and three-dimensional configurations of different classes of immunoglobulins are well known.

Native or naturally occurring antibodies are typically heterotetrameric glycoproteins of about 150,000 daltons composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains. The term "variable" refers to the fact that certain portions of the variable domains differ extensively in sequence among antibodies.

The terms "antigen binding fragment", "antigen binding portion" and "antibody portion" as used herein refer to one or more fragments of an intact antibody that retain the ability to bind to a given antigen (e.g., CXCR4). Antigen binding functions of an antibody can be performed by fragments of an intact antibody. Examples of antigen binding fragments include Fab; Fab'; $F(ab')_2$; an Fd fragment consisting of the VH and CH1 domains; an Fv fragment consisting of the VL and VH domains of a single arm of an antibody; a single domain antibody (dAb) fragment (Ward et al., Nature 341: 544-546, 1989), an isolated complementarity determining region (CDR), a nanobody and a heavy chain variable region containing a single variable domain and two constant domains. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv), see e g, Bird et al., Science 242:423-426 (1988), and Huston el al., PNAS 85: 5879-5883 (1988). Such single chain antibodies are also intended to be encompassed within the term "antigen binding portion" of an antibody. These antibody fragments are obtained using conventional techniques known to those with skill in the art, and the fragments are screened for utility in the same manner, as are intact antibodies.

The term "CDR" as used herein refers to a region in the variable domain of an antibody that confers its binding specificity. There are 3 CDRs on each heavy and light chain of an antibody. The amino acid residues within the variable region that make up the CDRs can be are identified using methods known in the art including, but not limited to, Kabat (Kabat et al., 1992, Sequences of Proteins of Immunological Interest, 5th ed., Public Health Service, NIH, Washington D.C.), Chothia (Chothia et al., 1989, Nature 342:877-883), the accumulation of both Kabat and Chothia, AbM definition (which is a compromise between Kabat and Chothia and is derived using Oxford Molecular's AbM antibody modeling software (now Accelrys®), contact definition (MacCallum et al., 1996, J. Mol. Biol., 262:732-745), and/or conformational definitions (Makabe et al., 2008, Journal of Biological Chemistry, 283:1156-1166). As used herein, a CDR may refer to CDRs defined by any approach known in the art, including combinations of approaches. The methods used herein may utilize CDRs defined according to any of these approaches.

The term "Fc region" as used herein refers to a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat (Kabat et al., Sequences of Proteins of Immunological Interest, 5th Ed. Public Health Service, National Institutes of Health, Bethesda, Md., 1991).

The terms "monoclonal antibody" and "mAb" as used herein refer to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

The term "isolated antibody" as used herein refers to an antibody that is substantially free of other antibodies having different antigenic specificities (e.g., an isolated antibody that specifically binds CXCR4 is substantially free of antibodies that specifically bind antigens other than CXCR4). An isolated antibody that specifically binds CXCR4 may, however, have cross-reactivity to other antigens, such as CXCR4 molecules from other species. Moreover, an isolated antibody may be substantially free of other cellular material and/or chemicals.

The terms "humanized antibody" and "CDR-grafted antibody" as used herein refers to forms of non-human (e.g., murine) antibodies that are chimeric immunoglobulins, immunoglobulin chains, or fragments thereof (such as Fv, Fab, Fab', $F(ab')_2$ or other antigen binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity.

In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

Humanization can be essentially performed following the method of Winter and co-workers (Jones et al. Nature 321:522-525 (1986); Riechmann et al. Nature 332:323-327 (1988); Verhoeyen et al. Science 239:1534-1536 (1988)), by substituting rodent or mutant rodent CDRs or CDR sequences for the corresponding sequences of a human antibody. See also U.S. Pat. Nos. 5,225,539; 5,585,089; 5,693,761; 5,693,762; 5,859,205; herein incorporated by reference. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al. Nature 331:522-525 (1986); Riechmann et al. Nature 332:323-329 (1988); and Presta Curr. Op. Struct. Biol. 2:593-596 (1992); herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

The term "human antibody" as used herein refers to an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, (1996); Sheets et al., Proc. Natl. Acad. Sci. (USA) 95:6157-6162, (1998); Hoogenboom and Winter, J. Mol. Biol., 227:381, (1991); Marks et al., J. Mol. Biol., 222:581, (1991)). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, (1985); Boerner et al., J. Immunol., 147 (1):86-95, (1991); and U.S. Pat. No. 5,750,373.

The term "chimeric antibody" as used herein refers to antibodies in which the variable region sequences are derived from one species and the constant region sequences are derived from another species, such as an antibody in which the variable region sequences are derived from a mouse antibody and the constant region sequences are derived from a human antibody. For veterinary applications, the constant domains of the chimeric antibody may be derived from that of other species, such as a cat or dog.

The terms "caninized antibody" and "felinized antibody" as used herein refer chimeric antibodies useful as therapeutics in canines and felines, respectively. In both cases, an antigen binding domain from a heterologous species donor antibody is combined with a non-antigen binding domain of a same species recipient antibody.

The terms "preferentially binds" or "specifically binds" as used herein when used in the context of the binding of an antibody to a target (e.g., CXCR4 protein) is a term well understood in the art. Methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CXCR4 epitope is an antibody that binds this epitope with greater affinity, avidity, more readily, and/or with greater duration than it binds to other CXCR4 epitopes or non-CXCR4 epitopes.

The term "binding affinity" and "$K_D$" as used herein is intended to refer to the equilibrium dissociation constant of a particular antigen-antibody interaction. The $K_D$ is the ratio of the rate of dissociation, also called the "off-rate" or "$k_d$", to the rate of association, or "on-rate" or "$k_a$". Thus, $K_D$ equals $k_d/k_a$ and is expressed as a molar concentration (M). It follows that the smaller the $K_D$, the stronger the binding affinity. Therefore, a $K_D$ of 1 μM indicates weak binding affinity compared to a $K_D$ of 1 nM. $K_D$ values for antibodies can be determined using methods well established in the art. One method for determining the $K_D$ of an antibody is by using surface plasmon resonance, typically using a biosensor system such as a BIACORE® system.

The term "compete" as used herein with regard to an antibody means that a first antibody binds to an epitope in a manner sufficiently similar to the binding of a second antibody such that the result of binding of the first antibody with its cognate epitope is detectably decreased in the presence of the second antibody compared to the binding of the first antibody in the absence of the second antibody. Antibodies that compete for epitope binding with an antibody of the invention are encompassed by the present invention. The skilled artisan would appreciate, based upon the teachings provided herein, that such competing antibodies can be useful for the methods disclosed herein.

The term "drug" as used herein refers to any substance having biological or detectable activity. The term drug is meant to encompass cytotoxic agents, therapeutic agents, immunomodulating agents, detectable labels, imaging agents, binding agents, prodrugs (which are metabolized to an active agent in vivo), growth factors, hormones, cytokines, anti-hormones, xanthines, interleukins, interferons, and cytotoxic drugs. Drug can be small molecules, polypeptides, oligonucleotides or biopolymers. Drug can be conjugated to an antibody of the invention via a linker to form an antibody-drug conjugate.

The term "effector function" as used herein refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, Clq binding, and down regulation of cell surface receptors (e.g., B cell receptor; BCR). See, e.g., U.S. Pat. No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 and/or Clq binding.

The term "epitope" as used herein includes any protein determinant capable of binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational". In a linear epitope, all of the points of interaction between the protein and the interacting molecule (such as an antibody) occur linearally along the primary amino acid sequence of the protein. In a conformational epitope, the points of interaction occur across amino acid residues on the protein that are separated from one another. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct competition studies to find antibodies that competitively bind with one another, i.e. the antibodies compete for binding to the epitope. A high throughput process for 'binning' antibodies based upon their competition is described in International patent application No. WO 03/48731. As used herein, the term 'binning' refers to a method to group antibodies based on their antigen binding characteristics.

The terms "polynucleotide," "nucleic acid/nucleotide," and "oligonucleotide" as used herein refer to polymeric forms of nucleotides of any length, either deoxyribonucleotides or ribonucleotides, analogs thereof, or any substrate that can be incorporated into a chain by DNA or RNA polymerase. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)$NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The terms "polypeptide", "oligopeptide", "peptide" and "protein" as used herein refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

Amino acids may be referred to herein by either their commonly known three letter symbols or by the one-letter symbols recommended by the IUPAC-IUB Biochemical.

The terms "amino acid" and "natural amino acid" as used herein refer to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine and valine.

The term "amino acid derivative" as used herein refers to an amino acid having substitutions or modifications by covalent attachment of a parent amino acid, such as, e.g., by alkylation, glycosylation, acetylation, phosphorylation, and the like. Further included within the definition of "derivative" is, for example, one or more analogs of an amino acid with substituted linkages, as well as other modifications known in the art.

The term "vector" as used herein refers to a construct capable of delivering, and preferably expressing, one or more genes or sequences of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "percent sequence identity" as used herein refers to the degree of similarity between two sequences. In the context of nucleic acid sequences, it means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, Methods Enzymol. 183:63-98 (1990); Pearson, Methods Mol. Biol. 132:185-219 (2000); Pearson, Methods Enzymol. 266:227-258 (1996); Pearson, J. Mol. Biol. 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

A reference to a nucleotide sequence encompasses its complement unless otherwise specified. Thus, a reference to a nucleic acid having a particular sequence should be understood to encompass its complementary strand, with its complementary sequence.

In the context of amino acid sequences, it means that two amino acid sequences, when optimally aligned, such as by the programs GAP or BESTFIT using default gap weights as supplied with the programs, share at least 70%, 75% or 80% sequence identity, preferably at least 90% or 95% sequence identity, and more preferably at least 97%, 98% or 99% sequence identity. In some substantially similar amino acid sequences, residue positions that are not identical differ by conservative amino acid substitutions.

Substantially similar polypeptides also include conservatively substituted variants in which one or more residues have been conservatively substituted with a functionally similar residue. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

A further indication that two proteins are substantially identical is that they share an overall three-dimensional structure, or are biologically functional equivalents.

The term "cytotoxic activity" as used herein refers to a cell-killing, a cytostatic or an anti-proliferative effect of an antibody, an ADC or an intracellular metabolite of said ADC. Cytotoxic activity may be expressed as the $IC_{50}$ value, which is the concentration (molar or mass) per unit volume at which half the cells survive.

The term "contacting" as used herein refers to bringing an antibody or antigen binding portion thereof of the present invention and a target CXCR4, or epitope thereof, together in such a manner that the antibody can affect the biological activity of the CXCR4. Such "contacting" can be accomplished "in vitro," i.e., in a test tube, a petri dish, or the like. In a test tube, contacting may involve only an antibody or antigen binding portion thereof and CXCR4 or epitope thereof or it may involve whole cells. Cells may also be maintained or grown in cell culture dishes and contacted with antibodies or antigen binding portions thereof in that environment. In this context, the ability of a particular antibody or antigen binding portion thereof to affect a CXCR4-related disorder, i.e., the $IC_{50}$ of the antibody, can be determined before use of the antibody in vivo with more complex living organisms is attempted. For cells outside the organism, multiple methods exist, and are well-known to those skilled in the art, to contact CXCR4 with the antibodies or antigen binding fragments thereof. In another embodiment, a significant amount of efficacy is generated by effector function. Immune effector functions which have been shown to contribute to an antibody-mediated cytotoxicity include but are not limited to antibody-dependent cell-mediated cytotoxicity (ADCC), antibody-dependent cell-mediated phagocytosis (ADCP), and complement-dependent cytotoxicity (CDC).

The term "acyl donor glutamine-containing tag" and "glutamine tag" as used herein refer to a polypeptide or a protein containing one or more Gin residue(s) that acts as a transglutaminase amine acceptor. See, e.g., WO2012059882.

The term "pharmaceutically acceptable carrier" and "pharmaceutical acceptable excipient" as used herein refer to any material which, when combined with an active ingredient, allows the ingredient to retain biological activity and is non-reactive with the subject's immune system. Examples include any and all solvents, dispersion media, coatings, antibacterial and antifungal agents, isotonic and absorption delaying agents, and the like that are physiologically compatible. The standard pharmaceutical carriers include but are not limited to a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 21st Ed. Mack Publishing, 2005). Preferably, the carrier is suitable for intravenous, intramuscular, subcutaneous, parenteral, spinal or epidermal administration (e.g., by injection or infusion). Depending on the route of administration, the active compound (e.g., monoclonal antibody, an antigen binding fragment thereof, antibody-drug conjugate) may be coated in a material to protect the compound from the action of acids and other natural conditions that may inactivate the compound.

The present invention also provides for compositions comprising, or alternatively consisting of, one, two, three, four, five, ten, fifteen, twenty, or more antibodies of the present invention (including molecules comprising, or alternatively consisting of, antibody fragments or variants thereof). A composition of the invention may comprise, or alternatively consist of, one, two, three, four, five, ten, fifteen, twenty, or more amino acid sequences of one or more antibodies or fragments or variants thereof. Alternatively, a composition of the invention may comprise, or alternatively consist of, nucleic acid molecules encoding one or more antibodies of the invention.

The term "CXCR4 associated disorder" is any condition wherein the pathology is due, at least in part, to increased or inappropriate expression of CXCR4 or inappropriate function of CXCR4. Examples of such disorders include, but are not limited to, cancer associated with increased expression of CXCR4 relative to normal, inflammatory and immune disorders, allergic disorders, infections (HIV infection, etc.), auto-immune disorders (e.g., rheumatoid arthritis), fibrosis disorders (e.g., pulmonary), and cardiovascular disorders.

The term "cancer" refers to the physiological condition or disorder in mammals that is typically characterized by unregulated cell growth. A hematological cancer refers to a cancer of the blood including, but not limited to, leukemia, lymphoma and myeloma among others. A solid cancer refers to a cancer of the body tissue other than blood including, but not limited to, bladder cancer, breast cancer, cervical cancer, choriocarcinoma, colon cancer, esophageal cancer, gastric cancer, glioblastoma, head and neck cancer, kidney cancer, lung cancer, oral cancer, ovarian cancer, pancreatic cancer, prostate cancer, skin cancer, liver cancer and hepatic carcinomas, and the like.

The term "patient" as used herein refers to a subject that suffers from a CXCR4 associated disorder. Patents can include, but are not limited to, humans, non-human primates (e.g. monkeys), rats, mice, guinea pigs, pigs, goats, cows, horses, dogs, cats, birds and fowl. In preferred embodiments, the patients administered an antibody or antibody-drug conjugate of the invention is a human.

The terms "effective amount" or "effective dose" as used herein refers to an amount of a drug, compound or pharmaceutical composition necessary to achieve one or more beneficial or desired therapeutic results. For prophylactic use, beneficial or desired results include eliminating or reducing the risk, lessening the severity, or delaying the outset of the disorder, including biochemical, histological and/or behavioral symptoms of the disorder, its complications and intermediate pathological phenotypes presenting during development of the disorder. For therapeutic use, beneficial or desired results include clinical results such as reducing incidence or amelioration of one or more symptoms of the disorder, ability to decrease the dose of other medications required to treat the disorder, enhancing the effect of another medication used to treat the disorder and/or delaying the progression of the disorder.

For purposes of this invention, beneficial or desired clinical results include, but are not limited to, one or more of the following: reducing the proliferation of (or destroying) neoplastic or cancerous cells in a CXCR4 associated disorder, reducing or inhibiting metastasis of neoplastic cells in a CXCR4 associated disorder, shrinking or decreasing the size of CXCR4 expressing tumor, remission of a CXCR4 associated disorder, increasing the life expectancy of an individual affected with a CXCR4 associated disorder, decreasing symptoms resulting from a CXCR4 associated disorder, increasing the quality of life of those suffering from a CXCR4 associated disorder, ability to decrease the dose of other medications required to treat a CXCR4 associated disorder without deleterious effect, delaying the progression of a CXCR4 associated disorder, curing a CXCR4 associated disorder and/or prolong survival of patients having a CXCR4 associated disorder.

Unless otherwise defined herein, scientific and technical terms used in connection with the present invention shall have the meanings that are commonly understood by those of ordinary skill in the art. For example, the terms "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Further, unless otherwise required by context, singular terms shall include pluralities and plural terms shall include the singular.

Reference to "about" a value or parameter herein includes (and describes) embodiments that are directed to that value or parameter per se. For example, description referring to "about X" includes description of "X." Numeric ranges are inclusive of the numbers defining the range. Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Unless otherwise defined, all technical and scientific terms used herein have the same meaning as commonly understood by one of ordinary skill in the art to which this invention belongs. In case of conflict, the present specification, including definitions, will control. Exemplary methods and materials are described herein, although methods and materials similar or equivalent to those described herein can also be used in the practice or testing of the present invention. The materials, methods, and examples are illustrative only and not intended to be limiting.

Anti-CXCR4 Antibodies and Methods of Making Thereof

The present invention provides anti-CXCR4 antibodies or antigen binding fragments that bind to human CXCR4. In this section of the specification, functional and structural characteristics of exemplary anti-CXCR4 antibodies, or antigen binding fragments of the disclosure are described in detail. It should be understood that antibodies or antigen binding fragments of the disclosure can be described based on any one or more (2, 3, 4, 5, 6, 7, 8, 9, etc.) of the structural and/or functional characteristics described herein. Throughout this portion of the disclosure, when a functional or structural characteristic is described with respect to antibodies of the disclosure, it should be understood that, except where context clearly indicates otherwise, such structural or functional characteristic may similarly be used to describe an antigen binding fragment of the disclosure.

The nucleotide sequence of the human CXCR4 cDNA and the predicted amino acid sequence of the human CXCR4 protein are shown as SEQ ID NOs: 104 and 105, respectively (Table 1). The human CXCR4 gene, which is approximately 1679 nucleotides in length, encodes a full-length protein having a molecular weight of approximately 38.7 kD and which is approximately 352 amino acid residues in length. Further description of the human CXCR4 nucleic acid and polypeptide sequences can be found in GenBank Accession Nos. NM_003467 and NP_003458, respectively; as well as in Federsppiel, B. et al. Genomics 16(3):707-712 (1993); Herzog, H. et al. DNA Cell Biol. 12(6):465-471 (1993); Jazin, E. E. et al. Regul. Pept 47(3):247-258 (1993); Nomura, H. et al. Int. Immunol. 5(10):1239-1249 (1993); Loetscher, M. et al. J. Biol. Chem. 269(1):232-237 (1994); Moriuchi, M. et al. J. Immunol. 159(9):4322-4329 (1997); Caruz, A. et al. FEBS Lett. 426(2):271-278 (1998); and Wegner, S. A. et al. J. Biol. Chem. 273(8):4754-4760 (1998).

TABLE 1

| GenBank Accession Nos. | SEQ ID No | Sequence |
|---|---|---|
| NM_003467.2 | 104 | AACTTCAGTTTGTTGGCTGCGGCAGCAGGTAGCAAAGTGAC<br>GCCGAGGGCCTGAGTGCTCCAGTAGCCAC<br>CGCATCTGGAGAACCAGCGGTTACC**ATG**GAGGGGATCAGTA<br>TATACACTTCAGATAACTACACCGAGGAA<br>ATGGGCTCAGGGGACTATGACTCCATGAAGGAACCCTGTTT<br>CCGTGAAGAAAATGCTAATTTCAATAAAA<br>TCTTCCTGCCCACCATCTACTCCATCATCTTCTTAACTGGCA<br>TTGTGGGCAATGGATTGGTCATCCTGGT<br>CATGGGTTACCAGAAGAAACTGAGAAGCATGACGGACAAGT<br>ACAGGCTGCACCTGTCAGTGGCCGACCTC<br>CTCTTTGTCATCACGCTTCCCTTCTGGGCAGTTGATGCCGTG<br>GCAAACTGGTACTTTGGGAACTTCCTAT<br>GCAAGGCAGTCCATGTCATCTACACAGTCAACCTCTACAGC<br>AGTGTCCTCATCCTGGCCTTCATCAGTCT<br>GGACCGCTACCTGGCCATCGTCCACGCCACCAACAGTCAGA<br>GGCCAAGGAAGCTGTTGGCTGAAAAGGTG<br>GTCTATGTTGGCGTCTGGATCCCTGCCCTCCTGCTGACTATT<br>CCCGACTTCATCTTTGCCAACGTCAGTG<br>AGGCAGATGACAGATATATCTGTGACCGCTTCTACCCCAATG<br>ACTTGTGGGTGGTTGTGTTCCAGTTTCA<br>GCACATCATGGTTGGCCTTATCCTGCCTGGTATTGTCATCCT<br>GTCCTGCTATTGCATTATCATCTCCAAG<br>CTGTCACACTCCAAGGGCCACCAGAAGCGCAAGGCCCTCAA<br>GACCACAGTCATCCTCATCCTGGCTTTCT<br>TCGCCTGTTGGCTGCCTTACTACATTGGGATCAGCATCGACT<br>CCTTCATCCTCCTGGAAATCATCAAGCA<br>AGGGTGTGAGTTTGAGAACACTGTGCACAAGTGGATTTCCA<br>TCACCGAGGCCCTAGCTTTCTTCCACTGT<br>TGTCTGAACCCCATCCTCTATGCTTTCCTTGGAGCCAAATTT<br>AAAACCTCTGCCCAGCACGCACTCACCT<br>CTGTGAGCAGAGGGTCCAGCCTCAAGATCCTCTCCAAAGGA<br>AAGCGAGGTGGACATTCATCTGTTTCCAC<br>TGAGTCTGAGTCTTCAAGTTTTCACTCCAGCTAACACAGATG<br>TAAAAGACTTTTTTTTATACGATAAATA<br>ACTTTTTTTTAAGTTACACATTTTTCAGATATAAAAGACTGAC<br>CAATATTGTACAGTTTTTATTGCTTGT<br>TGGATTTTTGTCTTGTGTTTCTTTAGTTTTTGTGAAGTTTAATT<br>GACTTATTTATATAAATTTTTTTTGT<br>TTCATATTGATGTGTGTCTAGGCAGGACCTGTGGCCAAGTTC<br>TTAGTTGCTGTATGTCTCGTGGTAGGAC<br>TGTAGAAAAGGGAACTGAACATTCCAGAGCGTGTAGTGAAT<br>CACGTAAAGCTAGAAATGATCCCCAGCTG<br>TTTATGCATAGATAATCTCTCCATTCCCGTGGAACGTTTTTCC<br>TGTTCTTAAGACGTGATTTTGCTGTAG<br>AAGATGGCACTTATAACCAAAGCCCAAAGTGGTATAGAAATG<br>CTGGTTTTTCAGTTTTCAGGAGTGGGTT<br>GATTTCAGCACCTACAGTGTACAGTCTTGTATTAAGTTGTTAA<br>TAAAAGTACATGTTAAACTTAAAAAAA<br>AAAAAAAAAAA |
| NP_003458 | 105 | MEGISIYTSDNYTEEMGSGDYDSMKEPCFREENANFNKIFLPTI<br>YSIIFLTGIVGNGLVILVMGYQKKLRSMTDKYRLHLSVADLLFVIT<br>LPFWAVDAVANWYFGNFLCKAVHVIYTVNLYSSVLILAFISLDRY<br>LAIVHATNSQRPRKLLAEKVVYVGVWIPALLLTIPDFIFANVSEA<br>DDRYICDRFYPNDLWVVVFQFQHIMVGLILPGIVILSCYCIIISKLS |

TABLE 1-continued

| GenBank Accession Nos. | SEQ ID No | Sequence |
|---|---|---|
| | | HSKGHQKRKALKTTVILILAFFACWLPYYIGISIDSFILLEIIKQGC<br>EFENTVHKWISITEALAFFHCCLNPILYAFLGAKFKTSAQHALTS<br>VSRGSSLKILSKGKRGGHSSVSTESESSSFHSS |

The human CXCR4 sequence as used herein may differ from human CXCR4 of SEQ ID NO: 105 by having, for example, conserved mutations or mutations in non-conserved regions and the CXCR4 has substantially the same biological function as the human CXCR4 of SEQ ID NO: 105. For example, a biological function of human CXCR4 is having an epitope in the extracellular domain of CXCR4 that is bound by an antibody of the instant disclosure or the biological function of human CXCR4 is chemokine binding or involvement in the metastatic process.

A particular human CXCR4 sequence will generally be at least 90% identical in amino acids sequence to human CXCR4 of SEQ ID NO: 105 and contain amino acid residues that identify the amino acid sequence as being human when compared to CXCR4 amino acid sequences of other species (e.g., murine). In certain cases, a human CXCR4 may be at least 95%, or even at least 96%, 97%, 98%, or 99% identical in amino acid sequence to CXCR4 of SEQ ID NO: 105. In some aspects of the invention, a human CXCR4 sequence will display no more than 10 amino acid differences from the CXCR4 of SEQ ID NO: 105. In certain aspects of the invention, the human CXCR4 may display no more than 5, or even no more than 4, 3, 2, or 1 amino acid difference from the CXCR4 of SEQ ID NO: 105. Percent identity can be determined as described herein.

The antibodies, antigen binding fragments thereof, and antibody-drug conjugates of the invention are characterized by any one or more of the following characteristics: (a) bind to CXCR4; (b) decrease or down-regulate the protein expression of CXCR4; (c) treat, prevent, ameliorate one or more symptoms of disorder associated with CXCR4 function or expression in a subject (e.g., cancer, such as NHL, AML, MM, CLL, T-ALL, gastric, head and neck, lung, ovarian, or pancreatic cancer); (d) decrease or inhibit tumor growth or progression in a subject (who has a CXCR4 expressing tumor); (e) decrease or inhibit metastasis of CXCR4 expressing cancer cells in a subject (who has one or more CXCR4 expressing cancer cells); (f) induce regression (e.g., long-term regression) of a CXCR4 expressing tumor; (g) exert cytotoxic activity in CXCR4 expressing cells; (h) deactivate or down-regulate the CXCR4 pathway; and (i) block CXCR4 interaction with CXCR4 extracellular binding partners. For example, the antibody, antigen binding fragment thereof, and antibody-drug conjugate of the invention blocks the function of SDF-I.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some aspects of the invention, the anti-CXCR4 antibody as described herein is a monoclonal antibody. For example, the anti-CXCR4 antibody is a humanized monoclonal antibody or a chimeric monoclonal antibody.

In some aspects of the invention, antibodies of the present invention cross-react with CXCR4 from species other than human, such as CXCR4 of mouse, rat, Canine, feline or primate, as well as different forms of CXCR4 (e.g., glycosylated CXCR4). In some aspects of the invention, the antibodies specific for human CXCR4 may be completely specific for human CXCR4 and may not exhibit species or other types of cross-reactivity.

In some aspects of the invention, the anti-CXCR4 antibody as described herein is a caninized antibody, or a felinized antibody. Antibodies according to the present invention that have been caninized or felinized are capable of binding to at least one of canine CXCR4 protein or feline CXCR4 protein. In one aspect, a monoclonal antibody of the present invention binds to canine CXCR4 protein or feline CXCR4 protein and prevents its binding to stromal cell-derived factor-1 (SDF-1).

In some aspects of the invention, the antibody comprises a modified constant region, such as, for example without limitation, a constant region that has increased potential for provoking an immune response. For example, the constant region may be modified to have increased affinity to an Fc gamma receptor such as, e.g., FcγRI, FcγRIIA, or FcγIII.

In some aspects of the invention, the antibody comprises a modified constant region, such as a constant region that has increased affinity to a human Fc gamma receptor, that is immunologically inert, that is, having a reduced potential for provoking an immune response. In some aspects of the invention, the constant region is modified as described in Eur. J. Immunol., 29:2613-2624, 1999; PCT Application No. PCT/GB99/01441; and/or UK Patent Application No. 98099518. The Fc can be human IgG1, human IgG2, human IgG3, or human IgG4. The Fc can be human IgG2 containing the mutation A330P331 to S330S331 (IgG2Δa), in which the amino acid residues are numbered with reference to the wild type IgG2 sequence. Eur. J.

Immunol., 29:2613-2624, 1999. In some aspects of the invention, the antibody comprises a constant region of $IgG_4$ comprising the following mutations (Armour et al., Molecular Immunology 40 585-593, 2003): E233F234L235 to P233V234A235 (IgG4Δc), in which the numbering is with reference to wild type IgG4. In still other aspects of the invention, the Fc is human IgG4 E233F234L235 to P233V234A235 with deletion G236 (IgG4Δb). In another aspect of the invention, the Fc is any human IgG4 Fc (IgG4, IgG4Δb or IgG4Δc) containing hinge stabilizing mutation S228 to P228 (Aalberse et al., Immunology 105, 9-19, 2002). In a particular aspect of the invention, the Fc can be aglycosylated Fc.

In some aspects of the invention, the constant region is aglycosylated by mutating the oligosaccharide attachment residue (such as Asn297) and/or flanking residues that are part of the glycosylation recognition sequence in the constant region. In some aspects of the invention, the constant region is aglycosylated for N-linked glycosylation enzymatically. The constant region may be aglycosylated for N-linked glycosylation enzymatically or by expression in a glycosylation deficient host cell.

One way of determining binding affinity of antibodies to CXCR4 is by measuring binding affinity of monofunctional Fab fragments of the antibody. To obtain monofunctional Fab fragments, an antibody (for example, IgG) can be cleaved with papain or expressed recombinantly. The affinity of a CXCR4 Fab fragment of an antibody can be determined by surface plasmon resonance (Biacore™3000™ surface plasmon resonance (SPR) system, Biacore™, INC, Piscataway N.J.) equipped with pre-immobilized streptavidin sensor chips (SA) or anti-mouse Fc or anti-human Fc using HBS-EP running buffer (0.01M HEPES, pH 7.4, 0.15 NaCl, 3 mM EDTA, 0.005% v/v Surfactant P20). Biotinylated WGA can be coated on the SA chip to facilitate capturing Lipoparticles containing CXCR4 proteins. A dilution series (5-membered, 3× dilution factor with a top concentration of 10 or 30 nM) of Fab was injected from low to high concentration (with a 3-minute association time for each concentration) to perform a kinetic analysis of the data using a "kinetic titration" methodology as described in Karlsson, et al., (Karlsson, R., Katsamba, P. S., Nordin, H., Pol, E. & Myszka, D. G. Analyzing a kinetic titration series using affinity biosensors. Anal. Biochem. 349, 136-147 (2006). For some analysis cycles buffer was injected over captured particles instead of Fab to provide blank cycles for double-referencing purposes (double-referencing was performed as described in Myszka et al.), (Myszka, D. G. Improving biosensor analysis. J. Mol. Recognit. 12, 279-284 (1999).

The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any CXCR4, including human CXCR4, CXCR4 of another mammal (such as mouse CXCR4, rat CXCR4, Canine CXCR4 or primate CXCR4), as well as different forms of CXCR4 (e.g., glycosylated CXCR4). Binding affinity of an antibody is generally measured at 25° C., but can also be measured at 37° C.

In some aspects of the invention, an antibody or antigen binding fragment thereof, binds CXCR4 has an MFI of less than 10,000 μg/mL. In particular aspects of the invention, an antibody or antigen binding fragment thereof, that binds CXCR4, has an MFI of less than 6000 μg/mL. In particular aspects of the invention, an antibody or antigen binding fragment thereof, that binds CXCR4, has an MFI of less than 5000 μg/mL. In particular aspects of the invention, In some aspects of the invention, an antibody or antigen binding fragment thereof, that binds CXCR, 4 has an MFI of in the range of 2000 μg/mL μg/mL to 5000 μg/mL.

As used herein, "MFI" refers to mean fluorescence intensity or median fluorescence intensity.

In some aspects of the invention, an antibody or antigen binding fragment thereof, that binds CXCR4 has an EC50 of less than 3.00E-09 M. In some aspects of the invention, an antibody or antigen binding fragment thereof, that binds CXCR4 has an EC50 within the range of about 1.00E-09 M to about 3.00E-09 M. For example, an antibody or antigen binding fragment thereof, binds CXCR4 has an EC50 of 2.00E-09 M.

In some aspects of the invention, an antibody or antigen binding fragment thereof, binds CXCR4, inhibits SDF-1 induced calcium flux. For example, an antibody or antigen binding fragment thereof, inhibits SDF-1 alpha induced Calcium flux, with IC50s for inhibition within the range of about 1 nM to 50 nM. In one aspect, an antibody or antigen binding fragment thereof, inhibits SDF-1 alpha induced Calcium flux, with IC50s for inhibition less than 30 nM. In one aspect, an antibody or antigen binding fragment thereof, inhibits SDF-1 alpha induced Calcium flux, with IC50s for inhibition less than 2 nM.

In some aspects of the invention, an antibody or antigen binding fragment thereof, significantly reduces the number of AML cells in AML cell models. For example, the number of human cell numbers was significantly decreased in animals treated with the anti-CXCR4 6B6 antibody. Further, the survival of the animals treated with the anti-CXCR4 antibodies of the present invention, were significantly increased.

In some aspects, antibodies of the present invention increased survival time and decreased tumor burden in a mouse systemic non-Hodgkin's lymphoma (NHL) and acute myeloid leukemia (AML) cell models. In one aspect, antibodies of the present invention increased survival in a mouse systemic chronic lymphocytic leukemia (CLL) tumor model. In one aspect, antibodies of the present invention inhibited NHL tumor growth in vivo. In some aspects, antibodies of the present invention increased survival time and decreased tumor burden in a mouse systemic multiple myeloma (MM) model.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50 (1999) and Fellouse, F. A., et al, J. Mol. Biol., 373(4):924-40 (2007)).

The anti-CXCR4 antibodies or antigen binding fragments thereof, as described herein may be made by any method known in the art. For example, for the production of hybridoma cell lines, the route and schedule of immunization of the host animal are generally in keeping with established and conventional techniques for antibody stimulation and production, as further described herein. General techniques for production of human and mouse antibodies are known in the art and/or are described herein.

It is contemplated that any mammalian subject including humans or antibody producing cells therefrom can be manipulated to serve as the basis for production of mammalian, including human and hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., Nature 256:495-497 (1975) or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the CXCR4 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for CXCR4, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a human CXCR4, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups, can yield a population of antibodies (e.g., monoclonal antibodies).

If desired, the anti-CXCR4 antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., J. Immunol. Methods 329, 112 (2008); U.S. Pat. No. 7,314,622.

In an alternative, the polynucleotide sequence may be used for genetic manipulation to "humanize" the antibody or to improve the affinity, or other characteristics of the antibody. For example, the constant region may be engineered to more nearly resemble human constant regions to avoid immune response if the antibody is used in clinical trials and treatments in humans. It may be desirable to genetically manipulate the antibody sequence to obtain greater affinity to CXCR4 and/or greater efficacy in inhibiting CXCR4.

There are four general steps to humanize a monoclonal antibody. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen binding site derived from a non-human immunoglobulin have been described, including chimeric antibodies having rodent or modified rodent V regions and their associated CDRs fused to human constant regions. See, for example, Winter et al. Nature 349:293-299 (1991), Lobuglio et al. Proc. Nat. Acad. Sci. USA 86:4220-4224 (1989), Shaw et al. J Immunol. 138:4534-4538 (19870, and Brown et al. Cancer Res. 47:3577-3583 (1987). Other references describe rodent CDRs grafted into a human supporting framework region (FR) prior to fusion with an appropriate human antibody constant region. See, for example, Riechmann et al. Nature 332:323-327 (1988), Verhoeyen et al. Science 239:1534-1536 (1988), and Jones et al. Nature 321:522-525 (1986). Another reference describes rodent CDRs supported by recombinantly engineered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476, 1991, and in U.S. Pat. Nos. 6,180,377; 6,054,297; 5,997,867; 5,866,692; 6,210,671; and 6,350,861; and in PCT Publication No. WO 01/27160.

The general principles related to humanized antibodies discussed above are also applicable to customizing antibodies for use, for example, in dogs, cats, primate, equines and bovines. Further, one or more aspects of humanizing an antibody described herein may be combined, e.g., CDR grafting, framework mutation and CDR mutation.

In some aspects of the invention, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Methods for obtaining human antibodies from transgenic mice are disclosed by Green et at, Nature Genet. 7: 13 (1994), Lonberg et at, Nature 368:856 (1994), and Taylor et at, Int. Immun. 6:519 (1994). A non-limiting example of such a system is the XenoMouse® {e.g., Green et al., J. Immunol. Methods 231: 11-23 (1999), incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along with accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., J. Immunol. Methods 231: 11-23 (1999)). The skilled artisan will realize that the claimed compositions and methods are not limited to use of the XenoMouse® system but may utilize any transgenic animal that has been genetically engineered to produce human antibodies.

In some aspects of the invention, an antibody can be prepared using an antibody having one or more of the VH and/or VL sequences disclosed herein as starting material to engineer a modified antibody, which modified antibody may have altered properties from the starting antibody. An antibody can be engineered by modifying one or more residues within one or both variable regions (VH and/or VL), for example within one or more CDR regions and/or within one or more framework regions. Additionally or alternatively, an antibody can be engineered by modifying residues within the constant region(s), for example to alter the effector function(s) of the antibody. In certain aspects, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L et al., Nature 332 323-327 (1995), Jones, P et al., Nature 32J. 522-525 (1986), Queen, C et al., Proc Natl Acad See U.S.A 86 10029-10033 (1989), U.S. Pat. Nos. 5,225,539; 5,530,101; 5,585,089; 5,693,762; and 6,180,370).

Such framework sequences can be obtained from public DNA databases or published references that include germline antibody gene sequences For example, germline DNA sequences for human heavy and light chain variable region genes can be found in the "VBase" human germline sequence database (available on the Internet at www mrc-cpe cam ac uk/vbase) as well as in Kabat, E A, et. al. (1991) Sequences of Proteins of Immunological Interest, Fifth Edition, U S. Department of Health and Human Services, NIH Publication No 91-3242, Tomlinson, I M, et al. (1992) "The Repertoire of Human Germline $V_H$ Sequences Reveals about Fifty Groups of VH Segments with Different Hypervariable Loops" Cox, J P L et al., J Mol. Biol TTL 776-798 (1994) "A Directory of Human Germ-line Vn Segments Reveals a Strong Bias in their Usage" Ew. J. Immunol 2A 827-836, the contents of each of which are expressly incorporated herein by reference As another example, the germline DNA sequences for human heavy and light chain variable region genes can be found in the Genbank database For example, the following heavy chain germline sequences found in the HCo7 HuMAb mouse are available in the accompanying Genbank accession numbers 1-69 (NG_0010109, NT_024637 and BC070333), 3-33 (NG_0010109 and NT_024637) and 3-7 (NG_0010109 and NT_024637). As another example, the following heavy chain germline sequences found in the HCol 2 HuMAb mouse are available in the accompanying Genbank accession numbers 1-69 (NG_0010109, NT_024637 and BC070333), 5-51 (NG_0010109 and NT_024637), 4-34 (NG_0010109 and NT_024637), 3-30 3 (CAJ556644) and 3-23 (AJ406678). Yet another source of human heavy and light chain germline sequences is the database of human immunoglobulin genes available from IMGT (http://imgt.cines.fr).

Preferred framework sequences for use in the antibodies of this disclosure are those that are structurally similar to the framework sequences used by selected antibodies of this disclosure. The VH CDR1, CDR2, and CDR3 sequences, and the VL CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. Another type of framework modification involves mutating one or more residues within the framework region, or even within one or more CDR regions, to remove T cell epitopes to thereby reduce the potential immunogenicity of the antibody. This approach is also referred to as "deimmunization" and is described in futher detail in U.S. Patent Publication No. 20030153043.

In addition or alternative to modifications made within the framework or CDR regions, antibodies of this disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of this disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat and/or Chothia. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762). In some aspects of the invention, the hinge region of CHI is modified such that the number of cysteine residues in the hinge region is altered, e.g., increased or decreased. This approach is described further in U.S. Pat. No. 5,677,425 by Bodmer el al. The number of cysteine residues in the hinge region of CHI is altered to, for example, facilitate assembly of the light and heavy chains or to increase or decrease the stability of the antibody. In some aspects of the invention, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding This approach is described in further detail in U.S. Pat. No. 6,165,745 by Ward et al.

In some aspects of the invention, the antibody is modified to increase its biological half-life. Various approaches are possible. For example, one or more of the following mutations can be introduced T252L, T254S, T256F, as described in U.S. Pat. No. 6,277,375. Alternatively, to increase the biological half-life, the antibody can be altered within the CHI or CL region to contain a salvage receptor binding epitope taken from two loops of a CH2 domain of an Fc region of an IgG, as described in U.S. Pat. Nos. 5,869,046 and 6,121,022 by Presta el al.

In some aspects of the invention, antibodies may be made recombinantly and expressed using any method known in the art. In another alternative, antibodies may be made recombinantly by phage display technology. See, for example, U.S. Pat. Nos. 5,565,332; 5,580,717; 5,733,743; and 6,265,150; and Winter et al., Annu. Rev. Immunol. 12:433-455 (1994). Alternatively, the phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571 (1993). Several sources of V-gene segments can be used for phage display. Clackson et al., Nature 352:624-628 (1991), isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597 (1991), or Griffith et al., EMBO J. 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al., Vaccine 19:2756, (2001); Lonberg, N. and D. Huszar Int. Rev. Immunol 13:65 (1995); and Pollock, et al., J Immunol Methods 231:147 (1999). Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for CXCR4.

The antibodies as described herein can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses, and magnetite. The nature of the carrier can be either soluble or insoluble for purposes of the invention. Those skilled in the art will know of other suitable carriers for binding antibodies, or will be able to ascertain such, using routine experimentation. In some aspects of the invention, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant regions in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a CXCR4 monoclonal antibody herein.

Methods for determining the binding specificity of an anti-CXCR4 antibody are well-known to those of skill in the art. General methods are provided, for example, by Mole, "Epitope Mapping," in METHODS IN MOLECULAR BIOLOGY, VOLUME 10: IMMUNOCHEMICAL PROTOCOLS, Manson (ed.), pages 105-116 (The Humana Press, Inc. 1992).

The anti-CXCR4 antibodies, or antigen binding fragments thereof, as described herein can be identified or characterized using methods known in the art, whereby reduction of CXCR4 expression levels is detected and/or measured. In some aspects of the invention, an anti-CXCR4 antibody, or antigen binding fragment thereof, is identified by incubating a candidate agent with CXCR4 and monitoring binding and/or attendant reduction of CXCR4 expression levels. The binding assay may be performed with purified CXCR4 polypeptide(s), or with cells naturally expressing, or transfected to express, CXCR4 polypeptide(s). In one aspect, the binding assay is a competitive binding assay, where the ability of a candidate antibody to compete with a known anti-CXCR4 antibody, or antigen binding fragment thereof, for CXCR4 binding is evaluated. The assay may be performed in various formats, including the ELISA format.

Following initial identification, the activity of a candidate anti-CXCR4 antibody, or antigen binding fragment thereof, can be further confirmed and refined by bioassays, known to test the targeted biological activities. Alternatively, bioassays can be used to screen candidates directly. Some of the methods for identifying and characterizing anti-CXCR4 antibodies, or antigen binding fragments thereof, are described in detail in the Examples.

Anti-CXCR4 antibodies, or antigen binding fragments thereof, may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an anti-CXCR4 antibody, or antigen binding fragment thereof, binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an anti-CXCR4 antibody, or antigen binding fragments thereof. In another example, the epitope to which the anti-CXCR4 antibody, or antigen-binding fragments thereof, binds can be determined in a systematic screening by using overlapping peptides derived from the CXCR4 sequence and determining binding by the anti-CXCR4 antibody, or antigen binding fragments thereof. According to the gene fragment expression assays, the open reading frame encoding CXCR4 is fragmented either randomly or by specific genetic constructions and the reactivity of the expressed fragments of CXCR4 with the antibody to be tested is determined. The gene fragments may, for example, be produced by PCR and then transcribed and translated into protein in vitro, in the presence of radioactive amino acids. The binding of the antibody to the radioactively labeled CXCR4 fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant CXCR4 in which various fragments of the CXCR4 protein have been replaced (swapped) with sequences from CXCR4 from another species (e.g., mouse), or a closely related, but antigenically distinct protein (e.g., CXCR4). By assessing binding of the antibody to the mutant CXCR4, the importance of the particular CXCR4 fragment to antibody binding can be assessed.

Yet another method which can be used to characterize an anti-CXCR4 antibody is to use competition assays with other antibodies known to bind to the same antigen, i.e., various fragments on CXCR4, to determine if the anti-CXCR4 antibody competes with and/or binds to the same epitope as other antibodies. Competition assays are well known to those of skill in the art.

In some aspects of the invention, an isolated antibody or antigen binding fragment thereof, that binds CXCR4, competes for binding to CXCR4 with and/or binds to the same epitope of CXCR4. Among antibodies that compete for binding to CXCR4 and/or bind to the same epitope of CXCR4 include antibodies comprising at least a heavy chain variable (VH) region comprising (i) a VH CDR1 selected from the group consisting of SEQ ID NOs:107, 113, 114, 108, 109, 115, 116, 117, 121 and 122; (ii) a VH CDR2 selected from the group consisting of SEQ ID NOs: 162, 128, 110, 111, 118, 119, 154, 123, 158, 124, 159, 125, 160, 126, 161, 127, 163, 164, 165, 166, 167, 168, 155, 129, 156, and 130, and, (iii) a VH CDR3 selected from the group consisting of SEQ ID NOs: 112; and 120; and/or; at least a light chain variable region (VL) region comprising (i) a VL CDR1 selected from the group consisting of SEQ ID NOs: 144, 131, 135, 138, 141, 142, 143, 146, 147, 148, 149, 150, and 151; (ii) a VL CDR2 selected from the group consisting of 145, 132, 136, and 152; and (iii) a VL CDR3 selected from the group consisting of SEQ ID NO: 139, 133, 137, 140, and 153.

In some aspects of the invention, an antibody competes for binding to CXCR4 with an antibody or antigen binding fragment thereof, comprising a heavy chain variable (VH) region comprising three CDRs set forth as SEQ ID NOs: 107, 162 and 112.

In some aspects of the invention, an antibody competes for binding to CXCR4 with an antibody or antigen binding fragment thereof, comprising a light chain variable (VL) region comprising three CDRs set forth as SEQ ID NOs: 144, 145 and 139.

In some aspects of the invention, an antibody competes for binding to CXCR4 with an antibody or antigen binding fragment thereof, comprising a) a heavy chain variable (VH) region comprising three CDRs set forth as SEQ ID NOs: 107, 162 and 112; and b) a light chain variable (VL) region comprising three CDRs set forth as SEQ ID NOs: 144, 145 and 139.

In some aspects of the invention, an antibody competes for binding to CXCR4 with an antibody or antigen binding fragment thereof, comprising a) a heavy chain variable (VH) region comprising VH CDR1, VH CDR2 and VH CDR3 from a VH region of SEQ ID NO: 33; and/or b) a light chain variable (VL) region comprising VL CDR1, VL CDR2 and VL CDR3 from a VL region of SEQ ID NO: 73.

In some aspects of the invention, an antibody competes for binding to CXCR4 with an antibody or antigen binding fragment thereof, comprising a) a heavy chain variable (VH) region of SEQ ID NO: 33; and/or b) a light chain variable (VL) region of SEQ ID NO: 73.

An expression vector can be used to direct expression of an anti-CXCR4 antibody, or antigen binding fragments thereof, One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another aspect of the invention, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol. 11:202 (1993); Chiou et al., Gene Therapeutics: Methods And Applications Of Direct Gene Transfer, J. A. Wolff, ed., 1994; Wu et al., J. Biol. Chem., 263:621 (1988); Wu et al., J. Biol. Chem., 269:542 (1994); Zenke et al., Proc. Natl. Acad. Sci. USA, 87:3655 (1990); and Wu et al., J. Biol. Chem., 266:338 (1991). Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly et al., Cancer Gene Therapy, 1:51 (1994); Kimura, Human Gene Therapy, 5:845 (1994); Connelly et al., Human Gene Therapy, 1:185 (1995); and Kaplitt, Nature Genetics, 6:148 (1994)). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Pat. No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel et al., Hum. Gene Ther., 3:147 (1992)); ligand-linked DNA (see, e.g., Wu, J. et al., Biol. Chem., 264:16985 (1989)); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip et al., Mol. Cell Biol., 14:2411 (1994) and in Woffendin et al., Proc. Natl. Acad. Sci., 91:1581 (1994).

In some aspects of the invention, the invention encompasses compositions, including pharmaceutical compositions, comprising antibodies described herein or made by the methods and having the characteristics described herein. As used herein, compositions comprise one or more antibodies that bind to CXCR4, and/or one or more polynucleotides comprising sequences encoding one or more these antibodies. These compositions may further comprise suitable excipients, such as pharmaceutically acceptable excipients including buffers, which are well known in the art.

Accordingly, the invention provides any of the following, or compositions (including pharmaceutical compositions) comprising any of the following sequences:

TABLE 2

| Descriptions | SEQ ID NO | Sequence |
|---|---|---|
| m6B6 VH Protein | 1 | HVEVKLVESGGGLVQPGGSLRLSCATS**GFTFTDY**YMS<br>WVRQPPGKALEWLGFI**RNKANGYT**TEYSASVKGRFTIS<br>RDNSQSILYLQMNTLRAEDSATYYCAR**DLPGFAY**WGQ<br>GTLVTVSS |
| m6B6 VH DNA | 2 | GAGGTAAAGTTGGTGGAGTCTGGAGGAGGCTTGGTA<br>CAGCCTGGGGGTTCTCTGAGACTCTCCTGTGCAACTT<br>CTGGGTTCACCTTCACTGATTACTACATGAGTTGGGT<br>CCGCCAGCCTCCAGGAAAGGCACTTGAGTGGTTGGG<br>TTTTATTAGAAACAAAGCTAATGGTTACACAACAGAGT<br>ACAGTGCATCTGTGAAGGGTCGGTTCACCATCTCCAG<br>AGATAATTCCCAAAGCATCCTCTATCTTCAAATGAACA<br>CCCTGAGAGCTGAGGACAGTGCCACTTATTACTGTGC<br>AAGAGATCTCCCGGGGTTTGCTTACTGGGGCCAAGG<br>GACTCTGGTCACCGTCTCCTCA |
| m6B6 VL Protein | 3 | DIVMSQSPSSLTVSAGEKVTMSC**KSSQSLYNSRTRKNY**<br>**LA**WYQQKPGQSPKLLIY**WASARES**GVPGRFTGSGSGT<br>DFALTISSVQAEDLAVYYC**KQSYNLRT**FGGGTKLEIK |
| m6B6 VL DNA | 4 | GACATAGTTATGTCGCAGTCTCCATCCTCCCTGACTG<br>TGTCAGCAGGAGAGAAGGTCACTATGAGCTGCAAAT<br>CCAGTCAGAGTCTGTACAACAGTAGAACCCGAAAGAA |

TABLE 2-continued

| Descriptions | SEQ ID NO | Sequence |
|---|---|---|
| | | CTACTTGGCTTGGTACCAGCAGAAACCAGGGCAGTC<br>TCCTAAACTGCTGATCTACTGGGCATCCGCTAGGGAA<br>TCTGGGGTCCCTGGTCGCTTCACAGGCAGTGGATCT<br>GGGACAGATTTCGCTCTCACCATCAGCAGTGTGCAG<br>GCTGAAGACCTGGCAGTTTATTACTGCAAGCAATCTT<br>ATAATCTTCGGACGTTCGGTGGAGGCACCAAGCTGG<br>AGATCAAA |
| h6B6 VH<br>Protein | 5 | EVQLVESGGGLVQPGGSLRLSCAAS**GFTFSDY**YMSWV<br>RQAPGKGLEWVGFI**RNKANGYT**TEYSASVKGRFTISRD<br>DSKNSLYLQMNSLKTEDTAVYYCAR**DLPGFAY**WGQGT<br>LVTVSS |
| h6B6 VH<br>DNA | 6 | GAAGTCCAGCTGGTTGAAAGTGGTGGCGGCCTGGTG<br>CAGCCGGGCGGCTCTCTGCGCCTGTCATGCGCTGCA<br>TCCGGCTTTACCTTCAGCGACTATTACATGAGCTGGG<br>TTCGCCAAGCGCCCGGCAAAGGCCTGGAATGGGTGG<br>GATTCATTCGAAATAAAGCGAACGGCTATACCACCGA<br>ATATAGCGCATCTGTCAAGGGCCGGTTCACCATCTCC<br>CGCGATGATTCCAAGAACAGCCTGTACCTGCAGATGA<br>ACTCCCTGAAGACGGAAGATACCGCCGTCTATTATTG<br>TGCCCGCGATCTGCCTGGCTTTGCCTATTGGGGCCA<br>AGGCACTCTGGTCACCGTCTCCTCA |
| h6B6 VL<br>Protein | 7 | DIVMTQSPDSLAVSLGERATINC**KSSQSLYNSRTRKNYL**<br>**A**WYQQKPGQPPKLLIY**WASARES**GVPDRFSGSGSGTD<br>FTLTISSLQAEDVAVYYC**KQSYNLRT**FGGGTKVEIK |
| h6B6 VL<br>DNA | 8 | GACATCGTTATGACACAGTCACCAGATAGCTTAGCCG<br>TGTCCCTGGGAGAACGTGCTACCATTAATTGCAAAAG<br>CTCCCAGAGCCTGTATAACAGCCGGACACGGAAGAA<br>TTATCTGGCATGGTATCAGCAGAAACCCGGACAGCC<br>GCCTAAGCTGCTGATTTATTGGGCCAGCGCACGCGA<br>AAGTGGTGTGCCCGACCGCTTTTCCGGCAGCGGTAG<br>TGGCACTGACTTCACCCTGACCATCTCAAGCTTGCAA<br>GCCGAAGACGTGGCAGTATATTATTGCAAGCAGTCGT<br>ACAATCTGCGCACCTTTGGCGGCGGCACAAAAGTGG<br>AGATCAAA |
| m12A11 VH<br>Protein | 9 | EIQLQQSGPELVKPGASVKVSCKAS**GYSFTDY**NIYWVK<br>QSHGQSLEWIGYI**DPYNGG**TRYNQKFKGKATLTVDKSS<br>STAFMHLNSLTSEDSAVYFCAR**TYGSRYVGAMDY**WGQ<br>GTSVTVSS |
| m12A11 VH<br>DNA | 10 | GAAATACAGTTGCAGCAGTCCGGGCCTGAGCTGGTG<br>AAGCCTGGGGCTTCAGTGAAGGTATCCTGCAAGGCT<br>TCTGGTTACTCATTCACTGACTATAATATATACTGGGT<br>GAAGCAGAGCCATGGACAGAGCCTTGAGTGGATTGG<br>ATATATTGATCCTTACAATGGTGGGACCAGGTATAAC<br>CAGAAGTTCAAGGGCAAGGCCACATTGACTGTTGACA<br>AGTCCTCCAGCACAGCCTTCATGCATCTCAACAGCCT<br>GACATCTGAGGACTCTGCAGTCTATTTTTGTGCAAGA<br>ACCTACGGTAGTCGGTACGTTGGGGCTATGGACTAC<br>TGGGGTCAAGGAACCTCGGTCACCGTCTCCTCA |
| m12A11 VL<br>Protein | 11 | DIVMTQAAPSVPVTPGESVSISC**RSSKSLLHSNGNTYLY**<br>WFLQRPGQSPQLLIY**RMSNPAS**GVPDRFSGSGSGTAF<br>TLRISRVEAEDVGVYYC**MQHLEYPLT**FGAGTKLELK |
| m12A11 VL<br>DNA | 12 | GATATCGTTATGACGCAGGCTGCACCCTCTGTACCTG<br>TCACTCCTGGAGAGTCAGTATCCATCTCCTGCAGGTC<br>TAGTAAGAGTCTCCTGCATAGTAATGGCAACACTTAC<br>TTATATTGGTTCCTGCAGAGGCCAGGCCAGTCTCCTC<br>AGCTCCTAATATATCGGATGTCCAACCCTGCCTCAGG<br>AGTCCCAGACAGGTTCAGTGGCAGTGGGTCAGGAAC<br>TGCTTTCACACTGAGAATCAGTCGAGTGGAGGCTGA<br>GGATGTGGGTGTTTATTACTGTATGCAACATCTAGAA<br>TATCCGCTCACGTTCGGTGCTGGGACCAAGCTGGAG<br>CTGAAA |
| h12A11 VH<br>Protein | 13 | QVQLVQSGAEVKKPGASVKVSCKAS**GYTFTDY**NIYWV<br>RQATGQGLEWMGYI**DPYNGG**TRYNQKFKGRVTMTRN<br>TSISTAYMELSSLRSEDTAVYYCAR**TYGSRYVGAMDY**W<br>GQGTLVTVSS |

TABLE 2-continued

| Descriptions | SEQ ID NO | Sequence |
|---|---|---|
| h12A11 VH DNA | 14 | CAGGTTCAGCTGGTGCAGAGCGGCGCCGAGGTGAA<br>GAAACCAGGCGCCAGCGTGAAAGTGTCCTGCAAGGC<br>GAGTGGATATACCTTCACCGATTACAATATTTATTGGG<br>TTCGCCAGGCCACCGGGCAGGGCCTGGAGTGGATG<br>GGCTACATTGATCCATATAACGGTGGCACCCGCTACA<br>ACCAGAAGTTTAAAGGCCGCGTGACCATGACCCGCA<br>ATACCTCGATCTCCACCGCCTATATGGAACTGAGCAG<br>CTTACGCTCTGAAGATACGGCCGTGTACTACTGTGCC<br>CGCACCTACGGGTCTCGCTACGTTGGCGCGATGGAT<br>TATTGGGGTCAGGGCACCCTGGTCACCGTCTCCTCA |
| h12A11 VL Protein | 15 | DIVMTQSPLSLPVTPGEPASISC**RSSKSLLHSNGNTYLY**<br>WYLQKPGQSPQLLIY**RMSNPAS**GVPDRFSGSGSGTDF<br>TLKISRVEAEDVGVYYC**MQHLEYPLT**FGGGTKVELK |
| h12A11 VL DNA | 16 | GACATCGTGATGACCCAGAGCCCGCTGTCTCTGCCA<br>GTGACCCCTGGTGAGCCAGCCAGTATTAGCTGCCGC<br>AGCAGCAAAAGTCTGCTGCACAGCAATGGAAACACCT<br>ACCTGTATTGGTATCTGCAGAAACCGGGTCAGTCACC<br>CCAGCTGCTGATCTACCGCATGTCTAACCCGGCCAG<br>CGGCGTCCCTGATCGCTTTAGCGGCAGCGGTTCCGG<br>AACCGATTTTACCCTGAAGATCTCCCGCGTTGAGGCC<br>GAAGACGTCGGCGTCTACTATTGCATGCAGCACCTG<br>GAATATCCGCTGACATTCGGTGGCGGTACCAAAGTG<br>GAACTCAAA |
| m3G10 VH Protein | 17 | EVKLVESGGGLVQPGSSLRLSCAAS**GFTFTDY**YMSWV<br>RQPPGKALEWLGFI**RHKANGYT**TEYSTSVKGRFTISRD<br>NSLSILYLQMNTLRPEDSATYYCAR**DLPGFAY**WGQGTL<br>VTVSS |
| m3G10 VH DNA | 18 | GAAGTGAAATTGGTGGAGTCTGGAGGAGGCTTGGTA<br>CAGCCTGGGAGTTCTCTGAGACTCTCCTGTGCAGCTT<br>CTGGGTTCACCTTCACTGATTACTACATGAGCTGGGT<br>CCGCCAGCCTCCAGGAAAGGCACTTGAGTGGTTGGG<br>TTTTATTAGACACAAGGCTAATGGTTACACAACAGAAT<br>ACAGTACATCTGTGAAGGGTCGGTTCACCATCTCCAG<br>AGATAATTCCCTAAGCATCCTCTATCTTCAAATGAACA<br>CCCTGAGACCTGAGGACAGTGCCACTTATTACTGTGC<br>AAGAGATCTCCCGGGGTTTGCTTACTGGGGCCAAGG<br>GACTCTGGTCACCGTCTCCTCA |
| m3G10 VL Protein | 19 | DIVMSQSPSSLAVSAGEKVTMTC**KSSQSLFNSRTRKNY**<br>**LA**WYQQKPGQSPKLLIY**WASARES**GVPDRFTGSGSGT<br>DFTLTISSVQAEDLAVYYC**KQSFNLRT**FGGGTKLEIK |
| m3G10 VL DNA | 20 | GATATTGTTATGTCGCAGTCGCCATCCTCCCTGGCTG<br>TGTCAGCAGGAGAGAAGGTCACTATGACCTGCAAATC<br>CAGTCAGAGTCTGTTCAACAGTAGAACCCGAAAGAAC<br>TACTTGGCTTGGTACCAGCAGAAACCCGGGCAGTCT<br>CCTAAACTGCTGATCTACTGGGCATCCGCTAGGGAAT<br>CTGGGGTCCCTGATCGCTTCACAGGCAGTGGATCTG<br>GGACAGATTTCACTCTCACCATCAGCAGTGTGCAGGC<br>TGAAGACCTGGCAGTTTATTACTGCAAGCAATCTTTTA<br>ATCTTCGGACGTTCGGTGGAGGCACCAAGCTGGAAA<br>TCAAA |
| h3G10 VH Protein | 21 | EVQLVESGGGLVQPGGSLRLSCAAS**GFTFSDY**YMSWV<br>RQAPGKGLEWVGFI**RHKANGYT**TEYSTSVKGRFTISRD<br>DSKNSLYLQMNSLKTEDTAVYYCAR**DLPGFAY**WGQGT<br>LVTVSS |
| h3G10 VH DNA | 22 | GAAGTCCAGCTGGTTGAAAGTGGTGGCGGCCTGGTG<br>CAGCCGGGCGGCTCTCTGCGCCTGTCATGCGCTGCA<br>TCCGGCTTTACCTTCAGCGACTATTACATGAGCTGGG<br>TTCGCCAAGCGCCCGGCAAAGGCCTGGAATGGGTGG<br>GATTCATTCGACATAAAGCGAACGGCTATACCACCGA<br>ATATAGCACATCTGTCAAGGGCCGGTTCACCATCTCC<br>CGCGATGATTCCAAGAACAGCCTGTACCTGCAGATGA<br>ACTCCCTGAAGACGGAAGATACCGCCGTCTATTATTG<br>TGCCCGCGATCTGCCTGGCTTTGCCTATTGGGGCCA<br>AGGCACTCTGGTCACCGTCTCCTCA |
| h3G10.A57 VH | 23 | EVQLVESGGGLVQPGGSLRLSCAAS**GFTFSDY**YMSWV<br>RQAPGKGLEWVGFI**RHKANFYT**TEYSTSVKGRFTISRD |

TABLE 2-continued

| Descriptions | SEQ ID NO | Sequence |
|---|---|---|
| Protein | | DSKNSLYLQMNSLKTEDTAVYYCAR**<u>DLPGFAY</u>**WGQGT LVTVSS |
| h3G10.A57 VH DNA | 24 | GAAGTCCAGCTGGTTGAAAGTGGTGGCGGCCTGGTG CAGCCGGGCGGCTCTCTGCGCCTGTCATGCGCTGCA TCCGGCTTTACCTTCAGCGACTATTACATGAGCTGGG TTCGCCAAGCGCCCGGCAAAGGCCTGGAATGGGTGG GATTCATTCGACATAAAGCGAACTTTTATACCACCGAA TATAGCACATCTGTCAAGGGCCGGTTCACCATCTCCC GCGATGATTCCAAGAACAGCCTGTACCTGCAGATGAA CTCCCTGAAGACGGAAGATACCGCCGTCTATTATTGT GCCCGCGATCTGCCTGGCTTTGCCTATTGGGGCCAA GGCACTCTGGTCACCGTCTCCTCA |
| h3G10.B44 VH Protein | 25 | EVQLVESGGGLVQPGGSLRLSCAAS**GFTFS<u>DY</u>**<u>YMS</u>WV RQAPGKGLEWVS<u>FI**RHKANFYT**TEYSTSVKG</u>RFTISRD NSKNTLYLQMNSLRAEDTAVYYCAK**<u>DLPGFAY</u>**WGQGT LVTVSS |
| h3G10.B44 VH DNA | 26 | GAAGTCCAGCTGGTTGAAAGTGGTGGCGGCCTGGTG CAGCCGGGCGGCTCTCTGCGCCTGTCATGCGCTGCA TCCGGCTTTACCTTCAGCGACTATTACATGAGCTGGG TTCGCCAAGCGCCCGGCAAAGGCCTGGAATGGGTGT CATTCATTCGACATAAAGCGAACTTTTATACCACCGAA TATAGCACATCTGTCAAGGGCCGGTTCACCATCTCCC GCGATAATTCCAAGAACACCCTGTACCTGCAGATGAA CTCCCTGAGGGCGGAAGATACCGCCGTCTATTATTGT GCCAAGGATCTGCCTGGCTTTGCCTATTGGGGCCAA GGCACTCTGGTCACCGTCTCTTCC |
| h3G10.1.7 VH Protein | 27 | EVQLVESGGGLVQPGGSLRLSCAAS**GFTFS<u>DY</u>**<u>YMS</u>WV RQAPGKGLEWVG<u>FI**RHKANKYT**TEYSTSVKG</u>RFTISRD DSKNSLYLQMNSLKTEDTAVYYCAR**<u>DLPGFAY</u>**WGQGT LVTVSS |
| h3G10.1.7 VH DNA | 28 | GAAGTCCAGCTGGTTGAAAGTGGTGGCGGCCTGGTG CAGCCGGGCGGCTCTCTGCGCCTGTCATGCGCTGCA TCCGGCTTTACCTTCAGCGACTATTACATGAGCTGGG TTCGCCAAGCGCCCGGCAAAGGCCTGGAATGGGTGG GATTCATTCGACATAAAGCGAACAAGTATACCACCGA ATATAGCACATCTGTCAAGGGCCGGTTCACCATCTCC CGCGATGATTCCAAGAACAGCCTGTACCTGCAGATGA ACTCCCTGAAGACGGAAGATACCGCCGTCTATTATTG TGCCCGCGATCTGCCTGGCTTTGCCTATTGGGGCCA AGGCACTCTGGTCACCGTCTCCTCA |
| h3G10.1.60 VH Protein | 29 | EVQLVESGGGLVQPGGSLRLSCAAS**GFTFS<u>DY</u>**<u>YMS</u>WV RQAPGKGLEWVG<u>FI**RHKANVYT**TEYSTSVKG</u>RFTISRD DSKNSLYLQMNSLKTEDTAVYYCAR**<u>DLPGFAY</u>**WGQGT LVTVSS |
| h3G10.1.60 VH DNA | 30 | GAAGTCCAGCTGGTTGAAAGTGGTGGCGGCCTGGTG CAGCCGGGCGGCTCTCTGCGCCTGTCATGCGCTGCA TCCGGCTTTACCTTCAGCGACTATTACATGAGCTGGG TTCGCCAAGCGCCCGGCAAAGGCCTGGAATGGGTGG GATTCATTCGACATAAAGCGAACGTGTATACCACCGA ATATAGCACATCTGTCAAGGGCCGGTTCACCATCTCC CGCGATGATTCCAAGAACAGCCTGTACCTGCAGATGA ACTCCCTGAAGACGGAAGATACCGCCGTCTATTATTG TGCCCGCGATCTGCCTGGCTTTGCCTATTGGGGCCA AGGCACTCTGGTCACCGTCTCCTCA |
| h3G10.2.5 VH Protein | 31 | EVQLVESGGGLVQPGGSLRLSCAAS**GFTFS<u>DY</u>**<u>YMS</u>WV RQAPGKGLEWVG<u>FI**RHKANIYT**TEYSTSVKG</u>RFTISRDD SKNSLYLQMNSLKTEDTAVYYCAR**<u>DLPGFAY</u>**WGQGTL VTVSS |
| h3G10.2.5 VH DNA | 32 | GAAGTCCAGCTGGTTGAAAGTGGTGGCGGCCTGGTG CAGCCGGGCGGCTCTCTGCGCCTGTCATGCGCTGCA TCCGGCTTTACCTTCAGCGACTATTACATGAGCTGGG TTCGCCAAGCGCCCGGCAAAGGCCTGGAATGGGTGG GATTCATTCGACATAAAGCGAACATTTATACCACCGA ATATAGCACATCTGTCAAGGGCCGGTTCACCATCTCC CGCGATGATTCCAAGAACAGCCTGTACCTGCAGATGA ACTCCCTGAAGACGGAAGATACCGCCGTCTATTATTG |

TABLE 2-continued

| Descriptions | SEQ ID NO | Sequence |
|---|---|---|
| | | TGCCCGCGATCTGCCTGGCTTTGCCTATTGGGGCCA<br>AGGCACTCTGGTCACCGTCTCCTCA |
| h3G10.1.91<br>VH<br>Protein | 33 | EVQLVESGGGLVQPGGSLRLSCAAS**GFTFSDY**YMSWV<br>RQAPGKGLEWVGFI**RHKANFET**TEYSTSVKGRFTISRD<br>DSKNSLYLQMNSLKTEDTAVYYCAR**DLPGFAY**WGQGT<br>LVTVSS |
| h3G10.1.91<br>VH<br>DNA | 34 | GAAGTCCAGCTGGTTGAAAGTGGTGGCGGCCTGGTG<br>CAGCCGGGCGGCTCTCTGCGCCTGTCATGCGCTGCA<br>TCCGGCTTTACCTTCAGCGACTATTACATGAGCTGGG<br>TTCGCCAAGCGCCCGGCAAAGGCCTGGAATGGGTGG<br>GATTCATTCGACATAAAGCGAACTTTGAGACCACCGA<br>ATATAGCACATCTGTCAAGGGCCGGTTCACCATCTCC<br>CGCGATGATTCCAAGAACAGCCTGTACCTGCAGATGA<br>ACTCCCTGAAGACGGAAGATACCGCCGTCTATTATTG<br>TGCCCGCGATCTGCCTGGCTTTGCCTATTGGGGCCA<br>AGGCACTCTGGTCACCGTCTCCTCA |
| h3G10.2.37<br>VH<br>Protein | 35 | EVQLVESGGGLVQPGGSLRLSCAAS**GFTFSDY**YMSWV<br>RQAPGKGLEWVGFI**RHKANFYT**REYSTSVKGRFTISRD<br>DSKNSLYLQMNSLKTEDTAVYYCAR**DLPGFAY**WGQGT<br>LVTVSS |
| h3G10.2.37<br>VH<br>DNA | 36 | GAAGTCCAGCTGGTTGAAAGTGGTGGCGGCCTGGTG<br>CAGCCGGGCGGCTCTCTGCGCCTGTCATGCGCTGCA<br>TCCGGCTTTACCTTCAGCGACTATTACATGAGCTGGG<br>TTCGCCAAGCGCCCGGCAAAGGCCTGGAATGGGTGG<br>GATTCATTCGACATAAAGCGAACTTTTATACCCGGGA<br>ATATAGCACATCTGTCAAGGGCCGGTTCACCATCTCC<br>CGCGATGATTCCAAGAACAGCCTGTACCTGCAGATGA<br>ACTCCCTGAAGACGGAAGATACCGCCGTCTATTATTG<br>TGCCCGCGATCTGCCTGGCTTTGCCTATTGGGGCCA<br>AGGCACTCTGGTCACCGTCTCCTCA |
| h3G10.2.45<br>VH<br>Protein | 37 | EVQLVESGGGLVQPGGSLRLSCAAS**GFTFSDY**YMSWV<br>RQAPGKGLEWVGFI**RHKANFYT**TEYSTWVKGRFTISRD<br>DSKNSLYLQMNSLKTEDTAVYYCAR**DLPGFAY**WGQGT<br>LVTVSS |
| h3G10.2.45<br>VH<br>DNA | 38 | GAAGTCCAGCTGGTTGAAAGTGGTGGCGGCCTGGTG<br>CAGCCGGGCGGCTCTCTGCGCCTGTCATGCGCTGCA<br>TCCGGCTTTACCTTCAGCGACTATTACATGAGCTGGG<br>TTCGCCAAGCGCCCGGCAAAGGCCTGGAATGGGTGG<br>GATTCATTCGACATAAAGCGAACTTTTATACCACCGG<br>GTATAGCACATCTGTCAAGGGCCGGTTCACCATCTCC<br>CGCGATGATTCCAAGAACAGCCTGTACCTGCAGATGA<br>ACTCCCTGAAGACGGAAGATACCGCCGTCTATTATTG<br>TGCCCGCGATCTGCCTGGCTTTGCCTATTGGGGCCA<br>AGGCACTCTGGTCACCGTCTCCTCA |
| h3G10.2.54<br>VH<br>Protein | 39 | EVQLVESGGGLVQPGGSLRLSCAAS**GFTFSDY**YMSWV<br>RQAPGKGLEWVGFI**RHKANFYT**TEYSTSVRGRFTISRD<br>DSKNSLYLQMNSLKTEDTAVYYCAR**DLPGFAY**WGQGT<br>LVTVSS |
| h3G10.2.54<br>VH<br>DNA | 40 | GAAGTCCAGCTGGTTGAAAGTGGTGGCGGCCTGGTG<br>CAGCCGGGCGGCTCTCTGCGCCTGTCATGCGCTGCA<br>TCCGGCTTTACCTTCAGCGACTATTACATGAGCTGGG<br>TTCGCCAAGCGCCCGGCAAAGGCCTGGAATGGGTGG<br>GATTCATTCGACATAAAGCGAACTTTTATACCACCGAA<br>TATAGCACATCTGTCCGTGGCCGGTTCACCATCTCCC<br>GCGATGATTCCAAGAACAGCCTGTACCTGCAGATGAA<br>CTCCCTGAAGACGGAAGATACCGCCGTCTATTATTGT<br>GCCCGCGATCTGCCTGGCTTTGCCTATTGGGGCCAA<br>GGCACTCTGGTCACCGTCTCCTCA |
| h3G10.2.42<br>HV<br>Protein | 41 | EVQLVESGGGLVQPGGSLRLSCAAS**GFTFSDY**YMSWV<br>RQAPGKGLEWVGFI**RHKVNFYT**TEYSTSVKGRFTISRD<br>DSKNSLYLQMNSLKTEDTAVYYCAR**DLPGFAY**WGQGT<br>LVTVSS |
| h3G10.2.42<br>VH<br>DNA | 42 | GAAGTCCAGCTGGTTGAAAGTGGTGGCGGCCTGGTG<br>CAGCCGGGCGGCTCTCTGCGCCTGTCATGCGCTGCA<br>TCCGGCTTTACCTTCAGCGACTATTACATGAGCTGGG<br>TTCGCCAAGCGCCCGGCAAAGGCCTGGAATGGGTGG |

TABLE 2-continued

| Descriptions | SEQ ID NO | Sequence |
|---|---|---|
| | | GATTCATTCGACATAAAGTGAACTTTTATACCACCGAA<br>TATAGCACATCTGTCAAGGGCCGGTTCACCATCTCCC<br>GCGATGATTCCAAGAACAGCCTGTACCTGCAGATGAA<br>CTCCCTGAAGACGGAAGATACCGCCGTCTATTATTGT<br>GCCCGCGATCTGCCTGGCTTTGCCTATTGGGGCCAA<br>GGCACTCTGGTCACCGTCTCCTCA |
| h3G10.1.33<br>VH<br>Protein | 43 | EVQLVESGGGLVQPGGSLRLSCAAS**GFTFSDY**YMSWV<br>RQAPGKGLEWVGFI**RHKANFYT**TEYSTSVTGRFTISRD<br>DSKNSLYLQMNSLKTEDTAVYYCAR**DLPGFAY**WGQGT<br>LVTVSS |
| h3G10.1.33<br>VH<br>DNA | 44 | GAAGTCCAGCTGGTTGAAAGTGGTGGCGGCCTGGTG<br>CAGCCGGGCGGCTCTCTGCGCCTGTCATGCGCTGCA<br>TCCGGCTTTACCTTCAGCGACTATTACATGAGCTGGG<br>TTCGCCAAGCGCCCGGCAAAGGCCTGGAATGGGTGG<br>GATTCATTCGACATAAAGCGAACTTTTATACCACCGAA<br>TATAGCACATCTGTCACGGGCCGGTTCACCATCTCCC<br>GCGATGATTCCAAGAACAGCCTGTACCTGCAGATGAA<br>CTCCCTGAAGACGGAAGATACCGCCGTCTATTATTGT<br>GCCCGCGATCTGCCTGGCTTTGCCTATTGGGGCCAA<br>GGCACTCTGGTCACCGTCTCCTCA |
| h3G10.3.25<br>VH<br>Protein | 45 | EVQLVESGGGLVQPGGSLRLSCAAS**GFTFSDY**YMSWV<br>RQAPGKGLEWVGFI**RHKANFYT**TEYSTSDKGRFTISRD<br>DSKNSLYLQMNSLKTEDTAVYYCAR**DLPGFAY**WGQGT<br>LVTVSS |
| h3G10.3.25<br>VH<br>DNA | 46 | GAAGTCCAGCTGGTTGAAAGTGGTGGCGGCCTGGTG<br>CAGCCGGGCGGCTCTCTGCGCCTGTCATGCGCTGCA<br>TCCGGCTTTACCTTCAGCGACTATTACATGAGCTGGG<br>TTCGCCAAGCGCCCGGCAAAGGCCTGGAATGGGTGG<br>GATTCATTCGACATAAAGCGAACTTTTATACCACCGAA<br>TATAGCACATCTGATAAGGGCCGGTTCACCATCTCCC<br>GCGATGATTCCAAGAACAGCCTGTACCTGCAGATGAA<br>CTCCCTGAAGACGGAAGATACCGCCGTCTATTATTGT<br>GCCCGCGATCTGCCTGGCTTTGCCTATTGGGGCCAA<br>GGCACTCTGGTCACCGTCTCCTCA |
| h3G10 VL<br>Protein | 47 | DIVMTQSPDSLAVSLGERATINC**KSSQSLFNSRTRKNYL**<br>**A**WYQQKPGQPPKLLIY**WASARES**GVPDRFSGSGSGTD<br>FTLTISSLQAEDVAVYYC**KQSFNLRT**FGGGTKVEIK |
| h3G10 VL<br>DNA | 48 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCGGACACGGAAGAA<br>TTATCTGGCATGGTATCAGCAGAAACCCGGACAGCC<br>GCCTAAGCTGCTGATTTATTGGGCCAGCGCACGCGA<br>AAGTGGTGTGCCCGACCGCTTTTCCGGCAGCGGTAG<br>TGGCACTGACTTCACCCTGACCATCTCAAGCTTGCAA<br>GCCGAAGACGTGGCAGTATATTATTGCAAGCAGTCGT<br>TCAATCTGCGCACCTTTGGCGGCGGCACAAAAGTGG<br>AGATCAAA |
| h3G10.2.72<br>VL<br>Protein | 49 | DIVMTQSPDSLAVSLGERATINC**KSSQSLFNSRTRKNYL**<br>**A**WYQQKPGQPPKLLIY**WASARES**GVPDRFSGSGSGTD<br>FTLTISSLQAEDVAVYYC**KQSFRLRT**FGGGTKVEIK |
| h3G10.2.72<br>VL<br>DNA | 50 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCGGACACGGAAGAA<br>TTATCTGGCATGGTATCAGCAGAAACCCGGACAGCC<br>GCCTAAGCTGCTGATTTATTGGGCCAGCGCACGCGA<br>AAGTGGTGTGCCCGACCGCTTTTCCGGCAGCGGTAG<br>TGGCACTGACTTCACCCTGACCATCTCAAGCTTGCAA<br>GCCGAAGACGTGGCAGTATATTATTGCAAGCAGTCGT<br>TCAGGCTGCGCACCTTTGGCGGCGGCACAAAAGTGG<br>AGATCAAA |
| h3G10.A11A<br>VL<br>Protein | 51 | DIVMTQSPDSLAVSLGERATINC**KSAQSLFNSRTRKNYL**<br>**A**WYQQKPGQPPKLLIY**WASARES**GVPDRFSGSGSGTD<br>FTLTISSLQAEDVAVYYC**KQSFRLRT**FGGGTKVEIK |
| h3G10.A11A<br>VL<br>DNA | 52 | GACATCGTTATGACACAGTCACCAGATAGCTTAGCCG<br>TGTCCCTGGGAGAACGTGCTACCATTAATTGCAAAAG<br>CGCTCAGAGCCTGTTTAACAGCCGGACACGGAAGAA |

TABLE 2-continued

| Descriptions | SEQ ID NO | Sequence |
| --- | --- | --- |
| | | TTATCTGGCATGGTATCAGCAGAAACCCGGACAGCC<br>GCCTAAGCTGCTGATTTATTGGGCCAGCGCACGCGA<br>AAGTGGTGTGCCCGACCGCTTTTCCGGCAGCGGTAG<br>TGGCACTGACTTCACCCTGACCATCTCAAGCTTGCAA<br>GCCGAAGACGTGGCAGTATATTATTGCAAGCAGTCGT<br>TCAGGCTGCGCACCTTTGGCGGCGGCACAAAAGTGG<br>AGATCAAA |
| h3G10.A18A<br>VL<br>Protein | 53 | DIVMTQSPDSLAVSLGERATINC**KSSWSLFNSRTRKNY**<br>**LA**WYQQKPGQPPKLLIY**WASARES**GVPDRFSGSGSGT<br>DFTLTISSLQAEDVAVYYC**KQSFRLRT**FGGGTKVEIK |
| h3G10.A18A<br>VL<br>DNA | 54 | GACATCGTTATGACACAGTCACCAGATAGCTTAGCCG<br>TGTCCCTGGGAGAACGTGCTACCATTAATTGCAAAAG<br>CTCCTGGAGCCTGTTTAACAGCCGGACACGGAAGAA<br>TTATCTGGCATGGTATCAGCAGAAACCCGGACAGCC<br>GCCTAAGCTGCTGATTTATTGGGCCAGCGCACGCGA<br>AAGTGGTGTGCCCGACCGCTTTTCCGGCAGCGGTAG<br>TGGCACTGACTTCACCCTGACCATCTCAAGCTTGCAA<br>GCCGAAGACGTGGCAGTATATTATTGCAAGCAGTCGT<br>TCAGGCTGCGCACCTTTGGCGGCGGCACAAAAGTGG<br>AGATCAAA |
| h3G10.A19A<br>VL<br>Protein | 55 | DIVMTQSPDSLAVSLGERATINC**KSSNSLFNSRTRKNYL**<br>**A**WYQQKPGQPPKLLIY**WASARES**GVPDRFSGSGSGTD<br>FTLTISSLQAEDVAVYYC**KQSFRLRT**FGGGTKVEIK |
| h3G10.A19A<br>VL<br>DNA | 56 | GACATCGTTATGACACAGTCACCAGATAGCTTAGCCG<br>TGTCCCTGGGAGAACGTGCTACCATTAATTGCAAAAG<br>CTCCAATAGCCTGTTTAACAGCCGGACACGGAAGAAT<br>TATCTGGCATGGTATCAGCAGAAACCCGGACAGCCG<br>CCTAAGCTGCTGATTTATTGGGCCAGCGCACGCGAA<br>AGTGGTGTGCCCGACCGCTTTTCCGGCAGCGGTAGT<br>GGCACTGACTTCACCCTGACCATCTCAAGCTTGCAAG<br>CCGAAGACGTGGCAGTATATTATTGCAAGCAGTCGTT<br>CAGGCTGCGCACCTTTGGCGGCGGCACAAAAGTGGA<br>GATCAAA |
| h3G10.A58A<br>VL<br>Protein | 57 | DIVMTQSPDSLAVSLGERATINC**KSSQSLFNSHTRKNYL**<br>**A**WYQQKPGQPPKLLIY**WASARGS**GVPDRFSGSGSGT<br>DFTLTISSLQAEDVAVYYC**KQSFRLRT**FGGGTKVEIK |
| h3G10.A58A<br>VL<br>DNA | 58 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCATACACGGAAGAAT<br>TATCTGGCATGGTATCAGCAGAAACCCGGACAGCCG<br>CCTAAGCTGCTGATTTATTGGGCCAGCGCACGCGGA<br>AGTGGTGTGCCCGACCGCTTTTCCGGCAGCGGTAGT<br>GGCACTGACTTCACCCTGACCATCTCAAGCTTGCAAG<br>CCGAAGACGTGGCAGTATATTATTGCAAGCAGTCGTT<br>CAGGCTGCGCACCTTTGGCGGCGGCACAAAAGTGGA<br>GATCAAA |
| h3G10.A65A<br>VL<br>Protein | 59 | DIVMTQSPDSLAVSLGERATINC**KSSQSLFNSRFRKNYL**<br>**A**WYQQKPGQPPKLLIY**WASARES**GVPDRFSGSGSGTD<br>FTLTISSLQAEDVAVYYC**KQSFRLRT**FGGGTKVEIK |
| h3G10.A65A<br>VL<br>DNA | 60 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCGGTTTCGGAAGAAT<br>TATCTGGCATGGTATCAGCAGAAACCCGGACAGCCG<br>CCTAAGCTGCTGATTTATTGGGCCAGCGCACGCGAA<br>AGTGGTGTGCCCGACCGCTTTTCCGGCAGCGGTAGT<br>GGCACTGACTTCACCCTGACCATCTCAAGCTTGCAAG<br>CCGAAGACGTGGCAGTATATTATTGCAAGCAGTCGTT<br>CAGGCTGCGCACCTTTGGCGGCGGCACAAAAGTGGA<br>GATCAAA |
| h3G10.B12A<br>VL<br>Protein | 61 | DIVMTQSPDSLAVSLGERATINC**KSSQSLFNSRTRKNYL**<br>**L**WYQQKPGQPPKLLIY**WASARES**GVPDRFSGSGSGTD<br>FTLTISSLQAEDVAVYYC**KQSFRLRT**FGGGTKVEIK |
| h3G10.B12A<br>VL<br>DNA | 62 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCGGACACGGAAGAA<br>TTATCTGCTTTGGTATCAGCAGAAACCCGGACAGCCG |

TABLE 2-continued

| Descriptions | SEQ ID NO | Sequence |
|---|---|---|
| | | CCTAAGCTGCTGATTTATTGGGCCAGCGCACGCGAA<br>AGTGGTGTGCCCGACCGCTTTTCCGGCAGCGGTAGT<br>GGCACTGACTTCACCCTGACCATCTCAAGCTTGCAAG<br>CCGAAGACGTGGCAGTATATTATTGCAAGCAGTCGTT<br>CAGGCTGCGCACCTTTGGCGGCGGCACAAAAGTGGA<br>GATCAAA |
| h3G10.B13A<br>VL<br>Protein | 63 | DIVMTQSPDSLAVSLGERATINC**KSSQSLFNSRTRKNYL**<br>**N**WYQQKPGQPPKLLIY**WASARES**GVPDRFSGSGSGTD<br>FTLTISSLQAEDVAVYYC**KQSFRLRT**FGGGTKVEIK |
| h3G10.B13A<br>VL<br>DNA | 64 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCGGACACGGAAGAA<br>TTATCTGAATTGGTATCAGCAGAAACCCGGACAGCCG<br>CCTAAGCTGCTGATTTATTGGGCCAGCGCACGCGAA<br>AGTGGTGTGCCCGACCGCTTTTCCGGCAGCGGTAGT<br>GGCACTGACTTCACCCTGACCATCTCAAGCTTGCAAG<br>CCGAAGACGTGGCAGTATATTATTGCAAGCAGTCGTT<br>CAGGCTGCGCACCTTTGGCGGCGGCACAAAAGTGGA<br>GATCAAA |
| h3G10.B18A<br>VL<br>Protein | 65 | DIVMTQSPDSLAVSLGERATINC**KSSQSLFNSRTRKNYL**<br>**M**WYQQKPGQPPKLLIY**WASARES**GVPDRFSGSGSGT<br>DFTLTISSLQAEDVAVYYC**KQSFRLRT**FGGGTKVEIK |
| h3G10.B18A<br>VL<br>DNA | 66 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCGGACACGGAAGAA<br>TTATCTGATGTGGTATCAGCAGAAACCCGGACAGCCG<br>CCTAAGCTGCTGATTTATTGGGCCAGCGCACGCGAA<br>AGTGGTGTGCCCGACCGCTTTTCCGGCAGCGGTAGT<br>GGCACTGACTTCACCCTGACCATCTCAAGCTTGCAAG<br>CCGAAGACGTGGCAGTATATTATTGCAAGCAGTCGTT<br>CAGGCTGCGCACCTTTGGCGGCGGCACAAAAGTGGA<br>GATCAAA |
| h3G10.A11B<br>VL<br>Protein | 67 | DIVMTQSPDSLAVSLGERATINC**KSAQSLFNSRTRKNYL**<br>**A**WYQQKPGQPPKLLIY**WASARES**GVPDRFSGSGSGTD<br>FTLTISSLQAEDVAVYYC**KQSFNLRT**FGGGTKVEIK |
| h3G10.A11B<br>VL<br>DNA | 68 | GACATCGTTATGACACAGTCACCAGATAGCTTAGCCG<br>TGTCCCTGGGAGAACGTGCTACCATTAATTGCAAAAG<br>CGCTCAGAGCCTGTTTAACAGCCGGACACGGAAGAA<br>TTATCTGGCATGGTATCAGCAGAAACCCGGACAGCC<br>GCCTAAGCTGCTGATTTATTGGGCCAGCGCACGCGA<br>AAGTGGTGTGCCCGACCGCTTTTCCGGCAGCGGTAG<br>TGGCACTGACTTCACCCTGACCATCTCAAGCTTGCAA<br>GCCGAAGACGTGGCAGTATATTATTGCAAGCAGTCGT<br>TCAATCTGCGCACCTTTGGCGGCGGCACAAAAGTGG<br>AGATCAAA |
| h3G10.A18B<br>VL<br>Protein | 69 | DIVMTQSPDSLAVSLGERATINC**KSSWSLFNSRTRKNY**<br>**LA**WYQQKPGQPPKLLIY**WASARES**GVPDRFSGSGSGT<br>DFTLTISSLQAEDVAVYYC**KQSFNLRT**FGGGTKVEIK |
| h3G10.A18B<br>VL<br>DNA | 70 | GACATCGTTATGACACAGTCACCAGATAGCTTAGCCG<br>TGTCCCTGGGAGAACGTGCTACCATTAATTGCAAAAG<br>CTCCTGGAGCCTGTTTAACAGCCGGACACGGAAGAA<br>TTATCTGGCATGGTATCAGCAGAAACCCGGACAGCC<br>GCCTAAGCTGCTGATTTATTGGGCCAGCGCACGCGA<br>AAGTGGTGTGCCCGACCGCTTTTCCGGCAGCGGTAG<br>TGGCACTGACTTCACCCTGACCATCTCAAGCTTGCAA<br>GCCGAAGACGTGGCAGTATATTATTGCAAGCAGTCGT<br>TCAATCTGCGCACCTTTGGCGGCGGCACAAAAGTGG<br>AGATCAAA |
| h3G10.A19B<br>VL<br>Protein | 71 | DIVMTQSPDSLAVSLGERATINC**KSSNSLFNSRTRKNYL**<br>**A**WYQQKPGQPPKLLIY**WASARES**GVPDRFSGSGSGTD<br>FTLTISSLQAEDVAVYYC**KQSFNLRT**FGGGTKVEIK |
| h3G10.A19B<br>VL<br>DNA | 72 | GACATCGTTATGACACAGTCACCAGATAGCTTAGCCG<br>TGTCCCTGGGAGAACGTGCTACCATTAATTGCAAAAG<br>CTCCAATAGCCTGTTTAACAGCCGGACACGGAAGAAT<br>TATCTGGCATGGTATCAGCAGAAACCCGGACAGCCG<br>CCTAAGCTGCTGATTTATTGGGCCAGCGCACGCGAA |

TABLE 2-continued

| Descriptions | SEQ ID NO | Sequence |
|---|---|---|
| | | AGTGGTGTGCCCGACCGCTTTTCCGGCAGCGGTAGT<br>GGCACTGACTTCACCCTGACCATCTCAAGCTTGCAAG<br>CCGAAGACGTGGCAGTATATTATTGCAAGCAGTCGTT<br>CAATCTGCGCACCTTTGGCGGCGGCACAAAAGTGGA<br>GATCAAA |
| h3G10.A58B<br>VL<br>Protein | 73 | DIVMTQSPDSLAVSLGERATINC**KSSQSLFNSHTRKNYL**<br>**A**WYQQKPGQPPKLLIY**WASARGS**GVPDRFSGSGSGT<br>DFTLTISSLQAEDVAVYYC**KQSFNLRT**FGGGTKVEIK |
| h3G10.A58B<br>VL<br>DNA | 74 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCATACACGGAAGAAT<br>TATCTGGCATGGTATCAGCAGAAACCCGGACAGCCG<br>CCTAAGCTGCTGATTTATTGGGCCAGCGCACGCGGA<br>AGTGGTGTGCCCGACCGCTTTTCCGGCAGCGGTAGT<br>GGCACTGACTTCACCCTGACCATCTCAAGCTTGCAAG<br>CCGAAGACGTGGCAGTATATTATTGCAAGCAGTCGTT<br>CAATCTGCGCACCTTTGGCGGCGGCACAAAAGTGGA<br>GATCAAA |
| h3G10.A65B<br>VL<br>Protein | 75 | DIVMTQSPDSLAVSLGERATINC**KSSQSLFNSRFRKNYL**<br>**A**WYQQKPGQPPKLLIY**WASARES**GVPDRFSGSGSGTD<br>FTLTISSLQAEDVAVYYC**KQSFNLRT**FGGGTKVEIK |
| h3G10.A65B<br>VL<br>DNA | 76 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCGGTTTCGGAAGAAT<br>TATCTGGCATGGTATCAGCAGAAACCCGGACAGCCG<br>CCTAAGCTGCTGATTTATTGGGCCAGCGCACGCGAA<br>AGTGGTGTGCCCGACCGCTTTTCCGGCAGCGGTAGT<br>GGCACTGACTTCACCCTGACCATCTCAAGCTTGCAAG<br>CCGAAGACGTGGCAGTATATTATTGCAAGCAGTCGTT<br>CAATCTGCGCACCTTTGGCGGCGGCACAAAAGTGGA<br>GATCAAA |
| h3G10.B12B<br>VL<br>Protein | 77 | DIVMTQSPDSLAVSLGERATINC**KSSQSLFNSRTRKNYL**<br>**L**WYQQKPGQPPKLLIY**WASARES**GVPDRFSGSGSGTD<br>FTLTISSLQAEDVAVYYC**KQSFNLRT**FGGGTKVEIK |
| h3G10.B12B<br>VL<br>DNA | 78 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCGGACACGGAAGAA<br>TTATCTGCTTTGGTATCAGCAGAAACCCGGACAGCCG<br>CCTAAGCTGCTGATTTATTGGGCCAGCGCACGCGAA<br>AGTGGTGTGCCCGACCGCTTTTCCGGCAGCGGTAGT<br>GGCACTGACTTCACCCTGACCATCTCAAGCTTGCAAG<br>CCGAAGACGTGGCAGTATATTATTGCAAGCAGTCGTT<br>CAATCTGCGCACCTTTGGCGGCGGCACAAAAGTGGA<br>GATCAAA |
| h3G10.B13B<br>VL<br>Protein | 79 | DIVMTQSPDSLAVSLGERATINC**KSSQSLFNSRTRKNYL**<br>**N**WYQQKPGQPPKLLIY**WASARES**GVPDRFSGSGSGTD<br>FTLTISSLQAEDVAVYYC**KQSFNLRT**FGGGTKVEIK |
| h3G10.B13B<br>VL<br>DNA | 80 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCGGACACGGAAGAA<br>TTATCTGAATTGGTATCAGCAGAAACCCGGACAGCCG<br>CCTAAGCTGCTGATTTATTGGGCCAGCGCACGCGAA<br>AGTGGTGTGCCCGACCGCTTTTCCGGCAGCGGTAGT<br>GGCACTGACTTCACCCTGACCATCTCAAGCTTGCAAG<br>CCGAAGACGTGGCAGTATATTATTGCAAGCAGTCGTT<br>CAATCTGCGCACCTTTGGCGGCGGCACAAAAGTGGA<br>GATCAAA |
| h3G10.B18B<br>VL<br>Protein | 81 | DIVMTQSPDSLAVSLGERATINC**KSSQSLFNSRTRKNYL**<br>**M**WYQQKPGQPPKLLIY**WASARES**GVPDRFSGSGSGT<br>DFTLTISSLQAEDVAVYYC**KQSFNLRT**FGGGTKVEIK |
| h3G10.B18B<br>VL<br>DNA | 82 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCGGACACGGAAGAA<br>TTATCTGATGTGGTATCAGCAGAAACCCGGACAGCCG<br>CCTAAGCTGCTGATTTATTGGGCCAGCGCACGCGAA<br>AGTGGTGTGCCCGACCGCTTTTCCGGCAGCGGTAGT |

TABLE 2-continued

| Descriptions | SEQ ID NO | Sequence |
|---|---|---|
| | | GGCACTGACTTCACCCTGACCATCTCAAGCTTGCAAG<br>CCGAAGACGTGGCAGTATATTATTGCAAGCAGTCGTT<br>CAATCTGCGCACCTTTGGCGGCGGCACAAAAGTGGA<br>GATCAAA |
| h3G10.2.25<br>VL<br>Protein | 83 | DIVMTQSPDSLAVSLGERATINC**RSSQSLFNSRTRKNYL**<br>**A**WYQQKPGQPPKLLIY**WASARES**GVPDRFSGSGSGTD<br>FTLTISSLQAEDVAVYYC**KQSFRLRT**FGGGTKVEIK |
| h3G10.2.25<br>VL<br>DNA | 84 | GACATCGTTATGACACAGTCACCAGATAGCTTAGCCG<br>TGTCCCTGGGAGAACGTGCTACCATTAATTGCAGGAG<br>CTCCCAGAGCCTGTTTAACAGCCGGACACGGAAGAA<br>TTATCTGGCATGGTATCAGCAGAAACCCGGACAGCC<br>GCCTAAGCTGCTGATTTATTGGGCCAGCGCACGCGA<br>AAGTGGTGTGCCCGACCGCTTTTCCGGCAGCGGTAG<br>TGGCACTGACTTCACCCTGACCATCTCAAGCTTGCAA<br>GCCGAAGACGTGGCAGTATATTATTGCAAGCAGTCGT<br>TCAGGCTGCGCACCTTTGGCGGCGGCACAAAAGTGG<br>AGATCAAA |
| h3G10.A59<br>VH<br>Protein | 85 | EVQLVESGGGLVQPGGSLRLSCAAS**GFTFSDY**YMSWV<br>RQAPGKGLEWVGF**IRHKANTYTT**EYSTSVKGRFTISRD<br>DSKNSLYLQMNSLKTEDTAVYYCAR**DLPGFAY**WGQGT<br>LVTVSS |
| h3G10.A59<br>VH<br>DNA | 86 | GAAGTCCAGCTGGTTGAAAGTGGTGGCGGCCTGGTG<br>CAGCCGGGCGGCTCTCTGCGCCTGTCATGCGCTGCA<br>TCCGGCTTTACCTTCAGCGACTATTACATGAGCTGGG<br>TTCGCCAAGCGCCCGGCAAAGGCCTGGAATGGGTGG<br>GATTCATTCGACATAAAGCGAACACGTATACCACCGA<br>ATATAGCACATCTGTCAAGGGCCGGTTCACCATCTCC<br>CGCGATGATTCCAAGAACAGCCTGTACCTGCAGATGA<br>ACTCCCTGAAGACGGAAGATACCGCCGTCTATTATTG<br>TGCCCGCGATCTGCCTGGCTTTGCCTATTGGGGCCA<br>AGGCACTCTGGTCACCGTCTCCTCA |
| >h3G10.A62<br>VH<br>Protein | 87 | EVQLVESGGGLVQPGGSLRLSCAAS**GFTFSDY**YMSWV<br>RQAPGKGLEWVGF**IRHKANLYTT**EYSTSVKGRFTISRD<br>DSKNSLYLQMNSLKTEDTAVYYCAR**DLPGFAY**WGQGT<br>LVTVSS |
| >h3G10.A62<br>VH<br>DNA | 88 | GAAGTCCAGCTGGTTGAAAGTGGTGGCGGCCTGGTG<br>CAGCCGGGCGGCTCTCTGCGCCTGTCATGCGCTGCA<br>TCCGGCTTTACCTTCAGCGACTATTACATGAGCTGGG<br>TTCGCCAAGCGCCCGGCAAAGGCCTGGAATGGGTGG<br>GATTCATTCGACATAAAGCGAACCTGTATACCACCGA<br>ATATAGCACATCTGTCAAGGGCCGGTTCACCATCTCC<br>CGCGATGATTCCAAGAACAGCCTGTACCTGCAGATGA<br>ACTCCCTGAAGACGGAAGATACCGCCGTCTATTATTG<br>TGCCCGCGATCTGCCTGGCTTTGCCTATTGGGGCCA<br>AGGCACTCTGGTCACCGTCTCCTCA |
| h3G10 VH<br>Mutated | 106 | EVQLVESGGGLVQPGGSLRLSCAASGFTFSDYYMSWV<br>RQAPGKGLEWV $X_1$FIRHK$X_2$N$X_3$$X_4$T$X_5$EYST $X_6$ $X_7$<br>$X_8$GRFTISRD $X_9$SKN $X_{10}$LYLQMNSL $X_{11}$<br>$X_{12}$EDTAVYYCA $X_{13}$DLPGFAYWGQGTLVTVSS<br>Wherein $X_1$ is G or S; $X_2$ is V or A; $X_3$ is G, F, K, V, T, L, or I; $X_4$ is E or Y; $X_5$ is T or R; $X_6$ is W or S; $X_7$ is D or V; $X_8$ is K, T, or R; $X_9$ is D or N; $X_{10}$ is T or S; $X_{11}$ is R or K; $X_{12}$ is A or T; and/or $X_{13}$ is K or R. (Kabat) |
| h3G10.L94D<br>VL<br>Protein | 169 | DIVMTQSPDSLAVSLGERATINC**KSSQSLFNSRTRKNYL**<br>**A**WYQQKPGQPPKLLIY**WASARES**GVPDRFSGSGSGTD<br>FTLTISSLQAEDVAVYYC**KQSFNDR**TFGGGTKVEIK |
| h3G10.L94D<br>VL<br>DNA | 134 | GACATCGTTATGACACAGTCACCAGATAGCTTAGCCG<br>TGTCCCTGGGAGAACGTGCTACCATTAATTGCAAAAG<br>CTCCCAGAGCCTGTTTAACAGCCGGACACGGAAGAA<br>TTATCTGGCATGGTATCAGCAGAAACCCGGACAGCC<br>GCCTAAGCTGCTGATTTATTGGGCCAGCGCACGCGA<br>AAGTGGTGTGCCCGACCGCTTTTCCGGCAGCGGTAG<br>TGGCACTGACTTCACCCTGACCATCTCAAGCTTGCAA<br>GCCGAAGACGTGGCAGTATATTATTGCAAGCAGTCGT |

TABLE 2-continued

| Descriptions | SEQ ID NO | Sequence |
|---|---|---|
| | | TCAATGATCGCACCTTTGGCGGCGGCACAAAAGTGG AGATCAAA |

In Table 2, the underlined sequences are CDR sequences according to Kabat and in bold according to Chothia.

The invention also provides CDR portions of antibodies to CXCR4 (including Chothia, Kabat CDRs, and CDR contact regions). Determination of CDR regions is well within the skill of the art. It is understood that in some aspects of the invention, CDRs can be a combination of the Kabat and Chothia CDR (also termed "combined CRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof. Tables 3 and 4 provide examples of CDR sequences provided herein.

TABLE 3

| | Heavy Chain | | |
|---|---|---|---|
| mAb | CDRH1 | CDRH2 | CDRH3 |
| m6B6 | DYYMS (SEQ ID NO: 107) (Kabat); GFTFTDY (SEQ ID NO: 108) (Chothia); GFTFTDYYMS (SEQ ID NO: 109) (extended) | FIRNKANGYTTEYSASVKG (SEQ ID NO: 110) (Kabat); RNKANGYT (SEQ ID NO: 111) (Chothia) | DLPGFAY (SEQ ID NO: 112) |
| h6B6 | DYYMS (SEQ ID NO: 107) (Kabat); GFTFSDY (SEQ ID NO: 113) (Chothia); GFTFSDYYMS (SEQ ID NO: 114) (extended) | FIRNKANGYTTEYSASVKG (SEQ ID NO: 110) (Kabat); RNKANGYT (SEQ ID NO: 111) (Chothia) | DLPGFAY (SEQ ID NO: 112) |
| m12A11 | DYNIY (SEQ ID NO: 115) (Kabat); GYSFTDY (SEQ ID NO: 116) (Chothia); GYSFTDYNIY (SEQ ID NO: 117) (extended) | YIDPYNGGTRYNQKFKG (SEQ ID NO: 118) (Kabat); DPYNGG (SEQ ID NO: 119) (Chothia) | TYGSRYVGAMDY (SEQ ID NO: 120) |
| h12A11 | DYNIY (SEQ ID NO: 115) (Kabat); GYTFTDY (SEQ ID NO: 121) (Chothia); GYTFTDYNIY (SEQ ID NO: 122) (extended) | YIDPYNGGTRYNQKFKG (SEQ ID NO: 118) (Kabat); DPYNGG (SEQ ID NO: 119) (Chothia) | TYGSRYVGAMDY (SEQ ID NO: 120) |
| m3G10 | DYYMS (SEQ ID NO: 107) (Kabat); GFTFTDY (SEQ ID NO: 108) (Chothia); GFTFTDYYMS (SEQ ID NO: 109) (extended) | FIRHKANGYTTEYSTSVKG (SEQ ID NO: 154) (Kabat); RHKANGYT (SEQ ID NO: 123) (Chothia) | DLPGFAY (SEQ ID NO: 112) |
| h3G10 | DYYMS (SEQ ID NO: 107) (Kabat); GFTFSDY (SEQ ID NO: 113) (Chothia); GFTFSDYYMS (SEQ ID NO: 114) (extended) | FIRHKANGYTTEYSTSVKG (SEQ ID NO: 154) (Kabat); RHKANGYT (SEQ ID NO: 123) (Chothia) | DLPGFAY (SEQ ID NO: 112) |

TABLE 3-continued

| Heavy Chain | | | |
|---|---|---|---|
| mAb | CDRH1 | CDRH2 | CDRH3 |
| h3G10.A57 | DYYMS (SEQ ID NO: 107) (Kabat); GFTFSDY (SEQ ID NO: 113) (Chothia); GFTFSDYYMS (SEQ ID NO: 114) (extended) | FIRHKANFYTTEYSTSVKG (SEQ ID NO: 158) (Kabat); RHKANFYT (SEQ ID NO: 124) (Chothia) | DLPGFAY (SEQ ID NO: 112) |
| h3G10.B44 | DYYMS (SEQ ID NO: 107) (Kabat); GFTFSDY (SEQ ID NO: 113) (Chothia); GFTFSDYYMS (SEQ ID NO: 114) (extended) | FIRHKANFYTTEYSTSVKG (SEQ ID NO: 158) (Kabat); RHKANFYT (SEQ ID NO: 124) (Chothia) | DLPGFAY (SEQ ID NO: 112) |
| h3G10.1.7 | DYYMS (SEQ ID NO: 107) (Kabat); GFTFSDY (SEQ ID NO: 113) (Chothia); GFTFSDYYMS (SEQ ID NO: 114) (extended) | FIRHKANKYTTEYSTSVKG (SEQ ID NO: 159) (Kabat); RHKANKYT (SEQ ID NO: 125) (Chothia) | DLPGFAY (SEQ ID NO: 112) |
| h3G10.1.60 | DYYMS (SEQ ID NO: 107) (Kabat); GFTFSDY (SEQ ID NO: 113) (Chothia); GFTFSDYYMS (SEQ ID NO: 114) (extended) | FIRHKANVYTTEYSTSVKG (SEQ ID NO: 160) (Kabat); RHKANVYT (SEQ ID NO: 126) (Chothia) | DLPGFAY (SEQ ID NO: 112) |
| h3G10.2.5 | DYYMS (SEQ ID NO: 107) (Kabat); GFTFSDY (SEQ ID NO: 113) (Chothia); GFTFSDYYMS (SEQ ID NO: 114) (extended) | FIRHKANIYTTEYSTSVKG (SEQ ID NO: 161) (Kabat); RHKANIYT (SEQ ID NO: 127) (Chothia) | DLPGFAY (SEQ ID NO: 112) |
| h3G10.1.91 | DYYMS (SEQ ID NO: 107) (Kabat); GFTFSDY (SEQ ID NO: 113) (Chothia); GFTFSDYYMS (SEQ ID NO: 114) (extended) | FIRHKANFETTEYSTSVKG (SEQ ID NO: 162) (Kabat); RHKANFET (SEQ ID NO: 128) (Chothia) | DLPGFAY (SEQ ID NO: 112) |
| h3G10.2.37 | DYYMS (SEQ ID NO: 107) (Kabat); GFTFSDY (SEQ ID NO: 113) (Chothia); GFTFSDYYMS (SEQ ID NO: 114) (extended) | FIRHKANFYTREYSTSVKG (SEQ ID NO: 163) (Kabat); RHKANFYT (SEQ ID NO: 124) (Chothia) | DLPGFAY (SEQ ID NO: 112) |
| h3G10.2.45 | DYYMS (SEQ ID NO: 107) (Kabat); GFTFSDY (SEQ ID NO: 113) (Chothia); | FIRHKANFYTTEYSTWVKG (SEQ ID NO: 164) (Kabat); RHKANFYT (SEQ ID NO: 124) (Chothia) | DLPGFAY (SEQ ID NO: 112) |

TABLE 3-continued

| Heavy Chain | | | |
|---|---|---|---|
| mAb | CDRH1 | CDRH2 | CDRH3 |
| | GFTFSDYYMS (SEQ ID NO: 114) (extended) | | |
| h3G10.2.54 | DYYMS (SEQ ID NO: 107) (Kabat); GFTFSDY (SEQ ID NO: 113) (Chothia); GFTFSDYYMS (SEQ ID NO: 114) (extended) | FIRHKANFYTTEYSTSVRG (SEQ ID NO: 165) (Kabat); RHKANFYT (SEQ ID NO: 124) (Chothia) | DLPGFAY (SEQ ID NO: 112) |
| h3G10.2.42 | DYYMS (SEQ ID NO: 107) (Kabat); GFTFSDY (SEQ ID NO: 113) (Chothia); GFTFSDYYMS (SEQ ID NO: 114) (extended) | FIRHKVNFYTTEYSTSVKG (SEQ ID NO: 166) (Kabat); RHKVNFYT (SEQ ID NO: 127) (Chothia) | DLPGFAY (SEQ ID NO: 112) |
| h3G10.1.33 | DYYMS (SEQ ID NO: 107) (Kabat); GFTFSDY (SEQ ID NO: 113) (Chothia); GFTFSDYYMS (SEQ ID NO: 114) (extended) | FIRHKANFYTTEYSTSVTG (SEQ ID NO: 167) (Kabat); RHKANFYT (SEQ ID NO: 124) (Chothia) | DLPGFAY (SEQ ID NO: 112) |
| h3G10.3.25 | DYYMS (SEQ ID NO: 107) (Kabat); GFTFSDY (SEQ ID NO: 113) (Chothia); GFTFSDYYMS (SEQ ID NO: 114) (extended) | FIRHKANFYTTEYSTSDKG (SEQ ID NO: 168) (Kabat); RHKANFYT (SEQ ID NO: 124) (Chothia) | DLPGFAY (SEQ ID NO: 112) |
| h3G10.A59 VH | DYYMS (SEQ ID NO: 107) (Kabat); GFTFSDY (SEQ ID NO: 113) (Chothia); GFTFSDYYMS (SEQ ID NO: 114) (extended) | FIRHKANTYTTEYSTSVKG (SEQ ID NO: 155) (Kabat); RHKANTYT (SEQ ID NO: 129) (Chothia) | DLPGFAY (SEQ ID NO: 112) |
| h3G10.A62 VH | DYYMS (SEQ ID NO: 107) (Kabat); GFTFSDY (SEQ ID NO: 113) (Chothia); GFTFSDYYMS (SEQ ID NO: 114) (extended) | FIRHKANLYTTEYSTSVKG (SEQ ID NO: 156) (Kabat); RHKANLYT (SEQ ID NO: 130) (Chothia) | DLPGFAY (SEQ ID NO: 112) |
| h3G10 HV Mutated | DYYMS (SEQ ID NO: 107) (Kabat) | FIRHK$X_2$N$X_3X_4$T$X_5$EYST $X_6$ $X_7$ $X_8$G Wherein $X_2$ is V or A; $X_3$ is G, F, K, V, T, L, or I; $X_4$ is E or Y; $X_5$ is T or R; $X_6$ is W or S; $X_7$ is D or V; and/or $X_8$ is K, T, or R. (SEQ ID NO: 157) (Kabat); | DLPGFAY (SEQ ID NO: 112) |

TABLE 4

| Light Chain | | | |
|---|---|---|---|
| mAb | CDRL1 | CDRL2 | CDRL3 |
| m6B6 | KSSQSLYNSRTRKNYLA (SEQ ID NO: 131) | WASARES (SEQ ID NO: 132) | KQSYNLRT (SEQ ID NO: 133) |
| h6B6 | KSSQSLYNSRTRKNYLA (SEQ ID NO: 131) | WASARES (SEQ ID NO: 132) | KQSYNLRT (SEQ ID NO: 133) |
| m12A11 | RSSKSLLHSNGNTYLY (SEQ ID NO: 135) | RMSNPAS (SEQ ID NO: 136) | MQHLEYPLT (SEQ ID NO: 137) |
| h12A11 | RSSKSLLHSNGNTYLY (SEQ ID NO: 135) | RMSNPAS (SEQ ID NO: 136) | MQHLEYPLT (SEQ ID NO: 137) |
| m3G10 | KSSQSLFNSRTRKNYLA (SEQ ID NO: 138) | WASARES (SEQ ID NO: 132) | KQSFNLRT (SEQ ID NO: 139) |
| h3G10 | KSSQSLFNSRTRKNYLA (SEQ ID NO: 138) | WASARES (SEQ ID NO: 132) | KQSFNLRT (SEQ ID NO: 139) |
| h3G10.2.72 | KSSQSLFNSRTRKNYLA (SEQ ID NO: 138) | WASARES (SEQ ID NO: 132) | KQSFRLRT (SEQ ID NO: 140) |
| h3G10.A11A | KSAQSLFNSRTRKNYLA (SEQ ID NO: 141) | WASARES (SEQ ID NO: 132) | KQSFRLRT (SEQ ID NO: 140) |
| h3G10.A18A | KSSWSLFNSRTRKNYLA (SEQ ID NO: 142) | WASARES (SEQ ID NO: 132) | KQSFRLRT (SEQ ID NO: 140) |
| h3G10.A19A | KSSNSLFNSRTRKNYLA (SEQ ID NO: 143) | WASARES (SEQ ID NO: 132) | KQSFRLRT (SEQ ID NO: 140) |
| h3G10.A58A | KSSQSLFNSHTRKNYLA (SEQ ID NO: 144) | WASARGS (SEQ ID NO: 145) | KQSFRLRT (SEQ ID NO: 140) |
| h3G10.A65A | KSSQSLFNSRFRKNYLA (SEQ ID NO: 146) | WASARES (SEQ ID NO: 132) | KQSFRLRT (SEQ ID NO: 140) |
| h3G10.B12A | KSSQSLFNSRTRKNYLL (SEQ ID NO: 147) | WASARES (SEQ ID NO: 132) | KQSFRLRT (SEQ ID NO: 140) |
| h3G10.B13A | KSSQSLFNSRTRKNYLN (SEQ ID NO: 148) | WASARES (SEQ ID NO: 132) | KQSFRLRT (SEQ ID NO: 140) |
| h3G10.B18A | KSSQSLFNSRTRKNYLM (SEQ ID NO: 149) | WASARES (SEQ ID NO: 132) | KQSFRLRT (SEQ ID NO: 140) |
| h3G10.A11B | KSAQSLFNSRTRKNYLA (SEQ ID NO: 141) | WASARES (SEQ ID NO: 132) | KQSFNLRT (SEQ ID NO: 139) |
| h3G10.A18B | KSSWSLFNSRTRKNYLA (SEQ ID NO: 142) | WASARES (SEQ ID NO: 132) | KQSFNLRT (SEQ ID NO: 139) |
| h3G10.A19B | KSSNSLFNSRTRKNYLA (SEQ ID NO: 143) | WASARES (SEQ ID NO: 132) | KQSFNLRT (SEQ ID NO: 139) |
| h3G10.A58B | KSSQSLFNSHTRKNYLA (SEQ ID NO: 144) | WASARGS (SEQ ID NO: 145) | KQSFNLRT (SEQ ID NO: 139) |
| h3G10.A65B | KSSQSLFNSRFRKNYLA (SEQ ID NO: 146) | WASARES (SEQ ID NO: 132) | KQSFNLRT (SEQ ID NO: 139) |
| h3G10.B12B | KSSQSLFNSRTRKNYLL (SEQ ID NO: 147) | WASARES (SEQ ID NO: 132) | KQSFNLRT (SEQ ID NO: 139) |
| h3G10.B13B | KSSQSLFNSRTRKNYLN (SEQ ID NO: 148) | WASARES (SEQ ID NO: 132) | KQSFNLRT (SEQ ID NO: 139) |
| h3G10.B18B | KSSQSLFNSRTRKNYLM (SEQ ID NO: 149) | WASARES (SEQ ID NO: 132) | KQSFNLRT (SEQ ID NO: 139) |
| h3G10.2.25 | RSSQSLFNSRTRKNYLA (SEQ ID NO: 150) | WASARES (SEQ ID NO: 132) | KQSFRLRT (SEQ ID NO: 140) |
| h3G10 VL Mutated | $X_1$S $X_2$ $X_3$ SLFNS$X_4X_5$RKNYL $X_6$ Wherein $X_1$ is R or K; $X_2$ is S or A; $X_3$ is W, N or Q; $X_4$ is H | WASAR $X_1$S Wherein $X_1$ is E or G. (SEQ ID NO: 152) | KQSF $X_1$LRT Wherein $X_1$ is N or R. (SEQ ID NO: 153) |

TABLE 4-continued

| Light Chain | | | |
|---|---|---|---|
| mAb | CDRL1 | CDRL2 | CDRL3 |
| | or R; $X_5$ is T or F; and $X_6$ is A, L, N, or M. (SEQ ID NO: 151) (Kabat) | (Kabat) | (Kabat) |
| h3G10.L94D | KSSQSLFNSRTRKNYLA (SEQ ID NO: 138) | WASARES (SEQ ID NO: 132) | KQSFNDR (SEQ ID NO: 170) |

In one aspect, the present invention provides an antibody that binds to CXCR4 and/or competes with the antibody as described herein, such as m6B6, h6B6, m12A11, h12A11, m3G10, h3G10, h3G10.A57, h3G10.B44, h3G10.1.7, h3G10.1.60, h3G10.2.5, h3G10.1.91, h3G10.2.37, h3G10.2.45, h3G10.2.42, h3G10.1.33, h3G10.3.25, h3G10, h3G10.2.72, h3G10.A11A, h3G10.A18A, h3G10.A19A, h3G10.A58A, h3G10.A65A, and h3G10.B12A, h3G10.B13A, h3G10.B18A, h3G10.A11B, h3G10.A18B, h3G10.A19B, h3G10.A58B, h3G10.A65B, h3G10.B12B, h3G10.B13B, h3G10.B18B, h3G10.2.25, h3G10.A59, h3G10.A62, or h3G10.L94D.

In another aspect, the antibody competes with the binding of CXCR4 with antibody m6B6, h6B6, m12A11, h12A11, m3G10, h3G10, h3G10.A57, h3G10.B44, h3G10.1.7, h3G10.1.60, h3G10.2.5, h3G10.1.91, h3G10.2.37, h3G10.2.45, h3G10.2.42, h3G10.1.33, h3G10.3.25, h3G10, h3G10.2.72, h3G10.A11A, h3G10.A18A, h3G10.A19A, h3G10.A58A, h3G10.A65A, and h3G10.B12A, h3G10.B13A, h3G10.B18A, h3G10.A11B, h3G10.A18B, h3G10.A19B, h3G10.A58B, h3G10.A65B, h3G10.B12B, h3G10.B13B, h3G10.B18B, h3G10.2.25, h3G10.A59, h3G10.A62, or h3G10.L94D.

In some aspects of the invention, the antibody competes with the binding of CXCR4 with an antibody of the present invention and has a monovalent antibody binding affinity ($K_D$) of about any of or less than about any of 6.5 nM, 6.0 nM, 5.5 nM, 5.0 nM, 4.5 nM, 4.0 nM, 3.5 nM, 3.0 nM, 2.5 nM, 2.0 nM, 1.5 nM, 1.0 nM, 0.5 nM, or 0.25 nM as measured by surface plasmon resonance. In some aspects of the invention, the antibody competes with the binding of CXCR4 with antibody h3G10 and has a monovalent antibody binding affinity ($K_D$) of about any of or less than about any of 30 nM, 25 nM, 22 nM, 20 nM, 15 nM, or 10 nM.

In some aspects, the invention also provides CDR portions of antibodies to anti-CXCR4 antibodies based on CDR contact regions. CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., J. Biol. Chem., 283:1156-1166, 2007. Determination of CDR contact regions is well within the skill of the art.

In some aspects of the invention, an isolated antibody, or an antigen binding fragment thereof, that binds to chemokine receptor 4 (CXCR4) comprises: a heavy chain variable (VH) region comprising (i) a VH CDR1 selected from the group consisting of SEQ ID NOs:107, 113, 114, 108, 109, 115, 116, 117, 121 and 122; (ii) a VH CDR2 selected from the group consisting of SEQ ID NOs: 162, 128, 110, 111, 118, 119, 154, 123, 158, 124, 159, 125, 160, 126, 161, 127, 163, 164, 165, 166, 167, 168, 155, 129, 156, and 130, and, (iii) a VH CDR3 selected from the group consisting of SEQ ID NOs: 112; and 120; and/or; b) a light chain variable region (VL) region comprising (i) a VL CDR1 selected from the group consisting of SEQ ID NOs: 144, 131, 135, 138, 141, 142, 143, 146, 147, 148, 149, 150, and 151; (ii) a VL CDR2 selected from the group consisting of 145, 132, 136, and 152; and (iii) a VL CDR3 selected from the group consisting of SEQ ID NO: 139, 133, 137, 140, and 153.

In one aspect, an antibody or an antigen binding fragment thereof that binds to CXCR4 comprises a heavy chain variable (VH) CDR regions comprising an amino acid sequence that is at least 90%, 92%, 94%, 95%, 96%, 97%, 98% or 99% identical to SEQ ID NOs: 107, 113, 114, 108, 109, 115, 116, 117, 121, 122; 162, 128, 110, 111, 118, 119, 154, 123, 158, 124, 159, 125, 160, 126, 161, 127, 163, 164, 165, 166, 167, 168, 155, 129, 156, 130, 112, and 120. In one aspect, an antibody or an antigen binding fragment thereof that binds to CXCR4 comprises a heavy chain variable (VL) CDR regions comprising an amino acid sequence that is at least 90%, 92%, 94%, 95%, 96%, 97%, 98% or 99% identical to SEQ ID NOs: 144, 131, 135, 138, 141, 142, 143, 146, 147, 148, 149, 150, 151, 145, 132, 136, and 152, 139, 133, 137, 140, and 153.

In some aspects of the invention, an isolated antibody, or an antigen binding fragment thereof, that binds to CXCR4 comprises: a) a heavy chain variable (VH) region comprising complementary determining regions selected from the group consisting of (i) a VH CDR1 comprising the sequence set forth as SEQ ID NOs: 107, 113, 114, 108, 109, 115, 116, 117, 121 AND 122; (ii) a VH CDR2 comprising the sequence set forth as SEQ ID NOs: 162, 128, 110, 111, 118, 119, 154, 123, 158, 124, 159, 125, 160, 126, 161, 127, 163, 164, 165, 166, 167, 168, 155, 129, 156, AND 130, and; (iii) a VH CDR3 comprising the sequence set forth as SEQ ID NOs: 112; or 120; and/or b) a light chain variable region (VL) region comprising complementary determining regions selected from the group consisting of (i) a VL CDR1 comprising the sequence set forth as SEQ ID NOs: 144, 131, 135, 138, 141, 142, 143, 146, 147, 148, 149, 150, or 151; (ii) a VL CDR2 comprising the sequence set forth as SEQ ID NOs 145, 132, 136, or 152; and (iii) a VL CDR3 comprising the sequence set forth as SEQ ID NOs: 139, 133, 137, 140, or 153. In some aspects of the invention, an isolated antibody, or an antigen binding fragment thereof, that binds to CXCR4 comprises: a) a light chain variable (VL) region comprising (i) VL CDR1 comprising the sequence $X_1SX_2X_3SLFNSX_4X_5RKNYLX_6$ wherein $X_1$ is R or K; $X_2$ is S or A; $X_3$ is W, N or Q; $X_4$ is H or R; $X_5$ is T or F; and/or $X_6$ is A, L, N, or M (SEQ ID NOs: 151); (ii) a VL CDR2 comprising the sequence $WASARX_1S$ Wherein $X_1$ is G or E (SEQ ID NOs: 152), and (iii) VL CDR3 comprising the sequence $KQSFX_1LRT$ Wherein $X_1$ is N or R (SEQ ID NO: 153); and/or b) a heavy chain variable (VH) region comprising (i) VH CDR1 comprising the sequence set forth as SEQ ID NOs:107, 108, 109, 113, or 114; (ii) a VH CDR2 comprising the sequence set forth as SEQ ID NO: 157 and (iii) a VH CDR3 comprising the sequence set forth as SEQ ID NO: 112.

In another aspect, the invention provides an isolated antibody, or an antigen binding fragment thereof, that binds to chemokine receptor 4 (CXCR4) and comprises: a heavy chain variable (VH) region sequence comprising: EVQLVESGGGLVQPGGSLRLSCAASGFTFSDYYMS WVRQAPGKGLEWV$X_1$FIRHK$X_2$ N$X_3X_4$T$X_5$EYST$X_6X_7X_8$GRFTISRD$X_9$SKN$X_{10}$LYLQM NS L$X_{11}X_{12}$E DTAVYYCA$X_{13}$DLPGF AYWGQGTLVTVSS (SEQ ID NO: 106), wherein $X_1$ is G or S; $X_2$ is V or A; $X_3$ is G, F, K, V, T, L, or I; $X_4$ is E or Y; $X_5$ is T or R; $X_6$ is W or S; $X_7$ is D or V; $X_8$ is K, T, or R; $X_9$ is D or N; $X_{10}$ is T or S; $X_{11}$ is R or K; $X_{12}$ is A or T; and $X_{13}$ is K or R.

In some aspects of the invention, an isolated antibody or antigen binding fragment thereof that binds to chemokine receptor 4 (CXCR4) is selected from the group consisting of: a) a heavy chain variable (VH) region having a VH CDR1 of SEQ ID NO: 107, 113 or 114; a VH CDR2 of SEQ ID NO:162 or 128 and a VH CDR3 of SEQ ID NO:112 and a light chain variable (VL) region having a VL CDR1 of SEQ ID NO:144; a VL CDR2 of SEQ ID NO:145 and a VL CDR3 of SEQ ID NO:139; b) a VH region having a VH CDR1 of SEQ ID NO:115, 116, 117, 121 or 122; a VH CDR2 of SEQ ID NO:118 or 119 and a VH CDR3 of SEQ ID NO:120 and a VL region having a VL CDR1 of SEQ ID NO:135; a VL CDR2 of SEQ ID NO:136 and a VL CDR3 of SEQ ID NO:137; c) a VH region having a VH CDR1 of SEQ ID NO:107, 108, 109, 113 or 114; a VH CDR2 of SEQ ID NO:110 or 111 and a VH CDR3 of SEQ ID NO:112 and a VL region having a VL CDR1 of SEQ ID NO:131; a VL CDR2 of SEQ ID NO:132 and a VL CDR3 of SEQ ID NO:133; d) a VH region having a VH CDR1 of SEQ ID NO:107, 108, 109, 113 or 114; a VH CDR2 of SEQ ID NO:154 or 123 and a VH CDR3 of SEQ ID NO:112 and a VL region having a VL CDR1 of SEQ ID NO:138; a VL CDR2 of SEQ ID NO:132 and a VL CDR3 of SEQ ID NO:139; and e) a VH region having a VH CDR1 of SEQ ID NO:107, 108, 109, 113 or 114; a VH CDR2 of SEQ ID NO:157 and a VH CDR3 of SEQ ID NO:112 and a VL region having a VL CDR1 of SEQ ID NO:151; a VL CDR2 of SEQ ID NO:152 and a VL CDR3 of SEQ ID NO:153.

In some aspects of the invention, an isolated antibody or antigen binding fragment thereof that binds to chemokine receptor 4 (CXCR4) is selected from the group consisting of: a) a heavy chain variable (VH) region having a VH CDR1 of SEQ ID NO:107; a VH CDR2 of SEQ ID NO:162 and a VH CDR3 of SEQ ID NO:112 and a light chain variable (VL) region having a VL CDR1 of SEQ ID NO:144; a VL CDR2 of SEQ ID NO:145 and a VL CDR3 of SEQ ID NO:139; b) a VH region having a VH CDR1 of SEQ ID NO:115; a VH CDR2 of SEQ ID NO:118 and a VH CDR3 of SEQ ID NO:120 and a VL region having a VL CDR1 of SEQ ID NO:135; a VL CDR2 of SEQ ID NO:136 and a VL CDR3 of SEQ ID NO:137; c) a VH region having a VH CDR1 of SEQ ID NO:107; a VH CDR2 of SEQ ID NO:110 and a VH CDR3 of SEQ ID NO:112 and a VL region having a VL CDR1 of SEQ ID NO:131; a VL CDR2 of SEQ ID NO:132 and a VL CDR3 of SEQ ID NO:133; d) a VH region having a VH CDR1 of SEQ ID NO:107; a VH CDR2 of SEQ ID NO:154 and a VH CDR3 of SEQ ID NO:112 and a VL region having a VL CDR1 of SEQ ID NO:138; a VL CDR2 of SEQ ID NO:132 and a VL CDR3 of SEQ ID NO:139; and e) a VH region having a VH CDR1 of SEQ ID NO:107; a VH CDR2 of SEQ ID NO:157 and a VH CDR3 of SEQ ID NO:112 and a VL region having a VL CDR1 of SEQ ID NO:151; a VL CDR2 of SEQ ID NO:152 and a VL CDR3 of SEQ ID NO:153.

In some aspects of the invention, an isolated antibody or antigen binding fragment thereof that binds to chemokine receptor 4 (CXCR4) is) selected from the group consisting of: a) a heavy chain variable (VH) region having a VH CDR1 of SEQ ID NO:107; a VH CDR2 of SEQ ID NO:158 and a VH CDR3 of SEQ ID NO:112 and a light chain variable (VL) region having a VL CDR1 of SEQ ID NO:138; a VL CDR2 of SEQ ID NO:132 and a VL CDR3 of SEQ ID NO:139; b) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:138; a VL CDR2 of SEQ ID NO:132 and a VL CDR3 of SEQ ID NO:140; c) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:150; a VL CDR2 of SEQ ID NO:132 and a VL CDR3 of SEQ ID NO:140; d) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:141; a VL CDR2 of SEQ ID NO:132 and a VL CDR3 of SEQ ID NO:140; e) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:144; a VL CDR2 of SEQ ID NO:145 and a VL CDR3 of SEQ ID NO:140; f) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:147; a VL CDR2 of SEQ ID NO:132 and a VL CDR3 of SEQ ID NO:140; g) a VH region having a VH CDR1 of SEQ ID NO:107; a VH CDR2 of SEQ ID NO:159 and a VH CDR3 of SEQ ID NO:112 and a VL region having a VL CDR1 of SEQ ID NO:138; a VL CDR2 of SEQ ID NO:132 and a VL CDR3 of SEQ ID NO:140; h) a VH region having a VH CDR1 of SEQ ID NO:107; a VH CDR2 of SEQ ID NO:160 and a VH CDR3 of SEQ ID NO:112 and a VL region having a VL CDR1 of SEQ ID NO:138; a VL CDR2 of SEQ ID NO:132 and a VL CDR3 of SEQ ID NO:140; i) a VH region having a VH CDR1 of SEQ ID NO:107; a VH CDR2 of SEQ ID NO:161 and a VH CDR3 of SEQ ID NO:112 and a VL region having a VL CDR1 of SEQ ID NO:138; a VL CDR2 of SEQ ID NO:132 and a VL CDR3 of SEQ ID NO:140; j) a VH region having a VH CDR1 of SEQ ID NO:107; a VH CDR2 of SEQ ID NO:162 and a VH CDR3 of SEQ ID NO:112 and a VL region having a VL CDR1 of SEQ ID NO:138; a VL CDR2 of SEQ ID NO:132 and a VL CDR3 of SEQ ID NO:140; k) a VH region having a VH CDR1 of SEQ ID NO:107; a VH CDR2 of SEQ ID NO:163 and a VH CDR3 of SEQ ID NO:112 and a VL region having a VL CDR1 of SEQ ID NO:138; a VL CDR2 of SEQ ID NO:132 and a VL CDR3 of SEQ ID NO:140; I) a VH region having a VH CDR1 of SEQ ID NO:107; a VH CDR2 of SEQ ID NO:164 and a VH CDR3 of SEQ ID NO:112 and a VL region having a VL CDR1 of SEQ ID NO:138; a VL CDR2 of SEQ ID NO:132 and a VL CDR3 of SEQ ID NO:140; m) a VH region having a VH CDR1 of SEQ ID NO:107; a VH CDR2 of SEQ ID NO:165 and a VH CDR3 of SEQ ID NO:112 and a VL region having a VL CDR1 of SEQ ID NO:138; a VL CDR2 of SEQ ID NO:132 and a VL CDR3 of SEQ ID NO:140; o) a VH region having a VH CDR1 of SEQ ID NO:107; a VH CDR2 of SEQ ID NO:166 and a VH CDR3 of SEQ ID NO:112 and a VL region having a VL CDR1 of SEQ ID NO:138; a VL CDR2 of SEQ ID NO:132 and a VL CDR3 of SEQ ID NO:140; p) a VH region having a VH CDR1 of SEQ ID NO:107; a VH CDR2 of SEQ ID NO:167 and a VH CDR3 of SEQ ID NO:112 and a VL region having a VL CDR1 of SEQ ID NO:138; a VL CDR2 of SEQ ID NO:132 and a VL CDR3 of SEQ ID NO:140; q) a VH region having a VH CDR1 of SEQ ID NO:107; a VH CDR2 of SEQ ID NO:168 and a VH CDR3 of SEQ ID NO:112 and a VL region having a VL CDR1 of SEQ ID NO:138; a VL CDR2 of SEQ ID NO:132 and a VL CDR3 of SEQ ID NO:140; r) a VH region having a VH CDR1 of SEQ ID NO:107; a VH CDR2 of SEQ ID NO:168 and a VH CDR3 of SEQ ID NO:112 and a VL region having a VL CDR1 of SEQ ID NO:138; a VL CDR2 of SEQ ID NO:132 and a VL CDR3 of SEQ ID NO:140; s) a VH region having a VH CDR1 of SEQ ID NO:107; a VH CDR2 of SEQ ID NO:163 and a VH CDR3 of SEQ ID NO:112 and a VL region having a VL CDR1 of SEQ ID NO:144; a VL CDR2 of SEQ ID NO:145 and a VL CDR3 of SEQ ID NO:140; t) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:144; a VL CDR2 of SEQ ID NO:145 and a VL CDR3 of SEQ ID NO:139; u) a VH region having a VH CDR1 of SEQ ID NO:107; a VH CDR2 of SEQ ID NO:162 and a VH CDR3 of SEQ ID NO:112 and a VL region having a VL CDR1 of SEQ ID NO:144; a VL CDR2 of SEQ ID NO:145 and a VL CDR3 of SEQ ID NO:139; v) a VH region having a VH CDR1 of SEQ ID NO:107; a VH CDR2 of SEQ ID NO:163 and a VH CDR3 of SEQ ID NO:112 and a VL region having a VL CDR1 of SEQ ID NO:144; a VL CDR2 of SEQ ID NO:145 and a VL CDR3 of SEQ ID NO:139; and w) a VH region having a VH CDR1 of SEQ ID NO:107; a VH CDR2 of SEQ ID NO:162 and a VH CDR3 of SEQ ID NO:112 and a VL region having a VL CDR1 of SEQ ID NO:144; a VL CDR2 of SEQ ID NO:145 and a VL CDR3 of SEQ ID NO:140.

In some aspects of the invention, an isolated antibody, or an antigen binding fragment thereof, comprises: a heavy chain variable (VH) region comprising three CDRs set forth as SEQ ID NOs: 107, 162 and 112. In some aspects of the invention, an isolated antibody, or an antigen binding fragment thereof, comprises: a light chain variable (VL) region comprising three CDRs set forth as SEQ ID NOs: 144, 145 and 139. In some aspects of the invention, an isolated antibody, or an antigen binding fragment thereof, comprises: a) a heavy chain variable (VH) region comprising three CDRs set forth as SEQ ID NOs: 107, 162 and 112; and b) a light chain variable (VL) region comprising three CDRs set forth as SEQ ID NOs: 144, 145 and 139.

In some aspects of the invention, an isolated antibody, or an antigen binding fragment thereof, comprises: a heavy chain variable (VH) region comprising VH CDR1, VH CDR2 and VH CDR3 from a VH region of SEQ ID NO: 33. In some aspects of the invention, an isolated antibody, or an antigen binding fragment thereof, comprises: a light chain variable (VL) region comprising VL CDR1, VL CDR2 and VL CDR3 from a VL region of SEQ ID NO: 73. In still other aspects of the invention, an isolated antibody, or an antigen binding fragment thereof, comprises: a) a heavy chain variable (VH) region comprising VH CDR1, VH CDR2 and VH CDR3 from a VH region of SEQ ID NO: 33; and b) a light chain variable (VL) region comprising VL CDR1, VL CDR2 and VL CDR3 from a VL region of SEQ ID NO: 73.

In some aspects of the invention, an isolated antibody, or an antigen binding fragment thereof, is selected from the group consisting of: a) an antibody or antigen-binding fragment thereof comprising a VH region of SEQ ID NO:33 and a VL region of SEQ ID NO:73; b) an antibody or antigen-binding fragment thereof comprising a VH region of SEQ ID NO:13 and a VL region of SEQ ID NO: 15; c) an antibody or antigen-binding fragment thereof comprising a VH region of SEQ ID NO: 5 and a VL region of SEQ ID NO:7; d) an antibody or antigen-binding fragment thereof comprising a VH region of SEQ ID NO:21 and a VL region of SEQ ID NO:47; and e) an antibody or antigen-binding fragment thereof comprising a VH region of SEQ ID NO:106 and a VL region having a VL CDR1 of SEQ ID NO:138; a VL CDR2 of SEQ ID NO:132 and a VL CDR3 of SEQ ID NO:139.

In one aspect of the invention, an isolated antibody, or an antigen binding fragment thereof, comprises: a) a heavy chain variable (VH) region of SEQ ID NO: 33; and/or b) a light chain variable (VL) region of SEQ ID NO: 73.

In one aspect, the present invention provides an antibody or an antigen binding fragment thereof, that binds to CXCR4, wherein the antibody comprises a heavy chain variable (VH) region comprising a sequence shown in SEQ ID NOs: 1, 5, 9, 13, 17, 21, 23, 25, 27, 29, 31, 33, 35, 37, 39, 41, 43, 45, 85, 87 or 106; and/or a light chain variable region (VL) region comprising a sequence shown in SEQ ID NOs: 3, 7, 11, 15, 19, 47, 49, 51, 53, 55, 57, 59, 61, 63, 65, 67, 69, 71, 73, 75, 77, 79, 81, 83, or 169. In one aspect, an antibody or an antigen binding fragment thereof that binds to CXCR4 comprises a heavy chain variable (VH) region comprising an amino acid sequence that is at least 90%, 92%, 94%, 95%, 96%, 97%, 98% or 99% identical to SEQ ID NOs: 1, 5, 9, 13, 17, 21, 23, 25, 27, 29, 31, 33, 35, 37, 39, 41, 43, 45, 85, 87 or 106. In one aspect, an antibody or an antigen binding fragment thereof that binds to CXCR4 comprises a light chain variable region (VL) region comprising an amino acid sequence that is at least 90%, 92%, 94%, 95%, 96%, 97%, 98% or 99% identical to SEQ ID NOs: 3, 7, 11, 15, 19, 47, 49, 51, 53, 55, 57, 59, 61, 63, 65, 67, 69, 71, 73, 75, 77, 79, 81, 83, or 169.

In some aspects of the invention, provided are the isolated antibody or antigen binding fragment thereof of claim 6 selected from the group selected from the group consisting of: a) an antibody or antigen-binding fragment thereof comprising a VH region of SEQ ID NO:33 and a VL region of SEQ ID NO:73; b) an antibody or antigen-binding fragment thereof comprising a VH region of SEQ ID NO:13 and a VL region of SEQ ID NO:15; c) an antibody or antigen-binding fragment thereof comprising a VH region of SEQ ID NO:5 and a VL region of SEQ ID NO:7; d) an antibody or antigen-binding fragment thereof comprising a VH region of SEQ ID NO:21 and a VL region of SEQ ID NO:47; and e) an antibody or antigen-binding fragment thereof comprising a VH region of SEQ ID NO:106 and a VL region having a VL CDR1 of SEQ ID NO:138; a VL CDR2 of SEQ ID NO:132; and a VL CDR3 of SEQ ID NO:139.

In some aspects of the invention, the antibody or antigen binding fragment thereof of comprises a) a heavy chain variable (VH) region of SEQ ID NO: 33; and/or b) a light chain variable (VL) region of SEQ ID NO: 73. In particular aspects, the antibody or the antigen binding fragment thereof comprises a heavy chain variable (VH) region produced by the expression vector with ATCC Accession No. PTA-121353. In other aspects, the antibody or the antigen binding fragment comprises a light chain variable (VL) region produced by the expression vector with ATCC Accession No. PTA-121354.

In some aspects of the invention, the antibody or antigen binding fragment thereof of that binds to chemokine receptor 4 (CXCR4) is selected from the group consisting of: a)

a heavy chain variable (VH) region having a VH CDR1 of SEQ ID NO:107; a VH CDR2 of SEQ ID NO:158 and a VH CDR3 of SEQ ID NO:112 and a light chain variable (VL) region having a VL CDR1 of SEQ ID NO:138; a VL CDR2 of SEQ ID NO:132 and a VL CDR3 of SEQ ID NO:139; b) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:138; a VL CDR2 of SEQ ID NO:132 and a VL CDR3 of SEQ ID NO:140; c) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:150; a VL CDR2 of SEQ ID NO:132 and a VL CDR3 of SEQ ID NO:140; d) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:141; a VL CDR2 of SEQ ID NO:132 and a VL CDR3 of SEQ ID NO:140; e) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:144; a VL CDR2 of SEQ ID NO:145 and a VL CDR3 of SEQ ID NO:140; f) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:147; a VL CDR2 of SEQ ID NO:132 and a VL CDR3 of SEQ ID NO:140; g) a VH region having a VH CDR1 of SEQ ID NO:107; a VH CDR2 of SEQ ID NO:159 and a VH CDR3 of SEQ ID NO:112 and a VL region having a VL CDR1 of SEQ ID NO:138; a VL CDR2 of SEQ ID NO:132 and a VL CDR3 of SEQ ID NO:140; h) a VH region having a VH CDR1 of SEQ ID NO:107; a VH CDR2 of SEQ ID NO:160 and a VH CDR3 of SEQ ID NO:112 and a VL region having a VL CDR1 of SEQ ID NO:138; a VL CDR2 of SEQ ID NO:132 and a VL CDR3 of SEQ ID NO:140; i) a VH region having a VH CDR1 of SEQ ID NO:107; a VH CDR2 of SEQ ID NO:161 and a VH CDR3 of SEQ ID NO:112 and a VL region having a VL CDR1 of SEQ ID NO:138; a VL CDR2 of SEQ ID NO:132 and a VL CDR3 of SEQ ID NO:140; j) a VH region having a VH CDR1 of SEQ ID NO:107; a VH CDR2 of SEQ ID NO:162 and a VH CDR3 of SEQ ID NO:112 and a VL region having a VL CDR1 of SEQ ID NO:138; a VL CDR2 of SEQ ID NO:132 and a VL CDR3 of SEQ ID NO:140; k) a VH region having a VH CDR1 of SEQ ID NO:107; a VH CDR2 of SEQ ID NO:163 and a VH CDR3 of SEQ ID NO:112 and a VL region having a VL CDR1 of SEQ ID NO:138; a VL CDR2 of SEQ ID NO:132 and a VL CDR3 of SEQ ID NO:140; I) a VH region having a VH CDR1 of SEQ ID NO:107; a VH CDR2 of SEQ ID NO:164 and a VH CDR3 of SEQ ID NO:112 and a VL region having a VL CDR1 of SEQ ID NO:138; a VL CDR2 of SEQ ID NO:132 and a VL CDR3 of SEQ ID NO:140; m) a VH region having a VH CDR1 of SEQ ID NO:107; a VH CDR2 of SEQ ID NO:165 and a VH CDR3 of SEQ ID NO:112 and a VL region having a VL CDR1 of SEQ ID NO:138; a VL CDR2 of SEQ ID NO:132 and a VL CDR3 of SEQ ID NO:140; n) a VH region having a VH CDR1 of SEQ ID NO:107; a VH CDR2 of SEQ ID NO:166 and a VH CDR3 of SEQ ID NO:112 and a VL region having a VL CDR1 of SEQ ID NO:138; a VL CDR2 of SEQ ID NO:132 and a VL CDR3 of SEQ ID NO:140; o) a VH region having a VH CDR1 of SEQ ID NO:107; a VH CDR2 of SEQ ID NO:167 and a VH CDR3 of SEQ ID NO:112 and a VL region having a VL CDR1 of SEQ ID NO:138; a VL CDR2 of SEQ ID NO:132 and a VL CDR3 of SEQ ID NO:140; p) a VH region having a VH CDR1 of SEQ ID NO:107; a VH CDR2 of SEQ ID NO:168 and a VH CDR3 of SEQ ID NO:112 and a VL region having a VL CDR1 of SEQ ID NO:138; a VL CDR2 of SEQ ID NO:132 and a VL CDR3 of SEQ ID NO:140; q) a VH region having a VH CDR1 of SEQ ID NO:107; a VH CDR2 of SEQ ID NO:168 and a VH CDR3 of SEQ ID NO:112 and a VL region having a VL CDR1 of SEQ ID NO:138; a VL CDR2 of SEQ ID NO:132 and a VL CDR3 of SEQ ID NO:140; r) a VH region having a VH CDR1 of SEQ ID NO:107; a VH CDR2 of SEQ ID NO:163 and a VH CDR3 of SEQ ID NO:112 and a VL region having a VL CDR1 of SEQ ID NO:144; a VL CDR2 of SEQ ID NO:145 and a VL CDR3 of SEQ ID NO:140; s) a VH region having a VH CDR1 of SEQ ID NO:107; a VH CDR2 of SEQ ID NO:158 and a VH CDR3 of SEQ ID NO:112 and a VL region having a VL CDR1 of SEQ ID NO:144; a VL CDR2 of SEQ ID NO:145 and a VL CDR3 of SEQ ID NO:139; t) a VH region having a VH CDR1 of SEQ ID NO:107; a VH CDR2 of SEQ ID NO:162 and a VH CDR3 of SEQ ID NO:112 and a VL region having a VL CDR1 of SEQ ID NO:144; a VL CDR2 of SEQ ID NO:145 and a VL CDR3 of SEQ ID NO:139; u) a VH region having a VH CDR1 of SEQ ID NO: 107; a VH CDR2 of SEQ ID NO:163 and a VH CDR3 of SEQ ID NO:112 and a VL region having a VL CDR1 of SEQ ID NO:144; a VL CDR2 of SEQ ID NO:145 and a VL CDR3 of SEQ ID NO:139; and v) a VH region having a VH CDR1 of SEQ ID NO:107; a VH CDR2 of SEQ ID NO:162 and a VH CDR3 of SEQ ID NO:112 and a VL region having a VL CDR1 of SEQ ID NO:144; a VL CDR2 of SEQ ID NO:145 and a VL CDR3 of SEQ ID NO:140.

In particular aspects of the invention, the antibody or antigen binding fragment thereof, comprises a VH region having a VH CDR1 of SEQ ID NO: 107; a VH CDR2 of SEQ ID NO: 162 and a VH CDR3 of SEQ ID NO: 112 and a VL region having a VL CDR1 of SEQ ID NO: 144; a VL CDR2 of SEQ ID NO: 145 and a VL CDR3 of SEQ ID NO:139.

The binding affinity ($K_D$) of the anti-CXCR4 antibody, or antigen-binding fragments thereof, as described herein to CXCR4 (such as human CXCR4) are about 0.002 to about 200 nM. In some aspects of the invention, the binding affinity is any of about 200 nM, about 100 nM, about 50 nM, about 45 nM, about 40 nM, about 35 nM, about 30 nM, about 25 nM, about 20 nM, about 15 nM, about 10 nM, about 8 nM, about 7.5 nM, about 7 nM, about 6.5 nM, about 6 nM, about 5.5 nM, about 5 nM, about 4 nM, about 3 nM, about 2 nM, about 1 nM, about 500 μM, about 100 μM, about 60 μM, about 50 μM, about 20 μM, about 15 μM, about 10 μM, about 5 μM, or about 2 μM. In some aspects of the invention, the binding affinity is less than any of about 250 nM, about 200 nM, about 100 nM, about 50 nM, about 30 nM, about 20 nM, about 10 nM, about 7.5 nM, about 7 nM, about 6.5 nM, about 6 nM, about 5 nM, about 4.5 nM, about 4 nM, about 3.5 nM, about 3 nM, about 2.5 nM, about 2 nM, about 1.5 nM, about 1 nM, about 500 μM, about 100 μM, about 50 μM, about 20 μM, about 10 μM, about 5 μM, or about 2 μM.

In some aspects of the invention, the binding affinity (e.g., monovalent antibody binding) of the antibodies as described herein is about 35 nM or less as measured by surface plasmon resonance. In some aspects of the invention, the binding affinity (e.g., monovalent antibody binding) of the antibodies as described herein is about 6.5 nM or less as measured by surface plasmon resonance.

The invention also provides methods of making any of these antibodies. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In another aspect of the invention, the antibodies can be made recombinantly using procedures that are well known in the art. In another aspect, a polynucleotide comprises a sequence encoding the heavy chain and/or the light chain variable regions of antibody m6B6, h6B6, m12A11, h12A11, m3G10, h3G10 (VH), h3G10.A57, h3G10.B44, h3G10.1.7, h3G10.1.60, h3G10.2.5, h3G10.1.91, h3G10.2.37, h3G10.2.45, h3G10.2.42, h3G10.1.33, h3G10.3.25, h3G10.2.54, h3G10.A59, h3G10.A62, h3G10 (VL), h3G10.2.72, h3G10.A11A, h3G10.A18A, h3G10.A19A, h3G10.A58A, h3G10.A65A, and h3G10.B12A, h3G10.B13A, h3G10.B18A, h3G10.A11B, h3G10.A18B, h3G10.A19B, h3G10.A58B, h3G10.A65B, h3G10.B12B, h3G10.B13B, h3G10.B18B, h3G10.2.25 or h3G10.L94D. The sequence encoding the antibody of interest may be maintained in a vector in a host cell and the host cell can then be expanded and frozen for future use. Vectors (including expression vectors) and host cells are further described herein.

The invention also encompasses scFv of antibodies of this invention. Single chain variable region fragments are made by linking light and/or heavy chain variable regions by using a short linking peptide (Bird et al., Science 242:423-426, 1988). An example of a linking peptide is $(GGGGS)_3$ (SEQ ID NO: 89), which bridges approximately 3.5 nm between the carboxy terminus of one variable region and the designed and used (Bird et al., 1988, supra). Linkers should be short, flexible polypeptides and preferably comprised of less than about 20 amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, amino terminus of the other variable region. Linkers of other sequences have been such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies or minibodies are also encompassed. Diabodies are bivalent, bispecific antibodies in which heavy chain variable (VH) and light chain variable (VL) domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., Proc. Natl. Acad Sci. USA 90:6444-6448 (1993); Poljak, R. J., et al., Structure 2:1121-1123 (1994)). Minibody includes the VL and VH domains of a native antibody fused to the hinge region and CH3 domain of the immunoglobulin molecule. See, e.g., U.S. Pat. No. 5,837,821.

A bispecific antibody is an antibody that can bind simultaneously to two different targets. Bispecific antibodies (bsAb) and bispecific antibody fragments (bsFab) may have at least one arm that binds to, for example, a tumor-associated antigen and at least one other arm that binds to a targetable conjugate that bears a therapeutic or diagnostic agent. A variety of bispecific fusion proteins can be produced using molecular engineering.

For example, bispecific antibodies, monoclonal antibodies that have binding specificities for at least two different antigens, can be prepared using the antibodies disclosed herein. Methods for making bispecific antibodies are known in the art (see, e.g., Suresh et al., Methods in Enzymology 121:210 (1986)). Traditionally, the recombinant production of bispecific antibodies was based on the coexpression of two immunoglobulin heavy chain-light chain pairs, with the two heavy chains having different specificities (Millstein and Cuello, Nature 305, 537-539 (1983)).

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some aspects of the invention, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 1994/004690.

In another aspect, the bispecific antibodies are composed of amino acid modification in the first hinge region in one arm, and the substituted/replaced amino acid in the first hinge region has an opposite charge to the corresponding amino acid in the second hinge region in another arm. This approach is described in PCT Publication No. WO 2011/143545.

In another aspect, the bispecific antibodies can be generated using a glutamine-containing peptide tag engineered to the antibody directed to an epitope (e.g., CXCR4) in one arm and another peptide tag (e.g., a Lys-containing peptide tag or a reactive endogenous Lys) engineered to a second antibody directed to a second epitope in another arm in the presence of transglutaminase. This approach is described in PCT Publication No. WO 2012/059882.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 1991/000360). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

The invention encompasses modifications to the antibodies and polypeptides of the invention variants shown in Table 2, including functionally equivalent antibodies which do not significantly affect their properties and variants which have enhanced or decreased activity and/or affinity. For example, the amino acid sequence may be mutated to obtain an antibody with the desired binding affinity to CXCR4. Modification of polypeptides is routine practice in the art and need not be described in detail herein. Examples of modified polypeptides include polypeptides with conservative sequence modifications. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions which do not significantly deleteriously change the functional activity, or which mature (enhance) the affinity of the polypeptide for its ligand, or use of chemical analogs.

Modifications can be introduced into an antibody of this disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of this disclosure can be replaced with other amino acid residues from the same side chain family and the altered antibody can be tested for retained function (i.e., the functions set forth above) using the functional assays described herein.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 5 under the heading of "conservative substitutions." If such substitutions result in a change in biological activity, then more substantial changes, denominated "exemplary substitutions" in Table 5, or as further described below in reference to amino acid classes, may be introduced and the products screened.

TABLE 5

Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring amino acid residues are divided into groups based on common side-chain properties:

(1) Non-polar: Norleucine, Met, Ala, Val, Leu, lie;
(2) Polar without charge: Cys, Ser, Thr, Asn, Gin;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some aspects of the invention, no more than one to five conservative amino acid substitutions are made within a CDR domain. In other aspects of the invention, no more than one to three conservative amino acid substitutions are made within a CDR domain.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, Chem. Immunol. 65:111-128 (1997); Wright and Morrison, TibTECH 15:26-32 (1997)). The oligosaccharide side chains of the immunoglobulins affect the protein's function (Boyd et al., Mol. Immunol. 32:1311-1318 (1996); Wittwe and Howard, Biochem. 29:4175-4180 (1990)) and the intramolecular interaction between portions of the glycoprotein, which can affect the conformation and presented three-dimensional surface of the glycoprotein (Jefferis and Lund, supra; Wyss and Wagner, Current Opin. Biotech. 7:409-416 (1996)). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of 13(1,4)-N-acetylglucosaminyltransferase III (GnTIII), a glycosyltransferase catalyzing formation of bisecting GlcNAc, was reported to have improved ADCC activity (Umana et al., Mature Biotech. 17:176-180 (1999)).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., J. Biol. Chem. 272:9062-9070 (1997)).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-polyethylene glycol or polyethylene glycol-maleimide. In certain aspects of the invention, the antibody to be pegylated is an aglycosylated antibody. Methods for pegylating proteins are known in the art and can be applied to the antibodies of this disclosure See for example, EP 0154316 by Nishimura et al., and EP0401384 by Ishikawa el al.

The present invention is not limited to traditional antibodies and includes the use of antibody fragments and antibody mimetics. Wide varieties of antibody fragment and antibody mimetic technologies have been developed and are known in the art. While a number of these technologies, such as domain antibodies, Nanobodies, and UniBodies make use of fragments of, or other modifications to, traditional antibody structures, there are also alternative technologies, such as Affibodies, DARPins, Avimers, Anticalins, and Versabodies that employ binding structures that, while they mimic traditional antibody binding, are generated from and function via distinct mechanisms.

Domain Antibodies (dAbs) are the smallest functional binding units of antibodies, corresponding to the variable regions of either the heavy (VH) or light (VL) chains of human antibodies. Domantis has developed a series of large and highly functional libraries of fully human VH and VL dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158, 6,582,915, 6,593,081, 6,172,197, and 6,696,245, U.S. Patent Application No. 2004/0110941, European Patent Application No. 1433846 and European Patents 0368684 & 0616640, WO05/035572, WO04/101790, WO04/081026, WO04/058821, WO04/003019 and WO03/002609, each of which is herein incorporated by reference in its entirety.

Nanobodies are antibody-derived therapeutic proteins that contain the unique structural and functional properties of naturally-occurring heavy-chain antibodies. These heavy-chain antibodies contain a single variable domain (VHH) and two constant domains (CH2 and CH3). The cloned and isolated VHH domain is a perfectly stable polypeptide harbouring the full antigen-binding capacity of the original heavy-chain antibody. Nanobodies have a high homology with the VH domains of human antibodies and can be further humanized without any loss of activity. Moreover, nanobodies combine the advantages of conventional antibodies with important features of small molecule drugs like conventional antibodies. Nanobodies show high target specificity, high affinity for their target and low inherent toxicity. Nanobodies are encoded by single genes and are efficiently produced in almost all prokaryotic and eukaryotic hosts e. g. *E. coli* (see e.g. U.S. Pat. No. 6,765,087, which is herein incorporated by reference in its entirety), molds (for example *Aspergillus* or Trrchoderma) and yeast (for example *Saccharomyces, Kluyveromyces, Hansenula* or *Pichia*) (see e.g., U.S. Pat. No. 6,838,254, which is herein incorporated by reference in its entirety).

In some aspects, the present invention provides the use of UniBodies. UniBodies are another antibody fragment technology, based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. For example, UniBodies may function to inhibit or silence, but not kill, the cells to which they are bound. Additionally, UniBody binding to cancer cells do not stimulate them to proliferate. Furthermore, because UniBodies are about half the size of traditional IgG4 antibodies, they may show better distribution over larger solid tumors with potentially advantageous efficacy UniBodies are cleared from the body at a similar rate to whole IgG4 antibodies and are able to bind with a similar affinity for their antigens as whole antibodies. Further details of UniBodies may be obtained by reference to PCT Publication WO2007/059782, which is herein incorporated by reference in its entirety.

In some aspects, the present invention encompasses Afibody molecules. Afibody molecules are a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunnettsson E, Ringdahl J, Stahl S, Uhlen M, Nygren P A, Binding proteins selected from combinatorial libraries of an $\alpha$-helical bacterial receptor domain, Nat Biotechnol 15 772-7 (1997), Ronmark J, Gronlund H, Uhlen M, Nygren P A, Human immunoglobulin A (IgA)-specific ligands from combinatorial engineering of protein A, Eur J Biochem., 269 2647-55 (2002)). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli*, J Immunol Methods, 261 199-211 (2002)) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng., 16 691-7 (2003)). Further details of Affibodies and methods of production thereof may be obtained by reference to U.S. Pat. No. 5,831,012 which is herein incorporated by reference in its entirety.

Another antibody mimetic technology useful in the context of the present invention is Avimers. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases Avimers with sub-nanomolar affinities have been obtained against a variety of targets. Additional information regarding Avimers can be found in U.S. Patent Application Publication Nos. 2006/0286603, 2006/0234299, 2006/02231 14, 2006/0177831, 2006/0008844, 2005/0221384, 2005/0164301, 2005/0089932, 2005/0053973, 2005/0048512, 2004/0175756, all of which are hereby incorporated by reference in their entirety.

Versabodies are another antibody mimetic technology that could be used in the context of the present invention. Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All these properties are well-known to affect immunogenicity, and together they are expected to cause a large decrease in immunogenicity. Additional information regarding Versabodies can be found in U.S.Patent Application Publication No. 2007/0191272 which is hereby incorporated by reference in its entirety.

The detailed description of antibody fragment and antibody mimetic technologies provided above is not intended to be a comprehensive list of all technologies that could be used in the context of the present specification. For example, and also not by way of limitation, a variety of additional technologies including alternative polypeptide-based technologies, such as fusions of complimentary determining regions as outlined in Qui et al., Nature Biotechnology, 25(8) 921-929 (2007), which is hereby incorporated by reference in its entirety, as well as nucleic acid-based technologies, such as the RNA aptamer technologies described in U.S. Pat. Nos. 5,789,157; 5,864,026; 5,712,375; 5,763,566; 6,013,443; 6,376,474; 6,613,526; 6,114,120; 6,261,774 and 6,387,620, all of which are hereby incorporated by reference, could be used in the context of the present invention.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some aspects of the invention, the antibody comprises a modified constant region, such as a constant region that has increased affinity to a human Fc gamma receptor, is immunologically inert or partially inert, e.g., does not trigger complement mediated lysis, does not stimulate antibody-dependent cell mediated cytotoxicity (ADCC), or does not activate macrophages; or has reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., Immunology 86:319-324 (1995); Lund et al., J. Immunology 157:4963-9 157:4963-4969 (1996); Idusogie et al., J. Immunology 164:4178-4184, (2000); Tao et al., J. Immunology 143: 2595-2601 (1989); and Jefferis et al., Immunological Reviews 163:59-76 (1998). In some aspects of the invention, the constant region is modified as described in Eur. J. Immunol., 29:2613-2624 (1999); PCT Publication No. WO1999/058572. In other aspects of the invention, the antibody comprises a human heavy chain IgG2 constant region comprising the following mutations: A330P331 to S330S331 (amino acid numbering with reference to the wild type IgG2 sequence). Eur. J. Immunol., 29:2613-2624 (1999). In still other aspects of the invention, the constant region is aglycosylated for N-linked glycosylation. In some aspects of the invention, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., J. Immunology 143: 2595-2601 (1989); and Jefferis et al., Immunological Reviews 163:59-76 (1998). In some aspects of the invention, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some aspects of the invention, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

The invention includes affinity matured antibodies. For example, affinity matured antibodies can be produced by procedures known in the art (Marks et al., Bio/Technology, 10:779-783 (1992); Barbas et al., Proc Nat. Acad. Sci, USA 91:3809-3813 (1994); Schier et al., Gene, 169:147-155 (1995); Yelton et al., J. Immunol., 155:1994-2004 (1995); Jackson et al., J. Immunol., 154(7):3310-9 (1995), Hawkins et al., J. Mol. Biol., 226:889-896 (1992); and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some aspects of the invention, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using Biacore™ surface plasmon resonance analysis, which detects differences in binding affinity of about 2-fold or greater. Biacore™ is particularly useful when the starting antibody already binds with a relatively high affinity, for example a $K_D$ of about 10 nM or lower. Screening using Biacore™ surface plasmon resonance is described in the Examples, herein.

In another aspect, the invention relates to antibody or antigen binding fragment thereof, that binds CXCR4, wherein the antibody or antigen binding fragment thereof has an EC50 of less than 100 nM. In yet another aspect, the invention relates to antibody or antigen binding fragment thereof, that binds CXCR4, wherein the antibody or antigen binding fragment thereof has an EC50 of less than 50 nM. In yet another aspect, the invention relates to antibody or antigen binding fragment thereof, that binds CXCR4, wherein the antibody or antigen binding fragment thereof has an EC50 of less than 1 nM. The term "EC50" means the concentration of the test antibody, antigen binding fragment thereof, or antibody-drug conjugate that is required for 50% inhibition of its maximum effect in vitro. The term "IC50" mean is defined as "the inhibitory concentration of 50%"

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some aspects of the invention, every amino acid position in a CDR is replaced (in some embodiments, one at a time) with all 20 natural amino acids using art recognized mutagenesis methods (some of which are described herein). This generates small libraries of clones (in some aspects of the invention, one for every amino acid position that is analyzed), each with a complexity of 20 members (if all 20 amino acids are substituted at every position).

In some aspects of the invention, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., Gene 137(1):109-18 (1993).

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore™ surface plasmon resonance analysis, and selection using any method known in the art for selection, including phage display, yeast display, and ribosome display.

The invention also encompasses fusion proteins comprising one or more fragments or regions from the antibodies of this invention. In some aspects of the invention, a fusion polypeptide is provided that comprises at least 10 contiguous amino acids of the VH region chain region shown in SEQ ID NOs: 1, 5, 9, 13, 17, 21, 23, 25, 27, 29, 31, 33, 35, 37, 39, 41, 43, 45, 85, 87 and 106; and/or at least 10 amino acids of the VL region shown in SEQ ID NOs: 3, 7, 11, 15, 19, 47, 49, 51, 53, 55, 57, 59, 61, 63, 65, 67, 69, 71, 73, 75, 77, 79, 81, 83, and 169. In various aspects of the invention, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another aspect, the fusion polypeptide comprises a light chain variable region and/or a heavy chain variable region, as shown in any of the sequence pairs in Table 2. For example, SEQ ID NOs:3 and 5; 3 and 9; 7 and 5; 11 and 13; 15 and 13; 19 and 17; 69 and 31; 49 and 37; and, 33 and 73. In some aspects, the fusion polypeptide comprises one or more CDR(s). In still other aspects, the fusion polypeptide comprises CDR H3 (VH CDR3) and/or CDR L3 (VL CDR3). For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

This invention also provides compositions comprising antibodies conjugated (for example, linked) to an agent that facilitate coupling to a solid support (such as biotin or avidin). For simplicity, reference will be made generally to antibodies with the understanding that these methods apply to any of the anti-CXCR4 antibody, or antigen-binding fragments thereof, embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The invention also provides isolated polynucleotides encoding the antibodies of the invention, and vectors and host cells comprising the polynucleotide.

Accordingly, the invention provides polynucleotides (or compositions, including pharmaceutical compositions), comprising polynucleotides encoding any of the following: m6B6, h6B6, m12A11, h12A11, m3G10, h3G10, h3G10.A57, h3G10.B44, h3G10.1.7, h3G10.1.60, h3G10.2.5, h3G10.1.91, h3G10.2.37, h3G10.2.45, h3G10.2.42, h3G10.1.33, h3G10.3.25, h3G10, h3G10.2.72, h3G10.A11A, h3G10.A18A, h3G10.A19A, h3G10.A58A, h3G10.A65A, and h3G10.B12A, h3G10.B13A, h3G10.B18A, h3G10.A11B, h3G10.A18B, h3G10.A19B, h3G10.A58B, h3G10.A65B, h3G10.B12B, h3G10.B13B, h3G10.B18B, h3G10.2.25, h3G10.A59 h3G10.A62, h3G10.L94D or any fragment or part thereof having the ability to bind CXCR4.

In some aspects, the invention provides polynucleotides encoding any of the antibodies (including antibody fragments) and polypeptides described herein, such as antibodies and polypeptides having impaired or improved effector function. Polynucleotides can be made and expressed by procedures known in the art.

In other aspects, the invention provides compositions (such as a pharmaceutical compositions) comprising any of the polynucleotides of the invention. In some aspects, the composition comprises an expression vector comprising a polynucleotide encoding any of the antibodies described herein. For example, the composition comprises either or both of the polynucleotides shown in SEQ ID NO: 2 and 4, or SEQ ID NO: 6 and 8, or SEQ ID NO: 86 and 68.

Expression vectors and administration of polynucleotide compositions are further described herein.

In other aspects, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., CABIOS 5:151-153 (1989); Myers, E. W. and Muller W., CABIOS 4:11-17 (1988); Robinson, E. D., Comb. Theor. 11:105 (1971); Santou, N., Nes, M., Mol. Biol. Evol. 4:406-425 (1987); Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., Proc. Natl. Acad. Sci. USA 80:726-730 (1983).

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein.

One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to CXCR4 or a CXCR4 domain (e.g., domains 1-4) is effected by an immunoassay or FACS. A cell overexpressing the antibody or protein of interest can be identified.

Anti-CXCR4 Antibody-Drug Conjugates

The present invention provides antibody-drug of the formula Ab-(T-L-D), wherein a) Ab is an antibody, or antigen-binding fragment thereof, that binds to CXCR4, b) T is an acyl donor glutamine-containing tag that can be optionally included; c) L is a linker; and d) D is a drug. Also provided are methods of preparing and manufacturing such antibody-drug conjugates, and use of the same in clinical applications. "Antibody-drug conjugate" or "ADC" refers to antibodies, or antigen-binding fragments thereof, including antibody derivatives that bind to CXCR4 and are conjugated to a drug.

In some aspects of the invention, the Ab is selected from the group consisting of: a) an antibody or antigen-binding fragment thereof comprising a VH region comprising CDRs of SEQ ID NOs: 107, 162 and 112 and a VL region comprising CDRs of SEQ ID NOs: 144, 145 and 139; b) an antibody or antigen-binding fragment thereof comprising a VH region comprising CDRs of SEQ ID NOs: 115, 118 and 120 and a VL region comprising CDRs of SEQ ID NOs:135, 136 and 137; c) an antibody or antigen-binding fragment thereof comprising a VH region comprising CDRs of SEQ ID NOs: 107, 110 and 112 and a VL region comprising CDRs of SEQ ID NOs:131, 132 and 133; d) an antibody or antigen-binding fragment thereof comprising a VH region comprising CDRs of SEQ ID NOs: 107, 154 and 112 and a VL region comprising CDRs of SEQ ID NOs:138, 132 and 139; e) an antibody or antigen-binding fragment thereof comprising a VH region comprising CDRs of SEQ ID NOs: 107, 157 and 112 and a VL region comprising CDRs of SEQ ID NOs:151, 152 and 153; f) an antibody or antigen-binding fragment thereof comprising a VH region of SEQ ID NO:33 and a VL region of SEQ ID NO:73; g) an antibody or antigen-binding fragment thereof comprising a VH region of SEQ ID NO:13 and a VL region of SEQ ID NO:15; h) an antibody or antigen-binding fragment thereof comprising a VH region of SEQ ID NO:5 and a VL region of SEQ ID NO:7; and i) an antibody or antigen-binding fragment thereof comprising a VH region of SEQ ID NO:21 and a VL region of SEQ ID NO:47.

Methods for conjugating cytotoxic agent or other therapeutic agents to antibodies have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, (2005), and Gentle et al., Bioconjug. Chem. 15:658-663, (2004). Reactive cysteine residues engineered at specific sites of antibodies for specific drug conjugation with defined stoichiometry have also been described. See, e.g., Junutula et al., Nature Biotechnology, 26:925-932, (2008). Conjugation using an acyl donor glutamine-containing tag and/or an endogenous glutamine made reactive (i.e., the ability to form a covalent bond as an acyl donor) by polypeptide engineering in the presence of transglutaminase and an amine (e.g., a cytotoxic agent comprising or attached to a reactive amine) is also described in International Patent Application Serial No. PCT/IB2011/054899 (WO2012/059882), Strop et al., Chem. Biol. 20(2):161-167 (2013), and Farias et al., Bioconjug. Chem. 25(2):245-250 (2014).

An example of a suitable conjugation procedure relies on the conjugation of hydrazides and other nucleophiles to the aldehydes generated by oxidation of the carbohydrates that naturally occur on antibodies. Hydrazone-containing conjugates can be made with introduced carbonyl groups that provide the desired drug-release properties. Conjugates can also be made with a linker that has a disulfide at one end, an alkyl chain in the middle, and a hydrazine derivative at the other end. The anthracyclines are one example of cytotoxins that can be conjugated to antibodies using this technology.

In other aspects of the invention, the anti-CXCR4 antibody, or antigen-binding fragments thereof, or the conjugate as described herein comprises an acyl donor glutamine-containing tag (T) engineered at a specific site of the antibody (e.g., a carboxyl terminus, an amino terminus, or at another site in the anti-CXCR4 antibody). In some aspects of the invention, the tag comprises an amino acid glutamine (Q) or an amino acid sequence LLQGG (SEQ ID NO: 171), GGLLQGG (SEQ ID NO: 90), LLQGA (SEQ ID NO: 91), GGLLQGA (SEQ ID NO: 92), LLQ, LLQGPGK (SEQ ID NO: 93), LLQGPG (SEQ ID NO: 94), LLQGPA (SEQ ID NO: 95), LLQGP (SEQ ID NO: 96), LLQP (SEQ ID NO: 97), LLQPGK (SEQ ID NO: 98), LLQGAPGK (SEQ ID NO: 99), LLQGAPG (SEQ ID NO: 100), LLQGAP (SEQ ID NO: 101), GGLLQGPP (SEQ ID NO: 172), LLQGPP (SEQ ID NO: 173), $LLQX_1X_2X_3X_4X_5$, wherein $X_1$ is G or P, wherein $X_2$ is A, G, P, or absent, wherein $X_3$ is A, G, K, P, or absent, wherein $X_4$ is K, G or absent, and wherein $X_5$ is K or absent (SEQ ID NO: 102), or $LLQX_1X_2X_3X_4X_5$, wherein $X_1$ is any naturally occurring amino acid and wherein $X_2$, $X_3$, $X_4$, and $X_5$ are any naturally occurring amino acids or absent (SEQ ID NO: 103). In particular aspect of the invention, T is selected from the group consisting of any of SEQ ID NOs: 91, 92 and 102.

In other aspects of the invention, provided is an isolated antibody comprising an acyl donor glutamine-containing tag and an amino acid modification at position 222, 340, or 370 of the antibody (EU numbering scheme), wherein the modification is an amino acid deletion, insertion, substitution, mutation, or any combination thereof. For example, the amino acid modification is K222R, K340R, and K370R.

In some aspect of the invention, a conjugate of the antibody or the antigen binding fragment is conjugated to a drug, wherein the drug is selected from the group consisting of a cytotoxic agent, an immunomodulating agent, an imaging agent, a therapeutic agent (e.g. therapeutic protein), a biopolymer, and an oligonucleotide.

In some aspects of the invention, a drug can be linked or conjugated to the anti-CXCR4 antibody, or the antigen binding fragment thereof as described herein for targeted local delivery of the drug to tumors (e.g., CXCR4 expressing tumor). In particular aspects of the invention, the drug is a cytotoxic agent. Examples of a cytotoxic agent include, but are not limited to, an anthracycline, an auristatin, a camptothecin, a combretastain, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, calicheamicin, and stereoisomers, isosteres, analogs or derivatives thereof. In some aspects of the invention, the anthracyclines are derived from bacteria Strepomyces and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., Antimicrob. Agents Chemother. 42:2961-2965 (1998). Exemplary dolastatins and auristatins include, but are not limited to, dolastatin 10, auristatin E, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other novel auristatins (such as the ones described in U.S. Publication No. 20130129753).

In particular aspects of the invention, the auristatin is selected from the group consisting of 0101 (2-methylalanyl-N-[(3R,4S,5S)-3-methoxy-1-{(2S)-2-[(1R,2R)-1-methoxy-2-methyl-3-oxo-3-{[(1 S)-2-phenyl-1-(1,3-thiazol-2-yl)ethyl]amino}propyl]pyrrolidin-1-yl}-5-methyl-1-oxoheptan-4-yl]-N-methyl-L-valinamide), MMAD (Monomethyl Auristatin D or monomethyl dolastatin 10 and 8261(2-Methylalanyl-N-[(3R,4S,5S)-1-{(2S)-2-[(1R,2R)-3-{[(1 S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide).

In some aspects of the present invention, the auristatin is 0101 (2-methylalanyl-N-[(3R,4S,5S)-3-methoxy-1-{(2S)-2-[(1R,2R)-1-methoxy-2-methyl-3-oxo-3-{[(1 S)-2-phenyl-1-(1,3-thiazol-2-yl)ethyl]amino}propyl]pyrrolidin-1-yl}-5-methyl-1-oxoheptan-4-yl]-N-methyl-L-valinamide) having the following structure:

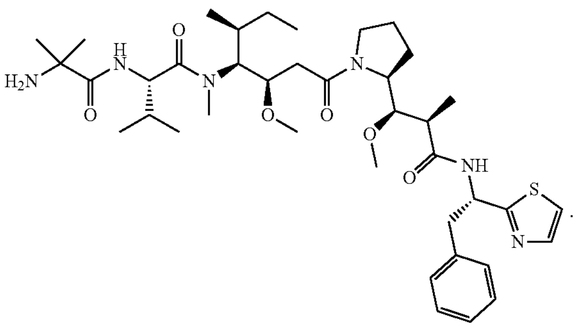 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)N)C(C)C]

In other aspects, the auristatin is 3377 (N,2-dimethylalanyl-N-{(1 S,2R)-4-{(2S)-2-[(1R,2R)-3-{[(1 S)-1-carboxyl-2-phenylethyl]amino}-1-methoxy-2-methyl-3-oxopropyl]pyrrolidin-1-yl}-2-methoxy-1-[(1 S)-1-methylpropyl]-4-oxobutyl}-N-methyl-L-valinamide) having the following structure:

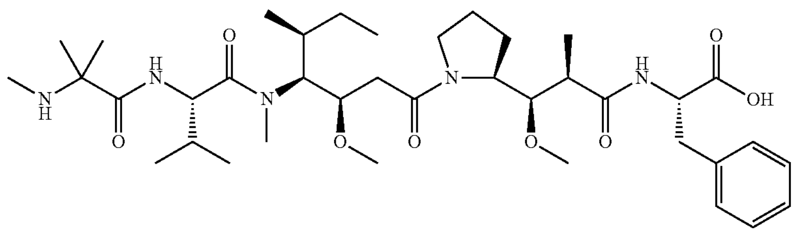 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)NC)C(C)C]

In other aspects of the invention, the auristatin is 0131 (2-methyl-L-proly-N-[(3R,4S,5S)-1-{(2S)-2-[(1R,2R)-3-{[(1 S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

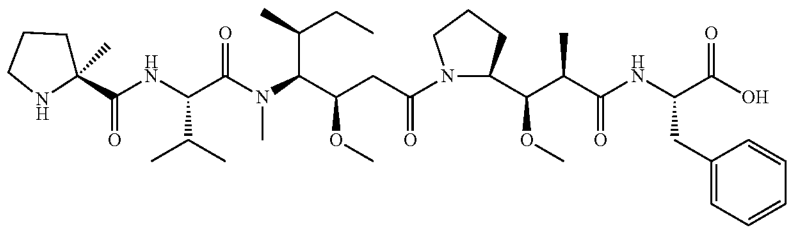 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCN1)C(C)C]

In some aspects, the auristatin is 0121 (2-methyl-L-proly-N-[(3R,4S,5S)-1-{(2S)-2-[(1R,2R)-3-{[(2S)-1-methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

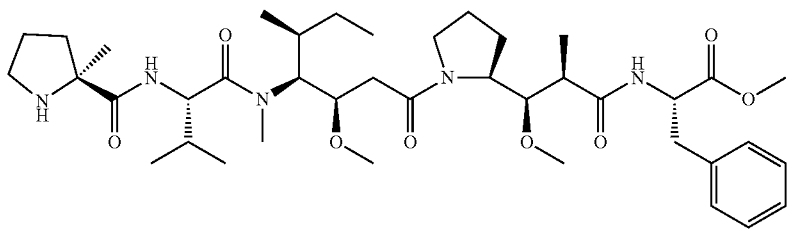 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@]1(C)CCCN1)C(C)C]

In other aspects, the auristatin is 8261, (8261 2-Methyl-alanyl-N-[(3R,4S,5S)-1-{(2S)-2-[(1R,2R)-3-{[(1 S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide), having the following structure:

$CF_3CO_2H$

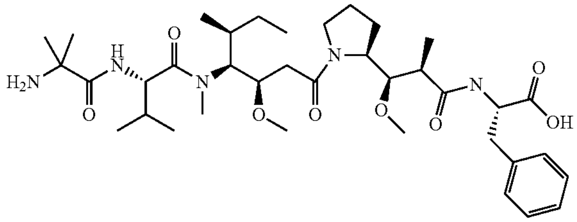

Camptothecin is a cytotoxic quinoline alkaloid which inhibits the enzyme topoisomerase I. Examples of camptothecin and its derivatives include, but are not limited to, topotecan and irinotecan, and their metabolites, such as SN-38.

Combretastatins are natural phenols with vascular disruption properties in tumors. Exemplary combretastatins and their derivatives include, but are not limited to, combretastatin A-4 (CA-4) and ombrabulin.

Duocarmycins are DNA alkylating agents with cytotoxic potency. See Boger and Johnson, PNAS 92:3642-3649 (1995). Exemplary duocarmycins include, but are not limited to, duocarmycin A, duocarmycin B1, duocarmycin B2, duocarmycin C1, duocarmycin C2, duocarmycin D, duocarmycin SA, and CC-1065. Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, and dynemicin.

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethylaminoethylamino-17-demethoxygeldanamycin).

Maytansines or their derivatives maytansinoids inhibit cell proliferation by inhibiting the microtubules formation during mitosis through inhibition of polymerization of tubulin. See Remillard et al., Science 189:1002-1005 (1975). Exemplary maytansines and maytansinoids include, but are not limited to, mertansine (DM1) and its derivatives as well as ansamitocin.

Pyrrolobenzodiazepine dimers (PBDs) and indolino-benzodiazepine dimers (IGNs) are anti-tumor agents that contain one or more immine functional groups, or their equivalents, that bind to duplex DNA. PBD and IGN molecules are based on the natural product athramycin, and interact with DNA in a sequence-selective manner, with a preference for purine-guanine-purine sequences. Exemplary PBDs and their analogs include, but are not limited to, SJG-136.

Spliceostatins and pladienolides are anti-tumor compounds which inhibit splicing and interacts with spliceosome, SF3b. Examples of spliceostatins include, but are not limited to, spliceostatin A, FR901464. Examples of pladienolides include, but are not limited to, Pladienolide B, Pladienolide D, and E7107.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Vinca alkyloids are also anti-tubulin agents. Exemplary vinca alkyloids include, but are not limited to, vincristine, vinblastine, vindesine, and vinorelbine.

In some aspects of the invention, the drug is an immunomodulating agent. Examples of an immunomodulating agent include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, cytokines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S 1 factor," erythropoietin and thrombopoietin, or a combination thereof.

In some aspects of the invention, the drug is an imaging agent (e.g., a fluorophore or a chelator), such as fluorescein, rhodamine, lanthanide phosphors, and their derivatives thereof. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101). Examples of chelators include, but are not limited to, 1,4,7,10-tetraazacyclododecane-N, N',N",N"'-tetraacetic acid (DOTA), 1,4,7-triazacyclononane-1,4,7-triacetic acid (NOTA), 1,4,7-triazacyclononane, 1-glutaric acid-4,7-acetic acid (NODAGA), diethylenetriaminepentaacetic acid (DTPA), and 1,2-bis(o-aminophenoxy) ethane-N,N,N',N'-tetraacetic acid) (BAPTA).

In some aspects of the invention, therapeutic or diagnostic radioisotopes or other labels (e.g., PET or SPECT labels) can be incorporated in the drug for conjugation to the anti-CXCR4 antibodies, or the antigen binding fragments as described herein. Examples of a radioisotope or other labels include, but are not limited to, $^{3}H$, $^{11}C$, $^{13}N$, $^{14}C$, $^{15}N$, $^{15}O$, $^{35}S$, $^{18}F$, $^{32}P$, $^{33}P$, $^{47}Sc$, $^{51}Cr$, $^{57}Co$, $^{58}Co$, $^{59}Fe$, $^{62}Cu$, $^{64}Cu$, $^{67}Cu$, $^{67}Ga$, $^{68}Ga$, $^{75}Se$, $^{76}Br$, $^{77}Br$, $^{86}Y$, $^{89}Zr$, $^{90}Y$, $^{94}Tc$, $^{95}Ru$, $^{97}Ru$, $^{99}Tc$, $^{103}Ru$, $^{105}Rh$, $^{105}Ru$, $^{107}Hg$, $^{109}Pd$, $^{111}Ag$, $^{111}In$, $^{113}In$, $^{121}Te$, $^{122}Te$, $^{123}I$, $^{124}I$, $^{125}I$, $^{125}Te$, $^{126}I$, $^{131}I$, $^{131}In$, $^{133}I$, $^{142}Pr$, $^{143}Pr$, $^{153}Pb$, $^{153}Sm$, $^{161}Tb$, $^{165}Tm$, $^{166}Dy$, $^{166}H$, $^{167}Tm$, $^{168}Tm$, $^{169}Yb$, $^{177}Lu$, $^{186}Re$, $^{188}Re$, $^{189}Re$, $^{197}Pt$, $^{198}Au$, $^{199}Au$, $^{201}Tl$, $^{203}Hg$, $^{211}At$, $^{212}Bi$, $^{212}Pb$, $^{213}Bi$, $^{223}Ra$, $^{224}Ac$, and $^{225}Ac$.

In some aspects of the invention, the drug is a therapeutic protein including, but is not limited to, a toxin, a hormone, an enzyme, and a growth factor.

Examples of a toxin protein (or polypeptide) include, but are not limited to, dipththeria (e.g., diphtheria A chain), *Pseudomonas* exotoxin and endotoxin, ricin (e.g., ricin A chain), abrin (e.g., abrin A chain), modeccin (e.g., modeccin A chain), alpha-sarcin, *Aleurites fordii* proteins, dianthin proteins, ribonuclease (RNase), DNase I, Staphylococcal enterotoxin-A, pokeweed antiviral protein, gelonin, diphtherin toxin, *Phytolaca americana* proteins (PAPI, PAPII, and PAP-S), *Momordica charantia* inhibitor, curcin, crotin, *Sapaonaria officinalis* inhibitor, mitogellin, restrictocin, phenomycin, enomycin, tricothecenes, inhibitor cystine knot (ICK) peptides (e.g., ceratotoxins), and conotoxin (e.g., KIIIA or SmIIIa).

In some aspects of the invention, the drug is a biocompatible polymer. The anti-CXCR4 antibodies or the antigen binding fragments as described herein can be conjugated to the biocompatible polymer to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

In some aspects of the invention, the drug is an oligonucleotide, such as antisense oligonucleotides.

In another aspect, the invention provides a conjugate of the antibody or the antigen binding fragment as described herein, wherein the antibody-drug conjugate comprises the formula: antibody-(acyl donor glutamine-containing tag)-(linker)-(drug), wherein the acyl donor glutamine-containing tag is engineered at a specific site of the antibody or the antigen binding fragment (e.g., at a carboxyl terminus of the heavy or light chain or at an another site), wherein the tag is conjugated to a linker (e.g., a linker containing one or more reactive amines (e.g., primary amine $NH_2$)), and wherein the linker is conjugated to a cytotoxic agent (e.g., MMAD or other auristatins as described herein). In some aspects of the invention, the antibody-drug conjugate does not comprise acyl donor glutamine-containing tag.

Examples of a linker containing one or more reactive amines include, but are not limited to, acetyl-lysine-valine-citrulline-p-aminobenzyloxycarbonyl (AcLys-VC-PABC) or amino PEG6-propionyl. See, e.g. WO2012/059882.

In some aspects of the invention, the linker can be a dipeptide linker, such as a valine-citrulline (val-cit), a phenylalanine-lysine (phe-lys) linker, or maleimidocapronic-valine-citruline-p-aminobenzyloxycarbonyl (vc) linker. In another aspect, the linker may be Sulfosuccinimidyl-4-[Nmaleimidomethyl] cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N terminus). Further, the linker may be maleimidocaproyl (mc). In some aspects of the invention, the acyl donor glutamine-containing tag comprises LLQGG (SEQ ID NO: 171), GGLLQGG (SEQ ID NO:90), LLQGA (SEQ ID NO:91), GGLLQGA (SEQ ID NO:92), LLQ, LLQGPGK (SEQ ID NO: 93), LLQGPG (SEQ ID NO: 94), LLQGPA (SEQ ID NO: 95), LLQGP (SEQ ID NO: 96), LLQP (SEQ ID NO: 97), LLQPGK (SEQ ID NO: 98), LLQGAPGK (SEQ ID NO: 99), LLQGAPG (SEQ ID NO: 100), LLQGAP (SEQ ID NO: 101), GGLLQGPP (SEQ ID NO: 172), LLQGPP (SEQ ID NO: 173), $LLQX_1X_2X_3X_4X_5$, wherein $X_1$ is G or P, wherein $X_2$ is A, G, P, or absent, wherein $X_3$ is A, G, K, P, or absent, wherein $X_4$ is K, G or absent, and wherein $X_5$ is K or absent (SEQ ID NO: 102), or $LLQX_1X_2X_3X_4X_5$, wherein $X_1$ is any naturally occurring amino acid and wherein $X_2$, $X_3$, $X_4$, and $X_5$ are any naturally occurring amino acids or absent (SEQ ID NO: 103).

In some aspects of the invention, the anti-CXCR4 antibody or the conjugate as described herein comprises an amino acid substitution from asparagine (N) to glutamine (Q) or from N to alanine (A) at position 297 of the anti-CXCR4 antibody.

In some aspects of the invention, the acyl donor glutamine-containing tag comprising, e.g., LLQ, SEQ ID NOs: 91, 90, 94, 95, 95, 97, 98, 99, 100, 171, 101, 172, or 173 is engineered at the C-terminus of the heavy chain of the antibody, wherein the lysine residue at the C-terminus is deleted. In other aspects, the acyl donor glutamine-containing tag (e.g., GGLLQGA (SEQ ID NO: 92)) is engineered at the C-terminus of the light chain of the antibody. Examples of the antibody include, but are not limited to, the m6B6, h6B6, m12A11, h12A11, m3G10, h3G10, h3G10.A57, h3G10.B44, h3G10.1.7, h3G10.1.60, h3G10.2.5, h3G10.1.91, h3G10.2.37, h3G10.2.45, h3G10.2.42, h3G10.1.33, h3G10.3.25, h3G10, h3G10.2.72, h3G10.A11A, h3G10.A18A, h3G10.A19A, h3G10.A58A, h3G10.A65A, and h3G10.B12A, h3G10.B13A, h3G10.B18A, h3G10.A11B, h3G10.A18B, h3G10.A19B, h3G10.A58B, h3G10.A65B, h3G10.B12B, h3G10.B13B, h3G10.B18B, h3G10.2.25, h3G10.A59, h3G10.A62 or h3G10.L94D.

In other aspects of the invention, the conjugate comprises the formula: antibody-(acyl donor glutamine-containing tag)-(L)-(cytotoxic agent). In some aspects of the invention, the conjugate is a) Ab-LLQGA (SEQ ID NO: 91)-(acetyl-lysine-valine-citrulline-p-aminobenzyloxycarbonyl (AcLys-VC-PABC))-0101; b) Ab-LLQGA (SEQ ID NO: 91)-(AcLys-VC-PABC)-M MAD; c) Ab-$LLQX_1X_2X_3X_4X_5$ (SEQ ID NO: 102)-(AcLys-VC-PABC)-0101; d) Ab-$LLQX_1X_2X_3X_4X_5$ (SEQ ID NO: 102)-(AcLys-VC-PABC)-MMAD; e) Ab-GGLLQGA (SEQ ID NO: 92)-(AcLys-VC-PABC)-0101; and f) Ab-GGLLQGA (SEQ ID NO: 92)-(AcLys-VC-PABC)-MMAD.

Examples of the antibody include, but are not limited to, the m6B6, h6B6, m12A11, h12A11, m3G10, h3G10, h3G10.A57, h3G10.B44, h3G10.1.7, h3G10.1.60, h3G10.2.5, h3G10.1.91, h3G10.2.37, h3G10.2.45, h3G10.2.42, h3G10.1.33, h3G10.3.25, h3G10, h3G10.2.72, h3G10.A11A, h3G10.A18A, h3G10.A19A, h3G10.A58A, h3G10.A65A, and h3G10.B12A, h3G10.B13A, h3G10.B18A, h3G10.A11B, h3G10.A18B, h3G10.A19B, h3G10.A58B, h3G10.A65B, h3G10.B12B, h3G10.B13B, h3G10.B18B, h3G10.2.25, h3G10.L94D, h3G10.A59, h3G10.A62 or h3G10.L94D.

In some aspects of the invention, Ab is an antibody or antigen-binding fragment thereof comprising a VH region comprising CDRs of SEQ ID NOs: 107, 162 and 112 and a VL region comprising CDRs of SEQ ID NOs: 144, 145 and 139.

In some aspects of the invention, the anti-CXCR4 antibody-drug conjugate induces tumor regression.

Methods of Using the Anti-CXCR4 Antibodies

Antigen-Binding Fragments Thereof or the Antibody-Drug Conjugates Thereof

The antibodies and antibody-drug conjugates of the present invention are useful in various applications including, but are not limited to, therapeutic treatment methods and diagnostic treatment methods.

In some aspects of the invention, when administered to a patient, the antibody or conjugate and pharmaceutically acceptable carriers are sterile. Water is an exemplary carrier when the compound or conjugate are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

The present compositions can take the form of solutions, pellets, powders, sustained-release formulations, or any other form suitable for use. Other examples of suitable pharmaceutical carriers are described in "Remington's Pharmaceutical Sciences" by E. W. Martin.

In some aspects, the antibody of the invention and/or antibody-drug conjugate thereof are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a compound of the invention and/or antibody-drug conjugate thereof is to be administered by infusion, it can be dispensed, for example, with an infusion bottle containing sterile pharmaceutical grade water or saline. Where the compound of the invention and/or antibody-drug conjugate thereof is administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer. In one aspect, the invention provides a method for treating a condition associated with CXCR4 expression in a subject. In some aspects of the invention, the method of treating a disorder associated with CXCR4 function or expression in a subject comprises administering to the subject in need thereof an effective amount of a composition (e.g., pharmaceutical composition) comprising the anti-CXCR4 antibodies, antigen-binding fragments thereof, or the anti-CXCR4 antibody-drug conjugates as described herein. The disorders associated with CXCR4 expression include, but are not limited to, abnormal CXCR4 expression, altered or aberrant CXCR4 expression, CXCR4 overexpression, and a proliferative disorder (e.g., cancer).

Accordingly, in some aspects provided is a method of treating a cancer in a subject comprising administering to the subject in need thereof an effective amount of a composition comprising an anti-CXCR4 antibody, antigen-binding fragments thereof or anti-CXCR4 antibody-drug conjugate as described herein. As used herein, cancers include, but are not limited to bladder, breast, cervical, choriocarcinoma, colon, esophageal, gastric, glioblastoma, head and neck, kidney, lung, oral, ovarian, pancreatic, prostate, skin and hematological cancer. In some aspects of the invention, provided is a method of decreasing tumor growth or progression in a subject who has a CXCR4 expressing tumor, comprising administering to the subject in need thereof an effective amount of a composition comprising an anti-CXCR4 antibody, or antigen-binding fragments thereof, or an anti-CXCR4 antibody-drug conjugate as described herein. In other aspects, provided is a method of decreasing metastasis of CXCR4 expressing cancer cells in a subject, comprising administering to the subject in need thereof an effective amount of a composition comprising an anti-CXCR4 antibody, antigen-binding fragments thereof, or an anti-CXCR4 antibody-drug conjugate as described herein. In other aspects, provided is a method of inducing regression of a CXCR4 expressing tumor regression in a subject, comprising administering to the subject in need thereof an effective amount of a composition comprising an anti-CXCR4 antibody, or antigen-binding fragments thereof, or an anti-CXCR4 antibody-drug conjugate as described herein.

In some aspects, the invention provides an isolated antibody, an antigen binding fragment or an antibody-drug conjugate of any one of antibodies as described herein for use in detecting, diagnosing and treating pathological disorders associated with function or expression of CXCR4. In one aspect, the disorders are oncogenic disorders associated with increased expression of CXCR4 relative to normal or any other pathology connected with the overexpression of CXCR4.

In some aspects of the invention, provided is a method of treating a cancer in a subject comprising administering to the subject in need thereof an effective amount of a composition comprising heavy chain variable (VH) region comprising (i) a VH CDR1 selected from the group consisting of SEQ ID NOs:107, 113, 114, 108, 109, 115, 116, 117, 121 and 122; (ii) a VH CDR2 selected from the group consisting of SEQ ID NOs: 162, 128, 110, 111, 118, 119, 154, 123, 158, 124, 159, 125, 160, 126, 161, 127, 163, 164, 165, 166, 167, 168, 155, 129, 156, and 130, and, (iii) a VH CDR3 selected from the group consisting of SEQ ID NOs: 112; and 120; and/or; b) a light chain variable region (VL) region comprising (i) a VL CDR1 selected from the group consisting of SEQ ID NOs: 144, 131, 135, 138, 141, 142, 143, 146, 147, 148, 149, 150, and 151; (ii) a VL CDR2 selected from the group consisting of 145, 132, 136, and 152; and (iii) a VL CDR3 selected from the group consisting of SEQ ID NO: 139, 133, 137, 140, and 153.

In some aspects of the invention, provided is a method of treating a cancer in a subject comprising administering to the subject in need thereof an effective amount of a composition comprising an antibody or antigen binding fragment thereof, wherein the antibody comprises: a heavy chain variable (VH) region comprising three CDRs set forth as SEQ ID NOs: 107, 162 and 112. In some aspects of the invention, provided is a method of treating a cancer in a subject comprising administering to the subject in need thereof an effective amount of a composition comprising an antibody or antigen binding fragment thereof, wherein the antibody comprises: a light chain variable (VL) region comprising three CDRs set forth as SEQ ID NOs: 144, 145 and 139.

In some aspects of the invention, provided is a method of treating a cancer in a subject comprising administering to the subject in need thereof an effective amount of a composition comprising an antibody or antigen binding fragment thereof of any one of the preceding claims, wherein the antibody comprises: heavy chain variable (VH) region comprising three CDRs set for as SEQ ID NOs: 107, 162 and 112; and a light chain variable (VL) region comprising three CDRs set forth as SEQ ID NOs: 144, 145 and 139.

In some aspects, the present invention provides a method of treating a cancer in a subject comprising administering to the subject in need thereof an effective amount of a composition comprising an isolated antibody, or an antigen binding fragment thereof, that binds to CXCR4 and comprises: a heavy chain variable (VH) region comprising VH CDR1, VH CDR2 and VH CDR3 from a VH region of SEQ ID NO: 33; and a light chain variable (VL) region comprising VL CDR1, VL CDR2 and VL CDR3 from a VL region of SEQ ID NO: 73.

In still other aspects, the present invention provides a method of treating a cancer in a subject comprising administering to the subject in need thereof an effective amount of a composition comprising an antibody or antigen binding fragment thereof of any one of the preceding claims, wherein the antibody comprises: a) a heavy chain variable (VH) region of SEQ ID NO: 33; and b) a light chain variable (VL) region of SEQ ID NO: 73.

In some aspects, the invention provides a use of an isolated antibody, an antigen binding fragment or an antibody-drug conjugate of any one of antibodies as described herein in the manufacture of a medicament for treating a disorder associated with CXCR4 function or expression. In one aspect, the disorders are oncogenic disorders associated with increased expression of CXCR4 relative to normal or any other pathology connected with the overexpression of CXCR4.

In other aspects of the invention, an anti-CXCR4 antibody-drug conjugate includes an antibody, or antigen-binding fragment thereof, having at least one heavy chain variable region and at least one light chain variable region, wherein the at least one heavy chain variable region includes three CDRs set forth as SEQ ID NOs: 107, 113, 114, 162, 128, and 112. In some aspects of the invention, an anti-CXCR4 antibody-drug conjugate includes an antibody, or antigen-binding fragment thereof, having at least one heavy chain variable region and at least one light chain variable region, wherein the at least one light chain variable region includes three CDRs set forth as SEQ ID NOs: 144, 145, and 139.

In some aspects of the invention, an antibody-drug conjugate, which binds to CXCR4, includes an antibody, or antigen-binding fragment thereof, having a heavy chain variable region set forth as any one of SEQ ID NOs: 33, 5, 9, 13, 17, 21, 23, 25, 27, 29, 31, 35, 37, 39, 41, 43, 45, 85, or 87, and/or a light chain variable region set forth as any one of SEQ ID NOs: 73, 3, 7, 11, 15, 19, 47, 49, 51, 53, 55, 57, 59, 61, 63, 65, 67, 69, 71, 75, 77, 79, 81, 83, or 169. For example, an anti-CXCR4 antibody-drug conjugate of the invention can include an antibody, or antigen-binding fragment thereof, having a heavy chain variable region having an amino acid sequence that is at least 90% identical to SEQ ID NO: 33 and a light chain variable region having an amino acid sequence that is at least 90% identical to SEQ ID NO: 73; or an antibody, or antigen-binding fragment thereof, having a heavy chain variable region set forth as SEQ ID NO: 33 and a light chain variable region having an amino acid sequence set forth as SEQ ID NO: 73.

In particular aspects of the invention, the antibody is not caninized or felinized.

The antibodies may also be modified, e.g. in the variable domains of the heavy and/or light chains, e.g., to alter a binding property of the antibody. For example, a mutation may be made in one or more of the CDR regions to increase or decrease the $K_D$ of an anti-CXCR4 antibody, to increase or decrease $k_{off}$, or to alter the binding specificity of the antibody. Techniques in site-directed mutagenesis are well-known in the art. See, e.g., Sambrook et al. and Ausubel et al., supra.

In some aspects of the invention, provided is a method of detecting, diagnosing, and/or monitoring a disorder associated with CXCR4 function or expression. For example, the anti-CXCR4 antibodies as described herein can be labeled with a detectable moiety such as an imaging agent and an enzyme-substrate label. The antibodies as described herein can also be used for in vivo diagnostic assays, such as in vivo imaging (e.g., PET or SPECT), or a staining reagent.

In one aspect of the invention, provided is a method of detecting, diagnosing, and/or monitoring a disorder associated with CXCR4 function or expression comprising the steps of: (i) obtaining a biological sample from a patient suspected of having a disorder associated with CXCR4 function or expression; (ii) contacting sample to be tested with the antibody or an antigen binding portion thereof under conditions that allow for formation of a complex between the antibody and the protein antigen CXCR4 (iii) detecting said antibody-protein antigen complex, wherein the presence of said detected antibody-protein antigen complex is indicative that said patient has a disorder associated with CXCR4 function or expression. In a particular aspect of the invention, the method further comprises administering to the patient a therapeutic effective amount of isolated antibody, antigen binding fragment, or antibody-drug conjugate of any one of antibodies as described herein.

In some aspects of the invention, an ADC can be used to target compounds (e.g. therapeutic agents, labels, cytotoxins, radiotoxins, immunossupressants, etc.) to cells which have CXCR4 cell surface receptors by linking such compounds to the antibody or a fragment there of. Thus, in some aspects of the invention, provided are methods for localizing ex-vivo or in vivo cells expressing CXCR4 (e.g. detectable label, such as radioisotope, fluorescent compound as enzyme. Alternatively the ADCs can be used to kill cells which have CXCR4 cell surface receptors by targeting cytotoxins or radiotoxins to CXCR4.

In some aspects of the invention, the methods described herein further comprise a step of treating a subject with an additional form of therapy. In some aspects, the additional form of therapy is an additional anti-cancer therapy including, but not limited to, chemotherapy, radiation, surgery, hormone therapy, and/or additional immunotherapy.

In some aspects of the invention, the additional form of therapy comprises administering one or more therapeutic agents in addition to an anti-CXCR4 antibody, antigen-binding fragments thereof, or an anti-CXCR4 antibody-drug conjugate as described herein. The therapeutic agents include, but are not limited to, a second antibody (e.g., an anti-VEGF antibody, an anti-HER2 antibody, anti-CD25 antibody, and/or an anti-CD20 antibody), an angiogenesis inhibitor, a cytotoxic agent, an anti-inflammatory agent (e.g., paclitaxel, docetaxel, cisplatin, doxorubicin, prednisone, mitomycin, progesterone, tamoxifen, or fluorouracil). In one aspect, the additional forms of therapy can administered simultaneously or sequentially or concurrently with an anti-CXCR4 antibody, antigen-binding fragments thereof, or an anti-CXCR4 antibody-drug conjugate as described herein.

The anti-CXCR4 antibody, antigen-binding fragments thereof, or anti-CXCR4 antibody-drug conjugate of the present invention can be administered to an individual via any suitable route. It should be understood by persons skilled in the art that the examples described herein are not intended to be limiting but to be illustrative of the techniques available. Accordingly, in some aspects of the invention, the anti-CXCR4 antibody, antigen-binding fragments thereof, or the anti-CXCR4 antibody-drug conjugate is administered to an individual in accord with known methods, such as intravenous administration, e.g., as a bolus or by continuous infusion over a period of time, by intramuscular, intraperitoneal, intracerebrospinal, intracranial, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, the anti-CXCR4 antibody, antigen-binding fragments thereof, or the anti-CXCR4 antibody-drug conjugate can be aerosolized using a fluorocarbon formulation and a metered dose inhaler, or inhaled as a lyophilized and milled powder. In some aspects of the invention, the anti-CXCR4 antibody, antigen-binding fragments thereof, or the anti-CXCR4 antibody-drug conjugate can be administered via inhalation, as described herein. In other aspects, the anti-CXCR4 antibody, antigen-binding fragments thereof, or the anti-CXCR4 antibody-drug conjugates of the present invention can be combined with pharmaceutically acceptable vehicles such as saline, Ringer's solution, dextrose solution, and the like. The particular dosage regimen, i.e., dose, timing and repetition, will depend on the particular individual and that individual's medical history.

In one aspect, the anti-CXCR4 antibody, antigen-binding fragments thereof, or the anti-CXCR4 antibody-drug conjugate is administered via site-specific or targeted local delivery techniques. Examples of site-specific or targeted local delivery techniques include various implantable depot sources of the anti-CXCR4 antibody, antigen-binding fragments thereof, or the anti-CXCR4 antibody-drug conjugate or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of the anti-CXCR4 antibody, antigen-binding fragments thereof, or the anti-CXCR4 antibody-drug conjugate may be used for administration. In some aspects of the invention, the anti-CXCR4 antibody, (antigen-binding fragments thereof, or the anti-CXCR4 antibody-drug conjugate) and a pharmaceutically acceptable excipient may be in various formulations. Some formulations of the present invention comprise pharmaceutically acceptable excipients. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

Generally, for administration of an anti-CXCR4 antibody, antigen-binding fragments thereof, and/or anti-CXCR4 antibody-drug conjugate, an initial candidate dosage can be about 2 mg/kg. For the purpose of the present invention, a typical daily dosage might range from about any of 3 μg/kg to 30 μg/kg to 300 μg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to inhibit or delay tumor growth/progression or metatstasis of cancer cells. An exemplary dosing regimen comprises administering an initial dose of about 2 mg/kg, followed by a weekly maintenance dose of about 1 mg/kg of the anti-CXCR4 antibody antigen-binding fragments thereof, or anti-CXCR4 antibody-drug conjugate, or followed by a maintenance dose of about 1 mg/kg every other week. Other exemplary dosing regimen comprises administering increasing doses (e.g., initial dose of 1 mg/kg and gradual increase to one or more higher doses every week or longer time period). Other dosage regimens may also be useful, depending on the pattern of pharmacokinetic decay that the practitioner wishes to achieve. For example, in some aspects, dosing from one to four times a week is contemplated. In other aspects dosing once a month or once every other month or every three months is contemplated. The progress of this therapy is easily monitored by conventional techniques and assays. The dosing regimen (including the anti-CXCR4 antibody, antigen-binding fragments thereof, or the anti-CXCR4 antibody-drug conjugate used) can vary over time.

For the purpose of the present invention, the appropriate dosage of an anti-CXCR4 antibody, antigen-binding fragments thereof, or an anti-CXCR4 antibody conjugate will depend on the anti-CXCR4 antibody, antigen-binding fragments thereof, or the CXCR4 antibody-drug conjugate (or compositions thereof) employed, the type and severity of symptoms to be treated, whether the agent is administered for therapeutic purposes, previous therapy, the patient's clinical history and response to the agent, the patient's clearance rate for the administered agent, and the discretion of the attending physician. Typically the clinician will administer an anti-CXCR4 antibody, antigen-binding fragments thereof, or an anti-CXCR4 antibody-drug conjugate until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., tumor growth inhibition or delay, etc. Alternatively, sustained continuous release formulations of anti-CXCR4 antibodies, antigen-binding fragments thereof, or anti-CXCR4 antibody-drug conjugates may be appropriate. Various formulations and devices for achieving sustained release are known in the art.

In some aspects of the invention, dosages for anti-CXCR4 antibody, antigen-binding fragments thereof, or anti-CXCR4 antibody-drug conjugate may be determined empirically in individuals who have been given one or more administration (s) of the anti-CXCR4 antibody, antigen-binding fragments thereof, or its anti-CXCR4 antibody-drug conjugate. Individuals are given incremental dosages of an anti-CXCR4 antibody, antigen-binding fragments thereof, or anti-CXCR4 antibody-drug conjugate. To assess efficacy, an indicator of the disease can be followed.

Administration of an anti-CXCR4 antibody, antigen-binding fragments thereof, or anti-CXCR4 antibody-drug conjugate in accordance with the method in the present invention can be continuous or intermittent, depending, for example, upon the recipient's physiological condition, whether the purpose of the administration is therapeutic or prophylactic, and other factors known to skilled practitioners. The administration of an anti-CXCR4 antibody, antigen-binding fragments thereof, or anti-CXCR4 antibody-drug conjugate may be essentially continuous over a preselected period of time or may be in a series of spaced doses.

In some aspects of the invention, more than one anti-CXCR4 antibody, antigen-binding fragments thereof, or anti-CXCR4 antibody-drug conjugate may be present. At least one, at least two, at least three, at least four, at least five different or more anti-CXCR4 antibody, antigen-binding fragments thereof, or anti-CXCR4 antibody-drug conjugate can be present. Generally, those anti-CXCR4 antibody, antigen-binding fragments thereof, or anti-CXCR4 antibody-drug conjugates may have complementary activities that do not adversely affect each other. For example, one or more of the following anti-CXCR4 antibody may be used: a first anti-CXCR4 antibody directed to one epitope on CXCR4 and a second anti-CXCR4 antibody directed to a different epitope on CXCR4.

Therapeutic formulations of the anti-CXCR4 antibody, antigen-binding fragments thereof, or anti-CXCR4 antibody-drug conjugate used in accordance with the present invention are prepared for storage by mixing an antibody having the desired degree of purity with optional pharmaceutically acceptable carriers, excipients or stabilizers (Remington, The Science and Practice of Pharmacy 21st Ed. Mack Publishing, 2005), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the anti-CXCR4 antibody, antigen-binding fragments thereof, or anti-CXCR4 antibody-drug conjugate are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 21st Ed. Mack Publishing, 2005.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic anti-CXCR4 antibody, antigen-binding fragments thereof, or anti-CXCR4 antibody-drug conjugate compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing an anti-CXCR4 antibody, antigen-binding fragments thereof, or anti-CXCR4 antibody-drug conjugate with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some aspects of the invention, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions

The compositions used in the methods of the invention comprise an effective amount of an anti-CXCR4 antibody, antigen-binding fragments thereof, or anti-CXCR4 antibody-drug conjugate as described herein. Examples of such compositions, as well as how to formulate, are also described in an earlier section and below. In some aspects of the invention, the composition comprises one or more anti-CXCR4 antibody, antigen-binding fragments thereof, or anti-CXCR4 antibody-drug conjugate. For example, the anti-CXCR4 antibody recognizes human CXCR4. In some aspects, the CXCR4 antibody is a human antibody, a CDR grafted, a humanized antibody, or a chimeric antibody. In other aspects, the anti-CXCR4 antibody comprises a constant region that is capable of triggering a desired immune response, such as antibody-mediated lysis or ADCC. In yet other aspects, the anti-CXCR4 antibody comprises a constant region that does not trigger an unwanted or undesirable immune response, such as antibody-mediated lysis or ADCC. In some aspects of the invention, the anti-CXCR4 antibody comprises one or more CDR(s) of an anti-CXCR4 antibody or an anti-CXCR4 or antigen-binding fragments thereof, as described herein (such as one, two, three, four, five, or, in some embodiments, all six CDRs).

It is understood that the compositions can comprise more than one anti-CXCR4 antibody, antigen-binding fragments thereof, or anti-CXCR4 antibody-drug conjugate (e.g., a mixture of anti-CXCR4 antibodies that recognize different epitopes of CXCR4). Other exemplary compositions comprise more than one anti-CXCR4 antibody, antigen-binding fragments thereof, or anti-CXCR4 antibody-drug conjugate that recognize the same epitope(s), or different species of anti-CXCR4 antibody, antigen-binding fragments thereof, or anti-CXCR4 antibody-drug conjugate that bind to different epitopes of CXCR4 (e.g., human CXCR4).

The composition used in the present invention can further comprise pharmaceutically acceptable carriers, excipients, or stabilizers (Remington: The Science and practice of Pharmacy 21st Ed., 2005, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

Kits

The invention also provides kits for use in the instant methods. Kits of the invention include one or more containers comprising an anti-CXCR4 antibody, antigen-binding fragments thereof, or anti-CXCR4 antibody-drug conjugate as described herein and instructions for use in accordance with any of the methods of the invention described herein. Generally, these instructions comprise a description of administration of the anti-CXCR4 antibody, antigen-binding fragments thereof, or anti-CXCR4 antibody-drug conjugate for the above described therapeutic treatments.

The instructions relating to the use of the anti-CXCR4 antibody, antigen-binding fragments thereof, or anti-CXCR4 antibody-drug conjugate, as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-CXCR4 antibody. The container may further comprise a second pharmaceutically active agent.

Kits may optionally provide additional components such as buffers and interpretive information. Normally, the kit comprises a container and a label or package insert(s) on or associated with the container.

Mutations and Modifications

To express the anti-CXCR4 antibodies or antigen-binding fragments thereof, of the present invention, DNA fragments encoding VH and VL regions can first be obtained using any of the methods described above. Various modifications, e.g. mutations, substitutions, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some aspects of the invention, the cysteine is canonical.

The antibodies may also be modified, e.g. in the variable domains of the heavy and/or light chains, e.g., to alter a binding property of the antibody. For example, a mutation may be made in one or more of the CDR regions to increase or decrease the $K_D$ of the antibody for CXCR4, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of an anti-CXCR4 antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

In a process known as “germlining”, certain amino acids in the VH and VL sequences can be mutated to match those found naturally in germline VH and $V_L$ sequences. In particular, the amino acid sequences of the framework regions in the $V_H$ and VL sequences can be mutated to match the germline sequences to reduce the risk of immunogenicity when the antibody is administered. Germline DNA sequences for human VH and VL genes are known in the art (see e.g., the “Vbase” human germline sequence database; see also Kabat, E. A., et al. (1991), Sequences of Proteins of Immunological Interest, Fifth Edition, U.S. Department of Health and Human Services, NIH Publication No. 91-3242; Tomlinson et al., J. Mol. Biol. 227:776-798 (1992); and Cox et al., Eur. J. Immunol. 24:827-836 (1994).

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of an anti-CXCR4 antibody of the invention can be cleaved. In various aspects of the invention, the heavy and light chains of the anti-CXCR4 antibodies may optionally include a signal sequence.

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term “operatively linked”, as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG2 constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the $V_H$-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH and VL encoding DNA fragments are operatively linked to another fragment encoding a flexible linker, e.g., encoding the amino acid sequence $(Gly_4\text{-}Ser)_3$, (SEQ ID NO: 80) such that the VH and VL sequences can be expressed as a contiguous single-chain protein, with the VL and VH regions joined by the flexible linker (See e.g., Bird et al., Science 242:423-426 (1988); Huston et al., Proc. Natl. Acad. Sci. USA 85:5879-5883 (1988); McCafferty et al., Nature 348:552-554 (1990). The single chain antibody may be monovalent, if only a single VH and VL are used, bivalent, if two VH and VL are used, or polyvalent, if more than two VH and VL are used. Bispecific or polyvalent antibodies may be generated that bind to CXCR4 and to another molecule.

In some aspects of the invention, a fusion antibody or immunoadhesin may be made that comprises all or a portion of an anti-CXCR4 antibody of the invention linked to another polypeptide. In other aspects, only the variable domains of the anti-CXCR4 antibody are linked to the polypeptide. In some aspects of the invention, the VH domain of an anti-CXCR4 antibody is linked to a first polypeptide, while the VL domain of an anti-CXCR4 antibody is linked to a second polypeptide that associates with the first polypeptide in a manner such that the VH and VL domains can interact with one another to form an antigen binding site. In other aspects, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In some aspects of the invention, other modified antibodies may be prepared using anti-CXCR4 antibody encoding nucleic acid molecules. For instance, "Kappa bodies" (111 et al., Protein Eng. 10:949-57 (1997)), "Minibodies" (Martin et al., EMBO J., 13:5303-9 (1994)), "Diabodies" (Holliger et al., Proc. Natl. Acad. Sci. USA 90:6444-6448 (1993)), or "Janusins" (Traunecker et al., EMBO J. 10:3655-3659 (1991) and Traunecker et al., Int. J. Cancer (Suppl.) 7:51-52 (1992)) may be prepared using standard molecular biological techniques following the teachings of the specification.

Bispecific antibodies or antigen binding fragments can be produced by a variety of methods including fusion of hybridomas or linking of Fab' fragments. See, e.g., Songsivilai & Lachmann, Clin. Exp. Immunol. 79:315-321 (1990), Kostelny et al., J. Immunol. 148:1547-1553 (1992). In addition, bispecific antibodies may be formed as "diabodies" or "Janusins." In some aspects of the invention, the bispecific antibody binds to two different epitopes of CXCR4. In some aspects, the modified antibodies described above are prepared using one or more of the variable domains or CDR regions from the anti-CXCR4 antibodies provided herein.

In one aspect, the present invention comprises the use of mulitspecific antibodies. A multispecific antibody is an antibody that can bind simultaneously to at least two targets that are of different structure, e.g., two different antigens, two different epitopes on the same antigen, or a hapten and/or an antigen or epitope. Multispecific, multivalent antibodies are constructs that have more than one binding site, and the binding sites are of different specificity.

Representative materials of the present invention were deposited in the American Type Culture Collection (ATCC) on Jun. 19, 2014. A vector having ATCC Accession No. PTA-121353 is a polynucleotide encoding a humanized anti-CXCR4 antibody heavy chain variable region, and vector having ATCC Accession No. PTA-121354 is a polynucleotide encoding a humanized anti-CXCR4 antibody light chain variable region. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The invention also relates to the use of these anti-CXCR4 antibodies, e.g., full-length antibodies, antigen binding fragments thereof, or anti-CXCR4 antibody-drug conjugates and pharmaceutical compositions comprising the CXCR4 receptor antibodies e.g., full-length antibodies or antigen binding fragments thereof, in the treatment of diseases and conditions associated with CXCR4 modulation such as bone marrow transplantation, chemosensitization, cancer, metastatic disease (e.g., cancer), auto-immune disease (e.g., rheumatoid arthritis), fibrosis disease (e.g., pulmonary), AIDS infection, cardiovascular disease, uveitis, inflammatory diseases, celiac disease HIV infection and stem cell-based regenerative medicine.

Cancer

CXCR4 receptor is over-expressed in a large number of cancers including but not limited to breast (Muller, A. et al. Nature 410:50-56 (2001)); ovarian (Scotton, C. et al. Br. J. Cancer 85:891-897 (2001); prostate (Taichman, R. S. et al. Cancer Res. 62:1832-1837 (2002); non-small cell lung (Spano J. P. et al. Ann. Oncol. 15:613-617 (2004)); pancreatic (Koshiba, T. et al. Clin. Cancer Res. 6:3530-3535 (2000)); thyroid (Hwang, J. H. et al. J. Clin. Endocrinol. Metab. 88:408-416 (2003)); nasopharyngeal carcinoma (Wang, N. et al. J. Transl. Med. 3:26-33 (2005)); melanoma (Scala, S. et al. Clin. Cancer Res. 11:1835-1841 (2005)); renal cell carcinoma (Staller, P. et al. Nature 425:307-311 (2003)); lymphoma (Bertolini, F. et al. Cancer Res. 62:3530-3535 (2002)); neuroblastoma (Geminder, H. et al. J. Immunol. 167:4747-4757 (2001)); glioblastoma (Rempel, S. A. et al. Clin. Cancer Res. 6:102-111 (2000)); rhabdomyosarcoma (Libura, J. et al. Blood 100:2597-2606 (2002)); colorectal (Zeelenberg, I. S. et al. Cancer Res. 63:3833-3839 (2003)); kidney (Schrader, A. J. et al. Br. J. Cancer 86:1250-1256 (2002)); osteosarcoma (Laverdiere, C. et al. Clin. Cancer Res. 11:2561-2567 (2005)); acute lymphoblastic leukemia (Crazzolara, R. et al. Br. J. Haematol. 115:545-553 (2001)); and acute myeloid leukemia (Rombouts, E. J. C. et al. Blood 104:550-557 (2004)).

In view of the foregoing, the anti-CXCR4 antibody, antigen-binding fragments thereof, or anti-CXCR4 antibody-drug conjugate of this disclosure can be used in the treatment of cancers, including but not limited to breast, ovarian, prostate, non-small cell lung, pancreatic, thyroid, nasopharyngeal carcinoma, melanoma, renal cell carcinoma, lymphoma, neuroblastoma, glioblastoma, rhabdomyosarcoma, colorectal, kidney, osteosarcoma, acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), Hodgkin's lymphoma, mantle cell lymphoma (MCL), follicular lymphoma, Waldenstrom's macroglobulinemia (WM), and B-cell lymphoma and diffuse large B-cell lymphoma (DLBCL). The antibody can be used alone or in combination with other cancer treatments, such as surgery and/or radiation, and/or with other anti-neoplastic agents, such as the anti-neoplastic agents discussed and set forth above, including chemotherapeutic drugs and other anti-tumor antigen antibodies, such as those that bind CD20, Her2, PSMA, Campath-1, EGFR and the like.

In some aspects, the anti-CXCR4 antibodies of the present invention can be used in combination with anti CD22 or anti CD33 antibodies, antibody-drug conjugates or compositions comprising such antibodies. For example, anti-CXCR4 antibodies of the present invention can be combined with inotuzumab ozogamicin or gemtuzumab ozogamicin (Mylotarg®).

"Combination therapy" or administration "in combination with" one or more further therapeutic agents includes simultaneous, concurrent, and consecutive administration in any order. The administration of the constituents of the combined preparations of the present invention can be made simultaneously, separately or sequentially.

According to the present invention there is provided a method for the treatment of cancers, comprising the simultaneous, concurrent or consecutive administration of anti-CXCR4 antibodies of the present invention and inotuzumab ozogamicin. For example, anti-CXCR4 antibodies can be administered before or after or simultaneously with inotuzumab ozogamicin. Additionally, the present invention provides herein a method for the treatment of cancers, such as AML, comprising the simultaneous, concurrent or consecutive administration of anti-CXCR4 antibodies of the present invention and Mylotarg. For example, anti-CXCR4 antibodies can be administered before or after or simultaneously with Mylotarg.

The anti-CXCR4 antibody, or a fragment thereof, can be conjugated to a therapeutic moiety and/or diagnostic agent, such as a cytotoxin, a drug (e.g., an immunosuppressant) or a radiotoxin. Such conjugates are referred to herein as antibody-drug conjugates. Antibody-drug conjugates can include one or more cytotoxins.

In some aspects of the invention, the treatment comprises administering an anti-CXCR4 antibody, antigen binding fragment thereof, or anti-CXCR4 antibody-drug conjugate of the present invention with one or more bioactive agents selected from antibodies, growth factors, hormones, cytokines, anti-hormones, xanthines, interleukins, interferons, and cytotoxic drugs. In particular aspects of the invention, the bioactive agent is an antibody, and is directed against a cell surface antigen expressed on B-cell malignancies.

In some aspects of the invention, the antibody directed against cell surface antigens expressed on B-cell malignancies is selected from a group consisting of anti-CD19, anti-CD20 and anti-CD33 antibodies. Such antibodies include the anti-CD20 antibody, rituximab (Rituxan™).

In some aspects of the invention, the bioactive agents are cytokines or growth factors and include, but are not limited to, interleukin 2 (IL-2), TNF, CSF, GM-CSF and G-CSF. In particular aspects of the invention, bioactive agents are hormones and include estrogens, androgens, progestins, and corticosteroids.

In some aspects of the invention, the drug is a drug selected from doxorubicin, daunorubicin, idarubicin, aclarubicin, zorubicin, mitoxantrone, epirubicin, carubicin, bendamustine, bevacizumab, bortesomib, lenalidomide, melphalan, nogalamycin, menogaril, pitarubicin, valrubicin, cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, adriamycin, cisplatin, carboplatin, cyclophosphamide, dacarbazine, vinblastine, vincristine, mitoxantrone, bleomycin, mechlorethamine, prednisone, procarbazine methotrexate, flurouracils, etoposide, taxol, taxol analogs, and mitomycin.

In some aspects of the invention, the therapeutically effective dose of the anti-CXCR4 antibody, a fragment thereof, or the anti-CXCR4 antibody-drug conjugateof the present invention is administered together with one or more combinations of tyrosine kinase inhibitors. Tyrosine kinase inhibitors include both protein and non-protein moieties. A tyrosine kinase inhibitor may be, for example, an antibody, a receptor ligand, or a small molecule inhibitor. Examples of tyrosine kinase inhibitors suitable for use in the methods of the present invention include, but are not limited to, gefitinib, sunitinib, erlotinib, lapatinib, canertinib, semaxinib, vatalanib, sorafenib, imatinib, dasatinib, leflunomide, vandetanib, derivatives thereof, analogs thereof, and combinations thereof. Additional tyrosine kinase inhibitors suitable for use in the present invention are as described, for example, in U.S. Pat. Nos. 5,618,829; 5,639,757; 5,728,868; 5,804,396; 6,100,254; 6,127,374; 6,245,759; 6,306,874; 6,313,138; 6,316,444, 6,329,380; 6,344,459; 6,420,382; 6,479,512; 6,498,165; 6,544,988; 6,562,818; 6,586,423; 6,586,424; 6,740,665; 6,794,393; 6,875,767, 6,927,293; and 6,958,340.

In some aspects, the therapeutically effective dose of the anti-CXCR4 antibody, a fragment thereof, or the anti-CXCR4 antibody-drug conjugate of the present invention is administered together with one or more combinations of drugs as a part of a treatment regimen, wherein the combination of cytotoxic agents is selected from: CHOPP (cyclophosphamide, doxorubicin, vincristine, prednisone, and procarbazine); CHOP (cyclophosphamide, doxorubicin, vincristine, and prednisone); COP (cyclophosphamide, vincristine, and prednisone); CAP-BOP (cyclophosphamide, doxorubicin, procarbazine, bleomycin, vincristine, and prednisone); m-BACOD (methotrexate, bleomycin, doxorubicin, cyclophosphamide, vincristine, dexamethasone, and leucovorin); ProMACE-MOPP (prednisone, methotrexate, doxorubicin, cyclophosphamide, etoposide, leucovorin, mechloethamine, vincristine, prednisone, and procarbazine); ProMACE-CytaBOM (prednisone, methotrexate, doxorubicin, cyclophosphamide, etoposide, leucovorin, cytarabine, bleomycin, and vincristine); MACOP-B (methotrexate, doxorubicin, cyclophosphamide, vincristine, prednisone, bleomycin, and leucovorin); MOPP (mechloethamine, vincristine, prednisone, and procarbazine); ABVD (adriamycin/doxorubicin, bleomycin, vinblastine, and dacarbazine); MOPP (mechloethamine, vincristine, prednisone and procarbazine) alternating with ABV (adriamycin/doxorubicin, bleomycin, and vinblastine); MOPP (mechloethamine, vincristine, prednisone, and procarbazine) alternating with ABVD (adriamycin/doxorubicin, bleomycin, vinblastine, and dacarbazine); ChlVPP (chlorambucil, vinblastine, procarbazine, and prednisone); IMVP-16 (ifosfamide, methotrexate, and etoposide); MIME (methyl-gag, ifosfamide, methotrexate, and etoposide); DHAP (dexamethasone, high-dose cytaribine, and cisplatin); ESHAP (etoposide, methylpredisolone, high-dose cytarabine, and cisplatin); CEPP(B) (cyclophosphamide, etoposide, procarbazine, prednisone, and bleomycin); CAMP (lomustine, mitoxantrone, cytarabine, and prednisone); CVP-1 (cyclophosphamide, vincristine, and prednisone), ESHOP (etoposide, methylprednisolone, high-dose cytarabine, vincristine and cisplatin); EPOCH (etoposide, vincristine, and doxorubicin for 96 hours with bolus doses of cyclophosphamide and oral prednisone), ICE (ifosfamide, cyclophosphamide, and etoposide), CEPP(B) (cyclophosphamide, etoposide, procarbazine, prednisone, and bleomycin), CHOP-B. (cyclophosphamide, doxorubicin, vincristine, prednisone, and bleomycin), CEPP-B (cyclophosphamide, etoposide, procarbazine, and bleomycin), and P/DOCE (epirubicin or doxorubicin, vincristine, cyclophosphamide, and prednisone).

In some aspects of the invention, the drug can be administered simultaneously or sequentially or concurrently with the anti-CXCR4 antibody, antigen-binding fragment thereof, or anti-CXCR4 antibody-drug conjugate as described herein. For example, the anti-CXCR4 antibody, antigen binding fragment thereof, or anti-CXCR4 antibody-drug-conjgate can be administered prior to the administration of one or more combinations of cytotoxic agents as a part of a treatment regimen. In some aspects of the invention, the therapeutically effective does of the anti-CXCR4 antibody, antigen binding fragment thereof, or anti-CXCR4 antibody-drug conjugate is administered subsequent to the administration of one or more combinations of cytotoxic agents as part of a treatment regimen.

In some aspects of the invention, the anti-CXCR4 antibody, antigen binding fragment thereof, or anti-CXCR4 antibody-drug conjugate is administered together with one or more combinations of cytotoxic agents as part of a treatment regimen.

The anti-CXCR4 antibody, antigen binding fragment thereof, or anti-CXCR4 antibody-drug conjugate of the present invention also can be administered in conjunction with nondrug treatments, such as surgery, radiation therapy, chemotherapy, immunotherapy and diet/exercise regimens. The other therapy may be administered before, concurrent with, or after treatment with the anti-CXCR4 antibody, a antigen binding fragment thereof, or anti-CXCR4 antibody-drug conjugate of the present invention. There may also be a delay of several hours, days and in some instances weeks between the administration of the different treatments, such that the anti-CXCR4 antibody, antigen binding fragment thereof, or anti-CXCR4 antibody-drug conjugate of the present invention may be administered before or after the other treatment.

Therapeutic Use of CXCR4

In accordance with various aspects of the invention, anti-CXCR4 antibodies, antigen-binding fragments thereof, or anti-CXCR4 antibody-drug may be used to treat, or produce medicaments to treat, a variety of disorders including various cancers, inflammatory disorders, allergic disorders, infections (HIV infection, etc.), auto-immune disorders (e.g., rheumatoid arthritis), fibrosis disorders (e.g., pulmonary), and cardiovascular disorders. Cancer disorders include solid tumor cancers (e.g., gastric, head and neck, lung, ovarian, and pancreatic cancers) and hematological cancers (e.g., Myelodysplastic syndromes, myeloproliferative disorders, and acute leukemias). Examples of hematopoietic disorders include non-B lineage derived, such as acute myeloid leukemia (AML), Chronic Myeloid Leukemia (CML), non-B cell acute lymphocytic leukemia (ALL), myelodysplastic disorders, myeloproliferative disorders, polycythemias, thrombocythemias, or non-B atypical immune lymphoproliferations. Examples of B-Cell or B cell lineage derived disorder include Chronic Lymphocytic Leukemia (CLL), B lymphocyte lineage leukemia, Multiple Myeloma, acute lymphoblastic leukemia (ALL), B-cell prolymphocytic leukemia, precursor B lymphoblastic leukemia, hairy cell leukemia or plasma cell disorders, e.g., amyloidosis or Waldenstrom's macroglobulinemia.

Hematological Disorders

Hematological disorders comprise diseases of the blood and all its constituents as well as diseases of organs and tissues involved in the generation or degradation of all the constituents of the blood. In some aspects of the invention, the hematological disorder include but are not limited to acute lymphocytic leukemia (ALL), acute myeloid leukemia (AML), chronic lymphocytic leukemia (CLL), small lymphocytic lymphoma (SLL), multiple myeloma (MM), non-Hodgkin's lymphoma (NHL), Hodgkin's lymphoma, mantle cell lymphoma (MCL), follicular lymphoma, Waldenstrom's macroglobulinemia (WM), B-cell lymphoma and diffuse large B-cell lymphoma (DLBCL). NHL may include indolent Non-Hodgkin's Lymphoma (iNHL) or aggressive Non-Hodgkin's Lymphoma (aNHL). In certain aspects, subjects are relapsed or refractory from other treatment. In certain aspects, subjects are relapsed or refractory from at least two or more other treatments. In some aspects of the invention, subjects are relapsed or refractory from at least three or more other treatments. In some aspects of the invention, subjects are relapsed or refractory from at least five or more other treatments.

The present invention contemplates the use of anti-CXCR4 antibody, antigen-binding fragment thereof, or anti-CXCR4 antibody-drug conjugate comprising anti-CXCR antibodies as the primary therapeutic composition for treatment of hematological disorders. Such composition can contain polyclonal anti-CXCR4 or monoclonal anti-CXCR4 antibodies. In addition, a therapeutic composition of the present invention can contain a mixture of monoclonal anti-CXCR4 antibodies directed to different, non-blocking CXCR4 epitopes or mixture of anti-CXCR4 antibody-drug conjugate or mixture of monoclonal anti-CXCR4 and anti-CXCR4 antibody-drug conjugates.

Chronic Lymphocytic Leukemia

CLL cells express high levels of CXCR4. (Burger J A, Burger M, Kipps T J. Chronic lymphocytic leukemia B cells express functional CXCR4 chemokine receptors that mediate spontaneous migration beneath bone marrow stromal cells. Blood. 94:3658-3667 (1999)). The present invention contemplates the use of an anti-CXCR4 antibody, antigen-binding fragment thereof, or anti-CXCR4 antibody-drug conjugate comprising an anti-CXCR antibody as the primary therapeutic composition for treatment of B-cell chronic lymphocytic leukemia (CLL). Such composition can contain polyclonal anti-CXCR4 or monoclonal anti-CXCR4 antibodies or mixture of polyclonal anti-CXCR4 or monoclonal anti-CXCR4 antibodies. In addition, a therapeutic composition of the present invention can contain a mixture of monoclonal anti-CXCR4 antibodies directed to different, non-blocking CXCR4 epitopes or mixture of anti-CXCR4 antibody-drug conjugates or mixture of monoclonal anti-CXCR4 and anti-CXCR4 antibody-drug conjugates.

Other B Cell Lymphomas

CXCR4 expression has been demonstrated in B-cell (Burger et. al., Chronic lymphocytic leukemia B cells express functional CXCR4 chemokine receptors that mediate spontaneous migration beneath bone marrow stromal cells. Blood. 94:3658-3667 (1999)). and T-cell (Trentin L, Agostini C, Facco M, et al. The chemokine receptor CXCR4 is expressed on malignant B cells and mediates chemotaxis. J Clin Invest. 104:115-121 (1999)) non-Hodgkin lymphoma (NHL). Malignant B cells from patients with B-NHL express functional CXCR4 receptors. The distinct pattern of chemokine receptor expression is thought to be involved in lymphoma cell trafficking and homing and may allow to distinguish different NHL subsets. (Jones D, Benjamin R J, Shahsafaei A, Dorfman D M. The chemokine receptor CXCR4 is expressed in a subset of B-cell lymphomas and is a marker of B-cell chronic lymphocytic leukemia. Blood. 95:627-632 (2000)). In an animal model, mice were challenged with T-cell hybridoma cells that were engineered to retain CXCR4 within the cytoplasm. In another mouse model of human high-grade NHL, CXCR4 neutralization by monoclonal antibodies inhibited homing of circulating NHL cells and improved survival. (Bertolini F, Dell'Agnola C, Mancuso P, et al. CXCR4 neutralization, a novel therapeutic approach for non-Hodgkin's lymphoma. Cancer Res. 62:3106-3112 (2002)) therefore suggested CXCR4 neutralization as a novel therapeutic approach in NHL. The present invention contemplates the use of anti-CXCR4 antibody, antigen-binding fragment thereof, or anti-CXCR4 antibody-drug conjugate comprising anti anti-CXCR4 antibodies as the primary therapeutic composition for treatment of B-cell chronic B cell lymphomas. Such composition can contain polyclonal anti-CXCR4 or monoclonal anti-CXCR4 antibodies. In addition, a therapeutic composition of the present invention can contain a mixture of monoclonal anti-CXCR4 antibodies directed to different, non-blocking CXCR4 epitopes or mixture of anti-CXCR4 antibody-drug conjugate or mixture of monoclonal anti-CXCR4 and anti-CXCR4 antibody-drug conjugates.

CXCR4 in Multiple Myeloma

Multiple myeloma (MM) is by large incurable neoplasm of plasma cells. Chemokine receptor CXCR4 is expressed by the majority of patients' MM cells. It promotes myeloma cell migration and homing to the bone marrow (BM) compartment, supports the tumor cells survival and protects the myeloma cells from chemotherapy-induced apoptosis. Accordingly, anti-CXCR4 antibody, antigen-binding fragment thereof, or anti-CXCR4 antibody-drug conjugate comprising an anti-CXCR antibody of the present invention that inhibits CXCR4 activity (e.g., antagonist antibodies) can be used in the treatment of hematological disorders, such as multiple myeloma. In addition, a therapeutic composition of the present invention can contain a mixture of monoclonal anti-CXCR4 antibodies directed to different, non-blocking CXCR4 epitopes or mixture of anti-CXCR4 antibody-drug conjugate or mixture of monoclonal anti-CXCR4 and anti-CXCR4 antibody-drug conjugate.

CXCR4 in Acute Leukemias

Because CXCR4 plays a critical role for retention of hematopoietic progenitors in the marrow, several groups have examined the role played by CXCR4 in progenitor cell leukemias. Precursor-B-cell acute lymphoblastic leukemia (ALL) expresses functional CXCR4 receptors (Bradstock K F, Makrynikola V, Bianchi A, Shen W, Hewson J, Gottlieb D J. Effects of the chemokine stromal cell-derived factor-1 on the migration and localization of precursor-B acute lymphoblastic leukemia cells within bone marrow stromal layers. Leukemia. 14:882-888 (2000)) that participate in homing of leukemia cells to the marrow in nonobese diabetic severe combined immunodeficient (NOD/SCID) mice. (Shen W, Bendall L J, Gottlieb D J, Bradstock K F. The chemokine receptor CXCR4 enhances integrin-mediated in vitro adhesion and facilitates engraftment of leukemic precursor-B cells in the bone marrow. Exp Hematol. 29:1439-1447 (2001).) In an elegant animal model, Sipkins et al (Sipkins D A, Wei X, Wu J W, et al. In vivo imaging of specialized bone marrow endothelial microdomains for tumour engraftment. Nature. 435: 969-973 (2005)) provided direct evidence that functional CXCR4 is necessary for the homing of ALL cells to the marrow microenvironment. The present invention contemplates the use of anti-CXCR4 antibody, antigen-binding fragment thereof, or anti-CXCR4 antibody-drug conjugate comprising anti-CXCR antibodies as the primary therapeutic composition for treatment of acute lymphoblastic leukemia (ALL). Such composition can contain polyclonal anti-CXCR4 or monoclonal anti-CXCR4 antibodies.

In addition, a therapeutic composition of the present invention can contain a mixture of monoclonal anti-CXCR4 antibodies directed to different, non-blocking CXCR4 epitopes or mixture of anti-CXCR4 antibody-drug conjugates or mixture of monoclonal anti-CXCR4 and anti-CXCR4 antibody-drug conjugates.

CXCR4 in Acute Myeloqenous Leukemia (AML)

Despite a general sensitivity to chemotherapy, long-term disease-free survival in AML remains low because a majority of patients relapse from minimal residual disease (MRD). CXCR4 appear to be central regulators of survival signals that account for anti-cancer drug resistance. This concept is supported by the finding that high-level expression of CXCR4 by leukemia cells is an adverse prognostic indicator in AML. Spoo A C, Wierda W G, Burger J A. The CXCR4 score: a new prognostic marker in acute myelogenous leukemia [abstract]. Blood. 104:304a (2004). The present invention contemplates the use of anti-CXCR4 antibody, antigen-binding fragment thereof, or anti-CXCR4 antibody-drug conjugate comprising anti-CXCR antibodies as the primary therapeutic composition for treatment of acute myelogenous leukemia (AML)._Such composition can contain polyclonal anti-CXCR4 or monoclonal anti-CXCR4 antibodies.

In addition, a therapeutic composition of the present invention can contain a mixture of monoclonal anti-CXCR4 antibodies directed to different, non-blocking CXCR4 epitopes or mixture of anti-CXCR4 antibody-drug conjugates or mixture of monoclonal anti-CXCR4 and anti-CXCR4 antibody-drug conjugates.

CXCR4 in Non-Hematopoietic Cancers

One of the most intriguing and perhaps important roles that chemokines and the chemokine receptors have is to regulate metastasis of solid tumors. CXCR4 is one of the best studied chemokine receptors, which selectively binds to the CXC chemokine stromal cell-derived factor 1 (SDF-1), also known as CXCL12 (Fredriksson et. al., Mol Pharmacol. 63:1256-72 (2003)). To date, CXCR4 have been demonstrated to be overexpressed in over 20 human malignancies, including breast cancer, prostate cancer, kidney cancer, colon cancer, thyroid cancer and pancreatic cancer (Miller et al., Nature 410: 50-6 (2001); Akashi et al. Cancer Sci. 99(3):539-542 (2008); Marechal et al. Br J Cancer, 100, 1444-51 (2009); Wang et al., Clin Exp Metastasis, 26, 1049-54. (2009); He X et al., Pathol Res Pract, 206, 712-5. (2010)).

The present invention contemplates the use of an anti-CXCR4 antibody, antigen-binding fragment thereof, or anti-CXCR4 antibody-drug conjugate comprising anti-CXCR antibodies as the primary therapeutic composition for treatment of non-hematopoietic cancers. Such composition can contain polyclonal anti-CXCR4 or monoclonal anti-CXCR4 antibodies. In addition, a therapeutic composition of the present invention can contain a mixture of monoclonal anti-CXCR4 antibodies directed to different, non-blocking CXCR4 epitopes or mixture of anti-CXCR4 antibody-drug conjugates or mixture of monoclonal anti-CXCR4 and anti-CXCR4 antibody-drug conjugates.

CXCR4 in Breast Cancer

High-level expression of CXCR4 on neoplastic cells is associated with relatively poor overall survival in patients with breast cancer. (Li Y M, Pan Y, Wei Y, et al. Upregulation of CXCR4 is essential for HER2-mediated tumor metastasis. Cancer Cell. 6:459-469 (2004)). High-level expression of HER2/neu, which is observed in about 30% of all breast cancers, also is associated with a relatively poor prognosis. Li et. al. recently demonstrated that HER2/neu enhances the expression and function of CXCR4 by inhibiting CXCR4 degradation. (Li Y M, Pan Y, Wei Y, et al. Up-regulation of CXCR4 is essential for HER2-mediated tumor metastasis. Cancer Cell. 6:459-469 (2004)). Therefore, the present invention contemplates the use of anti-CXCR4 antibody, antigen-binding fragment thereof, or anti-CXCR4 antibody-drug conjugate comprising anti-CXCR antibodies as the primary therapeutic composition for treatment of breast cancer. Such composition can contain polyclonal anti-CXCR4 or monoclonal anti-CXCR4 antibodies. In addition, a therapeutic composition of the present invention can contain a mixture of monoclonal anti-CXCR4 antibodies directed to different, non-blocking CXCR4 epitopes or mixture of anti-CXCR4 antibody-drug conjugate or mixture of monoclonal anti-CXCR4 and anti-CXCR4 antibody-drug conjugate.

CXCR4 in Lung Cancer

Small-cell lung cancer (SCLC) is an aggressive, rapidly metastasizing neoplasm with a high propensity for marrow involvement. Even with combination chemotherapy and radiotherapy treatments, the 5-year survival is only about 5% because of rapid development of drug resistance. In SCLC cells, CXCR4 activation induces migratory and invasive responses and adhesion to marrow stromal cells in a CXCR4- and integrin-dependent fashion. CXCR4 may direct the distinct metastatic pattern observed in patients with SCLC. Thus, the present invention contemplates the use of anti-CXCR4 antibody, antigen-binding fragment thereof, or anti-CXCR4 antibody-drug conjugate comprising anti-CXCR antibodies as the primary therapeutic composition for treatment of lung cancer. Such composition can contain polyclonal anti-CXCR4 or monoclonal anti-CXCR4 antibodies. In addition, a therapeutic composition of the present invention can contain a mixture of monoclonal anti-CXCR4 antibodies directed to different, non-blocking CXCR4 epitopes or mixture of anti-CXCR4 antibody-drug conjugates or mixture of monoclonal anti-CXCR4 and anti-CXCR4 antibody-drug conjugates.

CXCR4 in Renal Cell Carcinoma (RCC)

Recently, the role of CXCR4 in mRCC has been thoroughly elucidated. Results demonstrated that high expression of CXCR4 was strongly associated with poor survival of patients with mRCC (Wang et al., Clin Exp Metastasis, 26, 1049-54(2009); Zhao et al., Mol Biol Rep, 38, 1039-45 (2011)). Furthermore, results in a a murine model, where the metastatic capability of CXCR4-expressing RCC cells strongly correlated with CXCR4 protein level on cancer cells and the SDF-la expression in the target organs. (Motzer et. Al. The New England Journal of Medicine, vol. 335, no. 12, pp. 865-875 (1996)) Accordingly, CXCR4 might be an interesting therapeutic target in a multimodal therapy of renal clear cell carcinoma.

The present invention contemplates the use of anti-CXCR4 antibody, antigen-binding fragment thereof, or anti-CXCR4 antibody-drug conjugate comprising anti-CXCR antibodies as the primary therapeutic composition for treatment of renal cell carcinoma (RCC). Such composition can contain polyclonal anti-CXCR4 or monoclonal anti-CXCR4 antibodies.

In addition, a therapeutic composition of the present invention can contain a mixture of monoclonal anti-CXCR4 antibodies directed to different, non-blocking CXCR4 epitopes or mixture of anti-CXCR4 antibody-drug conjugates or mixture of monoclonal anti-CXCR4 and anti-CXCR4 antibody-drug conjugates.

CXCR4 in Non-Oncology Indications

Chemokine receptors are expressed at various specific cells and at a specific time. They are largely associated with the control of inflammatory- and immune-responses through a mechanism by which their effector cells accumulate in a site where chemokine is produced. For example, it has been shown that SDF-1 specifically inhibits infection of T cell-directed (X4) HIV in vitro (Bleul et al. Nature, 382:829-833 (1996), Oberlin et al. Nature, 833-835 (1996)). This may be considered that SDF-1 binds to CXCR4 prior to HIV, thereby taking away a scaffold for infecting a cell from HIV resulting in inhibition of HIV infection. Moreover, a HIV infection inhibitor was shown to be an antagonist of CXCR4 (Nat. Med., 4, 72 (1998)).

Accordingly, the present invention contemplates the use of anti-CXCR4 antibody, antigen-binding fragment thereof, or anti-CXCR4 antibody-drug conjugate anti-CXCR antibodies as a therapeutic composition for treatment of inflammatory and immune diseases, allergic diseases, infections (HIV infection, etc.), diseases associated with HIV infection (acquired immunodeficiency syndrome, etc.), Such composition can contain polyclonal anti-CXCR4 or monoclonal anti-CXCR4 antibodies.

In addition, a therapeutic composition of the present invention can contain a mixture of monoclonal anti-CXCR4 antibodies directed to different, non-blocking CXCR4 epitopes or mixture of anti-CXCR4 antibody-drug conjugates or mixture of monoclonal anti-CXCR4 and anti-CXCR4 antibody-drug conjugates.

WHIM Syndrome

WHIM syndrome is a rare congenital immunodeficiency disorder characterized by main clinical manifestations: warts, hypogammaglobulinemia, recurrent bacterial infections and myelokathexis [McDermott, D H et al. Blood 118 (18): 4957-4962 (2011); Mcermott D H et al. J. Cell. Mol.

Med. 15(10): 2071-2081 (2011)]. Myelokathexis can further be characterized as an unusual hematological disorder in which mature neutrophils fail to exit the bone marrow and B- and T-cell abundance or function is deficient (Zueler W W et al. N. Engl. J. Med. 270: 699-704 (1964)). Hernandez P A et al first described that mutations in the CXCR4 are associated with WHIM syndrome, wherein $CXCR4^{R334X}$ is the most common and best-studied variant (Hernandez P A et al. Nature Genetics 34: 70-74 (2003)). $CXCR4^{R334X}$, as a gain-of-function mutation, exhibits enhanced signaling capacity to the endogenous ligand CXCL12. Therefore, to tame $CXCR4^{R334X}$'s increased signaling capacity may be utilized to treat WHIM syndrome.

In some aspects of the invention, the present invention contemplates the use of antibody-drug conjugate comprising anti-CXCR4 antibodies as the primary therapeutic composition for treatment of WHIM syndrome, wherein the said composition can contain polyclonal anti-CXCR4 or monoclonal anti-CXCR4 antibodies. Furthermore, a therapeutic composition of the present invention can contain a mixture of monoclonal anti-CXCR4 antibodies directed to different, non-blocking CXCR4 epitopes or mixture of anti-CXCR4 antibody-drug conjugates or mixture of monoclonal anti-CXCR4 and anti-CXCR4 antibody-drug conjugates. Additionally, in some aspects, the therapeutic composition disclosed by the current invention may be administered alone or in combination with some current treatments for WHIM syndrome, such as G-CSF (filgrastim (Neupogen; Amgen Inc.)), intravenous immunoglobulin, and a small molecule CXCR4 antagonist AMD3100 (plerixafor, trade name Mozobil (Genyzme Corporation)).

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Example 1

Antibody Binding Affinity Determination for Chimeric Anti-CXCR4 Mouse Antibodies Binding of chimeric mouse anti-CXCR4 antibodies 12A11, 6B6 and 3G10 (expressed as hlgG1 subtype) were assessed on CXCR4-expressiing human Non-Hodgkin's Lymphoma (NHL) Ramos cells by flow cytometry. 100,000 cells were incubated with serially diluted anti-CXCR4 antibodies in 100 uL binding buffer (PBS+0.5% BSA), followed by incubation with Dylight488-conjugated goat anti-human Fc secondary antibody from Jackson Immunoresearch Laboratories. % was derived by normalizing MFI values of each dilution to the maximum value. EC50 was calculated by PRISM software.

TABLE 6

| μg/mL | 12A11 | 6B6 | 3G10 |
|---|---|---|---|
| 50 | 100.0% | 100.0% | 100.0% |
| 20 | 79.1% | 97.5% | 103.8% |
| 5 | 38.0% | 90.7% | 91.1% |
| 2 | 13.4% | 87.8% | 88.0% |
| 0.5 | 5.9% | 79.8% | 77.8% |
| 0.2 | 3.1% | 67.3% | 65.7% |
| 0.05 | 1.6% | 44.6% | 25.4% |
| 0.02 | 0.1% | 12.8% | 10.2% |

TABLE 6-continued

| μg/mL | 12A11 | 6B6 | 3G10 |
|---|---|---|---|
| 0.005 | 0.1% | 3.8% | 3.2% |
| 0.002 | 0.0% | 3.0% | 2.0% |
| EC50(μg/mL) | 7.28 | 0.09 | 0.13 |
| EC50(nM) | 48.51 | 0.63 | 0.89 |

Example 2

Binding of Humanized 3G10 Fab to CXCR4-Expressing HPB-ALL Cells

Binding of humanized 3G10 Fabs were assessed on CXCR4-expression HPB-ALL cells by Flow cytometry. 150,000 cells were incubated with various h3G10 Fabs at either 2.5 or 0.25 μg/mL in 100 uL binding buffer (PBS+0.5% BSA), followed by incubation with APC-conjugated goat anti-human Fab-specific secondary antibody from R&D systems.

TABLE 7

| Clone name | | MFI | |
|---|---|---|---|
| Heavy Chain | Light chain | 2.5 μg/ml | 0.25 μg/ml |
| m3G10 VH | m3G10 VL | 6198 | 2177 |
| h3G10 VH | h3G10 VL | 2464 | 563 |
| h3G10.A57 VH | h3G10 L | 4058 | 868 |
| h3G10.A57 VH | h3G10.2.72 VL | 4326 | 1216 |
| h3G10.A57 VH | h3G10.2.25 VL | 4998 | 1384 |
| h3G10.A57 VH | h3G10.A11 VL | 4521 | 1251 |
| h3G10.A57 VH | h3G10.A58A VL | 7402 | 3613 |
| h3G10.A57 VH | h3G10.B12 VL | 6830 | 2921 |
| h3G10.1.7 VH | h3G10.2.72 VL | 4124 | 768 |
| h3G10.1.60 VH | h3G10.2.72 VL | 2806 | 396 |
| h3G10.2.5 VH | h3G10.2.72 VL | 2793 | 390 |
| h3G10.1.91 VH | h3G10.2.72 VL | 7024 | 2673 |
| h3G10.2.37 VH | h3G10.2.72 VL | 6239 | 2919 |
| h3G10.2.45 VH | h3G10.2.72 VL | 2779 | 929 |
| h3G10.2.54 VH | h3G10.2.72 VL | 4611 | 1737 |
| h3G10.2.42 VH | h3G10.2.72 VL | 4724 | 1763 |
| h3G10.1.33 VH | h3G10.2.72 VL | 4138 | 848 |
| h3G10.3.25 VH | h3G10.2.72 VL | 2685 | 454 |
| h3G10.B44 VH | h3G10.2.72 VL | 8908 | 4513 |
| h3G10.B44 VH | h3G10.A11 VL | 8306 | 3792 |
| h3G10.B44 VH | h3G10.A58A VL | 9414 | 5123 |
| h3G10.B44 VH | h3G10.B12 VL | 8127 | 2094 |

Example 3

CXCR4 Antibody Binding: Cell Binding and Affinity Measurement of CXCR4 Ab Fabs Binding of CXCR4 Fabs to CXCR4-expressing cells were measured by flow cytometry on HPB-ALL (Human T cell leukemia) cells. 150,000 HPB-ALL cells were resuspended in 100 uL FACS buffer (1×PBS+0.5% BSA) on 96 well plates. Anti-CXCR4 Fabs were added to each well to the final concentration of 0.25 μg/mL and incubated at 4 degree for 30 min. After removing the primary antibodies the cells were washed twice with FACS buffer and then resuspended in FACS buffer and 2 uL (3 ug) of $2^{nd}$ Ab (Alexa Fluor 647-conjugated goat anti-human IgG, F(ab')2 specific, Jackson ImmunoResearch Laboratories, West Grove Pa.) was then added to each well. The plates were incubated at 4 degree for another 30 min. Fluorescence signals were acquired by cell analyzer LSRII (BD Biosciences, San Jose Calif.). Shown in the table are MFI (Mean Fluorescence Intensity) of each sample.

The binding affinity of each Fab was determined using human CXCR4-enriched lipoparticles (LEV101, Integral Molecular, Philadelphia Pa.). Biotinylated WGA (Sigma Aldrich, St. Louis Mo.)) can be coated on the SA chip to facilitate capturing lipoparticles containing CXCR4 proteins. A dilution series (5-membered, 3× dilution factor with a top concentration of 10 or 30 nM) of Fab was injected from low to high concentration (with a 3-minute association time for each concentration) to perform a kinetic analysis of the data using a "kinetic titration" methodology as described in Karlsson, et al. (Karlsson, R., Katsamba, P. S., Nordin, H., Pol, E. & Myszka, D. G. Analyzing a kinetic titration series using affinity biosensors. Anal. Biochem. 349, 136-147 (2006). For some analysis cycles buffer was injected over captured particles instead of Fab to provide blank cycles for double-referencing purposes (double-referencing was performed as described in Myszka et al. Improving biosensor analysis. J. Mol. Recognit. 12, 279-284 (1999).

TABLE 8

| Clone name | | FACS | Biosensor affinity measurement | | | |
|---|---|---|---|---|---|---|
| | | MFI at | Ka | Kd | t½ | KD |
| Heavy Chain | Light chain | 0.25 μg/mL | (1/MS) | (1/s) | (min) | (nM) |
| m3G10 VH | m3G10 VL | 2555 | 2.10E+06 | 1.40E−03 | 8.30 | 0.65 |
| h3G10 VH | h3G10 VL | 1363 | 1.60E+06 | 3.00E−03 | 3.90 | 1.90 |
| h3G10.A57 VH | h3G10 VL | 1345 | 1.17E+06 | 1.43E−03 | 8.08 | 1.22 |
| h3G10.A57 VH | h3G10.2.72 VL | 2769 | 1.10E+06 | 1.30E−03 | 9.00 | 1.12 |
| h3G10.1.91 VH | h3G10.2.72 VL | 2347 | 1.50E+06 | 4.90E−04 | 23.50 | 0.33 |
| h3G10.2.37 VH | h3G10.2.72 VL | 2887 | 2.30E+06 | 8.00E−04 | 14.40 | 0.35 |
| h3G10.A57 VH | h3G10.A58A VL | 3886 | 1.60E+06 | 6.30E−04 | 18.20 | 0.39 |
| h3G10.1.91 VH | h3G10.A58A VL | 5046 | 9.08E+05 | 3.41E−04 | 33.90 | 0.38 |
| h3G10.2.37 VH | h3G10.A58A VL | 4069 | 1.29E+06 | 4.18E−04 | 27.60 | 0.32 |
| h3G10.A57 VH | h3G10.A58B VL | 3089 | 6.88E+05 | 5.15E−04 | 22.40 | 0.75 |
| h3G10.1.91 VH | h3G10.A58B VL | 4627 | 8.03E+05 | 2.86E−04 | 40.40 | 0.36 |
| h3G10.2.37 VH | h3G10.A58B VL | 4551 | 7.97E+05 | 4.49E−04 | 25.70 | 0.56 |

Example 4

Binding of CXCR4 Ab to Monkey Cyno and Human CXCR4

Figure 3B:
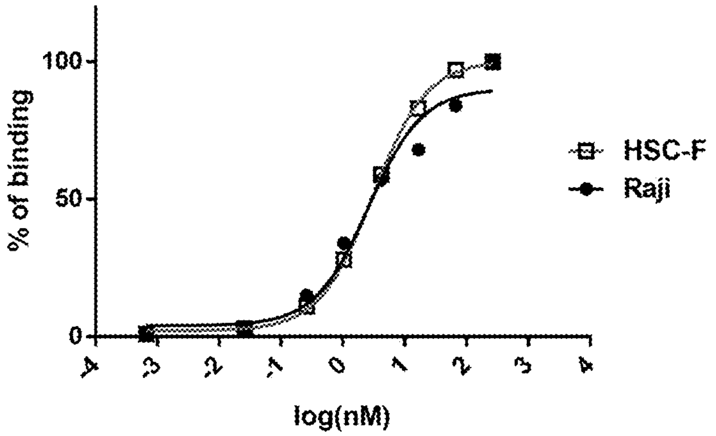
FIG. 3B shows the cross reactivity of anti-human CXCR4 Ab h3G10.1.91.A58B to the cynomolgus CXCR4 by flow cytometry in a dilution series (0.007-267 nM) on Raji (NHL; Human non-Hodgkin Lymphoma) and HSC-F (Cynomolgus T cell line).

Anti-human CXCR4 Ab h3G10.1.91.A58B was tested for its cross-reactivity to the cynomolgus CXCR4 by Flow cytometry in a dilution series (0.007-267 nM) on 1) HPB-ALL (Human T cell leukemia) and Cyno-CXCR4 transfected CHO cells and 2) Raji (Human non-Hodgkin Lymphoma) and HSC-F (Cynomolgus T cell line). Binding was detected by 2nd Ab (Alexa Fluor 647-conjugated goat anti-human IgG, Fcgamma specific, Jackson ImmunoResearch Laboratories, West Grove Pa.) and acquired with LSRFortessa cell analyzer (BD Biosciences, San Jose Calif.). Curve fit and EC50 calculation was performed with Prism software (GraphPad Software, La Jolla Calif.). Tables 9A and 9B and FIGS. 3A and 3B.

TABLE 9A

| | HPB-ALL | CHO-CynoCXCR4 |
|---|---|---|
| EC50 (nM) | 0.27 | 0.16 |

TABLE 9B

| | Raji | HSC-F |
|---|---|---|
| EC50 (nM) | 3.050 | 2.585 |

Example 5

Effector Function of CXCR4 Antibodies

Therapeutic naked antibodies rely on two types of functionalities to achieve clinical efficacy: target-specific binding by the Fab (antigen-binding fragment) domain and immune-mediated effector functions—such as antibody-dependent cell-mediated cytotoxicity (ADCC) and complement dependent cytotoxicity (CDC)—via interaction of the Fc domain of the antibody with Fc receptors on various cell types. In ADCC, the Fc region of the antibody binds to Fc receptors (FcγRs) on the surface of immune effector cells such as natural killers and macrophages, leading to the phagocytosis or lysis of the targeted cells. In CDC, the antibodies kill the targeted cells by triggering the complement cascade at the cell surface. The Fc portion of a therapeutic antibody may therefore have an important role in its mechanism of action through its influence on either ADCC or CDC.

Each subclass of human IgG (IgG1, IgG2, IgG3 and IgG4) exhibits a distinct profile of effector function, which is dictated by differential binding to each of the FcγRs and complement complex proteins. Whereas both IgG1 and IgG3 bind relatively strongly, IgG2 and IgG4 have much lower affinity to the Fc receptors, and do not elicit high levels of ADCC. IgG1 also has higher affinity for the complement complex proteins, with much lower CDC elicited by IgG2, IgG3 and IgG4.

The ADCC (antibody-dependent cytotoxicity) activity of anti-CXCR4 antibodies were determined with the cytoTox 96 non-radioactive cytotoxicity assay kit (Promega, Madison Wis.). CXCR4-expressing human tumor cells were seeded at 10,000 cells the day before the assay. Donor PBMC cells were isolated through Ficoll gradient and cultured overnight at 37° C. in x-vivo medium. The next day 10 or 20 μg/mL of antibodies were added to the wells with or without the addition of 1000,000 PBMC cells (E:T=100:1) in RPMI+5% FBS. The plates were then incubated at 37° C. for 4 hours. At 3 and half hours timepoint 20 uL of the lysis solution was added to the target cells alone wells. After spinning the plate at 8000 rpm for 3 min 50 uL of supernatants were transferred to another plate. 50 ul of substrate was then added to each well and the plate was incubated at room temperature for 30 min in the dark. The reaction was stopped by adding 50 uL of stop solution to each well. Plates were then read at 490 nm with a spectrophotometer (Molecular Devices). Percentages (%) of specific lysis were calculated with the following formula:

% specific lysis=(treatment LDH release−target cell spontaneous LDH release-effector cell spontaneous LDH release)/(target cell maximum LDH release−target cell spontaneous LDH release)×100

The CDC (complement-dependent cytotoxicity) activity of anti-CXCR4 antibodies were determined with the cyto-Tox 96 non-radioactive cytotoxicity assay kit (Promega, Madison Wis.). CXCR4-expressing human tumor cells were seeded at 10,000 cells the day before the assay. The next day 5-20 μg/mL of each Ab was added to the cells alone or with either 2.5%, 10% or 20% of donor AB complement (from Innovative Biotech or Sigma). The plates were developed and specific lysis analyzed similar to the ADCC assay.

Figure 4A:
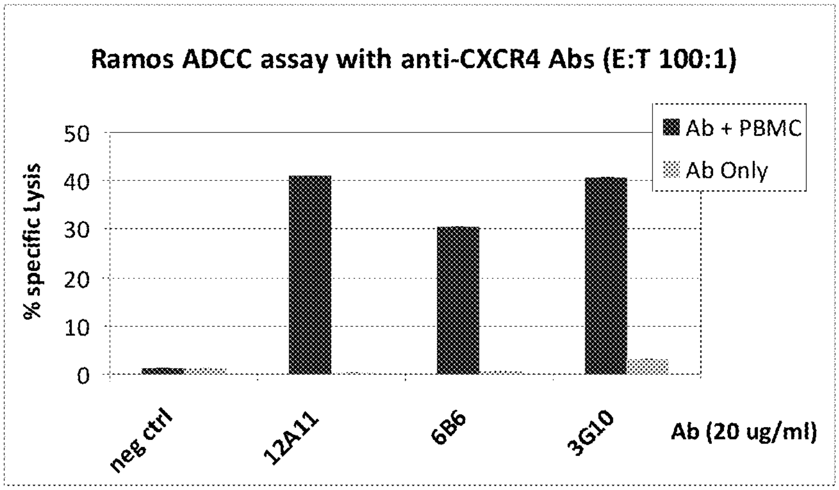
FIG. 4A shows the ADCC activities of 12A11, 6B6 and 3G10 anti-human CXCR4 antibodies on Ramos (NHL) cells.
Figure 4B:
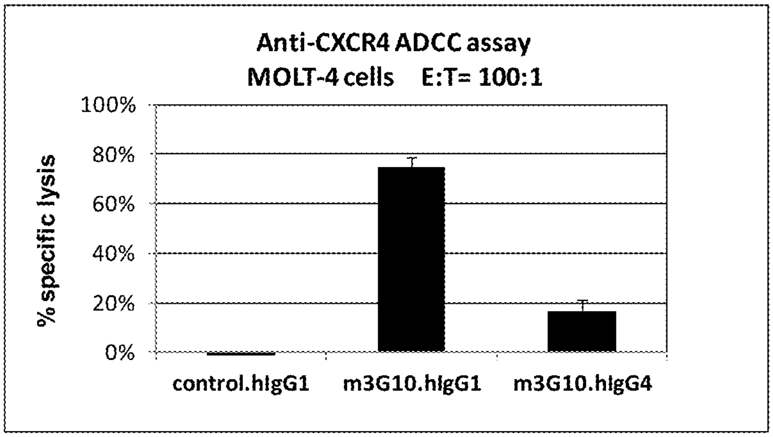
FIG. 4B shows ADCC activity comparison of m3G10-hlgG1 and m3G10-hlgG4 anti-human CXCR4 antibodies on MOLT-4 (T-acute lymphoblastic leukemia) cells.
Figure 4C:
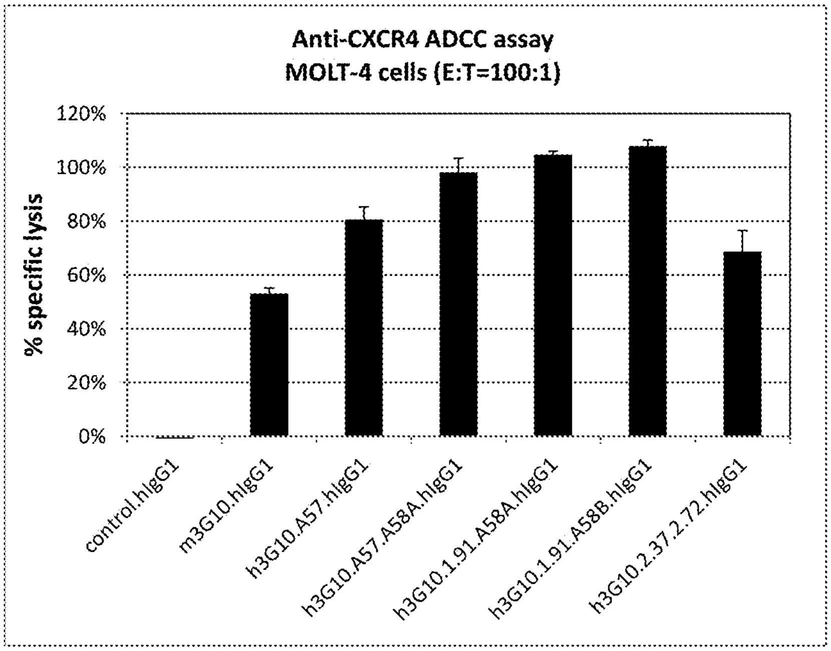
FIG. 4C shows ADCC activities of mouse (m3G10-) and humanized (h3G10-) anti-human CXCR4 antibodies on MOLT-4 (T-acute lymphoblastic leukemia) cells.

The ADCC assay was performed in CXCR4 expressing Ramos (NHL) or MOLT-4 (Human T cell leukemia) cells using 20 μg/mL (FIG. 4A) or 10 μg/mL (FIG. 4C) of antibody plus 100:1 (Effector:Target) ratio of normal donor PBMC cells. After 4 hours of incubation, ADCC activity was evident of anti-human CXCR4 mouse Abs 12A11, 6B6 and 3G10 produced as chimeric hlgG1 on Ramos (NHL) cells (FIG. 4A) or humanized 3G10 antibodies on MOLT-4 cells (FIG. 4C). Approximately 80% of cell lysis was seen from m3G10-hlgG1 treatment, as compared to −20% cell lysis from m3G10-hlgG4 subtype on MOLT-4 cells (FIG. 4B).

Figure 4D:
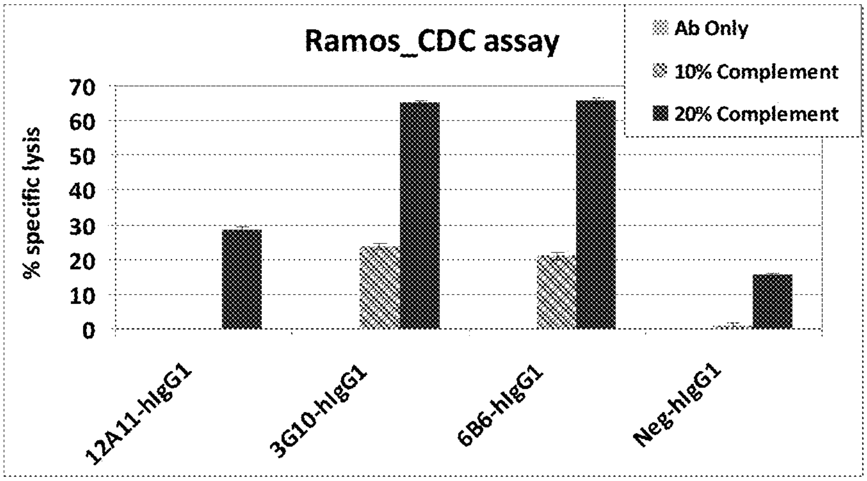
FIG. 4D shows CDC activities of 12A11, 6B6 and 3G10 anti-human CXCR4 antibodies on Ramos (NHL) cells.
Figure 4E:
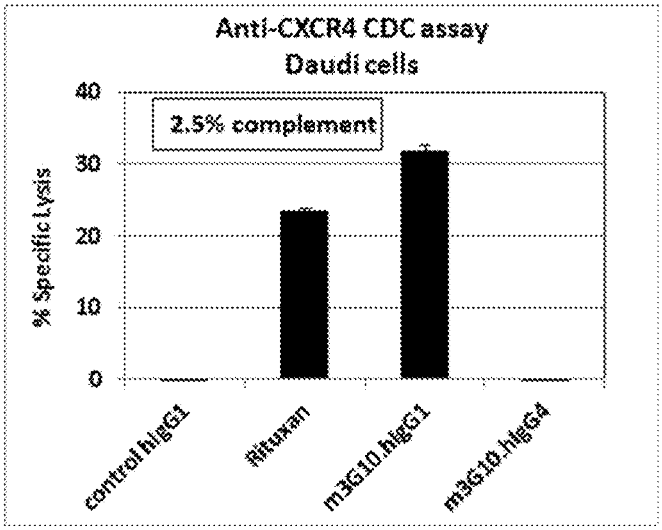
FIG. 4E shows CDC activity comparison of m3G10-hlgG1 and m3G10-hlgG4 anti-human CXCR4 antibodies on Daudi (NHL) cells.
Figure 4F:
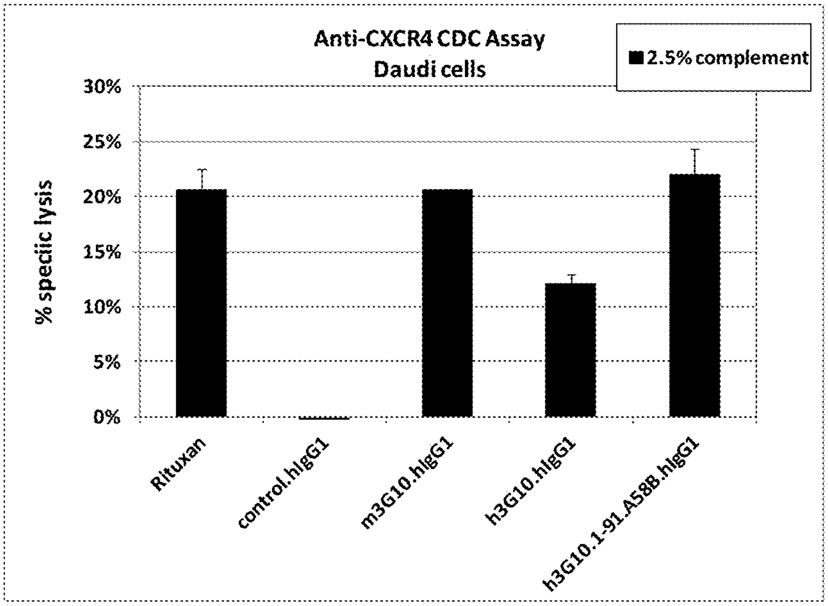
FIG. 4F shows CDC activities of mouse (m3G10-) and humanized (h3G10-) anti-human CXCR4 antibodies on Daudi (NHL) cells.

CDC activity was observed from treatment of 20 μg/mL of chimeric mouse 12A11-, 6B6- and 3G10-hlgG1 antibodies in CXCR4 expressing Ramos cells (FIG. 4D) and with 5 μg/mL humanized antibodies on Daudi (NHL) cells (FIG. 4F). Maximal 20-30% of specific lysis activity was detected with 5 μg/mL anti-CXCR4 3G10 antibody in IgG1 backbone, similar to the positive control antibody Rituxan on Daudi cells, while 3G10 in hlgG4 format showed no CDC activity (FIG. 4E)

Example 6

Inhibition of SDF-1 Induced Calcium Flux by Anti-CXCR4 Antibodies

Figure 5:
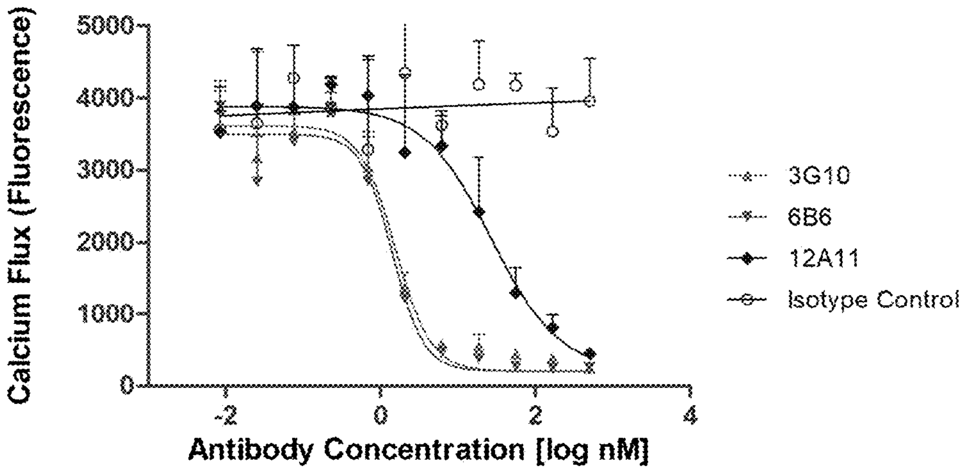
FIG. 5 shows the inhibition of Calcium flux by 3G10, 6B6 and 12A11 anti-human CXCR4 antibodies.

Upon binding of SDF-1 (ligand) to the CXCR4 receptor a Calcium flux reaction is triggered. As evidence for the functional antagonistic activity of the CXCR4 Abs, the ability of the anti-human CXCR4 antibodies to inhibit SDF-1 induced calcium flux, human T-cell leukemia (Jurkat) cells were used in conjunction with the Fluo-NW Calcium assay kit (Molecular Probes/life technologies). Cells were cultured to sub-confluence in RPMI 1640 media containing 10% fetal bovine serum, 1% Glutamine at 37° C. in a CO2 incubator. On the day of the assay, cells were plated in a black, clear bottom 384-well plate at 70,000 cells per well in 25 ul assay buffer. Kit assay dye was then added to the plates, 25 ul/well for 110 min at room temperature, protected from light. An 11 point 1:3 serial dilution was prepared in the Fluo-NW Ca assay kit buffer for each anti-human CXCR4 antibody, resulting in a concentration range from 500 nM to 8 μM. Cells were incubated with antibodies at room temperature for 20 minutes. Cells were then stimulated with SDF-1 alpha (Invitrogen) at a final concentration of 8 nM. Calcium flux was then measured for 95 seconds using a FLIPR Tetra (Molecular Devices). The positive control consisted of cells in presence of SDF-1 alpha and no antibody treatment. Baseline was measured from cells with no SDF-1 alpha and no antibody treatment. The SDF-1 alpha induction of calcium was measured by development of fluorescence signal over time. The data were exported and plotted using GraphPad Prism software and a non-linear curve fit with sigmoidal dose response formula was used to calculate EC50 values. The resulting inhibition of calcium flux by anti-human CXCR4 antibodies is shown in FIG. 5. Antibodies 3G10, 6B6 and 12A11 inhibited SDF-1 alpha induced Calcium flux, with IC50s for inhibition of 1.555 nM, 1.418 nM and 27.07 nM, respectively (Table 10). IC50s for humanized CXCR4 antibodies evaluated in the Calcium Flux Functional assay are summarized on Table 11 (average n=3 independent experiments/antibody). In summary, the potency of the humanized CXCR4 antibodies is similar to that of the chimeric m3G10 antibody in this assay.

TABLE 10

Calcium Flux activity of Chimeric CXCR4 Antibodies

| | 3G10 | 6B6 | 12A11 |
|---|---|---|---|
| IC50 | 1.555 | 1.418 | 27.07 |

TABLE 11

Calcium Flux Activity of Humanized CXCR4 antibodies

| Heavy Chain | Light Chain | Antibody Name | IC50 (M) |
|---|---|---|---|
| m3G10 VH | m3G10 VL | m3G10 | 1.25E−09 |
| h3G10 VH | h3G10 VL | h3G10 | 2.00E−09 |
| A57 | h3G10 VL | h3G10.A57 | 1.69E−09 |
| h3G10.2.37 VH | h3G10.2.72 VL | h3G10.2.37.2.72 | 1.36E−09 |
| h3G10.A57 VH | h3G10.A58A VL | h3G10.A57.A58A | 1.31E−09 |
| h3G10.1.91 VH | h3G10.A58A VL | h3G10.1.91.A58A | 2.35E−09 |
| h3G10.1.91 VH | h3G10.A58B VL | h3G10.1.91.A58B | 2.17E−09 |

Example 7

CXCR4 Antibodies Activity in a Cyclic AMP (cAMP) Cell Based Functional Assay Upon binding of CXCL12 (ligand) to the CXCR4 receptor cAMP is known to be inhibited. As evidence for the antagonist activity of the CXCR4 Abs, a cAMP assay was performed using CHO-K1 cells transfected with human CXCR4, purchased from DiscoveRx, Fremont, Calif. The cAMP Hunter eXpress GPCR assay kit (DiscoveRx) was used to perform the assay. In the absence of CXCR4 antibodies, treatment with CXCR4's ligand, CXCL12, inhibited cAMP production. Upon treatment with CXCR4 antibodies, this inhibition was abrogated, and cAMP production increased. The EC50 for this response is shown in Table 12. In summary, all CXCR4 antibodies tested had similar potent activity in this assay, ranging from 24.3 to 45.6 nM. This study confirms that the mouse (chimeric)

3G10 and the humanized 3G10 CXCR4 antibodies can compete and block the CXCR4 ligand activity in the cAMP functional assay.

TABLE 12

| Summary EC50s of anti-CXCR4 Abs in cAMP Assay | |
|---|---|
| Antibody Tested | EC50 (M) |
| Isotype Control Antibody | 9.80 E+10 |
| m3G10 | 4.56 E−08 |
| h3G10.1.91.A58B | 3.92 E−08 |
| h3G10.2.37.2.72 | 3.41 E−08 |
| h3G10.A57.A58A | 2.43 E−08 |

Example 8

Cell-Death Induction by Anti-CXCR4 Antibodies

Anti-CXCR4 antibodies were examined for the ability to induce cell-death in the human Non-Hodgkin's Lymphoma Ramos cell line. Cells were cultured to sub-confluency in RPMI 1640 media containing 10% fetal bovine serum and 2 nM Glutamine at 37° C. in a $CO_2$ incubator. Cells were seeded in growth media in a 48-well plates at $2.5\times10^6$ cells/mL. Anti-CXCR4 antibodies, diluted in PBS to concentrations indicated, were added to the cells and incubated for 24 hrs at 37° C. Cell-death was measured by Annexin V-PE and propidium iodide (PI) fluorescent signal measured in a LSRII Flow Cytometer (BD Biosciences). Total cell-death was determined by adding the Annexin V+/PI+(late) population with the Annexin V+/PI-(early) population.

Figure 6A:
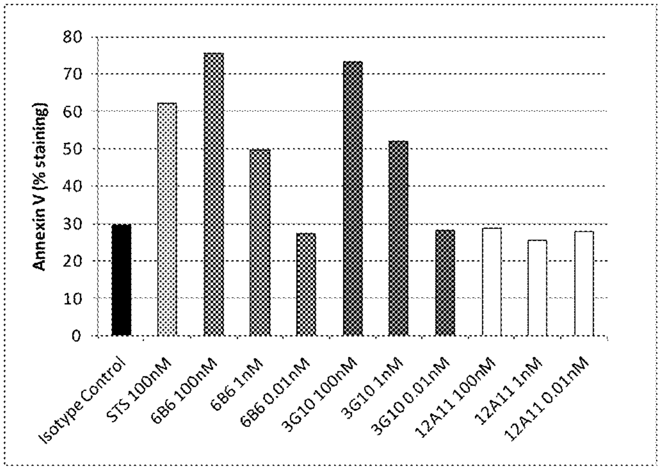
FIG. 6A shows that 3G10, 6B6 and 12A11 anti-human CXCR4 antibodies are capable of inducing cell-death in Ramos cells in a dose dependent manner.

The results on FIG. 6A demonstrate that 6B6 and 3G10 anti-CXCR4 antibodies are capable of inducing cell-death in Ramos cells in a dose dependent manner. At the highest concentration tested, 100 nM, 3G10 and 6B6 resulted in >70% cell-death. This effect was greater than the positive control Staurosporin (STS), a known potent cell-death inducer (approximately 60%). Untreated cells showed approximately 30% cell-death in this assay. The anti-CXCR4 12A11 antibody was not capable of inducing cell-death under the conditions tested. Similar results were observed when testing activity of these antibodies on Raji Non-Hodgkin's lymphoma cells.

Figure 6B:
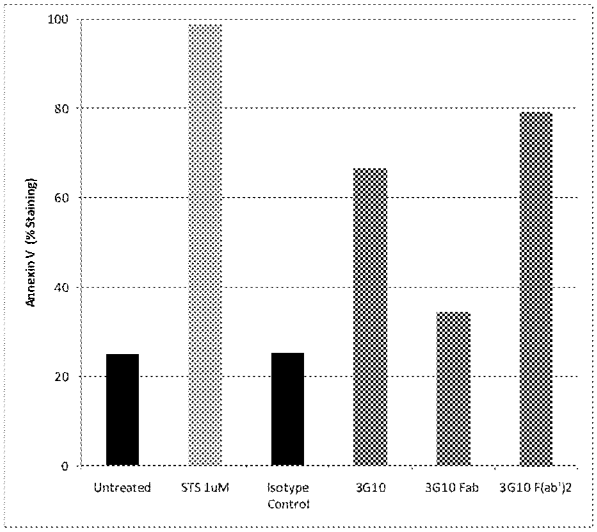
FIG. 6B shows that anti-human CXCR4 antibody 3G10's ability to induce cell-death is bivalency dependent.

In a similar study, single chain (Fab) and bivalent F(ab)2' were generated from the 3G10 antibody. The Fab is a single chain antibody (monovalent) and contains the immunoglobulin variable regions which are part of the antigen-binding site and the first immunoglogulin constant region. This fragment was obtained by digestion of the 3G10 antibody with the proteolytic enzyme papain. The F(ab')2 was generated by pepsin digestion to remove most of the Fc region while leaving intact some of the hinge region. $F(ab')_2$ fragments have two antigen-binding Fab portions linked together by disulfide bonds, and therefore are bivalent. The Fab and F(ab')2 were tested side by side with the bivalent full length 3G10 antibody for their ability to induce cell-death of Ramos cells. Results shown on FIG. 6B indicate that the ability to induce cell-death is bivalency dependent, with the intact antibody (3G10) and F(ab')2 antibodies capable of inducing cell-death, while the 3G10 Fab had very limited effect on cell-death.

Example 9

Figure 7:
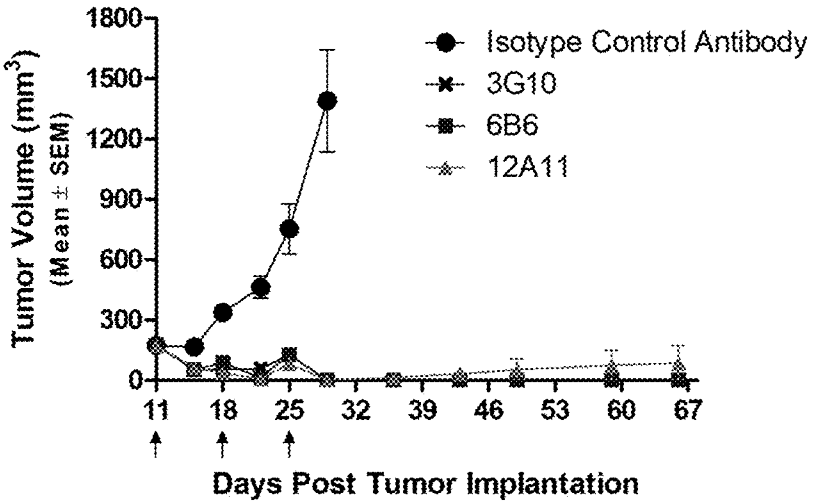
FIG. 7 shows that 3G10, 6B6 and 12A11 anti-human CXCR4 antibodies significantly inhibited tumor growth in a Non-Hodgkin's Lymphoma (NHL) model (Ramos) compared to the isotype control antibody.

Inhibition of Non-Hodgkin's Lymphoma Solid Tumor Growth in Vivo by Anti-CXCR4 Antibodies SDF-1/CXCR4 signaling is thought to play an important role in multiple stages of tumor development including tumor growth, angiogenesis, invasion, and metastasis. To evaluate the ability of the anti-human CXCR4 Abs to inhibit tumor growth, a tumor xenograft model using female 4-6 week-old CB17 SCID Beige mice (Jackson Laboratories) and human Non-Hodgkin's Lymphoma Ramos cells implanted subcutaneously was employed. Cells were cultured at 37° C. in a 5% $CO_2$ incubator in RPMI 1640 media containing 10% fetal bovine serum. In this study, $5\times10^6$ cells were implanted into the right rear flank region of each mouse and allowed to grow as solid tumors to the mean size volume of approximately 175 $mm^3$, calculated by the formula (volume=length×width$^2$)/2. The mice were then randomized in 4 different treatment groups, n=10 animals per group. Groups of mice were treated with intravenous (i.v.) injection of the antibodies in a solution of sterile PBS: (i) Isotype Control Ab (15 mg/kg); (ii) 3G10 (15 mg/kg); (iii) 6B6 (15 mg/kg); and (iv) 12A11 (15 mg/kg). Animals were dosed with antibodies once a week for 3 weeks, for a total of 3 doses. Tumor volumes were measured by caliper once to three times a week for the duration of the study. The results of the experiment are presented on FIG. 7. The results indicate that all 3 anti-CXCR4 antibodies tested significantly inhibited tumor growth compared to the isotype control antibody. The results indicate that the anti-CXCR4 antibodies are capable of inhibiting growth of an established solid tumor in vivo. This tumor growth inhibitory effect was sustained for long period of time (42 Days) after antibody dosing was stopped. Activity of all three anti-CXCR4 antibodies tested was comparable in this solid tumor model. FIG. 7.

Example 10

Increased Survival Time and Decreased Tumor Burden by Anti-CXCR4 Antibodies in a Mouse Systemic Non-Hodgkin's Lymphoma Cell Model Anti-tumor activity of anti-CXCR4 antibodies was further investigated in a hematological lymphoma model using Raji Non-Hodgkin's Lymphoma cells. The Raji cells used in this study were transfected with the luciferase gene (LUC) to allow for "in life" monitoring of tumor burden over time. Cells were cultured at 37° C. in a 5% $CO_2$ incubator in RPMI 1640 media containing 10% fetal bovine serum. The model was established by injecting $1\times10^6$ Raji-LUC cells into female 6-8 week old SCID Beige mice (from Charles River Laoratories) via tail vein. On Day 0 (implant day) Raji-LUC cells lodged in the lungs, indicative of accurate i.v. injection of the tumor cells in all animals. One day post-cell implantation mice were assigned into treatment groups (10 animals per group) based the presence of lung bioluminescence. Mice were treated with Isotype Control antibody, 3G10, 6B6 and 12A11 at 10 mg/kg in a solution of sterile PBS once a week intraperitoneally (i.p.), until Day 67. Tumor burden was monitored by bioluminescence imaging using Xenogen IVIS 200 imaging system. Mice were imaged every 5 days in ventral position, luciferin was delivered IP at 15 mg/ml, 200 ul injection and whole body bioluminescence was determined using Xenogen Living Image. When mice began to show hind limb paralysis or reached other humane endpoints they were euthanized. Both tumor burden (by bioluminescence) and survival were evaluated as endpoints.

Figure 8A:
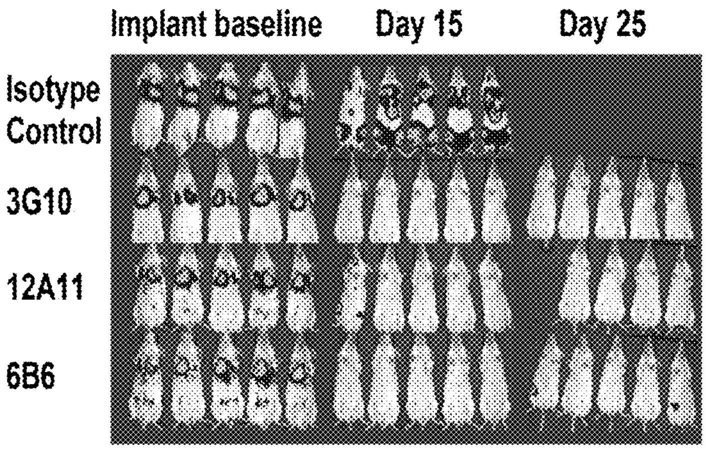
FIG. 8A shows that anti-human CXCR4 antibodies 3G10, 6B6 and 12A11 have a significant effect compared to the isotype control antibody on the tumor burden of animals systemically implanted with the Raji-LUC cells.
Figure 8B:
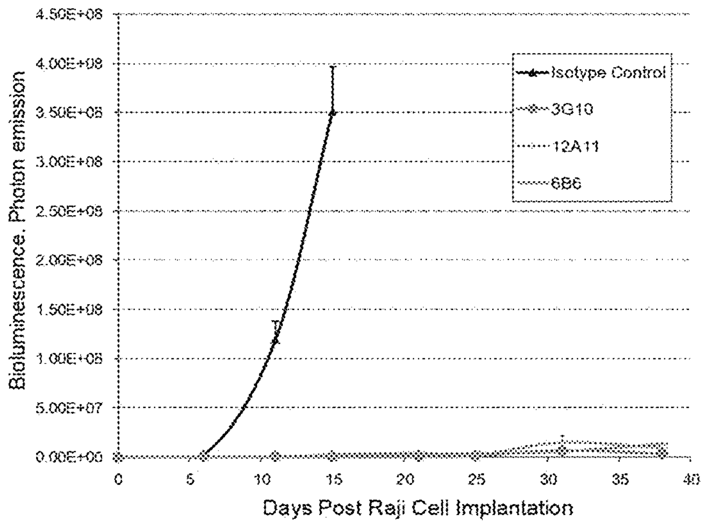
FIG. 8B shows that the treatment with anti-human CXCR4 antibodies 3G10, 6B6 and 12A11 had comparable and significant tumor growth inhibition (TGI) activity relative to isotype control antibody in this model.

FIGS. 8A and B show bioluminescence results of this study. Decrease in tumor burden is shown by a decrease in the level of bioluminescence over time. FIG. 8A shows representative imaging of 4-5 animals of each group on Days 0 (Implant Baseline), 15 and 25 of the study. All three anti-CXCR4 antibodies significantly decreased tumor burden as measured by level of luminescence. FIG. 8B shows that treatment with 3G10, 6B6 and 12A11 antibodies had comparable TGI activity relative to isotype control antibody in this model.

Figure 8C:
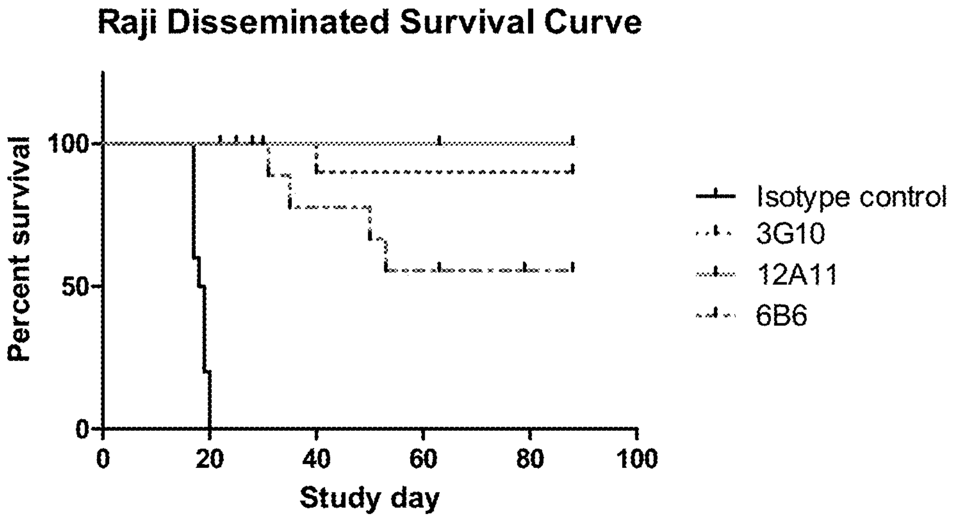
FIG. 8C is a survival curve showing a significant effect of anti-human CXCR4 antibodies 3G10, 6B6 and 12A11 compared to the isotype control antibody in the survival of animals implanted with the Raji-LUC cells systemically.

The survival curve shown in FIG. 8C demonstrates a very significant effect of anti-CXCR4 antibodies 3G10, 6B6 and 12A11 compared to the Isotype control antibody in the survival of animals implanted with the Raji-LUC cells systemically. While isoptype control treated animals showed median survival of 18 days, the animals treated with anti-CXCR4 antibodies did not reach median survival before termination of the study. The effect of all 3 anti-CXCR4 antibodies tested was comparable with no statistical difference between them. The survival of the anti-CXCR4 antibody treated animals was sustained well beyond Day 67, when last antibody dose was administered.

Example 11

Increased Survival Time and Decreased Tumor Burden by Anti-CXCR4 Antibodies in a Mouse Systemic Acute Myelopenous Leukemia (AML) Cell Model Anti-CXCR4 antibody 6B6 was tested for its ability to increase survival and reduce tumor burden of NSG mice using a disseminated/systemic intravenous model of AML. The human AML cancer line MV4-11 transduced with the luciferase gene (MV4-11-LUC) to allow for "in life" monitoring of tumor burden over time. Cells were cultured at 37° C. in a 5% $CO_2$ incubator in IMDM media containing 10% fetal bovine serum with 1 μg/mL puromycin for luciferase expression selection. 4-6 week old NSG female mice (from Jackson Laboratories) were injected intravenously with MV4-11-LUC AML cells ($1\times10^6$/animal).

On Day 13 post-cell implantation mice were randomized into three treatment groups (10 animals per group) based on total body bioluminescence intensity. Weekly subcutaneous (s.c.) antibody treatment at 10 mg/kg in a solution of sterile PBS was initiated on Day 13 (isotype control and anti-CXCR4 6B6 antibody) and on Day 20 (anti-CXCR4 6B6 antibody), as indicated in the figure (Day 13; Day 20). Tumor burden was assessed using Xenogen IVIS 200 imaging system. Mice were imaged every 7 days in a ventral position and whole body bioluminescence was determined using Xenogen Living Image software. When mice began to show hind limb paralysis or reached other humane endpoints they were euthanized. Both tumor burden (by bioluminescence) and survival were evaluated as endpoints. The number of human AML cells in circulation in the peripheral blood (PB) of mice (n=10 per group) was monitored on blood samples collected on Day 35 of the study. The AML CD45 and CD33 markers were used to determine the percentage of human AML cells in circulation by flow cytometry staining with anti-human CD45 and anti-human CD33 antibodies (from BD Biosciences)

Figure 9A:
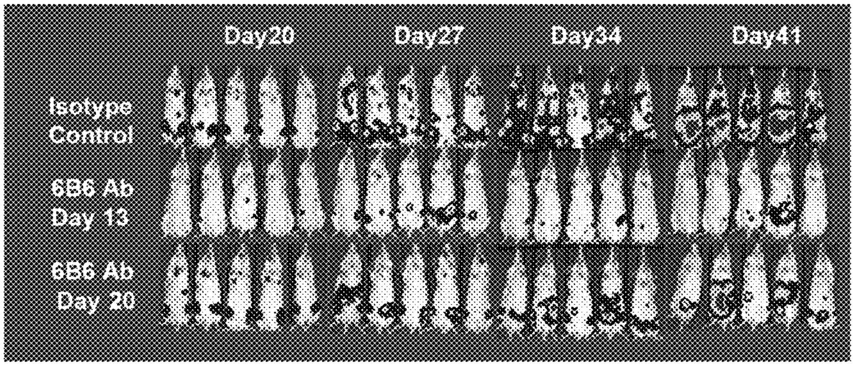
FIG. 9A shows effect of CXCR4 Ab 6B6 on tumor burden in an acute myelogenous leukemia (AML) model (MV4-11-LUC). Representative bioluminescence imaging of 5 animals/treatment group from Day 20 to Day 41 is shown.

FIG. 9A shows representative bioluminescence imaging of 5 animals/treatment group for this study (from Day 20 to Day 41). Decrease in tumor burden is shown by a decrease in the level of bioluminescence over time. Tumor burden inhibition with anti-CXCR4 6B6 antibody starting earlier (Day 13) was more pronounced than when it was initiated a week later (Day 20). 6B6 anti-CXCR4 antibody significantly decreased tumor burden in both treatment groups, compared to isotype control antibody, indicating that the anti-CXCR4 antibody is efficacious inhibiting tumor burden in a staged disseminated mouse model of human AML.

Figure 9B:
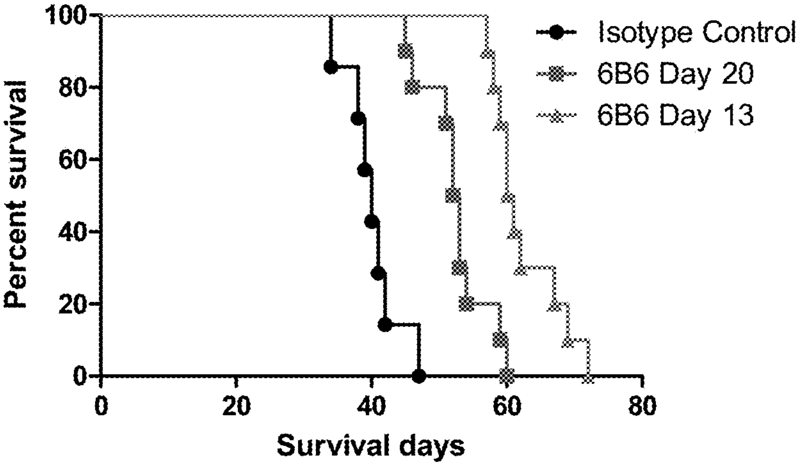
FIG. 9B shows a significant effect of anti-CXCR4 antibody 6B6 compared to the isotype control antibody in the survival of animals implanted with the MV4-11-LUC AML cells systemically.

The survival curve shown in FIG. 9B demonstrates a significant effect of anti-CXCR4 antibody 6B6 compared to the isotype control antibody in the survival of animals implanted with the MV4-11-LUC AML cells systemically. While isoptype control treated animals showed median survival of 40 days, the animals treated with anti-CXCR4 6B6 antibody on Day 13 and Day 20 had median survivals of 53 and 61 days, respectively. These differences were statistically significant ($p<0.05$) by Mantel-Cox test.

Figure 9C:
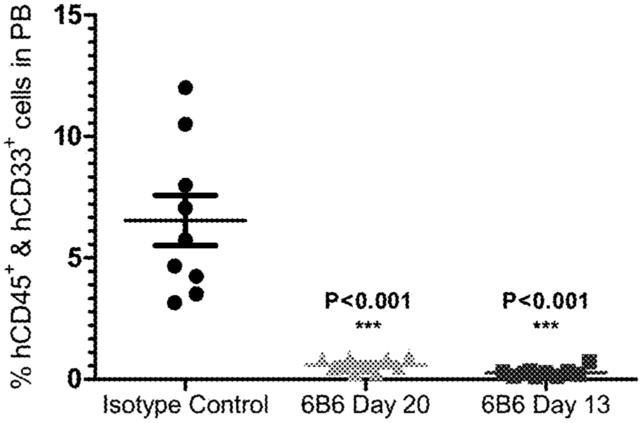
FIG. 9C shows a significant reduction of human AML tumor burden in Peripheral Blood (PB) of animals treated with the anti-CXCR4 6B6 antibody compared to isotype control treated animals at Day 35 of the study.

FIG. 9 C shows the significant reduction of human AML cell numbers in animals treated with the anti-CXCR4 6B6 antibody compared to isotype control treated animals at Day 35 of the study.

Example 12

Increased Survival by Anti-CXCR4 Antibody in a Mouse Systemic Chronic Lymphocytic Leukemia Tumor Model Anti-tumor activity of CXCR4 antibody was further investigated in a disseminated intravenous Chronic Lymphocytic Leukemia (CLL) model. The human JVM-13 tumor cell line stably transfected to express the luciferase gene was cultured at 37° C. in a 5% CO2 incubator in RPMI 1640 media containing 10% fetal bovine serum and 0.25 mg/mL Puromycin. The model was established by injecting $1\times10^6$ JVM-13-Luc cells into female 6-8 week old SCID Beige mice via tail vein. 21 days post-cell implantation mice were assigned into treatment groups (10 animals per group) based on bioluminescence (BLI) reading. Mice were treated with Isotype Control antibody and 3G10 were dosed at 10 mg/kg in a solution of sterile PBS, once a week subcutaneously (s.c.). Rituximab, an anti-CD20 Ab, approved for treatment of CLL patients, was used as positive control. Rituximab was dosed at 10 mg/kg in a solution of sterile PBS once a week, s.c. Tumor burden was assessed using Xenogen IVIS 200 imaging system. Mice were imaged every 7 days in a ventral position and whole body bioluminescence was determined using Xenogen Living Image software. When mice began to show hind limb paralysis or reached other humane endpoints they were euthanized. Both tumor burden (by bioluminescence) and survival were evaluated as endpoints.

Figure 10A:
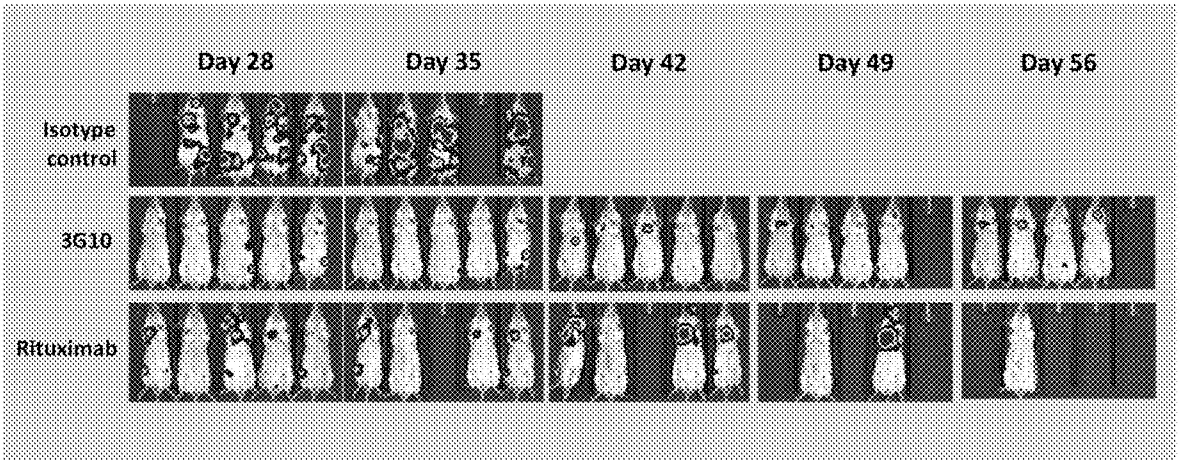
FIG. 10A shows representative luciferase imaging in mice with Systemic Chronic Lymphocytic Leukemia Tumors treated with the CXCR4 3G10 antibody.

FIG. 10A shows representative luciferase activity imaging for mice in each treatment each group on Days 28, 35, 42, 49, and 56 of the study. Treatment with 3G10 significantly decreased JVM-13-Luc tumor burden in large bones, as measured by level of luminescence over time, compared to isotype control antibody. Treatment with Rituximab also significantly reduced tumor burden compared to isotype control antibody.

Figure 10B:
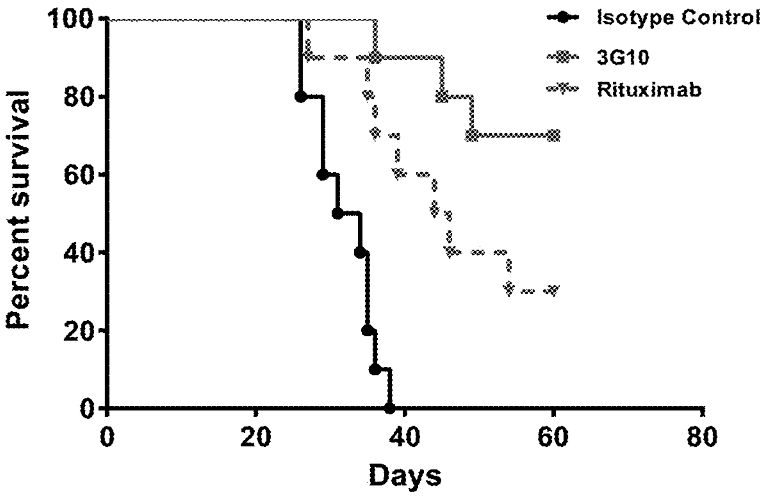
FIG. 10B is a survival curve showing a significant effect of anti-human CXCR4 antibody 3G10 compared to the isotype control antibody in the survival of animals implanted systemically with Chronic Lymphocytic Leukemia cells.

FIG. 10B shows a Kaplan-Meyer survival curve for this study. Significant increase in survival was observed for 3G10 and Rituximab antibodies compared to the Isotype control Ab ($p<0.0001$). While isoptype control antibody treated animals showed median survival of 32.5 days, animals treated with Rituxan showed median survival of 45 days and animals treated with 3G10 did not reach median survival before Day 60. Results from this study indicate that the anti-CXCR4 antibody is efficacious inhibiting tumor burden in a staged disseminated mouse model of human CLL.

Example 13

Figure 11:
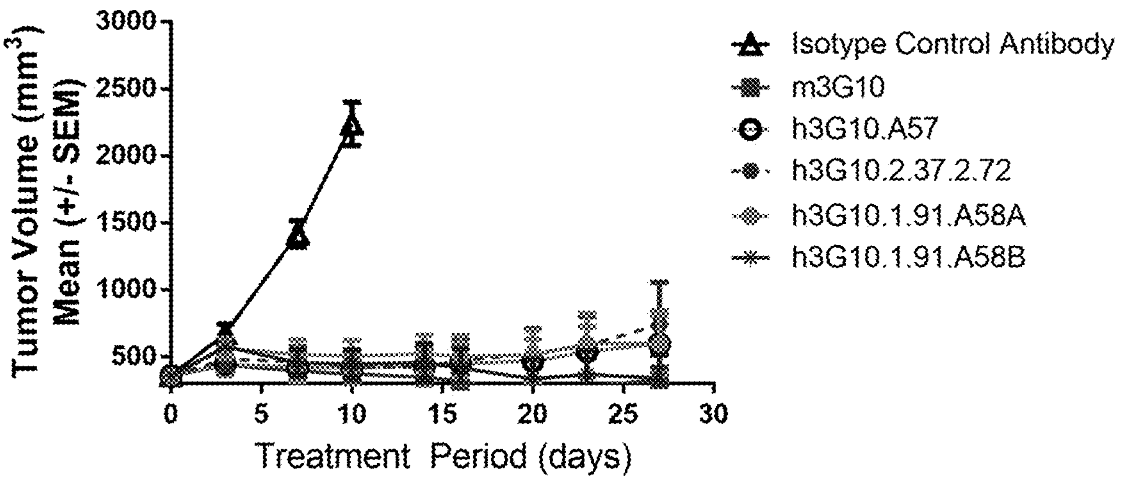
FIG. 11 shows that humanized anti-human CXCR4 antibodies significantly inhibited tumor growth in a Non-Hodgkin's Lymphoma (NHL) model (Ramos) compared to the isotype control antibody.

Inhibition of Ramos Non-Hodqkin's Lymphoma Tumor Growth In Vivo by Humanized Anti-CXCR4 Antibodies To evaluate the ability of humanized CXCR4 Abs to inhibit tumor growth, a tumor xenograft model using female 4-6 week-old CB17.cg-Prkdc SCID Beige mice (Charles River) and human Non-Hodgkin's Lymphoma Ramos cells implanted subcutaneously was employed. Cells were cultured at 37° C. in a 5% $CO_2$ incubator in RPMI 1640 media containing 10% fetal bovine serum. In this study, $5\times10^6$ cells were implanted into the right rear flank region of each mouse and allowed to grow as solid tumors to the mean size volume of approximately 350 $mm^3$, calculated by the formula (volume=length×width$^2$)/2. The mice were then randomized in 7 different treatment groups, n=10 animals per group. Groups of mice were treated with subcutaneously (s.c.) with 10 mg/kg of each antibody in a solution of sterile PBS: (Isotype Control Antibody; m3G10; h3G10.A57.WT; h3G10.2.37.2.72; h3G10.A57.A58; h3G10.1.91.A58A; h3G10.1.91.A58B. Animals were dosed with antibodies once a week for 2 weeks, for a total of 2 doses. Tumor volumes were measured by caliper twice a week for the duration of the study. The results of the experiment are presented on FIG. 11. The results indicate that all anti-CXCR4 antibodies tested significantly inhibited tumor growth compared to the isotype control antibody. The results indicate that the humanized CXCR4 antibodies tested have similar efficacy to that of the chimeric m3G10 antibody. Tumor growth inhibitory effect was sustained for several days after antibody dosing was stopped (Day 7).

Example 14

Increased Survival Time and Decreased Tumor Burden by Humanized Anti-CXCR4 Antibody in a Mouse Systemic Multiple Myeloma (MM) Model Humanized anti-CXCR4 antibody h3G10.1.91.A58B was tested for its ability to increase survival and reduce tumor burden of NSG mice using a disseminated/systemic intravenous model of MM. The human MM cancer line OPM-2 was transduced with the luciferase gene (OPM-2-LUC) to allow for "in life" monitoring of tumor burden over time. Cells were cultured at 37° C. in a 5% $CO_2$ incubator in RPMI 1640 media containing 10% fetal bovine serum with 0.5 μg/mL puromycin for luciferase expression selection. 4-6 week old NSG female mice were injected intravenously with OPM-2-Luc cells ($5\times10^6$/animal).

On Day 8 post-cell implantation mice were randomized into three treatment groups (10 animals per group) based on total body bioluminescence intensity. Weekly subcutaneous (s.c.) antibody treatment at 10 mg/kg in a solution of sterile PBS was initiated and carried out for 5 weeks. Melphalan, one of the approved drugs for treatment of multiple myeloma patients, was dosed at 1 mg/kg, twice/week carried out for 3 weeks. Tumor burden was assessed using Xenogen IVIS 200 imaging system. Mice were imaged every 7 days in a ventral position and whole body bioluminescence was determined using Xenogen Living Image software. When mice began to show hind limb paralysis or reached other humane endpoints they were euthanized. Both tumor burden (by bioluminescence) and survival were evaluated as endpoints.

Figure 12A:
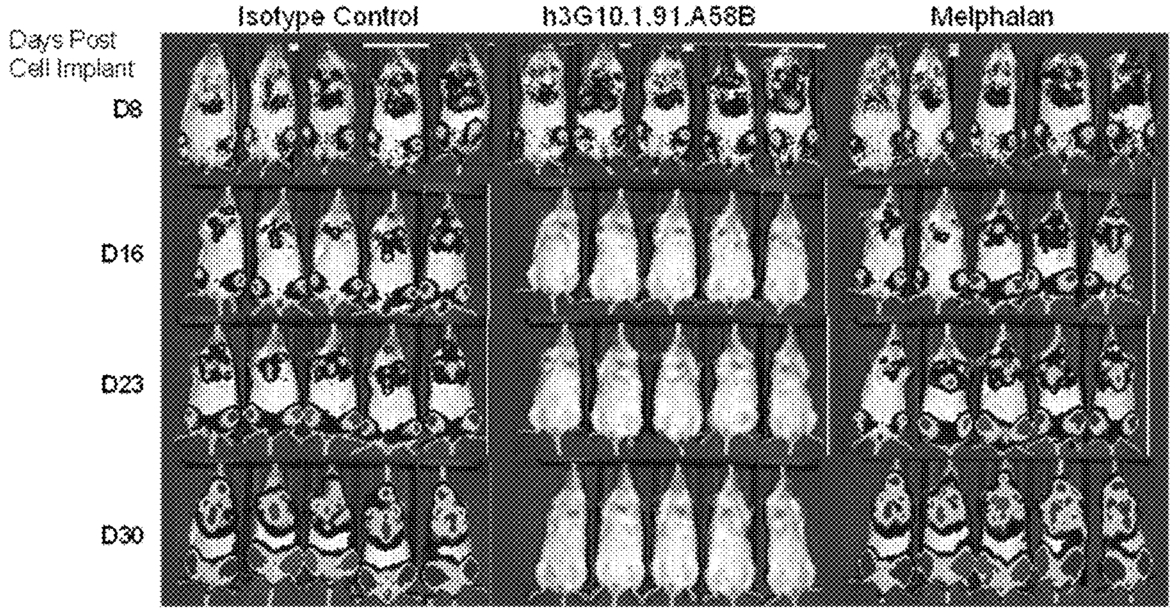
FIG. 12A shows effect of CXCR4 Ab h3G10.1.91.A58B on tumor burden in a multiple myeloma (MM) model (OPM-2-LUC). Representative bioluminescence imaging of 5 animals/treatment group from Day 8 to Day 30 is shown.
Figure 12B:
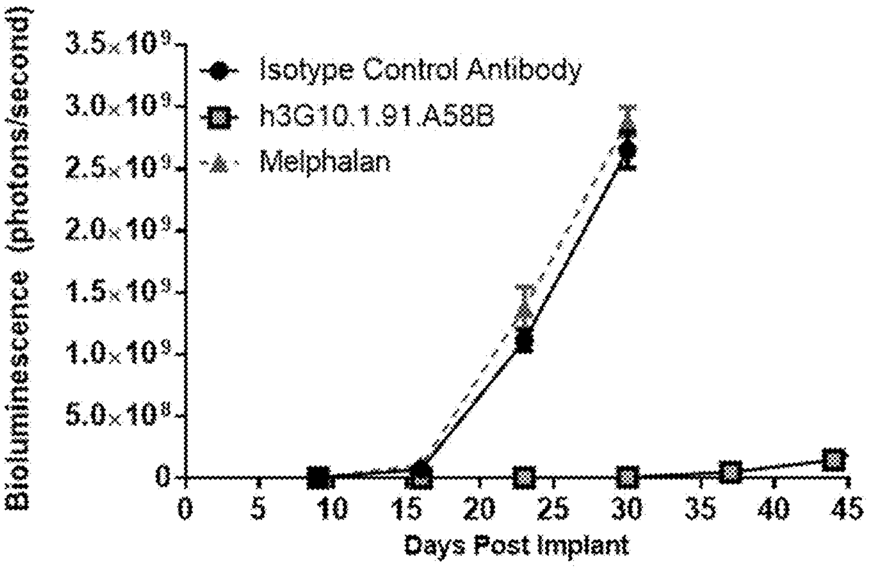
FIG. 12B shows quantification of the bioluminescence (Luciferase activity) in Mouse Systemic Multiple Myeloma (MM) Model treated with the anti-human CXCR4 antibody h3G10.1.91.A58B, compared to animals treated with Isopype Control antibody and Melphalan
Figure 12C:
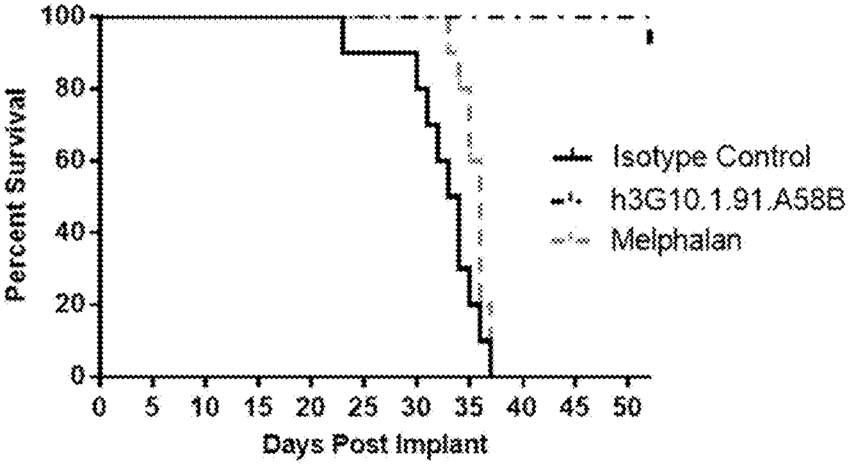
FIG. 12C is a survival curve showing a significant effect of anti-CXCR4 antibody h3G10.1.91.A58B compared to the isotype control antibody and Melphalan in mice systemically implanted with the OPM-2-Luc MM cells.

FIGS. 12 A and B show bioluminescence (Luciferase activity) results in this study. Decrease in tumor burden is shown by a decrease in the level of bioluminescence over time. FIG. 12A shows representative bioluminescence imaging of 5 animals/treatment group for this study. FIG. 12B shows that treatment with CXCR4 antibody h3G10.1.91.A58B significantly inhibited tumor growth compared to isotype control antibody over time ($p<0.0001$ on Day 30), indicating that the anti-CXCR4 antibody is efficacious inhibiting tumor burden in a staged disseminated xenograft model of human multiple myeloma. The survival curve for this study is shown in FIG. 12C demonstrates a significant effect of anti-CXCR4 antibody h3G10.1.91.A58B compared to the isotype control antibody in the survival of animals implanted with the OPM-2-Luc MM cells systemically. While isoptype control and Melphalan treated animals showed median survivals of 33.5 and 36 days respectively, the animals treated with h3G10.1.91.A58B CXCR4 antibody had median survival undefined, with no deaths observed by Day 50 of the study. Table 13. These differences were statistically significant ($p<0.0001$) by Mantel-Cox test.

TABLE 13

| | Isotype Control | h3G10.1.91.A58B | Melphalan |
|---|---|---|---|
| Median Survival (Days) | 33.5 | Undefined | 36 |

Example 15

Cytotoxicity of Anti-CXCR4-ADCs in CXCR4-Positive Cells

Anti-CXCR4 antibodies (e.g., 3G10) were expressed as human IgG1 subtypes and engineered with glutamine-containing transglutaminase ("Q") tag TG6(SEQ ID NO: 91 (LLQGA)) and conjugated with AcLys-vc-PABC-MMAD (Acetyl-Lysine-Valine-Citrulline-p-aminobenzyloxycarbonyl-MMAD), and AcLys-vc-PABC-0101 ((2-methylalanyl-N-[(3R,4S,5S)-3-methoxy-1-{(2 S)-2-[(1R,2R)-1-methoxy-2-methyl-3-oxo-3-{[(1 S)-2-phenyl-1-(1,3-thiazol-2-yl) ethyl]amino}propyl]pyrrolidin-1-yl}-5-methyl-1-oxoheptan-4-yl]-N-methyl-L-valinamide). The transglutaminase tags were engineered at the heavy chain C-terminus of the antibody. Anti-CXCR4 antibody conjugation to the cytotoxic agent MMAD or 0101 was then achieved via microbial transglutaminase-catalyzed transamidation reaction between the anti-CXCR4 antibody carrying a glutamine-containing tag at the specific site (e.g., carboxyl terminus of the heavy chain of the antibody) and an amine-containing derivative of the payload (e.g., MMAD or 0101). In some instances, the wild-type amino acid lysine at the carboxyl terminus (position 447 in accordance with EU numbering scheme) was deleted and replaced with the Q-tag. In other instances, the wild-type amino acid lysine at position 222, (in accordance with EU numbering scheme) was replaced with amino acid arginine ("K222R",). The K222R substitution provided the significant effect of resulting in more homogenous antibody and payload conjugate, and/or better intermolecular crosslinking between the antibody and the payload. In the transamidation reaction, the glutamine on the glutamine-containing tag acted as an acyl donor, and the amine-containing compound acted as an acyl acceptor (amine donor). Purified anti-CXCR4 antibody was incubated with excess acyl acceptor in the presence of Streptoverticillium mobaraense transglutaminase (ACTIVA™, Ajinomoto, Japan) in 150-900 mM NaCl, and 25 mM MES, HEPES [4-(2-hydroxyethyl)-1-piperazineethanesulfonic acid] or Tris HCl buffer at pH range 6.2-8.8. The reaction conditions were adjusted for individual acyl acceptor derivatives. Following incubation at room temperature for 2.5 hours, the antibody-drug conjugate was purified on MabSelect resin (GE Healthcare, Waukesha, Wis.) using standard affinity chromatography methods known to persons skilled in the art, such as commercial affinity chromatography from GE Healthcare.

CXCR4 expressing cells were then seeded on white walled clear bottom plates at 4000-8,000 cells/well for 24 hours before treatment. Cells were then treated with 4 fold serially diluted antibody-drug conjugates in triplicates. Cell viability was determined by CellTiter-Glo® Luminescent Cell Viability Assay 96 (Promega, Madison Wis.) 96 hours after treatment. Relative cell viability was determined as percentage of untreated control. IC50 was then calculated. The anti-CXCR4 antibodies conjugated to MMAD or 0101 through transglutaminase tag exert potent cell killing activity in CXCR4-expressing cells.

TABLE 14

Cytotoxicity of CXCR4 ADCs on CXCR4-expressing cells

| | ADC IC50 (nM) in CXCR4-expression tumor cells | | | | | | |
|---|---|---|---|---|---|---|---|
| conjugates | DAR (Drug-Ab-ratio) | Ramos (NHL) | MM1.S (MM) | RPMI-8226 (MM) | MOLP-8 (MM) | HPB-ALL (T-ALL) | MOLT-4 (T-ALL) |
| Neg ctrl-TG6-vcMMAD | 1.87 | >267 | n/d | n/d | n/d | n/d | n/d |
| 3G10-TG6-vcMMAD | 1.90 | 0.151 | n/d | n/d | n/d | n/d | n/d |
| 6B6-TG6-vcMMAD | 1.90 | 0.316 | n/d | n/d | n/d | n/d | n/d |
| 12A11-TG6-vcMMAD | 1.87 | 0.371 | n/d | n/d | n/d | n/d | n/d |
| Neg ctrl-TG6-vc0101 | 1.92 | 167.000 | 142.000 | 246.733 | 257.133 | 257.133 | 223.067 |
| 3G10-TG6-vc0101 | 1.86 | 0.066 | 8.533 | 0.138 | 0.045 | 0.059 | 0.062 |
| 6B6-TG6-vc0101 | 2.00 | 0.075 | 1.556 | 0.245 | 0.066 | 0.071 | 0.055 |

n/d: not determined

Example 16

In Vivo Anti-Tumor Activity of CXCR4-ADCs

Figure 13A:
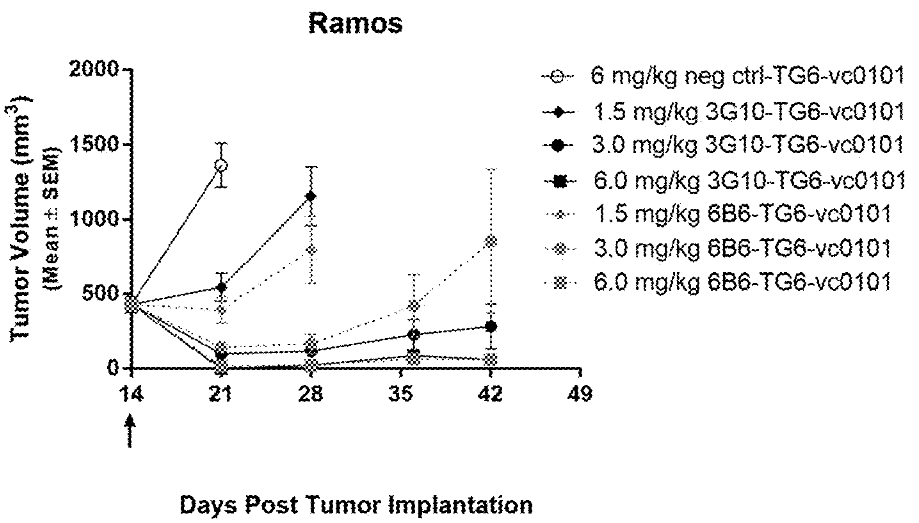
FIG. 13A shows a significant anti-tumor effect of CXCR4 ADCs 3G10-TG6-vc0101 and 6B6-TG6-vc0101 in Ramos (NHL) tumor model.
Figure 13B:
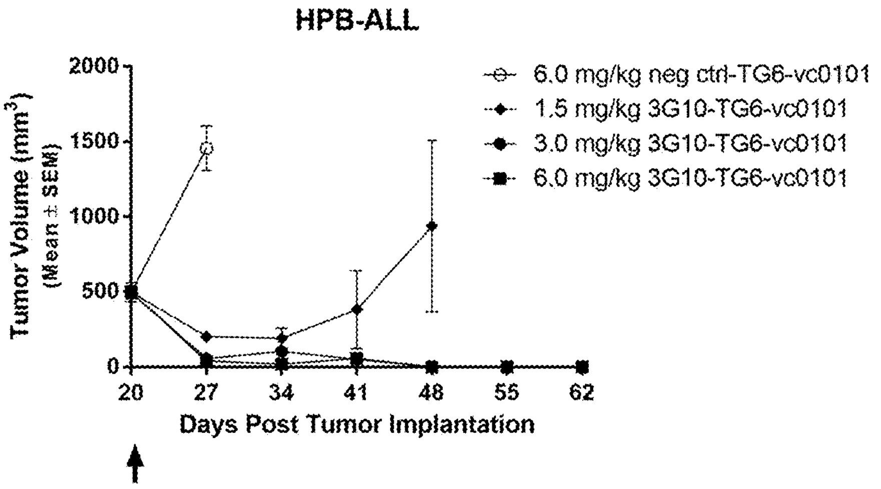
FIG. 13B shows a significant anti-tumor effect of CXCR4 ADC 3G10-TG6-vc0101 in HPB-ALL (T-ALL) tumor model.

The in vivo anti-tumor efficacy of CXCR4 ADCs was evaluated in xenograft models of Ramos (NHL) and HPB-ALL (T-ALL). Female 4-6 week-old CB17 SCID mice (Jackson Laboratories) were implanted subcutaneously with $5\times10^6$ Ramos (NHL) as described in Example 9 until mean size volume of approximately 500 $mm^3$, calculated by the formula (volume=length×width$^2$)/2. $10\times10^6$ HPB-ALL cells were implanted in female 4-6 week-old CB17 SCID mice until mean tumor size volume also reaches ~500 $mm^3$. In Ramos model, groups of mice were treated with single dose intravenous (i.v.) injection of either negative control ADC (neg ctrl-TG6-vc0101) at 6.0 mg/kg or CXCR4 ADCs (3G10-TG6-vc0101 and 6B6-TG6-vc0101) at 1.5, 3.0 or 6.0 mg/kg. Tumor volumes were measured by caliper once a week for the duration of the study. The results of the experiment are presented on FIG. 13A. The results indicate that both CXCR4 ADCs induced tumor regression at doses ≥3 mg/kg. The control ADC has no effect on tumor growth. In the HPB-ALL model, 1.5 mg/kg of single dose injection of 3G10-TG6-vc0101 is sufficient to induce tumor regression (FIG. 13B).

It is claimed:

1. An isolated polynucleotide comprising a nucleotide sequence encoding an antibody, or an antigen binding fragment thereof, that binds to chemokine receptor 4 (CXCR4) and comprises:

a) a heavy chain variable (VH) CDR1 comprising the amino acid sequence shown in SEQ ID NO: 107, 108, 109, 113 or 114; a VH CDR2 comprising the amino acid sequence shown in SEQ ID NO: 110 or 111; and a VH CDR3 comprising the amino acid sequence shown in SEQ ID NO: 112; and;

b) a light chain variable region (VL) CDR1 comprising SEQ ID NO: 131; a VL CDR2 comprising 132; and a VL CDR3 comprising SEQ ID NO: 133.

2. A vector comprising the polynucleotide of claim 1.

3. An isolated host cell that recombinantly produces the antibody or antigen binding fragment thereof of claim 1.

* * * * *

SEQUENCE LISTING

```
<160> NUMBER OF SEQ ID NOS: 173

<210> SEQ ID NO 1
<211> LENGTH: 120
<212> TYPE: PRT
<213> ORGANISM: Artificial Sequence
<220> FEATURE:
<223> OTHER INFORMATION: Synthetic Construct
```

<400> SEQUENCE: 1

His Val Glu Val Lys Leu Val Glu Ser Gly Gly Gly Leu Val Gln Pro
1               5                   10                  15

Gly Gly Ser Leu Arg Leu Ser Cys Ala Thr Ser Gly Phe Thr Phe Thr
            20                  25                  30

Asp Tyr Tyr Met Ser Trp Val Arg Gln Pro Pro Gly Lys Ala Leu Glu
        35                  40                  45

Trp Leu Gly Phe Ile Arg Asn Lys Ala Asn Gly Tyr Thr Thr Glu Tyr
    50                  55                  60

Ser Ala Ser Val Lys Gly Arg Phe Thr Ile Ser Arg Asp Asn Ser Gln
65                  70                  75                  80

Ser Ile Leu Tyr Leu Gln Met Asn Thr Leu Arg Ala Glu Asp Ser Ala
                85                  90                  95

Thr Tyr Tyr Cys Ala Arg Asp Leu Pro Gly Phe Ala Tyr Trp Gly Gln
            100                 105                 110

Gly Thr Leu Val Thr Val Ser Ser
            115                 120

<210> SEQ ID NO 2
<211> LENGTH: 354
<212> TYPE: DNA
<213> ORGANISM: Artificial Sequence
<220> FEATURE:
<223> OTHER INFORMATION: Synthetic Construct

<400> SEQUENCE: 2
gaggtaaagt tggtggagtc tggaggaggc ttggtacagc ctgggggttc tctgagactc      60
tcctgtgcaa cttctgggtt caccttcact gattactaca tgagttgggt ccgccagcct     120
ccaggaaagg cacttgagtg gttgggtttt attagaaaca aagctaatgg ttacacaaca     180
gagtacagtg catctgtgaa gggtcggttc accatctcca gagataattc ccaaagcatc     240
ctctatcttc aaatgaacac cctgagagct gaggacagtg ccacttatta ctgtgcaaga     300
gatctcccgg ggtttgctta ctggggccaa gggactctgg tcaccgtctc ctca           354

<210> SEQ ID NO 3
<211> LENGTH: 112
<212> TYPE: PRT
<213> ORGANISM: Artificial Sequence
<220> FEATURE:
<223> OTHER INFORMATION: Synthetic Construct

<400> SEQUENCE: 3

Asp Ile Val Met Ser Gln Ser Pro Ser Ser Leu Thr Val Ser Ala Gly
1               5                   10                  15

Glu Lys Val Thr Met Ser Cys Lys Ser Ser Gln Ser Leu Tyr Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Gly Arg Phe Thr Gly Ser Gly Ser Gly Thr Asp Phe Ala Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 4
<211> LENGTH: 336
<212> TYPE: DNA
<213> ORGANISM: Artificial Sequence
<220> FEATURE:
<223> OTHER INFORMATION: Synthetic Construct

<400> SEQUENCE: 4
gacatagtta tgtcgcagtc tccatcctcc ctgactgtgt cagcaggaga gaaggtcact 60
atgagctgca aatccagtca gagtctgtac aacagtagaa cccgaaagaa ctacttggct 120
tggtaccagc agaaaccagg gcagtctcct aaactgctga tctactgggc atccgctagg 180
gaatctgggg tccctggtcg cttcacaggc agtggatctg ggacagattt cgctctcacc 240
atcagcagtg tgcaggctga agacctggca gtttattact gcaagcaatc ttataatctt 300
cggacgttcg gtggaggcac caagctggag atcaaa 336

<210> SEQ ID NO 5
<211> LENGTH: 118
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Tyr Met Ser Trp Val Arg Gln Ala Pro Gly Lys Gly Leu Glu Trp Val
35 40 45

Gly Phe Ile Arg Asn Lys Ala Asn Gly Tyr Thr Thr Glu Tyr Ser Ala
50 55 60

Ser Val Lys Gly Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Ala Arg Asp Leu Pro Gly Phe Ala Tyr Trp Gly Gln Gly Thr
100 105 110

Leu Val Thr Val Ser Ser
115

<210> SEQ ID NO 6
<211> LENGTH: 354
<212> TYPE: DNA
<213> ORGANISM: Artificial Sequence
<220> FEATURE:
<223> OTHER INFORMATION: Synthetic Construct

<400> SEQUENCE: 6
gaagtccagc tggttgaaag tggtggcggc ctggtgcagc cgggcggctc tctgcgcctg 60
tcatgcgctg catccggctt taccttcagc gactattaca tgagctgggt tcgccaagcg 120
cccggcaaag gcctggaatg ggtgggattc attcgaaata aagcgaacgg ctataccacc 180
gaatatagcg catctgtcaa gggccggttc accatctccc gcgatgattc caagaacagc 240
ctgtacctgc agatgaactc cctgaagacg gaagataccg ccgtctatta ttgtgcccgc 300
gatctgcctg gctttgccta ttggggccaa ggcactctgg tcaccgtctc ctca 354

-continued

<210> SEQ ID NO 7
<211> LENGTH: 112
<212> TYPE: PRT
<213> ORGANISM: Artificial Sequence
<220> FEATURE:
<223> OTHER INFORMATION: Synthetic Construct

<400> SEQUENCE: 7

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Tyr Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Arg Thr Phe Gly Gly Gly Thr Lys Val Glu Ile Lys
            100                 105                 110
```

<210> SEQ ID NO 8
<211> LENGTH: 336
<212> TYPE: DNA
<213> ORGANISM: Artificial Sequence
<220> FEATURE:
<223> OTHER INFORMATION: Synthetic Construct

<400> SEQUENCE: 8

```
gacatcgtta tgacacagtc accagatagc ttagccgtgt ccctgggaga acgtgctacc      60

attaattgca aaagctccca gagcctgtat aacagccgga cacggaagaa ttatctggca     120

tggtatcagc agaaacccgg acagccgcct aagctgctga tttattgggc cagcgcacgc     180

gaaagtggtg tgcccgaccg cttttccggc agcggtagtg gcactgactt caccctgacc     240

atctcaagct tgcaagccga agacgtggca gtatattatt gcaagcagtc gtacaatctg     300

cgcacctttg gcggcggcac aaaagtggag atcaaa                                336
```

<210> SEQ ID NO 9
<211> LENGTH: 121
<212> TYPE: PRT
<213> ORGANISM: Artificial Sequence
<220> FEATURE:
<223> OTHER INFORMATION: Synthetic Construct

<400> SEQUENCE: 9

```
Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Asn Ile Tyr Trp Val Lys Gln Ser His Gly Gln Ser Leu Glu Trp Ile
        35                  40                  45

Gly Tyr Ile Asp Pro Tyr Asn Gly Gly Thr Arg Tyr Asn Gln Lys Phe
    50                  55                  60

Lys Gly Lys Ala Thr Leu Thr Val Asp Lys Ser Ser Ser Thr Ala Phe
65                  70                  75                  80

Met His Leu Asn Ser Leu Thr Ser Glu Asp Ser Ala Val Tyr Phe Cys
```

```
                85                  90                  95

Ala Arg Thr Tyr Gly Ser Arg Tyr Val Gly Ala Met Asp Tyr Trp Gly
            100                 105                 110

Gln Gly Thr Ser Val Thr Val Ser Ser
        115                 120


<210> SEQ ID NO 10
<211> LENGTH: 363
<212> TYPE: DNA
<213> ORGANISM: Artificial Sequence
<220> FEATURE:
<223> OTHER INFORMATION: Synthetic Construct

<400> SEQUENCE: 10

gaaatacagt tgcagcagtc cgggcctgag ctggtgaagc ctggggcttc agtgaaggta      60

tcctgcaagg cttctggtta ctcattcact gactataata tatactgggt gaagcagagc     120

catggacaga gccttgagtg gattggatat attgatcctt acaatggtgg gaccaggtat     180

aaccagaagt tcaagggcaa ggccacattg actgttgaca agtcctccag cacagccttc     240

atgcatctca acagcctgac atctgaggac tctgcagtct atttttgtgc aagaacctac     300

ggtagtcggt acgttggggc tatggactac tggggtcaag gaacctcggt caccgtctcc     360

tca                                                                   363


<210> SEQ ID NO 11
<211> LENGTH: 112
<212> TYPE: PRT
<213> ORGANISM: Artificial Sequence
<220> FEATURE:
<223> OTHER INFORMATION: Synthetic Construct

<400> SEQUENCE: 11

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Pro Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110


<210> SEQ ID NO 12
<211> LENGTH: 336
<212> TYPE: DNA
<213> ORGANISM: Artificial Sequence
<220> FEATURE:
<223> OTHER INFORMATION: Synthetic Construct

<400> SEQUENCE: 12

gatatcgtta tgacgcaggc tgcaccctct gtacctgtca ctcctggaga gtcagtatcc      60

atctcctgca ggtctagtaa gagtctcctg catagtaatg gcaacactta cttatattgg     120

ttcctgcaga ggccaggcca gtctcctcag ctcctaatat atcggatgtc caaccctgcc     180
```

tcaggagtcc cagacaggtt cagtggcagt gggtcaggaa ctgctttcac actgagaatc 240
agtcgagtgg aggctgagga tgtgggtgtt tattactgta tgcaacatct agaatatccg 300
ctcacgttcg gtgctgggac caagctggag ctgaaa 336

<210> SEQ ID NO 13
<211> LENGTH: 121
<212> TYPE: PRT
<213> ORGANISM: Artificial Sequence
<220> FEATURE:
<223> OTHER INFORMATION: Synthetic Construct

<400> SEQUENCE: 13

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Asn Ile Tyr Trp Val Arg Gln Ala Thr Gly Gln Gly Leu Glu Trp Met
35 40 45

Gly Tyr Ile Asp Pro Tyr Asn Gly Gly Thr Arg Tyr Asn Gln Lys Phe
50 55 60

Lys Gly Arg Val Thr Met Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Thr Tyr Gly Ser Arg Tyr Val Gly Ala Met Asp Tyr Trp Gly
100 105 110

Gln Gly Thr Leu Val Thr Val Ser Ser
115 120

<210> SEQ ID NO 14
<211> LENGTH: 363
<212> TYPE: DNA
<213> ORGANISM: Artificial Sequence
<220> FEATURE:
<223> OTHER INFORMATION: Synthetic Construct

<400> SEQUENCE: 14
caggttcagc tggtgcagag cggcgccgag gtgaagaaac caggcgccag cgtgaaagtg 60
tcctgcaagg cgagtggata taccttcacc gattacaata tttattgggt tcgccaggcc 120
accgggcagg gcctggagtg gatgggctac attgatccat ataacggtgg cacccgctac 180
aaccagaagt ttaaaggccg cgtgaccatg acccgcaata cctcgatctc caccgcctat 240
atggaactga gcagcttacg ctctgaagat acggccgtgt actactgtgc ccgcacctac 300
gggtctcgct acgttggcgc gatggattat tggggtcagg gcaccctggt caccgtctcc 360
tca 363

<210> SEQ ID NO 15
<211> LENGTH: 112
<212> TYPE: PRT
<213> ORGANISM: Artificial Sequence
<220> FEATURE:
<223> OTHER INFORMATION: Synthetic Construct

<400> SEQUENCE: 15

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Ser
20 25 30

```
Asn Gly Asn Thr Tyr Leu Tyr Trp Tyr Leu Gln Lys Pro Gly Gln Ser
        35                  40                  45

Pro Gln Leu Leu Ile Tyr Arg Met Ser Asn Pro Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gly Gly Thr Lys Val Glu Leu Lys
            100                 105                 110


<210> SEQ ID NO 16
<211> LENGTH: 336
<212> TYPE: DNA
<213> ORGANISM: Artificial Sequence
<220> FEATURE:
<223> OTHER INFORMATION: Synthetic Construct

<400> SEQUENCE: 16

gacatcgtga tgacccagag cccgctgtct ctgccagtga cccctggtga gccagccagt      60

attagctgcc gcagcagcaa aagtctgctg cacagcaatg gaaacaccta cctgtattgg     120

tatctgcaga aaccgggtca gtcaccccag ctgctgatct accgcatgtc taacccggcc     180

agcggcgtcc ctgatcgctt tagcggcagc ggttccggaa ccgattttac cctgaagatc     240

tcccgcgttg aggccgaaga cgtcggcgtc tactattgca tgcagcacct ggaatatccg     300

ctgacattcg gtggcggtac caaagtggaa ctcaaa                               336


<210> SEQ ID NO 17
<211> LENGTH: 118
<212> TYPE: PRT
<213> ORGANISM: Artificial Sequence
<220> FEATURE:
<223> OTHER INFORMATION: Synthetic Construct

<400> SEQUENCE: 17

Glu Val Lys Leu Val Glu Ser Gly Gly Gly Leu Val Gln Pro Gly Ser
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg His Lys Ala Asn Gly Tyr Thr Thr Glu Tyr Ser Thr
    50                  55                  60

Ser Val Lys Gly Arg Phe Thr Ile Ser Arg Asp Asn Ser Leu Ser Ile
65                  70                  75                  80

Leu Tyr Leu Gln Met Asn Thr Leu Arg Pro Glu Asp Ser Ala Thr Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115


<210> SEQ ID NO 18
<211> LENGTH: 354
<212> TYPE: DNA
<213> ORGANISM: Artificial Sequence
<220> FEATURE:
<223> OTHER INFORMATION: Synthetic Construct
```

<400> SEQUENCE: 18

```
gaagtgaaat tggtggagtc tggaggaggc ttggtacagc ctgggagttc tctgagactc     60

tcctgtgcag cttctgggtt caccttcact gattactaca tgagctgggt ccgccagcct    120

ccaggaaagg cacttgagtg gttgggtttt attagacaca aggctaatgg ttacacaaca    180

gaatacagta catctgtgaa gggtcggttc accatctcca gagataattc cctaagcatc    240

ctctatcttc aaatgaacac cctgagacct gaggacagtg ccacttatta ctgtgcaaga    300

gatctcccgg ggtttgctta ctggggccaa gggactctgg tcaccgtctc ctca          354
```

<210> SEQ ID NO 19
<211> LENGTH: 112
<212> TYPE: PRT
<213> ORGANISM: Artificial Sequence
<220> FEATURE:
<223> OTHER INFORMATION: Synthetic Construct

<400> SEQUENCE: 19

```
Asp Ile Val Met Ser Gln Ser Pro Ser Ser Leu Ala Val Ser Ala Gly
1               5                   10                  15

Glu Lys Val Thr Met Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Phe Asn Leu Arg Thr Phe Gly Gly Gly Thr Lys Leu Glu Ile Lys
            100                 105                 110
```

<210> SEQ ID NO 20
<211> LENGTH: 336
<212> TYPE: DNA
<213> ORGANISM: Artificial Sequence
<220> FEATURE:
<223> OTHER INFORMATION: Synthetic Construct

<400> SEQUENCE: 20

```
gatattgtta tgtcgcagtc gccatcctcc ctggctgtgt cagcaggaga gaaggtcact     60

atgacctgca aatccagtca gagtctgttc aacagtagaa cccgaaagaa ctacttggct    120

tggtaccagc agaaacccgg gcagtctcct aaactgctga tctactgggc atccgctagg    180

gaatctgggg tccctgatcg cttcacaggc agtggatctg ggacagattt cactctcacc    240

atcagcagtg tgcaggctga agacctggca gtttattact gcaagcaatc ttttaatctt    300

cggacgttcg gtggaggcac caagctggaa atcaaa                              336
```

<210> SEQ ID NO 21
<211> LENGTH: 118
<212> TYPE: PRT
<213> ORGANISM: Artificial Sequence
<220> FEATURE:
<223> OTHER INFORMATION: Synthetic Construct

<400> SEQUENCE: 21

```
Glu Val Gln Leu Val Glu Ser Gly Gly Gly Leu Val Gln Pro Gly Gly
```

-continued

```
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg His Lys Ala Asn Gly Tyr Thr Thr Glu Tyr Ser Thr
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115


<210> SEQ ID NO 22
<211> LENGTH: 354
<212> TYPE: DNA
<213> ORGANISM: Artificial Sequence
<220> FEATURE:
<223> OTHER INFORMATION: Synthetic Construct

<400> SEQUENCE: 22

gaagtccagc tggttgaaag tggtggcggc ctggtgcagc cgggcggctc tctgcgcctg     60

tcatgcgctg catccggctt taccttcagc gactattaca tgagctgggt tcgccaagcg    120

cccggcaaag gcctggaatg ggtgggattc attcgacata aagcgaacgg ctataccacc    180

gaatatagca catctgtcaa gggccggttc accatctccc gcgatgattc caagaacagc    240

ctgtacctgc agatgaactc cctgaagacg gaagataccg ccgtctatta ttgtgcccgc    300

gatctgcctg gctttgccta ttggggccaa ggcactctgg tcaccgtctc ctca          354


<210> SEQ ID NO 23
<211> LENGTH: 118
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg His Lys Ala Asn Phe Tyr Thr Thr Glu Tyr Ser Thr
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115
```

<210> SEQ ID NO 24
<211> LENGTH: 354
<212> TYPE: DNA
<213> ORGANISM: Artificial Sequence
<220> FEATURE:
<223> OTHER INFORMATION: Synthetic Construct

<400> SEQUENCE: 24
gaagtccagc tggttgaaag tggtggcggc ctggtgcagc cgggcggctc tctgcgcctg 60
tcatgcgctg catccggctt taccttcagc gactattaca tgagctgggt tcgccaagcg 120
cccggcaaag gcctggaatg ggtgggattc attcgacata aagcgaactt ttataccacc 180
gaatatagca catctgtcaa gggccggttc accatctccc gcgatgattc caagaacagc 240
ctgtacctgc agatgaactc cctgaagacg gaagataccg ccgtctatta ttgtgcccgc 300
gatctgcctg gctttgccta ttggggccaa ggcactctgg tcaccgtctc ctca 354

<210> SEQ ID NO 25
<211> LENGTH: 118
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Tyr Met Ser Trp Val Arg Gln Ala Pro Gly Lys Gly Leu Glu Trp Val
35 40 45

Ser Phe Ile Arg His Lys Ala Asn Phe Tyr Thr Thr Glu Tyr Ser Thr
50 55 60

Ser Val Lys Gly Arg Phe Thr Ile Ser Arg Asp Asn Ser Lys Asn Thr
65 70 75 80

Leu Tyr Leu Gln Met Asn Ser Leu Arg Ala Glu Asp Thr Ala Val Tyr
85 90 95

Tyr Cys Ala Lys Asp Leu Pro Gly Phe Ala Tyr Trp Gly Gln Gly Thr
100 105 110

Leu Val Thr Val Ser Ser
115

<210> SEQ ID NO 26
<211> LENGTH: 354
<212> TYPE: DNA
<213> ORGANISM: Artificial Sequence
<220> FEATURE:
<223> OTHER INFORMATION: Synthetic Construct

<400> SEQUENCE: 26
gaagtccagc tggttgaaag tggtggcggc ctggtgcagc cgggcggctc tctgcgcctg 60
tcatgcgctg catccggctt taccttcagc gactattaca tgagctgggt tcgccaagcg 120
cccggcaaag gcctggaatg ggtgtcattc attcgacata aagcgaactt ttataccacc 180
gaatatagca catctgtcaa gggccggttc accatctccc gcgataattc caagaacacc 240
ctgtacctgc agatgaactc cctgagggcg gaagataccg ccgtctatta ttgtgccaag 300
gatctgcctg gctttgccta ttggggccaa ggcactctgg tcaccgtctc ttcc 354

<210> SEQ ID NO 27
<211> LENGTH: 118
<212> TYPE: PRT
<213> ORGANISM: Artificial Sequence
<220> FEATURE:
<223> OTHER INFORMATION: Synthetic Construct

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg His Lys Ala Asn Lys Tyr Thr Thr Glu Tyr Ser Thr
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115
```

<210> SEQ ID NO 28
<211> LENGTH: 354
<212> TYPE: DNA
<213> ORGANISM: Artificial Sequence
<220> FEATURE:
<223> OTHER INFORMATION: Synthetic Construct

<400> SEQUENCE: 28

```
gaagtccagc tggttgaaag tggtggcggc ctggtgcagc cgggcggctc tctgcgcctg      60

tcatgcgctg catccggctt taccttcagc gactattaca tgagctgggt tcgccaagcg     120

cccggcaaag gcctggaatg ggtgggattc attcgacata aagcgaacaa gtataccacc     180

gaatatagca catctgtcaa gggccggttc accatctccc gcgatgattc caagaacagc     240

ctgtacctgc agatgaactc cctgaagacg gaagataccg ccgtctatta ttgtgcccgc     300

gatctgcctg gctttgccta ttggggccaa ggcactctgg tcaccgtctc ctca           354
```

<210> SEQ ID NO 29
<211> LENGTH: 118
<212> TYPE: PRT
<213> ORGANISM: Artificial Sequence
<220> FEATURE:
<223> OTHER INFORMATION: Synthetic Construct

<400> SEQUENCE: 29

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg His Lys Ala Asn Val Tyr Thr Thr Glu Tyr Ser Thr
    50                  55                  60

Ser Val Lys Gly Arg Phe Thr Ile Ser Arg Asp Asp Ser Lys Asn Ser
65                  70                  75                  80
```

```
Leu Tyr Leu Gln Met Asn Ser Leu Lys Thr Glu Asp Thr Ala Val Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115
```

<210> SEQ ID NO 30
<211> LENGTH: 354
<212> TYPE: DNA
<213> ORGANISM: Artificial Sequence
<220> FEATURE:
<223> OTHER INFORMATION: Synthetic Construct

<400> SEQUENCE: 30

```
gaagtccagc tggttgaaag tggtggcggc ctggtgcagc cgggcggctc tctgcgcctg      60

tcatgcgctg catccggctt taccttcagc gactattaca tgagctgggt tcgccaagcg     120

cccggcaaag gcctggaatg ggtgggattc attcgacata aagcgaacgt gtataccacc     180

gaatatagca catctgtcaa gggccggttc accatctccc gcgatgattc caagaacagc     240

ctgtacctgc agatgaactc cctgaagacg gaagataccg ccgtctatta ttgtgcccgc     300

gatctgcctg gctttgccta ttggggccaa ggcactctgg tcaccgtctc ctca           354
```

<210> SEQ ID NO 31
<211> LENGTH: 118
<212> TYPE: PRT
<213> ORGANISM: Artificial Sequence
<220> FEATURE:
<223> OTHER INFORMATION: Synthetic Construct

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg His Lys Ala Asn Ile Tyr Thr Thr Glu Tyr Ser Thr
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115
```

<210> SEQ ID NO 32
<211> LENGTH: 354
<212> TYPE: DNA
<213> ORGANISM: Artificial Sequence
<220> FEATURE:
<223> OTHER INFORMATION: Synthetic Construct

<400> SEQUENCE: 32

```
gaagtccagc tggttgaaag tggtggcggc ctggtgcagc cgggcggctc tctgcgcctg      60

tcatgcgctg catccggctt taccttcagc gactattaca tgagctgggt tcgccaagcg     120
```

-continued

```
cccggcaaag gcctggaatg ggtgggattc attcgacata aagcgaacat ttataccacc    180

gaatatagca catctgtcaa gggccggttc accatctccc gcgatgattc caagaacagc    240

ctgtacctgc agatgaactc cctgaagacg gaagataccg ccgtctatta ttgtgcccgc    300

gatctgcctg gctttgccta ttggggccaa ggcactctgg tcaccgtctc ctca          354


<210> SEQ ID NO 33
<211> LENGTH: 118
<212> TYPE: PRT
<213> ORGANISM: Artificial Sequence
<220> FEATURE:
<223> OTHER INFORMATION: Synthetic Construct

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg His Lys Ala Asn Phe Glu Thr Thr Glu Tyr Ser Thr
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115


<210> SEQ ID NO 34
<211> LENGTH: 354
<212> TYPE: DNA
<213> ORGANISM: Artificial Sequence
<220> FEATURE:
<223> OTHER INFORMATION: Synthetic Construct

<400> SEQUENCE: 34

gaagtccagc tggttgaaag tggtggcggc ctggtgcagc cgggcggctc tctgcgcctg     60

tcatgcgctg catccggctt taccttcagc gactattaca tgagctgggt tcgccaagcg    120

cccggcaaag gcctggaatg ggtgggattc attcgacata aagcgaactt tgagaccacc    180

gaatatagca catctgtcaa gggccggttc accatctccc gcgatgattc caagaacagc    240

ctgtacctgc agatgaactc cctgaagacg gaagataccg ccgtctatta ttgtgcccgc    300

gatctgcctg gctttgccta ttggggccaa ggcactctgg tcaccgtctc ctca          354


<210> SEQ ID NO 35
<211> LENGTH: 118
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
```

```
            20                  25                  30

Tyr Met Ser Trp Val Arg Gln Ala Pro Gly Lys Gly Leu Glu Trp Val
        35                  40                  45

Gly Phe Ile Arg His Lys Ala Asn Phe Tyr Thr Arg Glu Tyr Ser Thr
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115
```

<210> SEQ ID NO 36
<211> LENGTH: 354
<212> TYPE: DNA
<213> ORGANISM: Artificial Sequence
<220> FEATURE:
<223> OTHER INFORMATION: Synthetic Construct

<400> SEQUENCE: 36

```
gaagtccagc tggttgaaag tggtggcggc ctggtgcagc cgggcggctc tctgcgcctg      60

tcatgcgctg catccggctt taccttcagc gactattaca tgagctgggt tcgccaagcg     120

cccggcaaag gcctggaatg ggtgggattc attcgacata aagcgaactt ttatacccgg     180

gaatatagca catctgtcaa gggccggttc accatctccc gcgatgattc caagaacagc     240

ctgtacctgc agatgaactc cctgaagacg gaagataccg ccgtctatta ttgtgcccgc     300

gatctgcctg gctttgccta ttggggccaa ggcactctgg tcaccgtctc ctca           354
```

<210> SEQ ID NO 37
<211> LENGTH: 118
<212> TYPE: PRT
<213> ORGANISM: Artificial Sequence
<220> FEATURE:
<223> OTHER INFORMATION: Synthetic Construct

<400> SEQUENCE: 37

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg His Lys Ala Asn Phe Tyr Thr Thr Glu Tyr Ser Thr
    50                  55                  60

Trp Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115
```

<210> SEQ ID NO 38
<211> LENGTH: 354

<212> TYPE: DNA
<213> ORGANISM: Artificial Sequence
<220> FEATURE:
<223> OTHER INFORMATION: Synthetic Construct

<400> SEQUENCE: 38
gaagtccagc tggttgaaag tggtggcggc ctggtgcagc cgggcggctc tctgcgcctg 60
tcatgcgctg catccggctt taccttcagc gactattaca tgagctgggt tcgccaagcg 120
cccggcaaag gcctggaatg ggtgggattc attcgacata aagcgaactt ttataccacc 180
gggtatagca catctgtcaa gggccggttc accatctccc gcgatgattc caagaacagc 240
ctgtacctgc agatgaactc cctgaagacg gaagataccg ccgtctatta ttgtgcccgc 300
gatctgcctg gctttgccta ttggggccaa ggcactctgg tcaccgtctc ctca 354

<210> SEQ ID NO 39
<211> LENGTH: 118
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Tyr Met Ser Trp Val Arg Gln Ala Pro Gly Lys Gly Leu Glu Trp Val
35 40 45

Gly Phe Ile Arg His Lys Ala Asn Phe Tyr Thr Thr Glu Tyr Ser Thr
50 55 60

Ser Val Arg Gly Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Ala Arg Asp Leu Pro Gly Phe Ala Tyr Trp Gly Gln Gly Thr
100 105 110

Leu Val Thr Val Ser Ser
115

<210> SEQ ID NO 40
<211> LENGTH: 354
<212> TYPE: DNA
<213> ORGANISM: Artificial Sequence
<220> FEATURE:
<223> OTHER INFORMATION: Synthetic Construct

<400> SEQUENCE: 40
gaagtccagc tggttgaaag tggtggcggc ctggtgcagc cgggcggctc tctgcgcctg 60
tcatgcgctg catccggctt taccttcagc gactattaca tgagctgggt tcgccaagcg 120
cccggcaaag gcctggaatg ggtgggattc attcgacata aagcgaactt ttataccacc 180
gaatatagca catctgtccg tggccggttc accatctccc gcgatgattc caagaacagc 240
ctgtacctgc agatgaactc cctgaagacg gaagataccg ccgtctatta ttgtgcccgc 300
gatctgcctg gctttgccta ttggggccaa ggcactctgg tcaccgtctc ctca 354

<210> SEQ ID NO 41
<211> LENGTH: 118
<212> TYPE: PRT

<213> ORGANISM: Artificial Sequence
<220> FEATURE:
<223> OTHER INFORMATION: Synthetic Construct

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg His Lys Val Asn Phe Tyr Thr Thr Glu Tyr Ser Thr
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115
```

<210> SEQ ID NO 42
<211> LENGTH: 354
<212> TYPE: DNA
<213> ORGANISM: Artificial Sequence
<220> FEATURE:
<223> OTHER INFORMATION: Synthetic Construct

<400> SEQUENCE: 42

```
gaagtccagc tggttgaaag tggtggcggc ctggtgcagc cgggcggctc tctgcgcctg     60

tcatgcgctg catccggctt taccttcagc gactattaca tgagctgggt tcgccaagcg    120

cccggcaaag gcctggaatg ggtgggattc attcgacata aagtgaactt ttataccacc    180

gaatatagca catctgtcaa gggccggttc accatctccc gcgatgattc caagaacagc    240

ctgtacctgc agatgaactc cctgaagacg gaagataccg ccgtctatta ttgtgcccgc    300

gatctgcctg gctttgccta ttggggccaa ggcactctgg tcaccgtctc ctca          354
```

<210> SEQ ID NO 43
<211> LENGTH: 118
<212> TYPE: PRT
<213> ORGANISM: Artificial Sequence
<220> FEATURE:
<223> OTHER INFORMATION: Synthetic Construct

<400> SEQUENCE: 43

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg His Lys Ala Asn Phe Tyr Thr Thr Glu Tyr Ser Thr
    50                  55                  60

Ser Val Thr Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95
```

```
Tyr Cys Ala Arg Asp Leu Pro Gly Phe Ala Tyr Trp Gly Gln Gly Thr
            100                 105                 110

Leu Val Thr Val Ser Ser
        115


<210> SEQ ID NO 44
<211> LENGTH: 354
<212> TYPE: DNA
<213> ORGANISM: Artificial Sequence
<220> FEATURE:
<223> OTHER INFORMATION: Synthetic Construct

<400> SEQUENCE: 44

gaagtccagc tggttgaaag tggtggcggc ctggtgcagc cgggcggctc tctgcgcctg     60

tcatgcgctg catccggctt taccttcagc gactattaca tgagctgggt tcgccaagcg    120

cccggcaaag gcctggaatg ggtgggattc attcgacata aagcgaactt ttataccacc    180

gaatatagca catctgtcac gggccggttc accatctccc gcgatgattc caagaacagc    240

ctgtacctgc agatgaactc cctgaagacg gaagataccg ccgtctatta ttgtgcccgc    300

gatctgcctg gctttgccta ttggggccaa ggcactctgg tcaccgtctc ctca          354


<210> SEQ ID NO 45
<211> LENGTH: 118
<212> TYPE: PRT
<213> ORGANISM: Artificial Sequence
<220> FEATURE:
<223> OTHER INFORMATION: Synthetic Construct

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg His Lys Ala Asn Phe Tyr Thr Thr Glu Tyr Ser Thr
    50                  55                  60

Ser Asp Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115


<210> SEQ ID NO 46
<211> LENGTH: 354
<212> TYPE: DNA
<213> ORGANISM: Artificial Sequence
<220> FEATURE:
<223> OTHER INFORMATION: Synthetic Construct

<400> SEQUENCE: 46

gaagtccagc tggttgaaag tggtggcggc ctggtgcagc cgggcggctc tctgcgcctg     60

tcatgcgctg catccggctt taccttcagc gactattaca tgagctgggt tcgccaagcg    120

cccggcaaag gcctggaatg ggtgggattc attcgacata aagcgaactt ttataccacc    180
```

```
gaatatagca catctgataa gggccggttc accatctccc gcgatgattc caagaacagc    240

ctgtacctgc agatgaactc cctgaagacg gaagataccg ccgtctatta ttgtgcccgc    300

gatctgcctg gctttgccta ttggggccaa ggcactctgg tcaccgtctc ctca          354


<210> SEQ ID NO 47
<211> LENGTH: 112
<212> TYPE: PRT
<213> ORGANISM: Artificial Sequence
<220> FEATURE:
<223> OTHER INFORMATION: Synthetic Construct

<400> SEQUENCE: 47

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Asn Leu Arg Thr Phe Gly Gly Gly Thr Lys Val Glu Ile Lys
            100                 105                 110


<210> SEQ ID NO 48
<211> LENGTH: 336
<212> TYPE: DNA
<213> ORGANISM: Artificial Sequence
<220> FEATURE:
<223> OTHER INFORMATION: Synthetic Construct

<400> SEQUENCE: 48

gacatcgtta tgacacagtc accagatagc ttagccgtgt ccctgggaga acgtgctacc     60

attaattgca aaagctccca gagcctgttt aacagccgga cacggaagaa ttatctggca    120

tggtatcagc agaaacccgg acagccgcct aagctgctga tttattgggc cagcgcacgc    180

gaaagtggtg tgcccgaccg cttttccggc agcggtagtg gcactgactt caccctgacc    240

atctcaagct tgcaagccga agacgtggca gtatattatt gcaagcagtc gttcaatctg    300

cgcacctttg gcggcggcac aaaagtggag atcaaa                              336


<210> SEQ ID NO 49
<211> LENGTH: 112
<212> TYPE: PRT
<213> ORGANISM: Artificial Sequence
<220> FEATURE:
<223> OTHER INFORMATION: Synthetic Construct

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
```

50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Lys Gln
85 90 95

Ser Phe Arg Leu Arg Thr Phe Gly Gly Gly Thr Lys Val Glu Ile Lys
100 105 110

<210> SEQ ID NO 50
<211> LENGTH: 336
<212> TYPE: DNA
<213> ORGANISM: Artificial Sequence
<220> FEATURE:
<223> OTHER INFORMATION: Synthetic Construct

<400> SEQUENCE: 50
gacatcgtta tgacacagtc accagatagc ttagccgtgt ccctgggaga acgtgctacc 60
attaattgca aaagctccca gagcctgttt aacagccgga cacggaagaa ttatctggca 120
tggtatcagc agaaacccgg acagccgcct aagctgctga tttattgggc cagcgcacgc 180
gaaagtggtg tgcccgaccg cttttccggc agcggtagtg gcactgactt caccctgacc 240
atctcaagct tgcaagccga agacgtggca gtatattatt gcaagcagtc gttcaggctg 300
cgcacctttg gcggcggcac aaaagtggag atcaaa 336

<210> SEQ ID NO 51
<211> LENGTH: 112
<212> TYPE: PRT
<213> ORGANISM: Artificial Sequence
<220> FEATURE:
<223> OTHER INFORMATION: Synthetic Construct

<400> SEQUENCE: 51

Asp Ile Val Met Thr Gln Ser Pro Asp Ser Leu Ala Val Ser Leu Gly
1 5 10 15

Glu Arg Ala Thr Ile Asn Cys Lys Ser Ala Gln Ser Leu Phe Asn Ser
20 25 30

Arg Thr Arg Lys Asn Tyr Leu Ala Trp Tyr Gln Gln Lys Pro Gly Gln
35 40 45

Pro Pro Lys Leu Leu Ile Tyr Trp Ala Ser Ala Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Lys Gln
85 90 95

Ser Phe Arg Leu Arg Thr Phe Gly Gly Gly Thr Lys Val Glu Ile Lys
100 105 110

<210> SEQ ID NO 52
<211> LENGTH: 336
<212> TYPE: DNA
<213> ORGANISM: Artificial Sequence
<220> FEATURE:
<223> OTHER INFORMATION: Synthetic Contstruct

<400> SEQUENCE: 52
gacatcgtta tgacacagtc accagatagc ttagccgtgt ccctgggaga acgtgctacc 60
attaattgca aaagcgctca gagcctgttt aacagccgga cacggaagaa ttatctggca 120
tggtatcagc agaaacccgg acagccgcct aagctgctga tttattgggc cagcgcacgc 180
gaaagtggtg tgcccgaccg cttttccggc agcggtagtg gcactgactt caccctgacc 240
atctcaagct tgcaagccga agacgtggca gtatattatt gcaagcagtc gttcaggctg 300
cgcacctttg gcggcggcac aaaagtggag atcaaa 336

<210> SEQ ID NO 53
<211> LENGTH: 112
<212> TYPE: PRT
<213> ORGANISM: Artificial Sequence
<220> FEATURE:
<223> OTHER INFORMATION: Synthetic Construct

<400> SEQUENCE: 53

Asp Ile Val Met Thr Gln Ser Pro Asp Ser Leu Ala Val Ser Leu Gly
1 5 10 15

Glu Arg Ala Thr Ile Asn Cys Lys Ser Ser Trp Ser Leu Phe Asn Ser
20 25 30

Arg Thr Arg Lys Asn Tyr Leu Ala Trp Tyr Gln Gln Lys Pro Gly Gln
35 40 45

Pro Pro Lys Leu Leu Ile Tyr Trp Ala Ser Ala Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Lys Gln
85 90 95

Ser Phe Arg Leu Arg Thr Phe Gly Gly Gly Thr Lys Val Glu Ile Lys
100 105 110

<210> SEQ ID NO 54
<211> LENGTH: 336
<212> TYPE: DNA
<213> ORGANISM: Artificial Sequence
<220> FEATURE:
<223> OTHER INFORMATION: Synthetic Construct

<400> SEQUENCE: 54
gacatcgtta tgacacagtc accagatagc ttagccgtgt ccctgggaga acgtgctacc 60
attaattgca aaagctcctg gagcctgttt aacagccgga cacggaagaa ttatctggca 120
tggtatcagc agaaacccgg acagccgcct aagctgctga tttattgggc cagcgcacgc 180
gaaagtggtg tgcccgaccg cttttccggc agcggtagtg gcactgactt caccctgacc 240
atctcaagct tgcaagccga agacgtggca gtatattatt gcaagcagtc gttcaggctg 300
cgcacctttg gcggcggcac aaaagtggag atcaaa 336

<210> SEQ ID NO 55
<211> LENGTH: 112
<212> TYPE: PRT
<213> ORGANISM: Artificial Sequence
<220> FEATURE:
<223> OTHER INFORMATION: Synthetic Construct

<400> SEQUENCE: 55

Asp Ile Val Met Thr Gln Ser Pro Asp Ser Leu Ala Val Ser Leu Gly
1 5 10 15

Glu Arg Ala Thr Ile Asn Cys Lys Ser Ser Asn Ser Leu Phe Asn Ser
20 25 30

Arg Thr Arg Lys Asn Tyr Leu Ala Trp Tyr Gln Gln Lys Pro Gly Gln
35 40 45

-continued

```
Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Arg Leu Arg Thr Phe Gly Gly Gly Thr Lys Val Glu Ile Lys
            100                 105                 110


<210> SEQ ID NO 56
<211> LENGTH: 336
<212> TYPE: DNA
<213> ORGANISM: Artificial Sequence
<220> FEATURE:
<223> OTHER INFORMATION: Synthetic Construct

<400> SEQUENCE: 56

gacatcgtta tgacacagtc accagatagc ttagccgtgt ccctgggaga acgtgctacc      60

attaattgca aaagctccaa tagcctgttt aacagccgga cacggaagaa ttatctggca     120

tggtatcagc agaaacccgg acagccgcct aagctgctga tttattgggc cagcgcacgc     180

gaaagtggtg tgcccgaccg cttttccggc agcggtagtg gcactgactt caccctgacc     240

atctcaagct tgcaagccga agacgtggca gtatattatt gcaagcagtc gttcaggctg     300

cgcacctttg gcggcggcac aaaagtggag atcaaa                               336


<210> SEQ ID NO 57
<211> LENGTH: 112
<212> TYPE: PRT
<213> ORGANISM: Artificial Sequence
<220> FEATURE:
<223> OTHER INFORMATION: Synthetic Construct

<400> SEQUENCE: 57

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

His Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Gly Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Arg Leu Arg Thr Phe Gly Gly Gly Thr Lys Val Glu Ile Lys
            100                 105                 110


<210> SEQ ID NO 58
<211> LENGTH: 336
<212> TYPE: DNA
<213> ORGANISM: Artificial Sequence
<220> FEATURE:
<223> OTHER INFORMATION: Synthetic Construct

<400> SEQUENCE: 58

gacatcgtta tgacacagtc accagatagc ttagccgtgt ccctgggaga acgtgctacc      60

attaattgca aaagctccca gagcctgttt aacagccata cacggaagaa ttatctggca     120
```

tggtatcagc agaaacccgg acagccgcct aagctgctga tttattgggc cagcgcacgc 180
ggaagtggtg tgcccgaccg cttttccggc agcggtagtg gcactgactt caccctgacc 240
atctcaagct tgcaagccga agacgtggca gtatattatt gcaagcagtc gttcaggctg 300
cgcacctttg gcggcggcac aaaagtggag atcaaa 336

<210> SEQ ID NO 59
<211> LENGTH: 112
<212> TYPE: PRT
<213> ORGANISM: Artificial Sequence
<220> FEATURE:
<223> OTHER INFORMATION: Synthetic Construct

<400> SEQUENCE: 59

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Phe Asn Ser
20 25 30

Arg Phe Arg Lys Asn Tyr Leu Ala Trp Tyr Gln Gln Lys Pro Gly Gln
35 40 45

Pro Pro Lys Leu Leu Ile Tyr Trp Ala Ser Ala Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Lys Gln
85 90 95

Ser Phe Arg Leu Arg Thr Phe Gly Gly Gly Thr Lys Val Glu Ile Lys
100 105 110

<210> SEQ ID NO 60
<211> LENGTH: 336
<212> TYPE: DNA
<213> ORGANISM: Artificial Sequence
<220> FEATURE:
<223> OTHER INFORMATION: Synthetic Construct

<400> SEQUENCE: 60
gacatcgtta tgacacagtc accagatagc ttagccgtgt ccctgggaga acgtgctacc 60
attaattgca aaagctccca gagcctgttt aacagccggt ttcggaagaa ttatctggca 120
tggtatcagc agaaacccgg acagccgcct aagctgctga tttattgggc cagcgcacgc 180
gaaagtggtg tgcccgaccg cttttccggc agcggtagtg gcactgactt caccctgacc 240
atctcaagct tgcaagccga agacgtggca gtatattatt gcaagcagtc gttcaggctg 300
cgcacctttg gcggcggcac aaaagtggag atcaaa 336

<210> SEQ ID NO 61
<211> LENGTH: 112
<212> TYPE: PRT
<213> ORGANISM: Artificial Sequence
<220> FEATURE:
<223> OTHER INFORMATION: Synthetic Construct

<400> SEQUENCE: 61

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Phe Asn Ser
20 25 30

Arg Thr Arg Lys Asn Tyr Leu Leu Trp Tyr Gln Gln Lys Pro Gly Gln
35 40 45

```
Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Arg Leu Arg Thr Phe Gly Gly Gly Thr Lys Val Glu Ile Lys
            100                 105                 110


<210> SEQ ID NO 62
<211> LENGTH: 336
<212> TYPE: DNA
<213> ORGANISM: Artificial Sequence
<220> FEATURE:
<223> OTHER INFORMATION: Synthetic Construct

<400> SEQUENCE: 62

gacatcgtta tgacacagtc accagatagc ttagccgtgt ccctgggaga acgtgctacc      60

attaattgca aaagctccca gagcctgttt aacagccgga cacggaagaa ttatctgctt     120

tggtatcagc agaaacccgg acagccgcct aagctgctga tttattgggc cagcgcacgc     180

gaaagtggtg tgcccgaccg cttttccggc agcggtagtg gcactgactt caccctgacc     240

atctcaagct tgcaagccga agacgtggca gtatattatt gcaagcagtc gttcaggctg     300

cgcacctttg gcggcggcac aaaagtggag atcaaa                              336


<210> SEQ ID NO 63
<211> LENGTH: 112
<212> TYPE: PRT
<213> ORGANISM: Artificial Sequence
<220> FEATURE:
<223> OTHER INFORMATION: Synthetic Construct

<400> SEQUENCE: 63

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Arg Thr Arg Lys Asn Tyr Leu Asn Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Arg Leu Arg Thr Phe Gly Gly Gly Thr Lys Val Glu Ile Lys
            100                 105                 110


<210> SEQ ID NO 64
<211> LENGTH: 336
<212> TYPE: DNA
<213> ORGANISM: Artificial Sequence
<220> FEATURE:
<223> OTHER INFORMATION: Synthetic Construct

<400> SEQUENCE: 64

gacatcgtta tgacacagtc accagatagc ttagccgtgt ccctgggaga acgtgctacc      60

attaattgca aaagctccca gagcctgttt aacagccgga cacggaagaa ttatctgaat     120
```

-continued

```
tggtatcagc agaaacccgg acagccgcct aagctgctga tttattgggc cagcgcacgc    180

gaaagtggtg tgcccgaccg cttttccggc agcggtagtg gcactgactt caccctgacc    240

atctcaagct tgcaagccga agacgtggca gtatattatt gcaagcagtc gttcaggctg    300

cgcacctttg gcggcggcac aaaagtggag atcaaa                              336


<210> SEQ ID NO 65
<211> LENGTH: 112
<212> TYPE: PRT
<213> ORGANISM: Artificial Sequence
<220> FEATURE:
<223> OTHER INFORMATION: Synthetic Construct

<400> SEQUENCE: 65

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Arg Thr Arg Lys Asn Tyr Leu Met Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Arg Leu Arg Thr Phe Gly Gly Gly Thr Lys Val Glu Ile Lys
            100                 105                 110


<210> SEQ ID NO 66
<211> LENGTH: 336
<212> TYPE: DNA
<213> ORGANISM: Artificial Sequence
<220> FEATURE:
<223> OTHER INFORMATION: Synthetic Construct

<400> SEQUENCE: 66

gacatcgtta tgacacagtc accagatagc ttagccgtgt ccctgggaga acgtgctacc     60

attaattgca aaagctccca gagcctgttt aacagccgga cacggaagaa ttatctgatg    120

tggtatcagc agaaacccgg acagccgcct aagctgctga tttattgggc cagcgcacgc    180

gaaagtggtg tgcccgaccg cttttccggc agcggtagtg gcactgactt caccctgacc    240

atctcaagct tgcaagccga agacgtggca gtatattatt gcaagcagtc gttcaggctg    300

cgcacctttg gcggcggcac aaaagtggag atcaaa                              336


<210> SEQ ID NO 67
<211> LENGTH: 112
<212> TYPE: PRT
<213> ORGANISM: Artificial Sequence
<220> FEATURE:
<223> OTHER INFORMATION: Synthetic Construct

<400> SEQUENCE: 67

Asp Ile Val Met Thr Gln Ser Pro Asp Ser Leu Ala Val Ser Leu Gly
1               5                   10                  15

Glu Arg Ala Thr Ile Asn Cys Lys Ser Ala Gln Ser Leu Phe Asn Ser
            20                  25                  30

Arg Thr Arg Lys Asn Tyr Leu Ala Trp Tyr Gln Gln Lys Pro Gly Gln
```

```
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Asn Leu Arg Thr Phe Gly Gly Gly Thr Lys Val Glu Ile Lys
            100                 105                 110


<210> SEQ ID NO 68
<211> LENGTH: 336
<212> TYPE: DNA
<213> ORGANISM: Artificial Sequence
<220> FEATURE:
<223> OTHER INFORMATION: Synthetic Construct

<400> SEQUENCE: 68

gacatcgtta tgacacagtc accagatagc ttagccgtgt ccctgggaga acgtgctacc      60

attaattgca aaagcgctca gagcctgttt aacagccgga cacggaagaa ttatctggca     120

tggtatcagc agaaacccgg acagccgcct aagctgctga tttattgggc cagcgcacgc     180

gaaagtggtg tgcccgaccg cttttccggc agcggtagtg gcactgactt caccctgacc     240

atctcaagct tgcaagccga agacgtggca gtatattatt gcaagcagtc gttcaatctg     300

cgcacctttg gcggcggcac aaaagtggag atcaaa                               336


<210> SEQ ID NO 69
<211> LENGTH: 112
<212> TYPE: PRT
<213> ORGANISM: Artificial Sequence
<220> FEATURE:
<223> OTHER INFORMATION: Synthetic Construct

<400> SEQUENCE: 69

Asp Ile Val Met Thr Gln Ser Pro Asp Ser Leu Ala Val Ser Leu Gly
1               5                   10                  15

Glu Arg Ala Thr Ile Asn Cys Lys Ser Ser Trp Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Asn Leu Arg Thr Phe Gly Gly Gly Thr Lys Val Glu Ile Lys
            100                 105                 110


<210> SEQ ID NO 70
<211> LENGTH: 336
<212> TYPE: DNA
<213> ORGANISM: Artificial Sequence
<220> FEATURE:
<223> OTHER INFORMATION: Synthetic Construct

<400> SEQUENCE: 70

gacatcgtta tgacacagtc accagatagc ttagccgtgt ccctgggaga acgtgctacc      60
```

```
attaattgca aaagctcctg gagcctgttt aacagccgga cacggaagaa ttatctggca    120

tggtatcagc agaaacccgg acagccgcct aagctgctga tttattgggc cagcgcacgc    180

gaaagtggtg tgcccgaccg cttttccggc agcggtagtg gcactgactt caccctgacc    240

atctcaagct tgcaagccga agacgtggca gtatattatt gcaagcagtc gttcaatctg    300

cgcacctttg gcggcggcac aaaagtggag atcaaa                              336
```

<210> SEQ ID NO 71
<211> LENGTH: 112
<212> TYPE: PRT
<213> ORGANISM: Artificial Sequence
<220> FEATURE:
<223> OTHER INFORMATION: Synthetic Construct

<400> SEQUENCE: 71

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Asn Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Asn Leu Arg Thr Phe Gly Gly Gly Thr Lys Val Glu Ile Lys
            100                 105                 110
```

<210> SEQ ID NO 72
<211> LENGTH: 336
<212> TYPE: DNA
<213> ORGANISM: Artificial Sequence
<220> FEATURE:
<223> OTHER INFORMATION: Synthetic Construct

<400> SEQUENCE: 72

```
gacatcgtta tgacacagtc accagatagc ttagccgtgt ccctgggaga acgtgctacc     60

attaattgca aaagctccaa tagcctgttt aacagccgga cacggaagaa ttatctggca    120

tggtatcagc agaaacccgg acagccgcct aagctgctga tttattgggc cagcgcacgc    180

gaaagtggtg tgcccgaccg cttttccggc agcggtagtg gcactgactt caccctgacc    240

atctcaagct tgcaagccga agacgtggca gtatattatt gcaagcagtc gttcaatctg    300

cgcacctttg gcggcggcac aaaagtggag atcaaa                              336
```

<210> SEQ ID NO 73
<211> LENGTH: 112
<212> TYPE: PRT
<213> ORGANISM: Artificial Sequence
<220> FEATURE:
<223> OTHER INFORMATION: Synthetic Construct

<400> SEQUENCE: 73

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30
```

-continued

His Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Gly Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Asn Leu Arg Thr Phe Gly Gly Gly Thr Lys Val Glu Ile Lys
            100                 105                 110

<210> SEQ ID NO 74
<211> LENGTH: 336
<212> TYPE: DNA
<213> ORGANISM: Artificial Sequence
<220> FEATURE:
<223> OTHER INFORMATION: Synthetic Construct

<400> SEQUENCE: 74
gacatcgtta tgacacagtc accagatagc ttagccgtgt ccctgggaga acgtgctacc     60
attaattgca aaagctccca gagcctgttt aacagccata cacggaagaa ttatctggca    120
tggtatcagc agaaacccgg acagccgcct aagctgctga tttattgggc cagcgcacgc    180
ggaagtggtg tgcccgaccg cttttccggc agcggtagtg gcactgactt caccctgacc    240
atctcaagct tgcaagccga agacgtggca gtatattatt gcaagcagtc gttcaatctg    300
cgcacctttg gcggcggcac aaaagtggag atcaaa                              336

<210> SEQ ID NO 75
<211> LENGTH: 112
<212> TYPE: PRT
<213> ORGANISM: Artificial Sequence
<220> FEATURE:
<223> OTHER INFORMATION: Synthetic Construct

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Arg Phe Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Asn Leu Arg Thr Phe Gly Gly Gly Thr Lys Val Glu Ile Lys
            100                 105                 110

<210> SEQ ID NO 76
<211> LENGTH: 336
<212> TYPE: DNA
<213> ORGANISM: Artificial Sequence
<220> FEATURE:
<223> OTHER INFORMATION: Synthetic Construct

<400> SEQUENCE: 76
gacatcgtta tgacacagtc accagatagc ttagccgtgt ccctgggaga acgtgctacc     60

```
attaattgca aaagctccca gagcctgttt aacagccggt ttcggaagaa ttatctggca    120

tggtatcagc agaaacccgg acagccgcct aagctgctga tttattgggc cagcgcacgc    180

gaaagtggtg tgcccgaccg cttttccggc agcggtagtg gcactgactt caccctgacc    240

atctcaagct tgcaagccga agacgtggca gtatattatt gcaagcagtc gttcaatctg    300

cgcacctttg gcggcggcac aaaagtggag atcaaa                              336


<210> SEQ ID NO 77
<211> LENGTH: 112
<212> TYPE: PRT
<213> ORGANISM: Artificial Sequence
<220> FEATURE:
<223> OTHER INFORMATION: Synthetic Construct

<400> SEQUENCE: 77

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Arg Thr Arg Lys Asn Tyr Leu Leu Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Asn Leu Arg Thr Phe Gly Gly Gly Thr Lys Val Glu Ile Lys
            100                 105                 110


<210> SEQ ID NO 78
<211> LENGTH: 336
<212> TYPE: DNA
<213> ORGANISM: Artificial Sequence
<220> FEATURE:
<223> OTHER INFORMATION: Synthetic Construct

<400> SEQUENCE: 78

gacatcgtta tgacacagtc accagatagc ttagccgtgt ccctgggaga acgtgctacc     60

attaattgca aaagctccca gagcctgttt aacagccgga cacggaagaa ttatctgctt    120

tggtatcagc agaaacccgg acagccgcct aagctgctga tttattgggc cagcgcacgc    180

gaaagtggtg tgcccgaccg cttttccggc agcggtagtg gcactgactt caccctgacc    240

atctcaagct tgcaagccga agacgtggca gtatattatt gcaagcagtc gttcaatctg    300

cgcacctttg gcggcggcac aaaagtggag atcaaa                              336


<210> SEQ ID NO 79
<211> LENGTH: 112
<212> TYPE: PRT
<213> ORGANISM: Artificial Sequence
<220> FEATURE:
<223> OTHER INFORMATION: Synthetic Construct

<400> SEQUENCE: 79

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30
```

```
Arg Thr Arg Lys Asn Tyr Leu Asn Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Asn Leu Arg Thr Phe Gly Gly Gly Thr Lys Val Glu Ile Lys
            100                 105                 110
```

<210> SEQ ID NO 80
<211> LENGTH: 336
<212> TYPE: DNA
<213> ORGANISM: Artificial Sequence
<220> FEATURE:
<223> OTHER INFORMATION: Synthetic Construct

<400> SEQUENCE: 80

```
gacatcgtta tgacacagtc accagatagc ttagccgtgt ccctgggaga acgtgctacc      60

attaattgca aaagctccca gagcctgttt aacagccgga cacggaagaa ttatctgaat     120

tggtatcagc agaaacccgg acagccgcct aagctgctga tttattgggc cagcgcacgc     180

gaaagtggtg tgcccgaccg cttttccggc agcggtagtg gcactgactt caccctgacc     240

atctcaagct tgcaagccga agacgtggca gtatattatt gcaagcagtc gttcaatctg     300

cgcacctttg gcggcggcac aaaagtggag atcaaa                               336
```

<210> SEQ ID NO 81
<211> LENGTH: 112
<212> TYPE: PRT
<213> ORGANISM: Artificial Sequence
<220> FEATURE:
<223> OTHER INFORMATION: Synthetic Construct

<400> SEQUENCE: 81

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Arg Thr Arg Lys Asn Tyr Leu Met Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Asn Leu Arg Thr Phe Gly Gly Gly Thr Lys Val Glu Ile Lys
            100                 105                 110
```

<210> SEQ ID NO 82
<211> LENGTH: 336
<212> TYPE: DNA
<213> ORGANISM: Artificial Sequence
<220> FEATURE:
<223> OTHER INFORMATION: Synthetic Construct

<400> SEQUENCE: 82

-continued

```
gacatcgtta tgacacagtc accagatagc ttagccgtgt ccctgggaga acgtgctacc     60

attaattgca aaagctccca gagcctgttt aacagccgga cacggaagaa ttatctgatg    120

tggtatcagc agaaacccgg acagccgcct aagctgctga tttattgggc cagcgcacgc    180

gaaagtggtg tgcccgaccg cttttccggc agcggtagtg gcactgactt caccctgacc    240

atctcaagct tgcaagccga agacgtggca gtatattatt gcaagcagtc gttcaatctg    300

cgcacctttg gcggcggcac aaaagtggag atcaaa                              336
```

<210> SEQ ID NO 83
<211> LENGTH: 112
<212> TYPE: PRT
<213> ORGANISM: Artificial Sequence
<220> FEATURE:
<223> OTHER INFORMATION: Synthetic Construct

<400> SEQUENCE: 83

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Arg Leu Arg Thr Phe Gly Gly Gly Thr Lys Val Glu Ile Lys
            100                 105                 110
```

<210> SEQ ID NO 84
<211> LENGTH: 336
<212> TYPE: DNA
<213> ORGANISM: Artificial Sequence
<220> FEATURE:
<223> OTHER INFORMATION: Synthetic Construct

<400> SEQUENCE: 84

```
gacatcgtta tgacacagtc accagatagc ttagccgtgt ccctgggaga acgtgctacc     60

attaattgca ggagctccca gagcctgttt aacagccgga cacggaagaa ttatctggca    120

tggtatcagc agaaacccgg acagccgcct aagctgctga tttattgggc cagcgcacgc    180

gaaagtggtg tgcccgaccg cttttccggc agcggtagtg gcactgactt caccctgacc    240

atctcaagct tgcaagccga agacgtggca gtatattatt gcaagcagtc gttcaggctg    300

cgcacctttg gcggcggcac aaaagtggag atcaaa                              336
```

<210> SEQ ID NO 85
<211> LENGTH: 118
<212> TYPE: PRT
<213> ORGANISM: Artificial Sequence
<220> FEATURE:
<223> OTHER INFORMATION: Synthetic Construct

<400> SEQUENCE: 85

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
```

```
            20                  25                  30

Tyr Met Ser Trp Val Arg Gln Ala Pro Gly Lys Gly Leu Glu Trp Val
        35                  40                  45

Gly Phe Ile Arg His Lys Ala Asn Thr Tyr Thr Thr Glu Tyr Ser Thr
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115
```

<210> SEQ ID NO 86
<211> LENGTH: 354
<212> TYPE: DNA
<213> ORGANISM: Artificial Sequence
<220> FEATURE:
<223> OTHER INFORMATION: Synthetic Construct

<400> SEQUENCE: 86

```
gaagtccagc tggttgaaag tggtggcggc ctggtgcagc cgggcggctc tctgcgcctg     60

tcatgcgctg catccggctt taccttcagc gactattaca tgagctgggt tcgccaagcg    120

cccggcaaag gcctggaatg ggtgggattc attcgacata aagcgaacac gtataccacc    180

gaatatagca catctgtcaa gggccggttc accatctccc gcgatgattc caagaacagc    240

ctgtacctgc agatgaactc cctgaagacg gaagataccg ccgtctatta ttgtgcccgc    300

gatctgcctg gctttgccta ttggggccaa ggcactctgg tcaccgtctc ctca          354
```

<210> SEQ ID NO 87
<211> LENGTH: 118
<212> TYPE: PRT
<213> ORGANISM: Artificial Sequence
<220> FEATURE:
<223> OTHER INFORMATION: Synthetic Construct

<400> SEQUENCE: 87

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg His Lys Ala Asn Leu Tyr Thr Thr Glu Tyr Ser Thr
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Leu Pro Gly Phe Ala Tyr Trp Gly Gln Gly Thr
            100                 105                 110

Leu Val Thr Val Ser Ser
        115
```

<210> SEQ ID NO 88
<211> LENGTH: 354

<212> TYPE: DNA
<213> ORGANISM: Artificial Sequence
<220> FEATURE:
<223> OTHER INFORMATION: Synthetic Construct

<400> SEQUENCE: 88
gaagtccagc tggttgaaag tggtggcggc ctggtgcagc cgggcggctc tctgcgcctg 60
tcatgcgctg catccggctt taccttcagc gactattaca tgagctgggt tcgccaagcg 120
cccggcaaag gcctggaatg ggtgggattc attcgacata aagcgaacct gtataccacc 180
gaatatagca catctgtcaa gggccggttc accatctccc gcgatgattc caagaacagc 240
ctgtacctgc agatgaactc cctgaagacg gaagataccg ccgtctatta ttgtgcccgc 300
gatctgcctg gctttgccta ttggggccaa ggcactctgg tcaccgtctc ctca 354

<210> SEQ ID NO 89
<211> LENGTH: 15
<212> TYPE: PRT
<213> ORGANISM: Artificial Sequence
<220> FEATURE:
<223> OTHER INFORMATION: Synthetic Construct

<400> SEQUENCE: 89

Gly Gly Gly Gly Ser Gly Gly Gly Gly Ser Gly Gly Gly Gly Ser
1 5 10 15

<210> SEQ ID NO 90
<211> LENGTH: 7
<212> TYPE: PRT
<213> ORGANISM: Artificial Sequence
<220> FEATURE:
<223> OTHER INFORMATION: Synthetic Construct

<400> SEQUENCE: 90

Gly Gly Leu Leu Gln Gly Gly
1 5

<210> SEQ ID NO 91
<211> LENGTH: 5
<212> TYPE: PRT
<213> ORGANISM: Artificial Sequence
<220> FEATURE:
<223> OTHER INFORMATION: Synthetic Construct

<400> SEQUENCE: 91

Leu Leu Gln Gly Ala
1 5

<210> SEQ ID NO 92
<211> LENGTH: 7
<212> TYPE: PRT
<213> ORGANISM: Artificial Sequence
<220> FEATURE:
<223> OTHER INFORMATION: Synthetic Construct

<400> SEQUENCE: 92

Gly Gly Leu Leu Gln Gly Ala
1 5

<210> SEQ ID NO 93
<211> LENGTH: 7
<212> TYPE: PRT
<213> ORGANISM: Artificial Sequence
<220> FEATURE:
<223> OTHER INFORMATION: Synthetic Construct

<400> SEQUENCE: 93

Leu Leu Gln Gly Pro Gly Lys
1 5

<210> SEQ ID NO 94
<211> LENGTH: 6
<212> TYPE: PRT
<213> ORGANISM: Artificial Sequence
<220> FEATURE:
<223> OTHER INFORMATION: Synthetic Construct

<400> SEQUENCE: 94

Leu Leu Gln Gly Pro Gly
1 5

<210> SEQ ID NO 95
<211> LENGTH: 6
<212> TYPE: PRT
<213> ORGANISM: Artificial Sequence
<220> FEATURE:
<223> OTHER INFORMATION: Synthetic Construct

<400> SEQUENCE: 95

Leu Leu Gln Gly Pro Ala
1 5

<210> SEQ ID NO 96
<211> LENGTH: 5
<212> TYPE: PRT
<213> ORGANISM: Artificial Sequence
<220> FEATURE:
<223> OTHER INFORMATION: Synthetic Construct

<400> SEQUENCE: 96

Leu Leu Gln Gly Pro
1 5

<210> SEQ ID NO 97
<211> LENGTH: 4
<212> TYPE: PRT
<213> ORGANISM: Artificial Sequence
<220> FEATURE:
<223> OTHER INFORMATION: Synthetic Construct

<400> SEQUENCE: 97

Leu Leu Gln Pro
1

<210> SEQ ID NO 98
<211> LENGTH: 6
<212> TYPE: PRT
<213> ORGANISM: Artificial Sequence
<220> FEATURE:
<223> OTHER INFORMATION: Synthetic Construct

<400> SEQUENCE: 98

Leu Leu Gln Pro Gly Lys
1 5

<210> SEQ ID NO 99
<211> LENGTH: 8
<212> TYPE: PRT
<213> ORGANISM: Artificial Sequence
<220> FEATURE:
<223> OTHER INFORMATION: Synthetic Construct

<400> SEQUENCE: 99

-continued

Leu Leu Gln Gly Ala Pro Gly Lys
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic Construct

<400> SEQUENCE: 100

Leu Leu Gln Gly Ala Pro Gly
1               5

<210> SEQ ID NO 101
<211> LENGTH: 6
<212> TYPE: PRT
<213> ORGANISM: Artificial Sequence
<220> FEATURE:
<223> OTHER INFORMATION: Synthetic Construct

<400> SEQUENCE: 101

Leu Leu Gln Gly Ala Pro
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: G or P
<220> FEATURE:
<221> NAME/KEY: MISC_FEATURE
<222> LOCATION: (5)..(5)
<223> OTHER INFORMATION: A, G, P, or absent
<220> FEATURE:
<221> NAME/KEY: MISC_FEATURE
<222> LOCATION: (6)..(6)
<223> OTHER INFORMATION: A, G, K, P, or absent
<220> FEATURE:
<221> NAME/KEY: MISC_FEATURE
<222> LOCATION: (7)..(7)
<223> OTHER INFORMATION: K, G or absent
<220> FEATURE:
<221> NAME/KEY: MISC_FEATURE
<222> LOCATION: (8)..(8)
<223> OTHER INFORMATION: K or absent

<400> SEQUENCE: 102

Leu Leu Gln Xaa Xaa Xaa Xaa Xaa
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: any naturally occurring amino acids or absent
<220> FEATURE:
<221> NAME/KEY: MISC_FEATURE
<222> LOCATION: (5)..(8)
<223> OTHER INFORMATION: any naturally occurring amino acids or absent

<400> SEQUENCE: 103

Leu Leu Gln Xaa Xaa Xaa Xaa Xaa
1 5

<210> SEQ ID NO 104
<211> LENGTH: 1691
<212> TYPE: DNA
<213> ORGANISM: Homo sapiens

<400> SEQUENCE: 104
aacttcagtt tgttggctgc ggcagcaggt agcaaagtga cgccgagggc ctgagtgctc 60
cagtagccac cgcatctgga gaaccagcgg ttaccatgga ggggatcagt atatacactt 120
cagataacta caccgaggaa atgggctcag gggactatga ctccatgaag gaaccctgtt 180
tccgtgaaga aaatgctaat ttcaataaaa tcttcctgcc caccatctac tccatcatct 240
tcttaactgg cattgtgggc aatggattgg tcatcctggt catgggttac cagaagaaac 300
tgagaagcat gacggacaag tacaggctgc acctgtcagt ggccgacctc ctctttgtca 360
tcacgcttcc cttctgggca gttgatgccg tggcaaactg gtactttggg aacttcctat 420
gcaaggcagt ccatgtcatc tacacagtca acctctacag cagtgtcctc atcctggcct 480
tcatcagtct ggaccgctac ctggccatcg tccacgccac caacagtcag aggccaagga 540
agctgttggc tgaaaaggtg gtctatgttg gcgtctggat ccctgccctc ctgctgacta 600
ttcccgactt catctttgcc aacgtcagtg aggcagatga cagatatatc tgtgaccgct 660
tctaccccaa tgacttgtgg gtggttgtgt tccagtttca gcacatcatg gttggcctta 720
tcctgcctgg tattgtcatc ctgtcctgct attgcattat catctccaag ctgtcacact 780
ccaagggcca ccagaagcgc aaggccctca agaccacagt catcctcatc ctggctttct 840
tcgcctgttg gctgccttac tacattggga tcagcatcga ctccttcatc ctcctggaaa 900
tcatcaagca agggtgtgag tttgagaaca ctgtgcacaa gtggatttcc atcaccgagg 960
ccctagcttt cttccactgt tgtctgaacc ccatcctcta tgctttcctt ggagccaaat 1020
ttaaaacctc tgcccagcac gcactcacct ctgtgagcag agggtccagc ctcaagatcc 1080
tctccaaagg aaagcgaggt ggacattcat ctgtttccac tgagtctgag tcttcaagtt 1140
ttcactccag ctaacacaga tgtaaaagac tttttttttat acgataaata actttttttt 1200
aagttacaca tttttcagat ataaaagact gaccaatatt gtacagtttt tattgcttgt 1260
tggatttttg tcttgtgttt ctttagtttt tgtgaagttt aattgactta tttatataaa 1320
ttttttttgt ttcatattga tgtgtgtcta ggcaggacct gtggccaagt tcttagttgc 1380
tgtatgtctc gtggtaggac tgtagaaaag ggaactgaac attccagagc gtgtagtgaa 1440
tcacgtaaag ctagaaatga tccccagctg tttatgcata gataatctct ccattcccgt 1500
ggaacgtttt tcctgttctt aagacgtgat tttgctgtag aagatggcac ttataaccaa 1560
agcccaaagt ggtatagaaa tgctggtttt tcagttttca ggagtgggtt gatttcagca 1620
cctacagtgt acagtcttgt attaagttgt taataaaagt acatgttaaa cttaaaaaaa 1680
aaaaaaaaaa a 1691

<210> SEQ ID NO 105
<211> LENGTH: 352
<212> TYPE: PRT
<213> ORGANISM: Homo sapiens

<400> SEQUENCE: 105

-continued

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 106
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (49)..(49)
<223> OTHER INFORMATION: G or S
<220> FEATURE:
<221> NAME/KEY: MISC_FEATURE
<222> LOCATION: (55)..(55)
<223> OTHER INFORMATION: V or A
<220> FEATURE:
<221> NAME/KEY: MISC_FEATURE
<222> LOCATION: (57)..(57)
<223> OTHER INFORMATION: G , F, K, V, T, L or I
<220> FEATURE:
<221> NAME/KEY: MISC_FEATURE
<222> LOCATION: (58)..(58)
<223> OTHER INFORMATION: E or Y
<220> FEATURE:
<221> NAME/KEY: MISC_FEATURE
<222> LOCATION: (60)..(60)
<223> OTHER INFORMATION: T or R
<220> FEATURE:
<221> NAME/KEY: MISC_FEATURE
<222> LOCATION: (65)..(65)
<223> OTHER INFORMATION: W or S
<220> FEATURE:
<221> NAME/KEY: MISC_FEATURE
<222> LOCATION: (66)..(66)
<223> OTHER INFORMATION: D or V
<220> FEATURE:
<221> NAME/KEY: MISC_FEATURE
<222> LOCATION: (67)..(67)
<223> OTHER INFORMATION: K, T, or R
<220> FEATURE:
<221> NAME/KEY: MISC_FEATURE
<222> LOCATION: (76)..(76)
<223> OTHER INFORMATION: D or N
<220> FEATURE:
<221> NAME/KEY: MISC_FEATURE
<222> LOCATION: (80)..(80)
<223> OTHER INFORMATION: T or S
<220> FEATURE:
<221> NAME/KEY: MISC_FEATURE
<222> LOCATION: (89)..(89)
<223> OTHER INFORMATION: R or K
<220> FEATURE:
<221> NAME/KEY: MISC_FEATURE
<222> LOCATION: (90)..(90)
<223> OTHER INFORMATION: A or T
<220> FEATURE:
<221> NAME/KEY: MISC_FEATURE
<222> LOCATION: (100)..(100)
<223> OTHER INFORMATION: K or R

<400> SEQUENCE: 106

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Xaa Phe Ile Arg His Lys Xaa Asn Xaa Xaa Thr Xaa Glu Tyr Ser Thr
    50                  55                  60

Xaa Xaa Xaa Gly Arg Phe Thr Ile Ser Arg Asp Xaa Ser Lys Asn Xaa
65                  70                  75                  80

Leu Tyr Leu Gln Met Asn Ser Leu Xaa Xaa Glu Asp Thr Ala Val Tyr
                85                  90                  95

Tyr Cys Ala Xaa Asp Leu Pro Gly Phe Ala Tyr Trp Gly Gln Gly Thr
            100                 105                 110

Leu Val Thr Val Ser Ser
        115
```

<210> SEQ ID NO 107
<211> LENGTH: 5
<212> TYPE: PRT
<213> ORGANISM: Artificial Sequence
<220> FEATURE:

-continued

<223> OTHER INFORMATION: Synthetic Construct

<400> SEQUENCE: 107

Asp Tyr Tyr Met Ser
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic Construct

<400> SEQUENCE: 108

Gly Phe Thr Phe Thr Asp Tyr
1               5

<210> SEQ ID NO 109
<211> LENGTH: 10
<212> TYPE: PRT
<213> ORGANISM: Artificial Sequence
<220> FEATURE:
<223> OTHER INFORMATION: Synthetic Construct

<400> SEQUENCE: 109

Gly Phe Thr Phe Thr Asp Tyr Tyr Met Ser
1               5                   10

<210> SEQ ID NO 110
<211> LENGTH: 19
<212> TYPE: PRT
<213> ORGANISM: Artificial Sequence
<220> FEATURE:
<223> OTHER INFORMATION: Synthetic Construct

<400> SEQUENCE: 110

Phe Ile Arg Asn Lys Ala Asn Gly Tyr Thr Thr Glu Tyr Ser Ala Ser
1               5                   10                  15

Val Lys Gly

<210> SEQ ID NO 111
<211> LENGTH: 8
<212> TYPE: PRT
<213> ORGANISM: Artificial Sequence
<220> FEATURE:
<223> OTHER INFORMATION: Synthetic Construct

<400> SEQUENCE: 111

Arg Asn Lys Ala Asn Gly Tyr Thr
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic Construct

<400> SEQUENCE: 112

Asp Leu Pro Gly Phe Ala Tyr
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic Construct

<400> SEQUENCE: 113

Gly Phe Thr Phe Ser Asp Tyr
1 5

<210> SEQ ID NO 114
<211> LENGTH: 10
<212> TYPE: PRT
<213> ORGANISM: Artificial Sequence
<220> FEATURE:
<223> OTHER INFORMATION: Synthetic Construct

<400> SEQUENCE: 114

Gly Phe Thr Phe Ser Asp Tyr Tyr Met Ser
1 5 10

<210> SEQ ID NO 115
<211> LENGTH: 5
<212> TYPE: PRT
<213> ORGANISM: Artificial Sequence
<220> FEATURE:
<223> OTHER INFORMATION: Synthetic Construct

<400> SEQUENCE: 115

Asp Tyr Asn Ile Tyr
1 5

<210> SEQ ID NO 116
<211> LENGTH: 7
<212> TYPE: PRT
<213> ORGANISM: Artificial Sequence
<220> FEATURE:
<223> OTHER INFORMATION: Synthetic Construct

<400> SEQUENCE: 116

Gly Tyr Ser Phe Thr Asp Tyr
1 5

<210> SEQ ID NO 117
<211> LENGTH: 10
<212> TYPE: PRT
<213> ORGANISM: Artificial Sequence
<220> FEATURE:
<223> OTHER INFORMATION: Synthetic Construct

<400> SEQUENCE: 117

Gly Tyr Ser Phe Thr Asp Tyr Asn Ile Tyr
1 5 10

<210> SEQ ID NO 118
<211> LENGTH: 17
<212> TYPE: PRT
<213> ORGANISM: Artificial Sequence
<220> FEATURE:
<223> OTHER INFORMATION: Synthetic Construct

<400> SEQUENCE: 118

Tyr Ile Asp Pro Tyr Asn Gly Gly Thr Arg Tyr Asn Gln Lys Phe Lys
1 5 10 15

Gly

<210> SEQ ID NO 119
<211> LENGTH: 6
<212> TYPE: PRT

<213> ORGANISM: Artificial Sequence
<220> FEATURE:
<223> OTHER INFORMATION: Synthetic Construct

<400> SEQUENCE: 119

Asp Pro Tyr Asn Gly Gly
1               5

<210> SEQ ID NO 120
<211> LENGTH: 12
<212> TYPE: PRT
<213> ORGANISM: Artificial Sequence
<220> FEATURE:
<223> OTHER INFORMATION: Synthetic Construct

<400> SEQUENCE: 120

Thr Tyr Gly Ser Arg Tyr Val Gly Ala Met Asp Tyr
1               5                   10

<210> SEQ ID NO 121
<211> LENGTH: 7
<212> TYPE: PRT
<213> ORGANISM: Artificial Sequence
<220> FEATURE:
<223> OTHER INFORMATION: Synthetic Construct

<400> SEQUENCE: 121

Gly Tyr Thr Phe Thr Asp Tyr
1               5

<210> SEQ ID NO 122
<211> LENGTH: 10
<212> TYPE: PRT
<213> ORGANISM: Artificial Sequence
<220> FEATURE:
<223> OTHER INFORMATION: Synthetic Construct

<400> SEQUENCE: 122

Gly Tyr Thr Phe Thr Asp Tyr Asn Ile Tyr
1               5                   10

<210> SEQ ID NO 123
<211> LENGTH: 8
<212> TYPE: PRT
<213> ORGANISM: Artificial Sequence
<220> FEATURE:
<223> OTHER INFORMATION: Synthetic Construct

<400> SEQUENCE: 123

Arg His Lys Ala Asn Gly Tyr Thr
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic Construct

<400> SEQUENCE: 124

Arg His Lys Ala Asn Phe Tyr Thr
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic Construct

<400> SEQUENCE: 125

Arg His Lys Ala Asn Lys Tyr Thr
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic Construct

<400> SEQUENCE: 126

Arg His Lys Ala Asn Val Tyr Thr
1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic Construct

<400> SEQUENCE: 127

Arg His Lys Ala Asn Ile Tyr Thr
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic Construct

<400> SEQUENCE: 128

Arg His Lys Ala Asn Phe Glu Thr
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic Construct

<400> SEQUENCE: 129

Arg His Lys Ala Asn Thr Tyr Thr
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic Construct

<400> SEQUENCE: 130

Arg His Lys Ala Asn Leu Tyr Thr
1               5

<210> SEQ ID NO 131
<211> LENGTH: 17
<212> TYPE: PRT
<213> ORGANISM: Artificial Sequence
<220> FEATURE:

<223> OTHER INFORMATION: Synthetic Construct

<400> SEQUENCE: 131

Lys Ser Ser Gln Ser Leu Tyr Asn Ser Arg Thr Arg Lys Asn Tyr Leu
1               5                   10                  15

Ala

<210> SEQ ID NO 132
<211> LENGTH: 7
<212> TYPE: PRT
<213> ORGANISM: Artificial Sequence
<220> FEATURE:
<223> OTHER INFORMATION: Synthetic Construct

<400> SEQUENCE: 132

Trp Ala Ser Ala Arg Glu Ser
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic Construct

<400> SEQUENCE: 133

Lys Gln Ser Tyr Asn Leu Arg Thr
1               5

<210> SEQ ID NO 134
<211> LENGTH: 336
<212> TYPE: DNA
<213> ORGANISM: Artificial Sequence
<220> FEATURE:
<223> OTHER INFORMATION: Synthetic Construct

<400> SEQUENCE: 134
gacatcgtta tgacacagtc accagatagc ttagccgtgt ccctgggaga acgtgctacc 60
attaattgca aaagctccca gagcctgttt aacagccgga cacggaagaa ttatctggca 120
tggtatcagc agaaacccgg acagccgcct aagctgctga tttattgggc cagcgcacgc 180
gaaagtggtg tgcccgaccg cttttccggc agcggtagtg gcactgactt caccctgacc 240
atctcaagct tgcaagccga agacgtggca gtatattatt gcaagcagtc gttcaatgat 300
cgcacctttg gcggcggcac aaaagtggag atcaaa 336

<210> SEQ ID NO 135
<211> LENGTH: 16
<212> TYPE: PRT
<213> ORGANISM: Artificial Sequence
<220> FEATURE:
<223> OTHER INFORMATION: Synthetic Construct

<400> SEQUENCE: 135

Arg Ser Ser Lys Ser Leu Leu His Ser Asn Gly Asn Thr Tyr Leu Tyr
1               5                   10                  15

<210> SEQ ID NO 136
<211> LENGTH: 7
<212> TYPE: PRT
<213> ORGANISM: Artificial Sequence
<220> FEATURE:
<223> OTHER INFORMATION: Synthetic Construct

<400> SEQUENCE: 136

Arg Met Ser Asn Pro Ala Ser
1 5

<210> SEQ ID NO 137
<211> LENGTH: 9
<212> TYPE: PRT
<213> ORGANISM: Artificial Sequence
<220> FEATURE:
<223> OTHER INFORMATION: Synthetic Construct

<400> SEQUENCE: 137

Met Gln His Leu Glu Tyr Pro Leu Thr
1 5

<210> SEQ ID NO 138
<211> LENGTH: 17
<212> TYPE: PRT
<213> ORGANISM: Artificial Sequence
<220> FEATURE:
<223> OTHER INFORMATION: Synthetic Construct

<400> SEQUENCE: 138

Lys Ser Ser Gln Ser Leu Phe Asn Ser Arg Thr Arg Lys Asn Tyr Leu
1 5 10 15

Ala

<210> SEQ ID NO 139
<211> LENGTH: 8
<212> TYPE: PRT
<213> ORGANISM: Artificial Sequence
<220> FEATURE:
<223> OTHER INFORMATION: Synthetic Construct

<400> SEQUENCE: 139

Lys Gln Ser Phe Asn Leu Arg Thr
1 5

<210> SEQ ID NO 140
<211> LENGTH: 8
<212> TYPE: PRT
<213> ORGANISM: Artificial Sequence
<220> FEATURE:
<223> OTHER INFORMATION: Synthetic Construct

<400> SEQUENCE: 140

Lys Gln Ser Phe Arg Leu Arg Thr
1 5

<210> SEQ ID NO 141
<211> LENGTH: 17
<212> TYPE: PRT
<213> ORGANISM: Artificial Sequence
<220> FEATURE:
<223> OTHER INFORMATION: Synthetic Construct

<400> SEQUENCE: 141

Lys Ser Ala Gln Ser Leu Phe Asn Ser Arg Thr Arg Lys Asn Tyr Leu
1 5 10 15

Ala

<210> SEQ ID NO 142
<211> LENGTH: 17
<212> TYPE: PRT
<213> ORGANISM: Artificial Sequence
<220> FEATURE:

-continued

<223> OTHER INFORMATION: Synthetic Construct

<400> SEQUENCE: 142

Lys Ser Ser Trp Ser Leu Phe Asn Ser Arg Thr Arg Lys Asn Tyr Leu
1 5 10 15

Ala

<210> SEQ ID NO 143
<211> LENGTH: 17
<212> TYPE: PRT
<213> ORGANISM: Artificial Sequence
<220> FEATURE:
<223> OTHER INFORMATION: Synthetic Construct

<400> SEQUENCE: 143

Lys Ser Ser Asn Ser Leu Phe Asn Ser Arg Thr Arg Lys Asn Tyr Leu
1 5 10 15

Ala

<210> SEQ ID NO 144
<211> LENGTH: 17
<212> TYPE: PRT
<213> ORGANISM: Artificial Sequence
<220> FEATURE:
<223> OTHER INFORMATION: Synthetic Construct

<400> SEQUENCE: 144

Lys Ser Ser Gln Ser Leu Phe Asn Ser His Thr Arg Lys Asn Tyr Leu
1 5 10 15

Ala

<210> SEQ ID NO 145
<211> LENGTH: 7
<212> TYPE: PRT
<213> ORGANISM: Artificial Sequence
<220> FEATURE:
<223> OTHER INFORMATION: Synthetic Construct

<400> SEQUENCE: 145

Trp Ala Ser Ala Arg Gly Ser
1 5

<210> SEQ ID NO 146
<211> LENGTH: 17
<212> TYPE: PRT
<213> ORGANISM: Artificial Sequence
<220> FEATURE:
<223> OTHER INFORMATION: Synthetic Construct

<400> SEQUENCE: 146

Lys Ser Ser Gln Ser Leu Phe Asn Ser Arg Phe Arg Lys Asn Tyr Leu
1 5 10 15

Ala

<210> SEQ ID NO 147
<211> LENGTH: 17
<212> TYPE: PRT
<213> ORGANISM: Artificial Sequence
<220> FEATURE:
<223> OTHER INFORMATION: Synthetic Construct

<400> SEQUENCE: 147

Lys Ser Ser Gln Ser Leu Phe Asn Ser Arg Thr Arg Lys Asn Tyr Leu
1 5 10 15

Leu

<210> SEQ ID NO 148
<211> LENGTH: 17
<212> TYPE: PRT
<213> ORGANISM: Artificial Sequence
<220> FEATURE:
<223> OTHER INFORMATION: Synthetic Construct

<400> SEQUENCE: 148

Lys Ser Ser Gln Ser Leu Phe Asn Ser Arg Thr Arg Lys Asn Tyr Leu
1 5 10 15

Asn

<210> SEQ ID NO 149
<211> LENGTH: 17
<212> TYPE: PRT
<213> ORGANISM: Artificial Sequence
<220> FEATURE:
<223> OTHER INFORMATION: Synthetic Construct

<400> SEQUENCE: 149

Lys Ser Ser Gln Ser Leu Phe Asn Ser Arg Thr Arg Lys Asn Tyr Leu
1 5 10 15

Met

<210> SEQ ID NO 150
<211> LENGTH: 17
<212> TYPE: PRT
<213> ORGANISM: Artificial Sequence
<220> FEATURE:
<223> OTHER INFORMATION: Synthetic Construct

<400> SEQUENCE: 150

Arg Ser Ser Gln Ser Leu Phe Asn Ser Arg Thr Arg Lys Asn Tyr Leu
1 5 10 15

Ala

<210> SEQ ID NO 151
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: R or K
<220> FEATURE:
<221> NAME/KEY: MISC_FEATURE
<222> LOCATION: (3)..(3)
<223> OTHER INFORMATION: S or A
<220> FEATURE:
<221> NAME/KEY: MISC_FEATURE
<222> LOCATION: (4)..(4)
<223> OTHER INFORMATION: W, N or Q
<220> FEATURE:
<221> NAME/KEY: MISC_FEATURE
<222> LOCATION: (10)..(10)
<223> OTHER INFORMATION: H or R
<220> FEATURE:
<221> NAME/KEY: MISC_FEATURE
<222> LOCATION: (11)..(11)
<223> OTHER INFORMATION: T or F
<220> FEATURE:
<221> NAME/KEY: MISC_FEATURE
<222> LOCATION: (17)..(17)
<223> OTHER INFORMATION: A, L, N, or M

<400> SEQUENCE: 151

Xaa Ser Xaa Xaa Ser Leu Phe Asn Ser Xaa Xaa Arg Lys Asn Tyr Leu
1 5 10 15

Xaa

<210> SEQ ID NO 152
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: G or E

<400> SEQUENCE: 152

Trp Ala Ser Ala Arg Xaa Ser
1 5

<210> SEQ ID NO 153
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: N or R

<400> SEQUENCE: 153

Lys Gln Ser Phe Xaa Leu Arg Thr
1 5

<210> SEQ ID NO 154
<211> LENGTH: 19
<212> TYPE: PRT
<213> ORGANISM: Artificial Sequence
<220> FEATURE:
<223> OTHER INFORMATION: Synthetic Construct

<400> SEQUENCE: 154

Phe Ile Arg His Lys Ala Asn Gly Tyr Thr Thr Glu Tyr Ser Thr Ser
1 5 10 15

Val Lys Gly

<210> SEQ ID NO 155
<211> LENGTH: 19
<212> TYPE: PRT
<213> ORGANISM: Artificial Sequence
<220> FEATURE:
<223> OTHER INFORMATION: Synthetic Construct

<400> SEQUENCE: 155

Phe Ile Arg His Lys Ala Asn Thr Tyr Thr Thr Glu Tyr Ser Thr Ser
1 5 10 15

Val Lys Gly

<210> SEQ ID NO 156
<211> LENGTH: 19
<212> TYPE: PRT
<213> ORGANISM: Artificial Sequence
<220> FEATURE:
<223> OTHER INFORMATION: Synthetic Construct

<400> SEQUENCE: 156

Phe Ile Arg His Lys Ala Asn Leu Tyr Thr Thr Glu Tyr Ser Thr Ser
1 5 10 15

Val Lys Gly

<210> SEQ ID NO 157
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: V or A
<220> FEATURE:
<221> NAME/KEY: MISC_FEATURE
<222> LOCATION: (8)..(8)
<223> OTHER INFORMATION: G , F, K, V, T, L or I
<220> FEATURE:
<221> NAME/KEY: MISC_FEATURE
<222> LOCATION: (9)..(9)
<223> OTHER INFORMATION: E or Y
<220> FEATURE:
<221> NAME/KEY: MISC_FEATURE
<222> LOCATION: (11)..(11)
<223> OTHER INFORMATION: T or R
<220> FEATURE:
<221> NAME/KEY: MISC_FEATURE
<222> LOCATION: (16)..(16)
<223> OTHER INFORMATION: W or S
<220> FEATURE:
<221> NAME/KEY: MISC_FEATURE
<222> LOCATION: (17)..(17)
<223> OTHER INFORMATION: D or V
<220> FEATURE:
<221> NAME/KEY: MISC_FEATURE
<222> LOCATION: (18)..(18)
<223> OTHER INFORMATION: K, T or R

<400> SEQUENCE: 157

Phe Ile Arg His Lys Xaa Asn Xaa Xaa Thr Xaa Glu Tyr Ser Thr Xaa
1 5 10 15

Xaa Xaa Gly

<210> SEQ ID NO 158
<211> LENGTH: 19
<212> TYPE: PRT
<213> ORGANISM: Artificial Sequence
<220> FEATURE:
<223> OTHER INFORMATION: Synthetic Construct

<400> SEQUENCE: 158

Phe Ile Arg His Lys Ala Asn Phe Tyr Thr Thr Glu Tyr Ser Thr Ser
1 5 10 15

Val Lys Gly

<210> SEQ ID NO 159
<211> LENGTH: 19
<212> TYPE: PRT
<213> ORGANISM: Artificial Sequence
<220> FEATURE:
<223> OTHER INFORMATION: Synthetic Construct

<400> SEQUENCE: 159

Phe Ile Arg His Lys Ala Asn Lys Tyr Thr Thr Glu Tyr Ser Thr Ser
1 5 10 15

Val Lys Gly

<210> SEQ ID NO 160
<211> LENGTH: 19
<212> TYPE: PRT
<213> ORGANISM: Artificial Sequence
<220> FEATURE:
<223> OTHER INFORMATION: Synthetic Construct

<400> SEQUENCE: 160

Phe Ile Arg His Lys Ala Asn Val Tyr Thr Thr Glu Tyr Ser Thr Ser
1 5 10 15

Val Lys Gly

<210> SEQ ID NO 161
<211> LENGTH: 19
<212> TYPE: PRT
<213> ORGANISM: Artificial Sequence
<220> FEATURE:
<223> OTHER INFORMATION: Synthetic Construct

<400> SEQUENCE: 161

Phe Ile Arg His Lys Ala Asn Ile Tyr Thr Thr Glu Tyr Ser Thr Ser
1 5 10 15

Val Lys Gly

<210> SEQ ID NO 162
<211> LENGTH: 19
<212> TYPE: PRT
<213> ORGANISM: Artificial Sequence
<220> FEATURE:
<223> OTHER INFORMATION: Synthetic Construct

<400> SEQUENCE: 162

Phe Ile Arg His Lys Ala Asn Phe Glu Thr Thr Glu Tyr Ser Thr Ser
1 5 10 15

Val Lys Gly

<210> SEQ ID NO 163
<211> LENGTH: 19
<212> TYPE: PRT
<213> ORGANISM: Artificial Sequence
<220> FEATURE:
<223> OTHER INFORMATION: Synthetic Construct

<400> SEQUENCE: 163

Phe Ile Arg His Lys Ala Asn Phe Tyr Thr Arg Glu Tyr Ser Thr Ser
1 5 10 15

Val Lys Gly

<210> SEQ ID NO 164
<211> LENGTH: 19
<212> TYPE: PRT
<213> ORGANISM: Artificial Sequence
<220> FEATURE:
<223> OTHER INFORMATION: Synthetic Construct

<400> SEQUENCE: 164

Phe Ile Arg His Lys Ala Asn Phe Tyr Thr Thr Glu Tyr Ser Thr Trp
1 5 10 15

Val Lys Gly

<210> SEQ ID NO 165

<211> LENGTH: 19
<212> TYPE: PRT
<213> ORGANISM: Artificial Sequence
<220> FEATURE:
<223> OTHER INFORMATION: Synthetic Construct

<400> SEQUENCE: 165

Phe Ile Arg His Lys Ala Asn Phe Tyr Thr Thr Glu Tyr Ser Thr Ser
1 5 10 15

Val Arg Gly

<210> SEQ ID NO 166
<211> LENGTH: 19
<212> TYPE: PRT
<213> ORGANISM: Artificial Sequence
<220> FEATURE:
<223> OTHER INFORMATION: Synthetic Construct

<400> SEQUENCE: 166

Phe Ile Arg His Lys Val Asn Phe Tyr Thr Thr Glu Tyr Ser Thr Ser
1 5 10 15

Val Lys Gly

<210> SEQ ID NO 167
<211> LENGTH: 19
<212> TYPE: PRT
<213> ORGANISM: Artificial Sequence
<220> FEATURE:
<223> OTHER INFORMATION: Synthetic Construct

<400> SEQUENCE: 167

Phe Ile Arg His Lys Ala Asn Phe Tyr Thr Thr Glu Tyr Ser Thr Ser
1 5 10 15

Val Thr Gly

<210> SEQ ID NO 168
<211> LENGTH: 19
<212> TYPE: PRT
<213> ORGANISM: Artificial Sequence
<220> FEATURE:
<223> OTHER INFORMATION: Synthetic Construct

<400> SEQUENCE: 168

Phe Ile Arg His Lys Ala Asn Phe Tyr Thr Thr Glu Tyr Ser Thr Ser
1 5 10 15

Asp Lys Gly

<210> SEQ ID NO 169
<211> LENGTH: 112
<212> TYPE: PRT
<213> ORGANISM: Artificial Sequence
<220> FEATURE:
<223> OTHER INFORMATION: Synthetic Construct

<400> SEQUENCE: 169

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Phe Asn Ser
20 25 30

Arg Thr Arg Lys Asn Tyr Leu Ala Trp Tyr Gln Gln Lys Pro Gly Gln
35 40 45

Pro Pro Lys Leu Leu Ile Tyr Trp Ala Ser Ala Arg Glu Ser Gly Val
50 55 60

-continued

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Asn Asp Arg Thr Phe Gly Gly Gly Thr Lys Val Glu Ile Lys
            100                 105                 110


<210> SEQ ID NO 170
<211> LENGTH: 7
<212> TYPE: PRT
<213> ORGANISM: Artificial Sequence
<220> FEATURE:
<223> OTHER INFORMATION: Synthetic Construct

<400> SEQUENCE: 170

Lys Gln Ser Phe Asn Asp Arg
1               5


<210> SEQ ID NO 171
<211> LENGTH: 5
<212> TYPE: PRT
<213> ORGANISM: Artificial Sequence
<220> FEATURE:
<223> OTHER INFORMATION: Synthetic Construct

<400> SEQUENCE: 171

Leu Leu Gln Gly Gly
1               5


<210> SEQ ID NO 172
<211> LENGTH: 8
<212> TYPE: PRT
<213> ORGANISM: Artificial Sequence
<220> FEATURE:
<223> OTHER INFORMATION: Synthetic Construct

<400> SEQUENCE: 172

Gly Gly Leu Leu Gln Gly Pro Pro
1               5


<210> SEQ ID NO 173
<211> LENGTH: 6
<212> TYPE: PRT
<213> ORGANISM: Artificial Sequence
<220> FEATURE:
<223> OTHER INFORMATION: Synthetic Construct

<400> SEQUENCE: 173

Leu Leu Gln Gly Pro Pro
1               5
```